(12) United States Patent
Sheth et al.

(10) Patent No.: US 12,275,703 B2
(45) Date of Patent: **\*Apr. 15, 2025**

(54) HIGHLY PURIFIED BATCHES OF PHARMACEUTICAL GRADE MIGALASTAT AND METHODS OF PRODUCING THE SAME

(71) Applicant: Amicus Therapeutics, Inc., Philadelphia, PA (US)

(72) Inventors: Kamlesh Sheth, North Brunswick, NJ (US); Sergey Tesler, Monroe, NJ (US); James Cartwright, Middlesex (GB); Clive King, Middlesex (GB); Wendy Cross, Middlesex (GB)

(73) Assignee: Amicus Therapeutics, Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/214,002

(22) Filed: Jun. 26, 2023

(65) Prior Publication Data

US 2023/0348388 A1    Nov. 2, 2023

Related U.S. Application Data

(63) Continuation of application No. 17/551,806, filed on Dec. 15, 2021, now Pat. No. 11,685,718, which is a continuation-in-part of application No. 17/148,817, filed on Jan. 14, 2021, now Pat. No. 11,623,916.

(60) Provisional application No. 63/126,264, filed on Dec. 16, 2020.

(51) Int. Cl.
    *C07D 211/46*    (2006.01)

(52) U.S. Cl.
    CPC ........ *C07D 211/46* (2013.01); *C07B 2200/13* (2013.01)

(58) Field of Classification Search
    CPC .......................... C07D 211/46; C07B 2200/13
    See application file for complete search history.

(56) References Cited

U.S. PATENT DOCUMENTS

| 11,623,916 B2 * | 4/2023 | Sheth | A61J 1/035 |
| | | | 546/242 |
| 11,685,718 B2 * | 6/2023 | Sheth | C07D 211/46 |
| | | | 536/17.2 |

\* cited by examiner

*Primary Examiner* — D Margaret M Seaman
(74) *Attorney, Agent, or Firm* — Servilla Whitney LLC

(57) ABSTRACT

Provided are methods of producing Active Pharmaceutical Ingredient (API) grade migalastat hydrochloride, and for purifying intermediate grade migalastat hydrochloride. Further provided are methods of producing [(2R,3S,4R,5S)-1-butyl-2-(hydroxymethyl)piperidine-3,4,5-triol hydrochloride (lucerastat hydrochloride) and other 1-deoxygalactonojirimycin compounds, as well as methods of purifying intermediate grade lucerastat hydrochloride and other 1-deoxygalactonojirimycin compounds.

20 Claims, 26 Drawing Sheets

HIGHLY PURIFIED BATCHES OF PHARMACEUTICAL GRADE MIGALASTAT AND METHODS OF PRODUCING THE SAME

CROSS-REFERENCE TO RELATED APPLICATIONS

This application is a continuation of U.S. application Ser. No. 17/551,806, filed Dec. 15, 2021, which is a continuation-in-part application of U.S. application Ser. No. 17/148,817, filed Jan. 14, 2021, now U.S. Pat. No. 11,623,916, which claims the benefit of U.S. Provisional Application No. 63/126,264, filed Dec. 16, 2020. The contents of each of these applications are hereby incorporated by reference in their entirety.

BACKGROUND

Migalastat was developed for the treatment of Fabry disease. It is desirable to develop methods for producing batches of migalastat hydrochloride that have increased purity, and for purifying batches of migalastat hydrochloride of intermediate grade.

SUMMARY

Provided are methods of producing a batch of 1,2,3,6-tetrapivaloyl-D-galactofuranoside, the methods comprising: reacting D-(+)-galactose with pivaloyl imidazole to produce 1,2,3,6-tetrapivaloyl-D-galactofuranoside, wherein the 1,2,3,6-tetrapivaloyl-D-galactofuranoside contains 3% area or less of Compound B.

Also provided are methods of determining the purity of a batch of 1,2,3,6-tetrapivaloyl-D-galactofuranoside produced by reacting D-(+)-galactose with pivaloyl imidazole to produce 1,2,3,6-tetrapivaloyl-D-galactofuranoside, the method comprising performing a chromatographic test on the batch to determine that the batch has 3% or less of Compound B.

Some embodiments comprise performing high performance liquid chromatography (HPLC) on the batch to identify a peak associated with the Compound B, and determining that the area under the second peak is 3% or less of a total area under the identified HPLC peaks. In some embodiments, the batch has 2.9% area or less of the Compound B. In some embodiments, the batch has from 1.5-2.5% area of the Compound B.

Also provided are methods for determining an amount of Compound B in a 1,2,3,6-tetrapivaloyl-D-galactofuranoside sample, the methods comprising synthesizing Compound B and using the synthesized Compound B as a reference standard in high performance liquid chromatography (HPLC) test conducted to determine the amount of the Compound B in the 1,2,3,6-tetrapivaloyl-D-galactofuranoside sample.

Also provided are methods of producing a batch of 5-azido-5-deoxy-1,2,3,6-tetrapivaloyl-D-galactofuranoside, the methods comprising: activating 1,2,3,6-tetrapivaloyl-D-galactofuranoside with trifluoromethanesulfonic acid anhydride; reacting the activated 1,2,3,6-tetrapivaloyl-D-galactofuranoside with water to produce 1,2,3,6-tetrapivaloyl-α-L-altrofuranoside; activating the 1,2,3,6-tetrapivaloyl-α-L-altrofuranoside with trifluoromethanesulfonic acid anhydride; reacting the activated 1,2,3,6-tetrapivaloyl-α-L-altrofuranoside with sodium azide to produce 5-azido-5-deoxy-1,2,3,6-tetrapivaloyl-D-galactofuranoside; and isolating the 5-azido-5-deoxy-1,2,3,6-tetrapivaloyl-D-galactofuranoside, wherein the isolated 5-azido-5-deoxy-1,2,3,6-tetrapivaloyl-D-galactofuranoside contains 0.6% area or less of 1,2,3,6-tetrapivaloyl-D-galactofuranoside, 0.3% area or less of Compound E, 0.3% area or less of Compound G, 3% area or less of Compound J, 0.6% area or less of Compound I, 0.3% area or less of Compound K, 1% area or less of Compound N, and 0.3% area of less of Compound O.

Also provided are methods of determining the purity of a batch of 5-azido-5-deoxy-1,2,3,6-tetrapivaloyl-D-galactofuranoside produced from 1,2,3,6-tetrapivaloyl-D-galactofuranoside, the method comprising performing a chromatographic test on the batch to determine that the batch has 0.6% or less of 1,2,3,6-tetrapivaloyl-D-galactofuranoside, 0.3% or less of Compound E, 0.3% or less of Compound G, 3% or less of Compound J, 0.6% or less of Compound I, 0.3% or less of Compound K, 1% or less of Compound N, and 0.3% or less of Compound O.

Some embodiments comprise performing high performance liquid chromatography (HPLC) on the batch to identify one or more of a first peak associated with the 1,2,3,6-tetrapivaloyl-D-galactofuranoside, a second peak associated with the Compound E, a third peak associated with the Compound G, a fourth peak associated with the Compound J, a fifth peak associated with the Compound I, a sixth peak associated with the Compound K, a seventh peak associated with the Compound N, and an eighth peak associated with the Compound 0, and determining that one or more of the area under the first peak is 0.6% or less of a total area under identified HPLC peaks, the area under the second peak is 0.3% or less of the total area under identified HPLC peaks, the area under the third peak is 0.3% or less of the total area under identified HPLC peaks, the area under the fourth peak is 3% or less of the total area under identified HPLC peaks, the area under the fifth peak is 0.6% or less of the total area under identified HPLC peaks, the area under the sixth peak is 0.3% or less of the total area under identified HPLC peaks, the area under the seventh peak is 1% or less of the total area under identified HPLC peaks, and the area under the eighth peak is 0.3% or less of the total area under identified HPLC peaks.

In some embodiments, the batch has 0.16-0.36% area of 1,2,3,6-tetrapivaloyl-D-galactofuranoside, 0.06% area or less of Compound E, 0.03% area or less of Compound G, 0.86-1.67% area of Compound J, 0.35% area or less of Compound I, 0.08-0.11% area of Compound K, 0.06-0.28% area of Compound N, and 0.12-0.17% area of Compound O. In some embodiments, the batch has less than 12 µg of Compound F per g of 5-azido-5-deoxy-1,2,3,6-tetrapivaloyl-D-galactofuranoside.

In some embodiments, the sodium azide is in DMSO, and the 5-azido-5-deoxy-1,2,3,6-tetrapivaloyl-D-galactofuranoside is isolated by washing the 5-azido-5-deoxy-1,2,3,6-tetrapivaloyl-D-galactofuranoside with methanol and drying the 5-azido-5-deoxy-1,2,3,6-tetrapivaloyl-D-galactofuranoside under a vacuum, and the 5-azido-5-deoxy-1,2,3,6-tetrapivaloyl-D-galactofuranoside has 0.01% w/w or less of DMSO.

Also provided are methods for determining an amount of one or more of 1,2,3,6-tetrapivaloyl-D-galactofuranoside, Compound E, Compound G, Compound J, Compound I, Compound K, Compound N, and Compound O in a 5-azido-5-deoxy-1,2,3,6-tetrapivaloyl-D-galactofuranoside sample, the method comprising one or more of: synthesizing 1,2,3,6-tetrapivaloyl-D-galactofuranoside and using the synthesized 1,2,3,6-tetrapivaloyl-D-galactofuranoside as a reference standard in a high performance liquid chromatography (HPLC) test conducted to determine the amount of 1,2,3,6- tetrapivaloyl-D-galactofuranoside in the 5-azido-5-deoxy-1, 2,3,6-tetrapivaloyl-D-galactofuranoside sample; preparing Compound E from 1,2,3,6-tetrapivaloyl-D-galactofuranoside and using the Compound E as a reference standard in an HPLC test conducted to determine the amount of Compound E in the 5-azido-5-deoxy-1,2,3,6-tetrapivaloyl-D-galactofuranoside sample; synthesizing Compound G from 1,2,3, 6-tetrapivaloyl-D-galactofuranoside and using the synthesized Compound G as a reference standard in an HPLC test conducted to determine the amount of Compound G in the 5-azido-5-deoxy-1,2,3,6-tetrapivaloyl-D-galactofuranoside sample; isolating Compound J from a batch of 5-azido-5-deoxy-1,2,3,6-tetrapivaloyl-D-galactofuranoside produced from 1,2,3,6-tetrapivaloyl-D-galactofuranoside and using the isolated Compound J as a reference standard in an HPLC test conducted to determine the amount of Compound J in the 5-azido-5-deoxy-1,2,3,6-tetrapivaloyl-D-galactofuranoside sample; synthesizing Compound I from Compound D and then recrystallizing the Compound I in heptane, and using the recrystallized Compound I as a reference standard in an HPLC test conducted to determine the amount of Compound I in the 5-azido-5-deoxy-1,2,3,6-tetrapivaloyl-D-galactofuranoside sample; synthesizing Compound K from Compound F and then using the synthesized Compound K as a reference standard in an HPLC test conducted to determine the amount of Compound K in the 5-azido-5-deoxy-1,2,3,6-tetrapivaloyl-D-galactofuranoside sample; synthesizing Compound N from Compound F and then using the synthesized Compound N as a reference standard in an HPLC test conducted to determine the amount of Compound N in the 5-azido-5-deoxy-1,2,3,6-tetrapivaloyl-D-galactofuranoside sample; and isolating Compound O from a batch of 5-azido-5-deoxy-1,2,3,6-tetrapivaloyl-D-galactofuranoside produced from 1,2,3,6-tetrapivaloyl-D-galactofuranoside and using the isolated Compound O as a reference standard in an HPLC test conducted to determine the amount of Compound O in the 5-azido-5-deoxy-1,2,3, 6-tetrapivaloyl-D-galactofuranoside sample.

Also provided are methods of producing a batch of intermediate grade migalastat hydrochloride, the methods comprising: reducing 5-azido-5-deoxy-1,2,3,6-tetrapivaloyl-D-galactofuranoside using hydrogen and a palladium catalyst; allowing the reduced 5-azido-5-deoxy-1,2,3,6-tetrapivaloyl-D-galactofuranoside to undergo a rearrangement and hydrogenation to produce Compound S; adding sodium methoxide to the Compound S to produce migalastat; treating the migalastat with hydrochloric acid to produce an aqueous migalastat hydrochloride solution in hydrochloric acid; and isolating the intermediate grade migalastat hydrochloride from the aqueous migalastat hydrochloride solution; wherein the isolated intermediate grade migalastat hydrochloride contains 0.4% area or less of Compound U, 0.4% area or less of Compound V, 0.25% area or less of Compound Y, 0.15% area or less of Compound W, and 0.3% area or less of Compound BB.

In some embodiments, the batch of intermediate grade migalastat hydrochloride has 0.67% w/w or less of Compound U, 0.42% w/w or less of Compound V, 0.41% w/w or less of Compound Y, 0.15% w/w or less of Compound W, and 0.39% w/w or less of Compound BB, based on the weight of the intermediate grade migalastat hydrochloride. In some embodiments, the batch of intermediate grade migalastat hydrochloride contains 0.25% area or less of Compound Z and 0.15% area or less of Compound AA. In some embodiments, the batch of intermediate grade migalastat hydrochloride has 0.4% w/w or less of Compound Z and 0.41% w/w or less of Compound AA, based on the weight of the intermediate grade migalastat hydrochloride. In some embodiments, the batch of intermediate grade migalastat hydrochloride contains 1.0 µg or less of each of Compound Q and Compound P per gram of the isolated intermediate grade migalastat.

In some embodiments, the batch of intermediate grade migalastat hydrochloride contains 2.0 µg or less of Compound X per gram of the isolated intermediate grade migalastat.

In some embodiments, the batch of intermediate grade migalastat hydrochloride has one or more of: no detectable Compound U, 0.13% w/w or less of Compound V, 0.1% w/w or less of Compound Y, 0.04% w/w or less of Compound W, 0.15% w/w or less of Compound BB, 0.4% w/w or less of Compound Z, and 0.09% w/w or less of Compound AA, based on the weight of the intermediate grade migalastat hydrochloride.

In some embodiments, the intermediate grade migalastat hydrochloride has a residue on ignition of 7% w/w or less, based on the weight of the intermediate grade migalastat hydrochloride. In some embodiments, the intermediate grade migalastat hydrochloride has a residue on ignition of from 1.2% to 2.1% w/w, based on the weight of the intermediate grade migalastat hydrochloride.

In some embodiments, the step of reducing 5-azido-5-deoxy-1,2,3,6-tetrapivaloyl-D-galactofuranoside using hydrogen and a palladium catalyst is performed at a temperature of from 35° C.-55° C. In some embodiments, the step of reducing 5-azido-5-deoxy-1,2,3,6-tetrapivaloyl-D-galactofuranoside using hydrogen and a palladium catalyst is performed at a temperature of from 40° C.-50° C. In some embodiments, the step of reducing 5-azido-5-deoxy-1,2,3, 6-tetrapivaloyl-D-galactofuranoside using hydrogen and a palladium catalyst is performed at a temperature of 45° C.

In some embodiments, the step of reducing 5-azido-5-deoxy-1,2,3,6-tetrapivaloyl-D-galactofuranoside using hydrogen and a palladium catalyst is performed with a palladium catalyst quantity of from 0.5 mol % to 2.5 mol %.

In some embodiments, the step of reducing 5-azido-5-deoxy-1,2,3,6-tetrapivaloyl-D-galactofuranoside using hydrogen and a palladium catalyst is performed with a palladium catalyst quantity of from 0.007-0.013 molar equivalents. In some embodiments, the step of reducing 5-azido-5-deoxy-1,2,3,6-tetrapivaloyl-D-galactofuranoside using hydrogen and a palladium catalyst is performed with a palladium catalyst quantity of 0.013 molar equivalents.

In some embodiments, the step of reducing 5-azido-5-deoxy-1,2,3,6-tetrapivaloyl-D-galactofuranoside using hydrogen and a palladium catalyst is performed in 6-10 volumes of methanol. In some embodiments, the step of reducing 5-azido-5-deoxy-1,2,3,6-tetrapivaloyl-D-galactofuranoside using hydrogen and a palladium catalyst is performed in 7-9 volumes of methanol. In some embodiments, the step of reducing 5-azido-5-deoxy-1,2,3,6-tetrapivaloyl-D-galactofuranoside using hydrogen and a palladium catalyst is performed in 9 volumes of methanol.

In some embodiments, the step of reducing 5-azido-5-deoxy-1,2,3,6-tetrapivaloyl-D-galactofuranoside using hydrogen and a palladium catalyst is performed at a hydrogen pressure of from 6-10 bar gauge (5-9 bar absolute). In some embodiments, the step of reducing 5-azido-5-deoxy-1,2,3,6-tetrapivaloyl-D-galactofuranoside using hydrogen and a palladium catalyst is performed at a hydrogen pressure of from 7-9 bar gauge (8-10 bar absolute). In some embodiments, the step of reducing 5-azido-5-deoxy-1,2,3,6-tetrapivaloyl-D-galactofuranoside using hydrogen and a palladium catalyst is performed at a hydrogen pressure of 8 bar gauge.

In some embodiments, the step of reducing 5-azido-5-deoxy-1,2,3,6-tetrapivaloyl-D-galactofuranoside using hydrogen and a palladium catalyst is performed for 44 hours or more. In some embodiments, the step of reducing 5-azido-5-deoxy-1,2,3,6-tetrapivaloyl-D-galactofuranoside using hydrogen and a palladium catalyst is performed for 68 hours.

In some embodiments, the palladium catalyst is removed before adding the sodium methoxide.

In some embodiments, the step of treating the migalastat with hydrochloric acid comprises adding the hydrochloric acid to the migalastat to produce a migalastat/hydrochloric acid mixture, heating the migalastat/hydrochloric acid mixture for an age time to precipitate sodium chloride out of the mixture, cooling the mixture, and filtering out the sodium chloride.

In some embodiments, the filtering is at a filtration temperature of from 25° C. to 40° C.

In some embodiments, the hydrochloric acid has a concentration of from 35%-37% hydrochloric acid. In some embodiments, the hydrochloric acid has a concentration of 37% hydrochloric acid.

In some embodiments, the age time is from 1 to 10 hours.

In some embodiments, the heating is from 40° C. to 55° C.

In some embodiments, the step of adding sodium methoxide to the Compound S to produce migalastat further comprises adding methanol to the Compound S, wherein the method further comprises removing the methanol by distillation before adding the hydrochloric acid, and wherein the residual weight of the migalastat after distillation is 0.5-0.9 weights.

In some embodiments, the step of isolating the intermediate grade migalastat hydrochloride from the aqueous migalastat hydrochloride solution comprises treating the aqueous migalastat hydrochloride solution with charcoal and then crystallizing the intermediate grade migalastat hydrochloride with ethanol, wherein the ethanol is at a temperature of 15° C. or higher, and wherein the ethanol is added over a period of 12 minutes or more.

In some embodiments, the ethanol is at a temperature of from 15° C. to 25° C.

In some embodiments, the ethanol is added over a period of from 12 minutes to 50 minutes. In some embodiments, the ethanol is added over a period of 30 minutes or more.

Also provided are methods of determining the purity of a batch of intermediate grade migalastat hydrochloride produced from 5-azido-5-deoxy-1,2,3,6-tetrapivaloyl-D-galactofuranoside, the method comprising performing a chromatographic test on the batch to determine that the batch has 0.4% w/w or less of Compound U, 0.4% w/w or less of Compound V, 0.25% w/w or less of Compound Y, 0.15% w/w or less of Compound W, and 0.3% w/w or less of Compound BB, based on the weight of the intermediate grade migalastat hydrochloride.

Some embodiments comprise determining that batch of intermediate grade migalastat hydrochloride has 0.25% w/w or less of Compound Z and 0.15% w/w or less of Compound AA, based on the weight of the intermediate grade migalastat hydrochloride.

Some embodiments comprise performing high performance liquid chromatography (HPLC) on the batch of intermediate grade migalastat hydrochloride to identify one or more of a first peak associated with the Compound U, a second peak associated with the Compound V, a third peak associated with the Compound Y, a fourth peak associated with the Compound W, a fifth peak associated with the Compound BB, a sixth peak associated with the Compound Z, and a seventh peak associated with the Compound AA, and determining that one or more of the area under the first peak is 0.4% or less of a total area under identified HPLC peaks, the area under the second peak is 0.4% or less of the total area under identified HPLC peaks, the area under the third peak is 0.25% or less of the total area under identified HPLC peaks, the area under the fourth peak is 0.15% or less of the total area under identified HPLC peaks, the area under the fifth peak is 0.3% or less of the total area under identified HPLC peaks, the area under the sixth peak is 0.25% or less of the total area under identified HPLC peaks, and the area under the seventh peak is 0.15% or less of the total area under identified HPLC peaks.

Also provided are methods for determining an amount of one or more of Compound U, Compound V, Compound Y, Compound W, Compound BB, Compound Z, and Compound AA in an intermediate grade migalastat hydrochloride sample, the method comprising one or more of: preparing Compound U by hydrogenating 5-azido-5-deoxy-1,2,3,6-tetrapivaloyl-D-galactofuranoside and then treating it with sodium methoxide, and then using the prepared Compound U as a reference standard in a high performance liquid chromatography (HPLC) test conducted to determine the amount of Compound U in the intermediate grade migalastat hydrochloride sample; preparing Compound V by hydrogenation between migalastat hydrochloride and formaldehyde, and then using the prepared Compound V as a reference standard in an HPLC test conducted to determine the amount of Compound V in the intermediate grade migalastat hydrochloride sample; isolating Compound Y, from a filtrate obtained after recrystallizing a batch of intermediate grade migalastat hydrochloride, using hydrophilic interaction liquid chromatography, and then using the isolated Compound Y as a reference standard in an HPLC test conducted to determine the amount of Compound Y in the intermediate grade migalastat hydrochloride sample; preparing Compound W by hydrogenating migalastat hydrochloride in the presence of sodium methoxide and recrystallizing isolated crude, and then using the prepared Compound W as a reference standard in an HPLC test conducted to determine the amount of Compound W in the intermediate grade migalastat hydrochloride sample; isolating Compound BB, from a filtrate obtained after recrystallizing a batch of intermediate grade migalastat hydrochloride, using hydrophilic interaction liquid chromatography, and then using the isolated Compound BB as a reference standard in an HPLC test conducted to determine the amount of Compound BB in the intermediate grade migalastat hydrochloride sample; isolating Compound Z, from a filtrate obtained after recrystallizing a batch of intermediate grade migalastat hydrochloride, using hydrophilic interaction liquid chromatography, and then using the isolated Compound Z as a reference standard in an HPLC test conducted to determine the amount of Compound Z in the intermediate grade migalastat hydrochloride sample; and isolating Compound AA, from a filtrate obtained after recrystallizing a batch of intermediate grade migalastat hydrochloride, using hydrophilic interaction liquid chromatography, and then using the isolated Compound AA as a reference standard in an HPLC test conducted to determine the amount of Compound AA in the intermediate grade migalastat hydrochloride sample.

Also provided are methods of producing a batch of migalastat hydrochloride, the methods comprising: crystallizing intermediate grade migalastat hydrochloride twice in a mixture of water and ethanol to give migalastat hydrochloride, and isolating the batch of migalastat hydrochloride, wherein the batch of migalastat hydrochloride contains 0.15% w/w or less of Compound W, 0.15% w/w or less of Compound U, 0.15% w/w or less of Compound V, 0.15% w/w or less of Compound Y, 0.15% w/w or less of Compound BB, 0.3% w/w or less of methanol, 0.5% w/w or less of ethanol, 0.2% w/w or less of water, and 0.2% w/w or less of residue on ignition, each based on the weight of the migalastat hydrochloride, and 0.15 ppm or less of arsenic, 0.5 ppm or less of cadmium, 1.5 ppm or less of mercury, 0.5 ppm or less of lead, and 10 ppm or less of palladium.

Also provided are methods of determining the purity of a batch of migalastat hydrochloride, the methods comprising measuring an amount of Compound W, Compound U, Compound V, Compound Y, Compound BB, methanol, ethanol, water, residue on ignition, arsenic, cadmium, mercury, lead, and palladium in the batch of migalastat hydrochloride, wherein the batch of migalastat hydrochloride contains 0.15% w/w or less of Compound W, 0.15% w/w or less of Compound U, 0.15% w/w or less of Compound V, 0.15% w/w or less of Compound Y, 0.15% w/w or less of Compound BB, 0.3% w/w or less of methanol, 0.5% w/w or less of ethanol, 0.2% w/w or less of water, and 0.2% w/w or less of residue on ignition, each based on the weight of the migalastat hydrochloride, and 0.15 ppm or less of arsenic, 0.5 ppm or less of cadmium, 1.5 ppm or less of mercury, 0.5 ppm or less of lead, and 10 ppm or less of palladium.

In some embodiments, the batch of migalastat hydrochloride contains 0.10% w/w or less of any other particular impurity.

In some embodiments, the Compound W and Compound U are measured using high performance liquid chromatography (HPLC), and the Compound V, Compound Y, and Compound BB are measured using hydrophilic interaction liquid chromatography (HILIC), In some embodiments, total impurities measured using high performance liquid chromatography (HPLC) and hydrophilic interaction liquid chromatography (HILIC) are 0.5% w/w or less.

In some embodiments, the water is measured via Karl Fischer titration.

In some embodiments, the methanol and the ethanol are measured via gas chromatography.

In some embodiments, the arsenic, the cadmium, the mercury, the lead, and the palladium are measured via inductively coupled plasma mass spectroscopy.

In some embodiments, the migalastat hydrochloride is identified via (i) an infrared spectroscopy spectrum that is concordant with that of a migalastat hydrochloride reference material and (ii) a high performance liquid chromatography (HPLC) retention time that matches a migalastat hydrochloride reference standard.

In some embodiments, the migalastat hydrochloride contains 0.2% area or less of Compound CC, 1.4% area or less of Compound A, 0.6% area or less of Compound EE, and 4.1% area or less of Compound DD. In some embodiments, the migalastat hydrochloride has less than 0.1% w/w of each of Compound CC, Compound A, Compound EE, and Compound DD.

In some embodiments, each gram of the isolated migalastat hydrochloride contains less than 12 µg of each of Compound D, Compound F, 5-azido-5-deoxy-1,2,3,6-tetrapivaloyl-D-galactofuranoside, Compound N, Compound Q, Compound P, Compound X, ethyl chloride, and methyl chloride.

In some embodiments, the batch of migalastat hydrochloride is produced with a first crystallization step that comprises: admixing the intermediate grade migalastat hydrochloride in water at a first crystallization temperature to produce a first migalastat hydrochloride slurry or solution; adding ethanol to the first migalastat hydrochloride slurry or solution to induce a first crystallized migalastat hydrochloride; cooling the first migalastat hydrochloride slurry or solution to a first isolation temperature to isolate the first crystallized migalastat hydrochloride; then filtering the first crystallized migalastat hydrochloride; washing the filtered first crystallized migalastat hydrochloride with ethanol; and drying the washed first crystallized migalastat hydrochloride.

Some embodiments comprise methods of producing the migalastat hydrochloride that comprise a second crystallization step that comprises: dissolving the dried first crystallized migalastat hydrochloride in water at a second crystallization temperature to produce a second migalastat hydrochloride slurry or solution; adding a first portion of ethanol to the second migalastat hydrochloride slurry or solution to induce a second crystallized migalastat hydrochloride; adding a second portion of ethanol to the second migalastat hydrochloride slurry or solution after a hold time; then cooling the second migalastat hydrochloride slurry or solution to a second isolation temperature to isolate the second crystallized migalastat hydrochloride; then filtering the second crystallized migalastat hydrochloride; washing the filtered second crystallized migalastat hydrochloride with ethanol; and drying the washed second crystallized migalastat hydrochloride to produce the batch of migalastat hydrochloride.

Also provided are methods of producing a batch of migalastat hydrochloride, the methods comprising dissolving intermediate grade migalastat hydrochloride in water at a first crystallization temperature to produce a first migalastat hydrochloride slurry or solution; adding ethanol to the first migalastat hydrochloride slurry or solution to induce a first crystallized migalastat hydrochloride; cooling the first migalastat hydrochloride slurry or solution to a first isolation temperature to isolate the first crystallized migalastat hydrochloride; filtering the first crystallized migalastat hydrochloride; washing the filtered first crystallized migalastat hydrochloride with ethanol; drying the washed first crystallized migalastat hydrochloride; dissolving the dried first crystallized migalastat hydrochloride in water at a second crystallization temperature to produce a second migalastat hydrochloride slurry or solution; adding a first portion of ethanol to the second migalastat hydrochloride slurry or solution to induce a second crystallized migalastat hydrochloride; adding a second portion of ethanol to the second migalastat hydrochloride slurry or solution after a hold time; cooling the second migalastat hydrochloride slurry or solution to a second isolation temperature to isolate the second crystallized migalastat hydrochloride; filtering the second crystallized migalastat hydrochloride; washing the filtered second crystallized migalastat hydrochloride with ethanol; and drying the washed second crystallized migalastat hydrochloride to produce the batch of migalastat hydrochloride.

In some embodiments, the dissolving the intermediate grade migalastat hydrochloride and/or the dried first crystallized migalastat hydrochloride is in from 1.0-1.6 weights of water. In some embodiments, the dissolving the intermediate grade migalastat hydrochloride and/or the dried first crystallized migalastat hydrochloride is in from 1.1-1.4 weights of water. In some embodiments, the dissolving the intermediate grade migalastat hydrochloride and/or the dried first crystallized migalastat hydrochloride is in 1.3 weights of water.

In some embodiments, the first crystallization temperature and/or the second crystallization temperature is within a range of from 30° C. to 60° C. In some embodiments, the first crystallization temperature and/or the second crystallization temperature is within a range of from 40° C. to 60° C. In some embodiments, the first crystallization temperature and/or the second crystallization temperature is 50° C.

In some embodiments, the ethanol added to the first migalastat hydrochloride slurry or solution and/or the combination of the first portion of ethanol and second portion of ethanol added to the second migalastat hydrochloride slurry or solution is from 1-11.4 weights of ethanol. In some embodiments, the ethanol added to the first migalastat hydrochloride slurry or solution and/or the combination of the first portion of ethanol and second portion of ethanol added to the second migalastat hydrochloride slurry or solution is from 4.8-11.4 weights of ethanol. In some embodiments, the ethanol added to the first migalastat hydrochloride slurry or solution and/or the combination of the first portion of ethanol and second portion of ethanol added to the second migalastat hydrochloride slurry or solution is from 8.4-10.6 weights of ethanol. In some embodiments, the ethanol added to the first migalastat hydrochloride slurry or solution and/or the combination of the first portion of ethanol and second portion of ethanol added to the second migalastat hydrochloride slurry or solution is 9.5 weights of ethanol.

In some embodiments, the first isolation temperature and/or the second isolation temperature is within a range of from 5° C. to 35° C. In some embodiments, the first isolation temperature and/or the second isolation temperature is 20° C.

In some embodiments, the combination of the first portion of ethanol and the second portion of ethanol is from 1.0-11.4 weights of ethanol. In some embodiments, the first portion of ethanol comprises 1.8 to 2.0 weights of ethanol. In some embodiments, the first portion of ethanol is 1.9 weights of ethanol. In some embodiments, the second portion of ethanol comprises 6.7 to 8.4 weights of ethanol.

In some embodiments, the ethanol is added to the first migalastat hydrochloride slurry or solution over a period of from 0 to 65 min. In some embodiments, the ethanol is added to the first migalastat hydrochloride slurry or solution over a period of 60 min.

In some embodiments, the first portion of ethanol is added over a period of 5 min or more. In some embodiments, the first portion of ethanol is added over a period of from 5 min to 60 min.

In some embodiments, the hold time is 5 min or more. In some embodiments, the hold time is from 5 min to 60 min.

In some embodiments, the second portion of ethanol is added over a period of from 15 min to 60 min.

In some embodiments, the batch of migalastat hydrochloride comprises 0.6 kg or more of migalastat hydrochloride. In some embodiments, the batch of migalastat hydrochloride comprises 23 kg or more of migalastat hydrochloride.

Another aspect of the disclosure describes a method of purifying intermediate grade 1-deoxygalactonojirimycin compound. In some embodiments, the method comprises (i) performing a first crystallization comprising crystallizing intermediate grade 1-deoxygalactonojirimycin compound in a first mixture comprising water and a first C1 to C4 alcohol to give a first crystallized 1-deoxygalactonojirimycin compound; (ii) isolating the first crystallized 1-deoxygalactonojirimycin compound from the first mixture to give an isolated first crystallized 1-deoxygalactonojirimycin compound; (iii) performing a second crystallization comprising crystallizing the isolated first crystallized 1-deoxygalactonojirimycin compound in a second mixture comprising water and a second C1 to C4 alcohol to give a second crystallized 1-deoxygalactonojirimycin compound; and (iv) isolating the second crystallized 1-deoxygalactonojirimycin compound from the second mixture to give an active pharmaceutical ingredient (API) grade 1-deoxygalactonojirimycin compound.

In some embodiments, the 1-deoxygalactonojirimycin compound comprises 1-deoxygalactonojirimycin derivatives and salts thereof. In some embodiments, the 1-deoxygalactonojirimycin derivative comprises N-alkyldeoxygalactonojirimycin. In some embodiments, the 1-deoxygalactonojirimycin derivative comprises migalastat, N-methyldeoxygalactonojirimycin, N-ethyldeoxygalactonojirimycin, N-propyldeoxygalactonojirimycin, N-butyldeoxygalactonojirimycin (lucerastat) or salt thereof. In some embodiments, the 1-deoxygalactonojirimycin derivatives comprises hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methane-sulphonate, naphthalene-2-sulphonate, phthalate, salicylate, sorbate, stearate, succinate, tartrate or toluene-p-sulphonate salt.

In some embodiments, the intermediate grade 1-deoxygalactonojirimycin compound, the isolated first crystallized 1-deoxygalactonojirimycin compound, or both, are admixed with an amount of water which is from about 1.0 to about 1.6 times the weight of the corresponding 1-deoxygalactonojirimycin compound.

In some embodiments, the first C1 to C4 alcohol is ethanol, the second C1 to C4 alcohol is ethanol, or both the first and the second C1 to C4 alcohol are ethanol. In some embodiments, the first C1 to C4 alcohol is present in the first mixture in an amount from about 1 to about 11.4 times the weight of the intermediate 1-deoxygalactonojirimycin compound. In some embodiments, the second C1 to C4 alcohol is present in the second mixture in an amount from about 1 to about 11.4 times the weight of the isolated first crystallized 1-deoxygalactonojirimycin compound.

In some embodiments, performing the first crystallization comprises admixing the intermediate grade 1-deoxygalactonojirimycin compound in water to produce a first 1-deoxygalactonojirimycin compound slurry or solution; adding the first C1 to C4 alcohol to the first 1-deoxygalactonojirimycin compound slurry or solution to produce a second 1-deoxygalactonojirimycin compound slurry or solution at a first crystallization temperature for inducing crystallization; and cooling the second 1-deoxygalactonojirimycin compound slurry or solution to a first isolation temperature to complete crystallization, providing the first mixture. In some embodiments, the first C1 to C4 alcohol is added to the first 1-deoxygalactonojirimycin compound slurry or solution in an amount from about 1 to about 11.4 times the weight of the intermediate 1-deoxygalactonojirimycin compound over a period of time ranging from about 0 to about 65 minutes. In some embodiments, the first isolation temperature is within a range from about 5° C. to about 35° C., or is about 20° C. In some embodiments, the first crystallization temperature, the second crystallization temperature, or both, is within a range of from about 30° C. to about 70° C.

In some embodiments, isolating the first crystallized 1-deoxygalactonojirimycin compound comprises filtering the first mixture to provide the first crystallized 1-deoxygalactonojirimycin compound; washing the first crystallized 1-deoxygalactonojirimycin compound with the first C1 to C4 alcohol to provide a washed first crystallized 1-deoxygalactonojirimycin compound; and optionally, drying the washed first crystallized 1-deoxygalactonojirimycin compound to give the isolated first crystallized 1-deoxygalactonojirimycin compound.

In some embodiments, performing the second crystallization comprises admixing the isolated first crystallized 1-deoxygalactonojirimycin compound in water to produce a third 1-deoxygalactonojirimycin compound slurry or solution; adding a first portion of the second C1 to C4 alcohol to the third 1-deoxygalactonojirimycin compound slurry or solution to produce a fourth 1-deoxygalactonojirimycin compound slurry or solution at a second crystallization temperature for inducing crystallization; adding a second portion of the second C1 to C4 alcohol to the fourth 1-deoxygalactonojirimycin compound slurry or solution after a hold time; and cooling the fourth 1-deoxygalactonojirimycin compound slurry or solution to a second isolation temperature to complete crystallization, providing the second mixture. In some embodiments, the hold time is from about 5 minutes to about 60 minutes. In some embodiments, the first portion of the second C1 to C4 alcohol is about 1.8 to about 2.0 times the weight of the 1-deoxygalactonojirimycin compound present in the fourth 1-deoxygalactonojirimycin compound slurry or solution. In some embodiments, the first portion of C1 to C4 alcohol is added to the third 1-deoxygalactonojirimycin compound slurry or solution over a period from about 5 minutes to about 60 minutes. In some embodiments, the second portion of the C1 to C4 alcohol is about 6.7 to about 8.4 times the weight of the 1-deoxygalactonojirimycin compound present in the fourth 1-deoxygalactonojirimycin compound slurry or solution. In some embodiments, the second isolation temperature is within a range from about 5° C. to about 35° C., or is about 20° C.

In some embodiments, isolating the second crystallized 1-deoxygalactonojirimycin compound comprises filtering the second mixture to isolate the second crystallized 1-deoxygalactonojirimycin compound; washing the second crystallized 1-deoxygalactonojirimycin compound with the second C1 to C4 alcohol; and drying the washed second crystallized 1-deoxygalactonojirimycin compound to give the API grade 1-deoxygalactonojirimycin compound.

Another aspect of the disclosure describes a method of producing active pharmaceutical ingredient (API) grade. In some embodiments, the method comprises (i) performing a first crystallization comprising crystallizing intermediate grade 1-deoxygalactonojirimycin compound in a first mixture comprising water and a first C1 to C4 alcohol to give a first crystallized 1-deoxygalactonojirimycin compound; (ii) isolating the first crystallized 1-deoxygalactonojirimycin compound from the first mixture to give an isolated first crystallized 1-deoxygalactonojirimycin compound; (iii) performing a second crystallization comprising crystallizing the isolated first crystallized 1-deoxygalactonojirimycin compound in a second mixture comprising water and a second C1 to C4 alcohol to give a second crystallized 1-deoxygalactonojirimycin compound; and (iv) isolating the second crystallized 1-deoxygalactonojirimycin compound from the second mixture to give an active pharmaceutical ingredient (API) grade 1-deoxygalactonojirimycin compound.

In some embodiments, the active pharmaceutical ingredient (API) grade 1-deoxygalactonojirimycin compound comprises 1-deoxygalactonojirimycin derivatives or salts thereof. In some embodiments, the 1-deoxygalactonojirimycin derivative comprises N-alkyldeoxygalactonojirimycin. In some embodiments, the 1-deoxygalactonojirimycin derivative comprises migalastat, N-methyldeoxygalactonojirimycin, N-ethyldeoxygalactonojirimycin, N-propyldeoxygalactonojirimycin, N-butyldeoxygalactonojirimycin (lucerastat) or salt thereof. In some embodiments, the active pharmaceutical ingredient (API) grade 1-deoxygalactonojirimycin derivatives comprises hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, naphthalene-2-sulphonate, phthalate, salicylate, sorbate, stearate, succinate, tartrate or toluene-p-sulphonate salt.

Another aspect of the disclosure describes a method of purifying intermediate grade 1-deoxygalactonojirimycin compound. In a specific embodiments, the method comprises: (i) admixing the intermediate grade 1-deoxygalactonojirimycin compound in water to produce a first 1-deoxygalactonojirimycin compound slurry or solution; (ii) adding a first C1 to C4 alcohol to the first 1-deoxygalactonojirimycin compound slurry or solution at a first crystallization temperature to produce a second 1-deoxygalactonojirimycin compound slurry or solution and induce crystallization; (iii) cooling the second 1-deoxygalactonojirimycin compound slurry or solution to a first isolation temperature to complete crystallization, providing a first mixture comprising a first crystallized 1-deoxygalactonojirimycin compound; (iv) filtering the first mixture to isolate an isolated first crystallized 1-deoxygalactonojirimycin compound; (v) washing the isolated first crystallized 1-deoxygalactonojirimycin compound with the first C1 to C4 alcohol to provide a washed first crystallized 1-deoxygalactonojirimycin compound; (vi) optionally, drying the washed first crystallized 1-deoxygalactonojirimycin compound; (vii) dissolving the washed and optionally dried first crystallized 1-deoxygalactonojirimycin compound in water to produce a third 1-deoxygalactonojirimycin compound slurry or solution; (viii) adding a portion of a second C1 to C4 alcohol to the third 1-deoxygalactonojirimycin compound slurry or solution to produce a fourth 1-deoxygalactonojirimycin compound slurry or solution at a second crystallization temperature to initiate crystallization; (ix) adding a second portion of the second C1 to C4 alcohol to the fourth 1-deoxygalactonojirimycin compound slurry or solution after a hold time to further induce crystallization; (x) cooling the fourth 1-deoxygalactonojirimycin compound slurry or solution to a second isolation temperature to complete crystallization, providing a second mixture comprising a second crystallized 1-deoxygalactonojirimycin compound; (xi) filtering the second mixture to isolate the second crystallized 1-deoxygalactonojirimycin compound; (xii) washing the second crystallized 1-deoxygalactonojirimycin compound with the second C1 to C4 alcohol; and (xiii) drying the washed second crystallized 1-deoxygalactonojirimycin compound to give active pharmaceutical ingredient (API) grade 1-deoxygalactonojirimycin compound. In some embodiments, the 1-deoxygalactonojirimycin compound comprises 1-deoxygalactonojirimycin derivatives and salts thereof. In some embodiments, the 1-deoxygalactonojirimycin derivative comprises N-alkyldeoxygalactonojirimycin. In some embodiments, the 1-deoxygalactonojirimycin derivative comprises migalastat, N-methyldeoxygalactonojirimycin, N-ethyldeoxygalactonojirimycin, N-propyldeoxygalactonojirimycin, N-butyldeoxygalactonojirimycin (lucerastat) or salt thereof. In some embodiments, the active pharmaceutical ingredient (API) grade 1-deoxygalactonojirimycin derivatives comprises hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, naphthalene-2-sulphonate, phthalate, salicylate, sorbate, stearate, succinate, tartrate or toluene-p-sulphonate salt.

Also provided is a method of purifying intermediate grade migalastat salt, the method comprising:
i) performing a first crystallization comprising crystallizing intermediate grade migalastat salt in a first mixture comprising water and a first C1 to C4 alcohol to give a first crystallized migalastat salt;
ii) isolating the first crystallized migalastat salt from the first mixture to give an isolated first crystallized migalastat salt;
iii) performing a second crystallization comprising crystallizing the isolated first crystallized migalastat salt in a second mixture comprising water and a second C1 to C4 alcohol to give a second crystallized migalastat salt; and
iv) isolating the second crystallized migalastat salt from the second mixture to give an active pharmaceutical ingredient (API) grade migalastat salt.

In some embodiments, the first crystallization comprises: admixing the intermediate grade migalastat salt in water to produce a first migalastat salt slurry or solution; adding the first C1 to C4 alcohol to the first migalastat salt slurry or solution to produce a second migalastat salt slurry or solution at a first crystallization temperature for inducing crystallization; and cooling the second migalastat salt slurry or solution to a first isolation temperature to complete crystallization, providing the first mixture.

In some embodiments, the isolating in ii) comprises: filtering the first mixture to provide the first crystallized migalastat salt; washing the first crystallized migalastat salt with the first C1 to C4 alcohol to provide a washed first crystallized migalastat salt; and optionally, drying the isolated first crystallized migalastat salt.

In some embodiments, the second crystallization comprises: admixing the isolated first crystallized migalastat salt in water to produce a third migalastat salt slurry or solution; adding a portion of the C1 to C4 alcohol to the third migalastat salt slurry or solution to produce a fourth migalastat salt slurry or solution at a second crystallization temperature for inducing crystallization; adding a second portion of the C1 to C4 alcohol to the fourth migalastat salt slurry or solution after a hold time; then cooling the fourth migalastat salt slurry or solution to a second isolation temperature to complete crystallization, providing the second mixture.

In some embodiments, the isolating in iv) comprises: filtering the second mixture to isolate the second crystallized migalastat salt; washing the second crystallized migalastat salt with the second C1 to C4 alcohol; and drying the washed second crystallized migalastat salt to give the API grade migalastat salt.

In some embodiments, the first C1 to C4 alcohol is ethanol. In some embodiments, the second C1 to C4 alcohol is ethanol. In some embodiments, the first and second C1 to C4 alcohol are both ethanol.

In some embodiments, the intermediate grade migalastat salt, the first crystallized migalastat salt, or both, is admixed in an amount of water which is from about 1.0 to about 1.6 times the weight of the corresponding migalastat salt. In some embodiments, the amount of water is from about 1.1 to about 1.4 times the weight of the corresponding migalastat salt. In some embodiments, the amount of water is about 1.3 times the weight of the corresponding migalastat salt.

In some embodiments, the first crystallization temperature, the second crystallization temperature, or both, is within a range from about 30° C. to about 70° C. In some embodiments, the first crystallization temperature, the second crystallization temperature, or both, is within a range of from about 40° C. to about 60° C. In some embodiments, the first crystallization temperature, the second crystallization temperature, or both, is about 50° C.

In some embodiments, the amount of first C1 to C4 alcohol present in the first mixture is from about 1 to about 11.4 times the weight of migalastat salt present in the first mixture In some embodiments, the amount of first C1 to C4 alcohol is from about 4.8 to about 11.4 times the weight of the migalastat salt. In some embodiments, the amount of first C1 to C4 alcohol is from about 8.4 to about 10.6 times the weight of the migalastat salt, or is about 9.5 times the weight of migalastat salt.

In some embodiments, a total amount of the second C1 to C4 alcohol present in the second mixture is from about 1 to about 11.4 times the weight of migalastat salt present in the second mixture. In some embodiments, the total amount of second C1 to C4 alcohol, is from about 4.8 to about 11.4 times the weight of the migalastat salt. In some embodiments, the total amount of second C1 to C4 alcohol is from about 8.4 to about 10.6 times the weight of the corresponding migalastat salt. In some embodiments, the total amount of second C1 to C4 alcohol is about 9.5 times the weight of the migalastat salt.

In some embodiments, a first portion of the second C1 to C4 alcohol is added which is about 1.8 to about 2.0 times the weight of the migalastat salt present in the third migalastat salt slurry or solution. In some embodiments, the first portion of second C1 to C4 alcohol is about 1.9 times the weight of the migalastat salt present in the third migalastat salt slurry or solution.

In some embodiments, a second portion of the second C1 to C4 alcohol is added which is about 6.7 to about 8.4 times the weight of the migalastat salt present in the fourth migalastat salt slurry or solution.

In some embodiments, the first isolation temperature, the second isolation temperature, or both, is within a range from about 5° C. to about 35° C. In some embodiments, the first isolation temperature, the second isolation temperature, or both, is about 20° C. In some embodiments, the first C1 to C4 alcohol is added to the first migalastat salt slurry or solution in an amount from about 1 to about 11.4 times the weight of the intermediate migalastat salt over a period of time ranging from about 0 to about 65 minutes. In some embodiments, the first C1 to C4 alcohol is added to the first migalastat salt slurry or solution over a period of time of about 60 minutes.

In some embodiments, the first portion of second C1 to C4 alcohol is added to the third migalastat salt slurry or solution over a period from about 5 minutes to about 60 minutes.

In some embodiments, the hold time is from about 5 minutes to about 60 minutes.

In some embodiments, the migalastat salt comprises hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methane-sulphonate, naphthalene-2-sulphonate, phthalate, salicylate, sorbate, stearate, succinate, tartrate or toluene-p-sulphonate salt.

In another aspect is provided a method of producing active pharmaceutical ingredient (API) grade migalastat salt, the method comprising:
i) performing a first crystallization comprising crystallizing intermediate grade migalastat salt in a first mixture comprising water and a first C1 to C4 alcohol to give a first crystallized migalastat salt;
ii) isolating the first crystallized migalastat salt from the first mixture to give an isolated first crystallized migalastat salt;
iii) performing a second crystallization comprising crystallizing the isolated first crystallized migalastat salt in a second mixture comprising water and a second C1 to C4 alcohol to give a second crystallized migalastat salt; and
iv) isolating the second crystallized migalastat salt from the second mixture to give active pharmaceutical ingredient (API) grade migalastat salt.

In some embodiments, the migalastat salt comprises hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methane-sulphonate, naphthalene-2-sulphonate, phthalate, salicylate, sorbate, stearate, succinate, tartrate or toluene-p-sulphonate salt In another aspect is provided a method of purifying intermediate grade migalastat salt, the method comprising:
i) admixing the intermediate grade migalastat salt in water to produce a first migalastat salt slurry or solution;
ii) adding a first C1 to C4 alcohol to the first migalastat salt slurry or solution at a first crystallization temperature to give a second migalastat salt slurry or solution and induce crystallization;
iii) cooling the second migalastat salt slurry or solution to a first isolation temperature to complete crystallization, providing a first mixture comprising a first crystallized migalastat salt;
iv) filtering the first mixture to isolate an isolated first crystallized migalastat salt;
v) washing the isolated first crystallized migalastat salt with the first C1 to C4 alcohol to provide a washed first crystallized migalastat salt;
vi) optionally, drying the washed first crystallized migalastat salt;
vii) admixing the washed and optionally dried first crystallized migalastat salt in water to produce a third migalastat salt slurry or solution;
viii) adding a portion of a second C1 to C4 alcohol to the third migalastat salt slurry or solution at a second crystallization temperature to initiate crystallization;
ix) adding a second portion of the second C1 to C4 alcohol to the fourth migalastat salt slurry or solution after a hold time to further induce crystallization;
x) cooling the fourth migalastat salt slurry or solution to a second isolation temperature to complete crystallization, providing a second mixture comprising a second crystallized migalastat salt;
xi) filtering the second mixture to isolate the second crystallized migalastat salt;
xii) washing the second crystallized migalastat salt with the second C1 to C4 alcohol; and
xiii) drying the washed second crystallized migalastat salt to give active pharmaceutical ingredient (API) grade migalastat salt.

In some embodiments, the migalastat salt comprises hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methane-sulphonate, naphthalene-2-sulphonate, phthalate, salicylate, sorbate, stearate, succinate, tartrate or toluene-p-sulphonate salt.

Some embodiments comprise preparing the batch of migalastat salt, or a portion thereof, for commercial sale.

Some embodiments comprise packaging the batch of migalastat salt, or a portion thereof. Some embodiments comprise packing a portion of the migalastat salt in polyvinyl chloride (PVC)/polychlorotrifluoroethylene (PCTFE)/PVC laminate film with aluminum foil lidding blister packs.

Some embodiments comprise performing an integrity test on the packaged migalastat salt. In some embodiments, the integrity test comprises a water vapor permeation test.

Some embodiments comprise distributing the batch of migalastat salt, or a portion thereof.

Also provided are methods of distributing a commercial batch of migalastat salt, the methods comprising: (i) producing a batch of migalastat salt; (ii) validating the batch of migalastat salt by determining that the batch contains 0.15% w/w or less of Compound W, 0.15% w/w or less of Compound U, 0.15% w/w or less of Compound V, 0.15% w/w or less of Compound Y, 0.15% w/w or less of Compound BB, 0.3% w/w or less of methanol, 0.5% w/w or less of ethanol, 0.2% w/w or less of water, and 0.2% w/w or less of residue on ignition, each based on the weight of the migalastat salt, and 0.15 ppm or less of arsenic, 0.5 ppm or less of cadmium, 1.5 ppm or less of mercury, 0.5 ppm or less of lead, and 10 ppm or less of palladium; and (iii) distributing the validated commercial batch, or a portion thereof, for medical use in a human subject.

Some embodiments comprise tracking the distributed migalastat salt, or a portion thereof. In some embodiments, the tracking comprises scanning a barcode associated with the migalastat salt, or a portion thereof. In some embodiments, the barcode encodes information that includes one or more of a name of a product, a strength and dosage form of the product, a NDC number of the product, a container size, a number of containers, a lot number of the product, a date of a transaction, a date of the shipment, and a business name and address of a person from whom and to whom ownership of the migalastat salt, or portion thereof, is being transferred.

Some embodiments comprise storing the migalastat salt, or a portion thereof, at a storage temperature of from 20° C. to 25° C.

Also provided are methods of assessing the suitability of migalastat salt for medical use in a human subject, the methods comprising: (i) performing high performance liquid chromatography (HPLC) on the migalastat salt to determine that the migalastat salt contains 0.15% w/w or less of Compound W and 0.15% w/w or less of Compound U; (ii) performing hydrophilic interaction liquid chromatography (HILIC) on the migalastat salt to determine that the migalastat salt contains 0.15% w/w or less of Compound V, 0.15% w/w or less of Compound Y, and 0.15% w/w or less of Compound BB; (iii) performing a Karl Fischer titration on the migalastat salt to determine that the migalastat salt contains 0.2% w/w or less of water; (iv) performing gas chromatography on the migalastat salt to determine that the migalastat salt contains 0.3% w/w or less of methanol and 0.5% w/w or less of ethanol; and (v) performing inductively coupled plasma mass spectroscopy on the migalastat salt to determine that the migalastat salt contains 0.15 ppm or less of arsenic, 0.5 ppm or less of cadmium, 1.5 ppm or less of mercury, 0.5 ppm or less of lead, and 10 ppm or less of palladium, wherein the migalastat salt is suitable for medical use in a human subject.

In yet another aspect is provided a method of purifying intermediate grade lucerastat salt, the method comprising:
i) performing a first crystallization comprising crystallizing intermediate grade lucerastat salt in a first mixture comprising water and a first C1 to C4 alcohol to give a first crystallized lucerastat salt;
ii) isolating the first crystallized lucerastat salt from the first mixture;
iii) performing a second crystallization comprising crystallizing the first crystallized lucerastat salt in a second mixture comprising water and a second C1 to C4 alcohol to give a second crystallized lucerastat salt; and
iv) isolating the second crystallized lucerastat salt from the second mixture to give active pharmaceutical ingredient (API) grade lucerastat salt.

In some embodiments, the first crystallization comprises: admixing the intermediate grade lucerastat salt in water to produce a first lucerastat salt slurry or solution; adding the C1 to C4 alcohol to the first lucerastat salt slurry or solution to produce a second lucerastat salt solution or slurry at a first crystallization temperature for inducing crystallization; and cooling the second lucerastat salt slurry or solution to a first isolation temperature to complete crystallization, providing the first mixture.

In some embodiments, the isolating in ii) comprises: filtering the mixture to provide the first crystallized lucerastat salt; washing the first crystallized lucerastat salt with the first C1 to C4 alcohol to provide a washed first crystallized lucerastat salt; and optionally, drying the washed first crystallized lucerastat salt to give the isolated first crystallized lucerastat salt.

In some embodiments, the second crystallization comprises: admixing the isolated first crystallized lucerastat salt in water to produce a third lucerastat salt slurry or solution; adding a first portion of the second C1 to C4 alcohol to the third lucerastat salt slurry or solution to produce a fourth lucerastat salt slurry or solution at a second crystallization temperature to induce crystallization; adding a second portion of the second C1 to C4 alcohol to the fourth lucerastat salt slurry or solution after a hold time; and cooling the fourth lucerastat salt slurry or solution to a second isolation temperature to complete crystallization, providing the second mixture.

In some embodiments, the isolating in iv) comprises: filtering the second mixture to isolate an isolated second crystallized lucerastat salt; washing the isolated second crystallized lucerastat salt with the second C1 to C4 alcohol; and drying the washed second crystallized lucerastat salt to give the API grade lucerastat salt.

In some embodiments, the first C1 to C4 alcohol is ethanol. In some embodiments, the second C1 to C4 alcohol is ethanol. In some embodiments, both the first and second C1 to C4 alcohols are ethanol.

In some embodiments, the lucerastat salt comprises hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methane-sulphonate, naphthalene-2-sulphonate, phthalate, salicylate, sorbate, stearate, succinate, tartrate or toluene-p-sulphonate salt.

The disclosure includes, without limitations, the following embodiments.

Embodiment 1: A method of purifying intermediate grade 1-deoxygalactonojirimycin compound, the method comprising:
i) performing a first crystallization comprising crystallizing intermediate grade migalastat salt in a first mixture comprising water and a first C1 to C4 alcohol to give a first crystallized migalastat salt;
ii) isolating the first crystallized migalastat salt from the first mixture to give an isolated first crystallized migalastat salt;
iii) performing a second crystallization comprising crystallizing the isolated first crystallized migalastat salt in a second mixture comprising water and a second C1 to C4 alcohol to give a second crystallized migalastat salt; and
iv) isolating the second crystallized migalastat salt from the second mixture to give an active pharmaceutical ingredient (API) grade migalastat salt.

Embodiment 2: The method of embodiment 1, wherein the 1-deoxygalactonojirimycin compound comprises 1-deoxygalactonojirimycin derivatives and salts thereof.

Embodiment 3: The method of embodiment 2, wherein the 1-deoxygalactonojirimycin derivative comprises N-alkyldeoxygalactonojirimycin.

Embodiment 4: The method of embodiment 2 or 3, wherein the 1-deoxygalactonojirimycin derivative comprises migalastat, N-methyldeoxygalactonojirimycin, N-ethyldeoxygalactonojirimycin, N-propyldeoxygalactonojirimycin, N-butyldeoxygalactonojirimycin (lucerastat) or salt thereof.

Embodiment 5: The method of any one of embodiments 2-4, wherein the 1-deoxygalactonojirimycin derivatives comprises hydrochloride, hydrobromide, nitrate, perchlorate, phosphate, sulphate, formate, acetate, aconate, ascorbate, benzenesulphonate, benzoate, cinnamate, citrate, embonate, enantate, fumarate.

Embodiment 6: The method of any one of embodiment 1-5, the first crystallization comprises: admixing the intermediate grade 1-deoxygalactonojirimycin compound in water to produce a first 1-deoxygalactonojirimycin compound slurry or solution; adding the first C1 to C4 alcohol to the first 1-deoxygalactonojirimycin compound slurry or solution to produce a second 1-deoxygalactonojirimycin compound slurry or solution at a first crystallization temperature for inducing crystallization; and cooling the second 1-deoxygalactonojirimycin compound slurry or solution to a first isolation temperature to complete crystallization, providing the first mixture Embodiment 7: The method of any one of embodiment 1-6, wherein the isolating in ii) comprises: filtering the first mixture to provide the first crystallized 1-deoxygalactonojirimycin compound; washing the first crystallized 1-deoxygalactonojirimycin compound with the first C1 to C4 alcohol to provide a washed first crystallized 1-deoxygalactonojirimycin compound; and optionally, drying the washed first crystallized 1-deoxygalactonojirimycin compound to give the isolated first crystallized 1-deoxygalactonojirimycin compound.

Embodiment 8: The method of any one of embodiment 1-7, wherein the second crystallization comprises: admixing the isolated first crystallized 1-deoxygalactonojirimycin compound in water to produce a third 1-deoxygalactonojirimycin compound slurry or solution; adding a first portion of the second C1 to C4 alcohol to the third 1-deoxygalactonojirimycin compound slurry or solution to produce a fourth 1-deoxygalactonojirimycin compound slurry or solution at a second crystallization temperature for inducing crystallization; adding a second portion of the second C1 to C4 alcohol to the fourth 1-deoxygalactonojirimycin compound slurry or solution after a hold time; and cooling the fourth 1-deoxygalactonojirimycin compound slurry or solution to a second isolation temperature to complete crystallization, providing the second mixture.

Embodiment 9: The method of any one of embodiment 1-8, wherein the isolating in iv) comprises: filtering the second mixture to isolate the second crystallized 1-deoxygalactonojirimycin compound; washing the second crystallized 1-deoxygalactonojirimycin compound with the second C1 to C4 alcohol; and drying the washed second crystallized 1-deoxygalactonojirimycin compound to give the API grade 1-deoxygalactonojirimycin compound.

Embodiment 10: The method of any one or embodiments 1-9, wherein the first C1 to C4 alcohol is ethanol, the second C1 to C4 alcohol is ethanol, or both the first and the second C1 to C4 alcohol are ethanol.

Embodiment 11: The method of any one of embodiments 1-10, wherein the intermediate grade 1-deoxygalactonojirimycin compound, the isolated first crystallized 1-deoxygalactonojirimycin compound, or both, are admixed with an amount of water which is from about 1.0 to about 1.6 times the weight of the corresponding 1-deoxygalactonojirimycin compound.

Embodiment 12: The method of any one of embodiments 1-11, wherein the first crystallization temperature, the second crystallization temperature, or both, is within a range of from about 30° C. to about 70° C.

Embodiment 13: The method of any one of embodiments 1-12, wherein the first C1 to C4 alcohol is present in the first mixture in an amount from about 1 to about 11.4 times the weight of the intermediate 1-deoxygalactonojirimycin compound.

Embodiment 14: The method of any one of embodiments 1-13, wherein the second C1 to C4 alcohol is present in the second mixture in an amount from about 1 to about 11.4 times the weight of the isolated first crystallized 1-deoxygalactonojirimycin compound.

Embodiment 15: The method of embodiment 8, wherein the first portion of the second C1 to C4 alcohol is about 1.8 to about 2.0 times the weight of the 1-deoxygalactonojirimycin compound present in the fourth 1-deoxygalactonojirimycin compound slurry or solution.

Embodiment 16: The method of embodiment 8 or 15, wherein the second portion of the C1 to C4 alcohol is about 6.7 to about 8.4 times the weight of the 1-deoxygalactonojirimycin compound present in the fourth 1-deoxygalactonojirimycin compound slurry or solution.

Embodiment 17: The method of embodiment 6, wherein the first isolation temperature is within a range from about 5° C. to about 35° C., or is about 20° C.

Embodiment 18: The method of embodiment 8, wherein the second isolation temperature is within a range from about 5° C. to about 35° C., or is about 20° C.

Embodiment 19: The method of embodiment 6, wherein the first C1 to C4 alcohol is added to the first 1-deoxygalactonojirimycin compound slurry or solution in an amount from about 1 to about 11.4 times the weight of the intermediate 1-deoxygalactonojirimycin compound over a period of time ranging from about 0 to about 65 minutes.

Embodiment 20: The method of embodiment 8 or 15, wherein the first portion of C1 to C4 alcohol is added to the third 1-deoxygalactonojirimycin compound slurry or solution over a period from about 5 minutes to about 60 minutes.

Embodiment 21: The method of embodiment 8, wherein the hold time is from about 5 minutes to about 60 minutes.

Embodiment 22: A method of producing active pharmaceutical ingredient (API) grade 1-deoxygalactonojirimycin compound, the method comprising:
  i) performing a first crystallization comprising crystallizing intermediate grade 1-deoxygalactonojirimycin compound in a first mixture comprising water and a first C1 to C4 alcohol to give a first crystallized 1-deoxygalactonojirimycin compound;
  ii) isolating the first crystallized 1-deoxygalactonojirimycin compound from the first mixture to give an isolated first crystallized 1-deoxygalactonojirimycin compound;
  iii) performing a second crystallization comprising crystallizing the isolated first crystallized 1-deoxygalactonojirimycin compound in a second mixture comprising water and a second C1 to C4 alcohol to give a second crystallized 1-deoxygalactonojirimycin compound; and
  iv) isolating the second crystallized 1-deoxygalactonojirimycin compound from the second mixture to give active pharmaceutical ingredient (API) grade 1-deoxygalactonojirimycin compound.

Embodiment 23: The method of embodiment 22, wherein 1-deoxygalactonojirimycin compound comprises 1-deoxygalactonojirimycin derivatives and salts thereof.

Embodiment 24: The method of embodiment 23, wherein the 1-deoxygalactonojirimycin derivative comprises N-alkyldeoxygalactonojirimycin.

Embodiment 25: The method of embodiment 23 or 24, wherein the 1-deoxygalactonojirimycin derivative comprises migalastat, N-methyldeoxygalactonojirimycin, N-ethyldeoxygalactonojirimycin, N-propyldeoxygalactonojirimycin, N-butyldeoxygalactonojirimycin (lucerastat) or salt thereof.

Embodiment 26: The method of any one of embodiments 23-25, wherein 1-deoxygalactonojirimycin derivatives comprises hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methane-sulphonate, naphthalene-2-sulphonate, phthalate, salicylate, sorbate, stearate, succinate, tartrate or toluene-p-sulphonate salt.

Embodiment 27: A method of purifying intermediate grade 1-deoxygalactonojirimycin compound, the method comprising:
  i) admixing the intermediate grade 1-deoxygalactonojirimycin compound in water to produce a first 1-deoxygalactonojirimycin compound slurry or solution;
  ii). adding a first C1 to C4 alcohol to the first 1-deoxygalactonojirimycin compound slurry or solution at a first crystallization temperature to produce a second 1-deoxygalactonojirimycin compound slurry or solution and induce crystallization;
  iii) cooling the second 1-deoxygalactonojirimycin compound slurry or solution to a first isolation temperature to complete crystallization, providing a first mixture comprising a first crystallized 1-deoxygalactonojirimycin compound;
  iv) filtering the first mixture to isolate an isolated first crystallized 1-deoxygalactonojirimycin compound;

v) washing the isolated first crystallized 1-deoxygalactonojirimycin compound with the first C1 to C4 alcohol to provide a washed first crystallized 1-deoxygalactonojirimycin compound;

vi) optionally, drying the washed first crystallized 1-deoxygalactonojirimycin compound;

vii) dissolving the washed and optionally dried first crystallized 1-deoxygalactonojirimycin compound in water to produce a third 1-deoxygalactonojirimycin compound slurry or solution;

viii) adding a portion of a second C1 to C4 alcohol to the third 1-deoxygalactonojirimycin compound slurry or solution to produce a fourth 1-deoxygalactonojirimycin compound slurry or solution at a second crystallization temperature to initiate crystallization;

ix) adding a second portion of the second C1 to C4 alcohol to the fourth 1-deoxygalactonojirimycin compound slurry or solution after a hold time to further induce crystallization;

x) cooling the fourth 1-deoxygalactonojirimycin compound slurry or solution to a second isolation temperature to complete crystallization, providing a second mixture comprising a second crystallized 1-deoxygalactonojirimycin compound;

xi) filtering the second mixture to isolate the second crystallized 1-deoxygalactonojirimycin compound;

xii) washing the second crystallized 1-deoxygalactonojirimycin compound with the second C1 to C4 alcohol; and xiii) drying the washed second crystallized 1-deoxygalactonojirimycin compound to give active pharmaceutical ingredient (API) grade 1-deoxygalactonojirimycin compound.

Embodiment 28: The method of embodiment 27, wherein 1-deoxygalactonojirimycin compound comprises 1-deoxygalactonojirimycin derivatives and salts thereof.

Embodiment 29: The method of embodiment 28, wherein the 1-deoxygalactonojirimycin derivative comprises N-alkyldeoxygalactonojirimycin.

Embodiment 30: The method of embodiment 28 or 29, wherein the 1-deoxygalactonojirimycin derivative comprises migalastat, N-methyldeoxygalactonojirimycin, N-ethyldeoxygalactonojirimycin, N-propyldeoxygalactonojirimycin, N-butyldeoxygalactonojirimycin (lucerastat) or salt thereof.

Embodiment 31: The method of any one of embodiments 28-30, wherein 1-deoxygalactonojirimycin derivatives comprises hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methane-sulphonate, naphthalene-2-sulphonate, phthalate, salicylate, sorbate, stearate, succinate, tartrate or toluene-p-sulphonate salt.

Embodiment 32: A method of purifying intermediate grade migalastat salt, the method comprising:

i) performing a first crystallization comprising crystallizing intermediate grade migalastat salt in a first mixture comprising water and a first C1 to C4 alcohol to give a first crystallized migalastat salt;

ii) isolating the first crystallized migalastat salt from the first mixture to give an isolated first crystallized migalastat salt;

iii) performing a second crystallization comprising crystallizing the isolated first crystallized migalastat salt in a second mixture comprising water and a second C1 to C4 alcohol to give a second crystallized migalastat salt; and iv) isolating the second crystallized migalastat salt from the second mixture to give an active pharmaceutical ingredient (API) grade migalastat salt.

Embodiment 33: The method of embodiment 32, wherein the first crystallization comprises: admixing the intermediate grade migalastat salt in water to produce a first migalastat salt slurry or solution; adding the first C1 to C4 alcohol to the first migalastat salt slurry or solution to produce a second migalastat salt slurry or solution at a first crystallization temperature for inducing crystallization; and cooling the second migalastat salt slurry or solution to a first isolation temperature to complete crystallization, providing the first mixture.

Embodiment 34: The method of embodiment 32 or 33, wherein the isolating in ii) comprises: filtering the first mixture to provide the first crystallized migalastat salt; washing the first crystallized migalastat salt with the first C1 to C4 alcohol to provide a washed first crystallized migalastat salt; and optionally, drying the washed first crystallized migalastat salt to give the isolated first crystallized migalastat salt.

Embodiment 35: The method of any one of embodiments 32-34, wherein the second crystallization comprises: admixing the isolated first crystallized migalastat salt in water to produce a third migalastat salt slurry or solution; adding a first portion of the second C1 to C4 alcohol to the third migalastat salt slurry or solution to produce a fourth migalastat salt slurry or solution at a second crystallization temperature for inducing crystallization; adding a second portion of the second C1 to C4 alcohol to the fourth migalastat salt slurry or solution after a hold time; and cooling the fourth migalastat salt slurry or solution to a second isolation temperature to complete crystallization, providing the second mixture.

Embodiment 36: The method of any one of embodiments 32-35, wherein the isolating in iv) comprises: filtering the second mixture to isolate the second crystallized migalastat salt; washing the second crystallized migalastat salt with the second C1 to C4 alcohol; and drying the washed second crystallized migalastat salt to give the API grade migalastat salt.

Embodiment 37: The method of any one of embodiments 32-36, wherein the first C1 to C4 alcohol is ethanol, the second C1 to C4 alcohol is ethanol, or both the first and the second C1 to C4 alcohol is ethanol.

Embodiment 38: The method of any one of embodiments 32-37, wherein the intermediate grade migalastat salt, the isolated first crystallized migalastat salt, or both, is admixed in an amount of water which is from 1.0 to 1.6 times the weight of the corresponding migalastat salt.

Embodiment 39: The method of any one of embodiments 32-38, wherein the amount of water is from 1.1 to 1.4 times the weight of the corresponding migalastat salt.

Embodiment 40: The method of any one of embodiments 32-39, wherein the amount of water is 1.3 times the weight of the corresponding migalastat salt.

Embodiment 41: The method of any one of embodiments 32-40, wherein the first crystallization temperature, the second crystallization temperature, or both, is within a range from about 30° C. to about 70° C.

Embodiment 42: The method of any one of embodiments 32-41, wherein the first crystallization temperature, the second crystallization temperature, or both, is within a range of from 40° C. to 60° C.

Embodiment 43: The method of any one of embodiments 32-42, wherein the first crystallization temperature, the second crystallization temperature, or both, is about 50° C.

Embodiment 44: The method of any one of embodiments 32-43, wherein the first C1 to C4 alcohol is present in the first mixture in an amount from about 1 to about 11.4 times the weight of the intermediate migalastat salt.

Embodiment 45: The method of embodiment 44, wherein the first C1 to C4 alcohol is present in an amount from about 4.8 to about 11.4 times the weight of the corresponding migalastat salt.

Embodiment 46: The method of embodiment 44, wherein the first C1 to C4 alcohol is present in an amount from about 8.4 to about 10.6 times the weight of the corresponding migalastat salt.

Embodiment 47: The method of embodiment 44, wherein the first C1 to C4 alcohol is used in a total amount of about 9.5 times the weight of the corresponding migalastat salt.

Embodiment 48: The method of any one of embodiments 32-47, wherein the second C1 to C4 alcohol is present in the second mixture in an amount from about 1 to about 11.4 times the weight of the isolated first crystallized migalastat salt.

Embodiment 49: The method of any one of embodiments 32-48, wherein the second C1 to C4 alcohol is present in an amount from about 4.8 to about 11.4 times the weight of the corresponding migalastat salt.

Embodiment 50: The method of any one of embodiments 32-49, wherein the second C1 to C4 alcohol is present in an amount from about 8.4 to about 10.6 times the weight of the corresponding migalastat salt.

Embodiment 51: The method of any one of embodiments 32-50, wherein the second C1 to C4 alcohol is used in a total amount of about 9.5 times the weight of the corresponding migalastat salt.

Embodiment 52: The method of any one of embodiments 32-51, wherein the first portion of the second C1 to C4 alcohol is about 1.8 to about 2.0 times the weight of the migalastat salt present in the third migalastat salt slurry or solution.

Embodiment 53: The method of any one of embodiments 32-52, wherein the first portion of the C1 to C4 alcohol is about 1.9 times the weight of the migalastat salt present in the third migalastat salt slurry or solution.

Embodiment 54: The method of any one of embodiments 32-53, wherein the second portion of the C1 to C4 alcohol is about 6.7 to about 8.4 times the weight of the migalastat salt present in the second migalastat salt solution.

Embodiment 55: The method of any one of embodiments 32-54, wherein the first isolation temperature is within a range from about 5° C. to about 35° C., or is about 20° C.

Embodiment 56: The method of any one of embodiments 32-55, wherein the second isolation temperature is within a range from about 5° C. to about 35° C., or is about 20° C.

Embodiment 57: The method of any one of embodiments 32-56, wherein the first C1 to C4 alcohol is added to the first migalastat salt slurry or solution in an amount from about 1 to about 11.4 times the weight of the intermediate migalastat salt over a period of time ranging from about 0 to about 65 minutes.

Embodiment 58: The method of any one of embodiments 32-57, wherein the first C1 to C4 alcohol is added to the first migalastat salt slurry or solution over a period of time of about 60 minutes.

Embodiment 59: The method of any one of embodiments 32-58, wherein the first portion of the second C1 to C4 alcohol is added to the third migalastat salt slurry or solution over a period from about 5 minutes to about 60 minutes.

Embodiment 60: The method of any one of embodiments 32-59, wherein the hold time is from about 5 minutes to about 60 minutes.

Embodiment 61: The method of any one of embodiments 32-60, wherein the migalastat salt comprises hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methane-sulphonate, naphthalene-2-sulphonate, phthalate, salicylate, sorbate, stearate, succinate, tartrate or toluene-p-sulphonate salt.

Embodiment 62: A method of producing active pharmaceutical ingredient (API) grade migalastat salt, the method comprising:
  i) performing a first crystallization comprising crystallizing intermediate grade migalastat salt in a first mixture comprising water and a first C1 to C4 alcohol to give a first crystallized migalastat salt;
  ii) isolating the first crystallized migalastat salt from the first mixture to give an isolated first crystallized migalastat salt;
  iii) performing a second crystallization comprising crystallizing the isolated first crystallized migalastat salt in a second mixture comprising water and a second C1 to C4 alcohol to give a second crystallized migalastat salt; and
  iv) isolating the second crystallized migalastat salt from the second mixture to give active pharmaceutical ingredient (API) grade migalastat salt.

Embodiment 63: The method of embodiment 62, wherein the migalastat salt comprises hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methane-sulphonate, naphthalene-2-sulphonate, phthalate, salicylate, sorbate, stearate, succinate, tartrate or toluene-p-sulphonate salt.

Embodiment 64. A method of purifying intermediate grade migalastat salt, the method comprising:
  i) admixing the intermediate grade migalastat salt in water to produce a first migalastat salt slurry or solution;
  ii). adding a first C1 to C4 alcohol to the first migalastat salt slurry or solution at a first crystallization temperature to give a second migalastat salt slurry or solution and induce crystallization;
  iii) cooling the second migalastat salt slurry or solution to a first isolation temperature to complete crystallization, providing a first mixture comprising a first crystallized migalastat salt;
  iv) filtering the first mixture to isolate an isolated first crystallized migalastat salt;
  v) washing the isolated first crystallized migalastat salt with the first C1 to C4 alcohol to provide a washed first crystallized migalastat salt;
  vi) optionally, drying the washed first crystallized migalastat salt;
  vii) admixing the washed and optionally dried first crystallized migalastat salt in water to produce a third migalastat salt slurry or solution;
  viii) adding a portion of a second C1 to C4 alcohol to the third migalastat salt slurry or solution to produce a fourth migalastat salt slurry or solution at a second crystallization temperature to initiate crystallization;

ix) adding a second portion of the second C1 to C4 alcohol to the fourth migalastat salt slurry or solution after a hold time to further induce crystallization;

x) cooling the fourth migalastat salt slurry or solution to a second isolation temperature to complete crystallization, providing a second mixture comprising a second crystallized migalastat salt;

xi) filtering the second mixture to isolate the second crystallized migalastat salt;

xii) washing the second crystallized migalastat salt with the second C1 to C4 alcohol; and xiii) drying the washed second crystallized migalastat salt to give active pharmaceutical ingredient (API) grade migalastat salt.

Embodiment 65: The method of embodiment 64, wherein the migalastat salt comprises hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, naphthalene-2-sulphonate, phthalate, salicylate, sorbate, stearate, succinate, tartrate or toluene-p-sulphonate salt.

Embodiment 66. A method of purifying intermediate grade lucerastat salt, the method comprising:

i) performing a first crystallization comprising crystallizing intermediate grade lucerastat salt in a first mixture comprising water and a first C1 to C4 alcohol to give a first crystallized lucerastat salt;

ii) isolating the first crystallized lucerastat salt from the first mixture;

iii) performing a second crystallization comprising crystallizing the first crystallized lucerastat salt in a second mixture comprising water and a second C1 to C4 alcohol to give a second crystallized lucerastat salt; and iv) isolating the second crystallized lucerastat salt from the second mixture to give active pharmaceutical ingredient (API) grade lucerastat salt.

Embodiment 67. The method of embodiment 66, wherein the first crystallization comprises: admixing the intermediate grade lucerastat salt in water to produce a first lucerastat salt slurry or solution; adding the C1 to C4 alcohol to the first lucerastat salt slurry or solution to produce a second lucerastat salt slurry or solution at a first crystallization temperature for inducing crystallization; and cooling the second lucerastat salt slurry or solution to a first isolation temperature to complete crystallization, providing the first mixture.

Embodiment 68. The method of embodiment 66 or 67, wherein the isolating in ii) comprises: filtering the first mixture to provide the first crystallized lucerastat salt; washing the first crystallized lucerastat salt with the first C1 to C4 alcohol to provide a washed first crystallized lucerastat salt; and optionally, drying the washed first crystallized lucerastat salt to give the isolated first crystallized lucerastat salt.

Embodiment 69. The method of any one of embodiments 66-68, wherein the second crystallization comprises: admixing the isolated first crystallized lucerastat salt in water to produce a third lucerastat salt slurry or solution; adding a first portion of the second C1 to C4 alcohol to the third lucerastat salt slurry or solution to produce a fourth lucerastat salt slurry or solution at a second crystallization temperature for inducing crystallization; adding a second portion of the second C1 to C4 alcohol to the fourth lucerastat salt slurry or solution after a hold time; and cooling the fourth lucerastat salt slurry or solution to a second isolation temperature to complete crystallization, providing the second mixture.

Embodiment 70. The method of any one of embodiments 66-69, wherein the isolating in iv) comprises: filtering the second mixture to isolate an isolated second crystallized lucerastat salt; washing the isolated second crystallized lucerastat salt with the second C1 to C4 alcohol; and drying the washed second crystallized lucerastat salt to give the API grade lucerastat salt.

Embodiment 71. The method of embodiment 66, wherein the first C1 to C4 alcohol, the second C1 to C4 alcohol, or both the first and second C1 to C4 alcohol is ethanol.

Embodiment 72. The method of embodiment 67, wherein the first C1 to C4 alcohol, the second C1 to C4 alcohol, or both the first and second C1 to C4 alcohol is ethanol.

Embodiment 73. The method of embodiment 68, wherein the first C1 to C4 alcohol, the second C1 to C4 alcohol, or both the first and second C1 to C4 alcohol is ethanol.

Embodiment 74. The method of embodiment 69, wherein the first C1 to C4 alcohol, the second C1 to C4 alcohol, or both the first and second C1 to C4 alcohol is ethanol.

Embodiment 75. The method of embodiment 70, wherein the first C1 to C4 alcohol, the second C1 to C4 alcohol, or both the first and second C1 to C4 alcohol is ethanol.

Embodiment 76: The method of any one of embodiments 66-75, wherein the lucerastat salt comprises hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methane-sulphonate, naphthalene-2-sulphonate, phthalate, salicylate, sorbate, stearate, succinate, tartrate or toluene-p-sulphonate salt.

DETAILED DESCRIPTION

Figure 1:
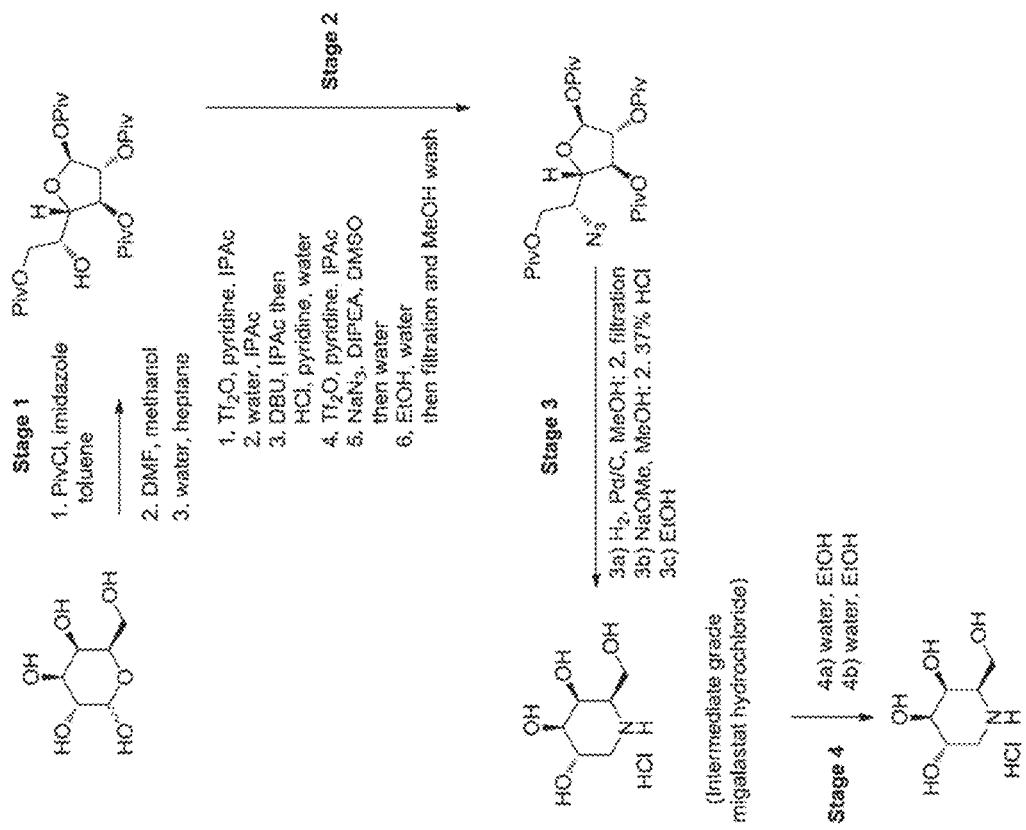
FIG. 1 sets forth a diagram showing an exemplary migalastat hydrochloride synthesis scheme.

Technical and scientific terms used herein have the meanings commonly understood by one of ordinary skill in the art to which the present invention pertains, unless otherwise defined.

Materials to which reference is made in the following description and examples are obtainable from commercial sources, unless otherwise noted.

As used herein, the singular forms "a," "an," and "the" designate both the singular and the plural, unless expressly stated to designate the singular only.

It is noted that in this disclosure and particularly in the claims and/or paragraphs, terms such as "comprises," "comprising," "consists of," "consisting of," "consists essentially of," and "consisting essentially of" can have the meaning attributed to it in U.S. patent law. It is contemplated that features set forth using any of such terms can instead be set forth using another of such terms. For instance, if a feature is set forth using "comprising" language, alternative embodiments setting forth the feature using "consisting of" or "consisting essentially of" language is within the scope of the present disclosure.

The term "about" means that the number comprehended is not limited to the exact number set forth herein, and is intended to refer to numbers substantially around the recited number while not departing from the scope of the invention. As used herein, "about" will be understood by persons of ordinary skill in the art and will vary to some extent on the context in which it is used. In the context of numerical values, "about" will mean up to plus or minus 10% of the particular numerical value unless otherwise noted. As used herein, "approximately" in the context of a numerical value or range means+/−5% of the numerical value. It is contemplated that disclosed numerical values can be modified to include ranges that are about or approximately the numerical value.

"Intermediate grade" as used herein means that a substance does not comply with regulatory requirements for a finished pharmaceutical product, e.g., because it does not meet specification criteria for one or more of drug identity, strength, quality, and purity.

"Pharmaceutical grade" or "Active Pharmaceutical Ingredient (API) grade" as used herein means that a substance (e.g., an API) complies with regulatory requirements (e.g., FDA, EMA, and/or PMDA requirements) for incorporation into a finished drug product, e.g., related to identity, strength, quality, and purity.

A "critical quality attribute" (CQA) is a physical, chemical, biological, or microbiological property or characteristic that should be within an appropriate limit, range, or distribution to ensure the desired product quality. CQAs of solid oral dosage forms are typically those aspects affecting product purity, strength, drug release, and/or stability. For drug substances, raw materials, and intermediates, the CQAs can additionally include those properties (e.g., particle size distribution, bulk density) that affect drug product CQAs.

A "critical process parameter" (CPP) is process parameter whose variability has an impact on a critical quality attribute.

The term "Fabry disease" refers to an X-linked inborn error of glycosphingolipid catabolism due to deficient lysosomal α-Gal A activity. This defect causes accumulation of the substrate globotriaosylceramide ("GL-3", also known as $Gb_3$ or ceramide trihexoside) and related glycosphingolipids in vascular endothelial lysosomes of the heart, kidneys, skin, and/or other tissues. Another substrate of the enzyme is plasma globotriaosylsphingosine ("plasma lyso-$Gb_3$").

A "carrier" is a female who has one X chromosome with a defective α-Gal A gene and one X chromosome with the normal gene and in whom X chromosome inactivation of the normal allele is present in one or more cell types. A carrier can be diagnosed with Fabry disease.

A "patient" refers to a subject who has been diagnosed with or is suspected of having a particular disease. The patient may be human or animal.

A "Fabry patient" refers to an individual who has been diagnosed with or suspected of having Fabry disease and has a mutated α-Gal A as defined further below. Characteristic markers of Fabry disease can occur in male hemizygotes and female carriers with the same prevalence, although females typically are less severely affected.

The term "ERT-naive patient" refers to a Fabry patient that has never received enzyme replacement therapy (ERT) or has not received ERT for at least 6 months prior to initiating migalastat therapy.

The term "ERT-experienced patient" refers to a Fabry patient that was receiving ERT immediately prior to initiating migalastat therapy. In some embodiments, the ERT-experienced patient has received at least 12 months of ERT immediately prior to initiating migalastat therapy.

Human α-galactosidase A (α-Gal A) refers to an enzyme encoded by the human GLA gene. The full DNA sequence of α-Gal A, including introns and exons, is available in GenBank Accession No. X14448.1. The human α-Gal A enzyme consists of 429 amino acids and is available in GenBank Accession Nos. X14448.1 and U78027.1.

The term "mutant protein" includes a protein which has a mutation in the gene encoding the protein which results in the inability of the protein to achieve a stable conformation under the conditions normally present in the endoplasmic reticulum (ER). The failure to achieve a stable conformation result in a substantial amount of the enzyme being degraded, rather than being transported to the lysosome. Such a mutation is sometimes called a "conformational mutant." Such mutations include, but are not limited to, missense mutations, and in-frame small deletions and insertions.

The term "mutant α-Gal A" includes an α-Gal A which has a mutation in the gene encoding α-Gal A which results in the inability of the enzyme to achieve a stable conformation under the conditions normally present in the ER. The failure to achieve a stable conformation result in a substantial amount of the enzyme being degraded, rather than being transported to the lysosome.

"Deficient α-Gal A activity" refers to α-Gal A activity in cells from a patient which is below the normal range as compared (using the same methods) to the activity in cells from normal individuals not having Fabry.

The term "α-Gal A activity" refers to the normal physiological function of a wild-type α-Gal A in a cell. For example, α-Gal A activity includes hydrolysis of GL-3.

The terms "enhance α-Gal A activity" or "increase α-Gal A activity" refer to increasing the amount of α-Gal A that adopts a stable conformation in a cell contacted with a pharmacological chaperone specific for the α-Gal A, relative to the amount in a cell (preferably of the same cell-type or the same cell, e.g., at an earlier time) not contacted with the pharmacological chaperone specific for the α-Gal A. This term also refers to increasing the trafficking of α-Gal A to the lysosome in a cell contacted with a pharmacological chaperone specific for the α-Gal A, relative to the trafficking of α-Gal A not contacted with the pharmacological chaperone specific for the protein. These terms refer to both wild-type and mutant α-Gal A. In one embodiment, the increase in the amount of α-Gal A in the cell is measured by measuring the hydrolysis of an artificial substrate in lysates from cells that have been treated with the PC. An increase in hydrolysis is indicative of increased α-Gal A activity.

A "responder" is an individual diagnosed with or suspected of having a lysosomal storage disorder, such as Fabry disease, whose cells exhibit sufficiently increased α-Gal A activity, respectively, and/or amelioration of symptoms or enhancement in surrogate markers, in response to contact with a pharmaceutical chaperone. Non-limiting examples of enhancements in surrogate markers for Fabry are lyso-Gb$_3$ and those disclosed in U.S. Patent Application Publication No. US 2010/0113517, which is hereby incorporated by reference in its entirety.

"Weights" is referred to as a relative amount of a component or compound, and it is defined relative to a reference material. For instance, for 1 g of a reference material, 2 weights of a compound means 2 g of the compound. Other relative amounts, such as "molar equivalents" and "volumes" are also determined with reference to a reference material.

The production of migalastat hydrochloride can result in a plurality of impurities, especially when produced at a large scale (bulk) quantity. Provided are methods of producing migalastat hydrochloride with controlled levels of impurities. Also provided are methods of producing intermediates used in the production of migalastat hydrochloride. Also provided are methods of purifying intermediate grade migalastat hydrochloride. Also provided are methods useful for validating, releasing, and or distributing a batch of migalastat hydrochloride, or a portion thereof. The methods are also useful for validating, releasing, and or distributing a batch of an intermediate of migalastat hydrochloride, or a portion thereof.

1-deoxygalactonojirimycin (Migalastat)1-deoxygalactonojirimycin, also known as migalastat or (2R,3S,4R,5S)-2-(hydroxymethyl) piperdine-3,4,5-triol, refers to a compound having the following free base structures:

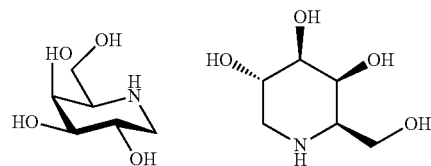

As used herein, the term "1-deoxygalactonojirimycin compound" refers to 1-deoxygalactonojirimycin and derivatives thereof in both the free base form and any pharmaceutically acceptable salt forms. Accordingly, in some embodiments, 1-deoxygalactonojirimycin derivative comprises N-alkyl derivatives of 1-deoxygalactonojorimycin such as C1-C4 N-alkyl derivatives. In some embodiments, N-alkyldeoxygalactonojirimycin comprises N-methyldeoxygalactonojirimycin, N-ethyldeoxygalactonojirimycin, N-propyldeoxygalactonojirimycin and N-butyldeoxygalactonojirimycin. N-butyldeoxygalactonojirimycin is also known as lucerasate. In some embodiments, 1-deoxygalactonojirimycin compound comprises migalastat, N-methyldeoxygalactonojirimycin, N-ethyldeoxygalactonojirimycin, N-propyldeoxygalactonojirimycin, N-butyldeoxygalactonojirimycin (lucerastat) or salt thereof. In one or more embodiments, the 1-deoxygalactonojirimycin compound refers to migalastat or a salt thereof. Although specific reference to reagents, intermediates and/or impurities below may be specific to a particular 1-deoxygalactonojirimycin compound (e.g. migalastat), the methods and compositions described herein can utilize corresponding reagents, intermediates and/or impurities for other relevant 1-deoxygalactonojirimycin compounds.

In some embodiments, the 1-deoxygalactonojirimycin compound comprises hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methane-sulphonate, naphthalene-2-sulphonate, phthalate, salicylate, sorbate, stearate, succinate, tartrate, toluene-p-sulphonate, and the like salts of 1-deoxygalactonojirimycin compounds.

The term migalastat generally encompasses both the free base form and any pharmaceutically acceptable salt forms of unsubstituted 1-deoxygalactonojirimycin (DGJ). For example, the hydrochloride salt of unsubstituted 1-deoxygalactonojirimycin is known as migalastat hydrochloride.

Migalastat hydrochloride has the following structure:

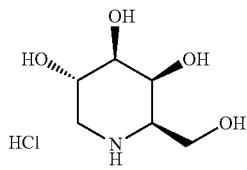 [SMILES: Cl ; OC[C@H]1NC[C@H](O)[C@@H](O)[C@H]1O]

As used herein, the term "free base equivalent" or "FBE" refers to the amount of DGJ present in the DGJ or salt thereof. In other words, the term "FBE" means either an amount of DGJ free base, or the equivalent amount of DGJ free base that is provided by a salt of DGJ. For example, due to the weight of the chloride anion, 150 mg of DGJ HCl provides as much DGJ as 123 mg of the free base form of DGJ. Other salts will have different conversion factors, depending on the molecular weight of the counter ion. While migalastat hydrochloride is referenced throughout, also provided are methods and compositions that instead use other salts, such as hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methane-sulphonate, naphthalene-2-sulphonate, phthalate, salicylate, sorbate, stearate, succinate, tartrate, toluene-p-sulphonate, and the like.

The term "1-deoxygalactonojirimycin compound" encompasses pharmaceutical grade 1-deoxygalactonojirimycin compound, intermediate grade 1-deoxygalactonojirimycin compound, and pre-intermediate grade 1-deoxygalactonojirimycin compound (e.g., in aqueous solution). However, unless specifically noted to refer to intermediate grade 1-deoxygalactonojirimycin compound, or unless it would be apparent to the person skilled in the art to refer to intermediate grade 1-deoxygalactonojirimycin compound or pre-intermediate grade 1-deoxygalactonojirimycin compound based on context, the term 1-deoxygalactonojirimycin compound will implicate a degree of purity sufficient for pharmaceutical use.

In some embodiments, 1-deoxygalactonojirimycin compound is purified according to a first purification method. The first purification method can be any of the method known to the person skilled in the art. In some embodiments, the purification method comprises chromatography, sublimation, crystallization, fractional extraction and distillation. In some embodiments, the chromatography comprises size exclusion chromatography, ion-exchange chromatography, affinity chromatography, normal-phase liquid chromatography and reverse-phase liquid chromatography. In some embodiments, the ion-exchange chromatography comprises anion exchange chromatography and cation exchange chromatography.

In some embodiments, the 1-deoxygalactonojirimycin compound is optionally treated to protect one or more chemical groups. In some embodiments, 1-deoxygalactonojirimycin compound with one or more protected chemical groups provide better purification.

In some embodiments, 1-deoxygalactonojirimycin compound is converted into a pharmaceutically acceptable salt according to any of the known methods. In some embodiments, the pharmaceutically acceptable salt provides better purification.

the term migalastat hydrochloride encompasses pharmaceutical grade migalastat hydrochloride, intermediate grade migalastat hydrochloride, and pre-intermediate grade migalastat hydrochloride (e.g., in aqueous solution). However, unless specifically noted to refer to intermediate grade migalastat hydrochloride, or unless it would be apparent to the person skilled in the art to refer to intermediate grade migalastat hydrochloride or pre-intermediate grade migalastat hydrochloride based on context, the term migalastat hydrochloride will implicate a degree of purity sufficient for pharmaceutical use.

Migalastat hydrochloride generally has a white to almost white appearance and is in solid form.

1-deoxygalactonojirimycin compound can be produced in four general stages, each of which are discussed below. Compounds formed throughout Stages 1-3 of the process can be considered to be intermediates of pharmaceutical grade 1-deoxygalactonojirimycin compound.

The stage 4 process can produce pharmaceutical grade drug substance.

Stage 1: Preparation of
1,2,3,6-tetrapivaloyl-D-galactofuranoside

Stage 1 of 1-deoxygalactonojirimycin compound production can be performed by reacting pivaloyl imidazole with D-(+)-galactose to give 1,2,3,6-tetrapivaloyl-D-galactofuranoside. To the extent amounts of Stage 1 components are described using relative terms (e.g., weights or molar equivalents), those amounts are relative to D-(+)-galactose unless indicated otherwise.

In some embodiments, D-(+)-galactose is dissolved by heating in N,N-Dimethylformamide (DMF). In some embodiments, the D-(+)-galactose is dissolved in at least about 12 weights (expressed relative to D-(+)-galactose) of DMF, such as about 12 weights to about 18 weights, about 12.10 to about 17.08 weights, about 12 weights, about 13 weights, about 14 weights, about 15 weights, about 16 weights, or about 17 weights of DMF. In some embodiments, the D-(+)-galactose is dissolved at least 12 weights of DMF, such as 12 weights to 18 weights, 12.10 to 17.08 weights, 12 weights, 13 weights, 14 weights, 15 weights, 16 weights, or 17 weights of DMF.

In some embodiments, the galactose is dissolved in DMF at a temperature of from about 80° C. to about 100° C., about 85° C. to about 90° C., about 88° C. to about 92° C., about 88° C., about 89° C., about 90° C., about 91° C., or about 92° C. In some embodiments, the galactose is dissolved in DMF at a temperature of from 80° C. to 100° C., 85° C. to 90° C., 88° C. to 92° C., 88° C., 89° C., 90° C., 91° C., or 92° C.

In some embodiments, a solution of pivaloyl imidazole in toluene is added to the solution of D-(+)-galactose, and then the mixture is treated with methanol. In some embodiments, the solution of pivaloyl imidazole contains about 15 to about 35% w/w pivaloyl imidazole, about 18 to about 30% w/w, about 18.4 to about 28.3% w/w, about 19% w/w, about 20% w/w, about 21% w/w, about 22% w/w, about 23% w/w, about 24% w/w, about 25% w/w, about 26% w/w, about 27% w/w, or about 28% w/w pivaloyl imidazole, based on the total weight of the solution. In some embodiments, the solution of pivaloyl imidazole contains 15 to 35% w/w pivaloyl imidazole, 18 to 30% w/w, 18.4 to 28.3% w/w, 19% w/w, 20% w/w, 21% w/w, 22% w/w, 23% w/w, 24% w/w, 25% w/w, 26% w/w, 27% w/w, or 28% w/w pivaloyl imidazole, based on the total weight of the solution.

In some embodiments, about 3.5 to about 5.5 molar equivalents of pivaloyl imidazole is added to the solution of D-(+)-galactose, such as about 4 to about 5 molar equivalents, about 4.5 to about 5 molar equivalents, about 4.6 to about 4.8 molar equivalents, about 4.6 molar equivalents, about 4.7 molar equivalents, or about 4.8 molar equivalents of pivaloyl imidazole. In some embodiments, 3.5 to 5.5 molar equivalents of pivaloyl imidazole is added to the solution of D-(+)-galactose, such as 4 to 5 molar equivalents, 4.5 to 5 molar equivalents, 4.5 to 4.8 molar equivalents, 4.6 molar equivalents, 4.7 molar equivalents, or 4.8 molar equivalents of pivaloyl imidazole.

In some embodiments, the pivaloyl imidazole is reacted with the D-(+)-galactose at a temperature of from about 70° C. to about 90° C., such as from about 75° C. to about 85° C., about 77° C. to about 85° C., about 77° C., about 78° C., about 79° C., about 80° C., about 81° C., about 82° C., about 83° C., about 84° C., or about 85° C. In some embodiments, the pivaloyl imidazole is reacted with the D-(+)-galactose at a temperature of from 70° C. to 90° C., such as from 75° C. to 85° C., 77° C. to 85° C., 77° C., 78° C., 79° C., 80° C., 81° C., 82° C., 83° C., 84° C., or 85° C.

In some embodiments, the mixture of pivaloyl imidazole and D-(+)-galactose is treated with methanol. In some embodiments, the mixture is treated with from about 0.25 to about 5 weights of methanol, such as about 0.5 to about 4 weights, about 0.5 to about 3 weights, about 0.5 weights, about 1 weight, about 2 weights, or about 3 weights of methanol. In some embodiments, the mixture is treated with from 0.25 to 5 weights of methanol, such as 0.5 to 4 weights, 0.5 to 3 weights, 0.5 weights, 1 weight, 2 weights, or 3 weights of methanol.

In some embodiments, the resultant mixture is washed with water and the organic layer is separated. In some embodiments, the solution is concentrated and heptane is added and then the mixture is seeded and cooled. In some embodiments, about 5 to about 10 weights of heptane is added, such as about 6 to about 9.5 weights, about 6.27 to about 9.4 weights, about 6.27 weights, about 7 weights, about 8 weights, about 9 weights, or about 9.4 weights of heptane is added. In some embodiments, 5 to 10 weights of heptane are added, such as 6 to 9.5 weights, 6.27 to 9.4 weights, 6.27 weights, 7 weights, 8 weights, 9 weights, or 9.4 weights of heptane.

In some embodiments, the solution is crystallized at a temperature of from about −60° to about −5° C., such as about −55° C. to about −10° C., about −50° C. to about −15° C., about −50° C., about −45° C., about −40° C., about −35° C., about −30° C., about −25° C., about −20° C., or about −15° C. In some embodiments, the solution is crystallized at a temperature of from −60° to −5° C., such as −55° C. to −10° C., −50° C. to −15° C., −50° C., −45° C., −40° C., −35° C., −30° C., −25° C., −20° C., or −15° C.

In some embodiments, the yield of 1,2,3,6-tetrapivaloyl-D-galactofuranoside is about 15% or more, such as about 20% or more, about 23% or more, about 25% or more, about 30% or more, about 33% or more, about 15% to about 40%, about 20% to about 35%, about 23% to about 33%, about 23%, about 25%, about 30%, or about 33%. In some embodiments, the yield of 1,2,3,6-tetrapivaloyl-D-galactofuranoside is 15% or more, such as 20% or more, 23% or more, 25% or more, 30% or more, 33% or more, 15% to 40%, 20% to 35%, 23% to 33%, 23%, 25%, 30%, or 33%.

1,2,3,6-tetrapivaloyl-D-galactofuranoside Purity

Purity of 1,2,3,6-tetrapivaloyl-D-galactofuranoside can be expressed using an amount of total or specific impurities. Amounts can be calculated, inter alia, using % w/w (e.g., based on the weight of the 1,2,3,6-tetrapivaloyl-D-galactofuranoside) or % area (e.g., based on the area under a chromatograph peak, such as an HPLC peak, of the impurity or impurities as compared to the total area under chromatographic peaks). A particularly disclosed impurity percentage is meant to encompass amounts as calculated based on % w/w and/or % area. In other words: in some embodiments, the % impurity is calculated based on % w/w; in some embodiments the % impurity is calculated based on % area; in some embodiments the % impurity is calculated based on % w/w and % area.

In some embodiments, the produced 1,2,3,6-tetrapivaloyl-D-galactofuranoside has about 5% or less of total impurities, such as about 4% or less, about 3% or less, about 2.9% or less, about 2% or less, about 1% or less, or about 1.5% to about 2.5% of total impurities. In some embodiments, the produced 1,2,3,6-tetrapivaloyl-D-galactofuranoside has 5% or less total impurities, such as 4% or less, 3% or less, 2.9% or less, 2% or less, 1% or less, or 1.5% to 2.5% of total impurities. In some embodiments, the produced 1,2,3,6-tetrapivaloyl-D-galactofuranoside has about 5% or less of Compound B, such as about 4% or less, about 3% or less, about 2.9% or less, about 2% or less, about 1% or less, or about 1.5% to about 2.5% of Compound B. In some embodiments, the produced 1,2,3,6-tetrapivaloyl-D-galactofuranoside has 5% or less of Compound B, such as 4% or less, 3% or less, 2.9% or less, 2% or less, 1% or less, or 1.5% to 2.5% of Compound B.

In some embodiments, 1,2,3,6-tetrapivaloyl-D-galactofuranoside is purified according to a second purification method. The second purification method can be any of the method known to the person skilled in the art. In some embodiments, the second purification method comprises chromatography, sublimation, crystallization, fractional extraction and distillation. In some embodiments, the chromatography comprises size exclusion chromatography, ion-exchange chromatography, affinity chromatography, normal-phase liquid chromatography and reverse-phase liquid chromatography. In some embodiments, the ion-exchange chromatography comprises anion exchange chromatography and cation exchange chromatography. In some embodiments, the second purification removes impurity comprising Compound B.

In some embodiments, 1,2,3,6-tetrapivaloyl-D-galactofuranoside is converted into a pharmaceutically acceptable salt according to any of the known methods. In some embodiments, the pharmaceutically acceptable salt provides better purification.

In some embodiments, 1,2,3,6-tetrapivaloyl-D-galactofuranoside is optionally treated to protect one or more chemical groups. In some embodiments, 1,2,3,6-tetrapivaloyl-D-galactofuranoside with one or more protected chemical groups provide better purification.

Stage 2: Preparation of 5-azido-5-deoxy-1,2,3,6-tetrapivaloyl-D-galactofuranoside Stage 2 of 1-deoxygalactonojirimycin compound production can be performed by activating 1,2,3,6-tetrapivaloyl-D-galactofuranoside with trifluoromethanesulfonic acid anhydride and then reacting it with water to give 1,2,3,6-tetrapivaloyl-α-L-altrofuranoside. The resulting intermediate can be activated with trifluoromethanesulfonic acid anhydride and then reacted with sodium azide to give 5-azido-5-deoxy-1,2,3,6-tetrapivaloyl-D-galactofuranoside. To the extent amounts of Stage 2 components are described using relative terms (e.g., weights or molar equivalents), those amounts are relative to 1,2,3,6-tetrapivaloyl-D-galactofuranoside unless indicated otherwise.

In some embodiments, the trifluoromethanesulfonic acid anhydride in either of the above-mentioned steps is independently from about 0.5 to about 3 molar equivalents, such as from about 0.75 to about 2 molar equivalents, about 1 to about 1.6 molar equivalents, about 1 molar equivalent, about 1.5 molar equivalents, or about 1.6 molar equivalents. In some embodiments, the trifluoromethanesulfonic acid anhydride in either of the above-mentioned steps is independently from 0.5 to 3 molar equivalents, such as from 0.75 to 2 molar equivalents, 1 to 1.6 molar equivalents, 1 molar equivalent, 1.5 molar equivalents, or 1.6 molar equivalents.

Some embodiments comprise adding trifluoromethanesulfonic acid anhydride and pyridine to a solution of 1,2,3,6-tetrapivaloyl-D-galactofuranoside in isopropyl acetate (IPAc). In some embodiments, about 0.75 to about 3 weights of pyridine is added to the solution, such as about 1 weight to about 2 weights, about 1.15 weights to about 1.73 weights, about 1.15 weights, about 1.25 weights, about 1.5 weights, or about 1.73 weights. In some embodiments, 0.75 to 3 weights of pyridine are added to the solution, such as 1 weight to 2 weights, 1.15 weights to 1.73 weights, 1.15 weights, 1.25 weights, 1.5 weights, or 1.73 weights of pyridine.

In some embodiments, water is added to the mixture of trifluoromethanesulfonic acid anhydride, pyridine, 1,2,3,6-tetrapivaloyl-D-galactofuranoside, and IPAc. In some embodiments, the mixture is then heated, e.g., to a temperature of from about 45° C. to about 70° C., such as from about 50° C. to about 65° C., about 55° C. to about 60° C., about 55° C., about 56° C., about 57° C., about 58° C., about 59° C., or about 60° C. In some embodiments, the mixture is heated to a temperature of from 45° C. to 70° C., such as from 50° C. to 65° C., 55° C. to 60° C., 55° C., 56° C., 57° C., 58° C., 59° C., or 60° C.

In some embodiments, the aqueous layer is separated and the organic layer is dried by azeotropic distillation before adding IPAc and then 1,8-diazabicycloundec-7-ene (DBU) to produce Compound E. Some embodiments comprise adding from about 0.02 to about 0.08 weights of DBU, such as from about 0.03 to about 0.07, from about 0.033 to about 0.066, about 0.033, about 0.04, about 0.05, about 0.06, or about 0.066 weights of DBU. Some embodiments comprise adding from 0.02 to 0.08 weights of DBU, such as from 0.03 to 0.07, from 0.033 to 0.066, 0.033, 0.04, 0.05, 0.06, or 0.066 weights of DBU.

Some embodiments comprise washing the IPAc solution of Compound E with aqueous acid, such as aqueous hydrochloric acid (HCl), and then with aqueous pyridine. In some embodiments, the aqueous pyridine comprises about 0.75 to about 3 weights of pyridine, such as about 1 weight to about 2 weights, about 1.15 weights to about 1.73 weights, about 1.15 weights, about 1.25 weights, about 1.5 weights, or about 1.73 weights of pyridine. In some embodiments, 0.75 to 3 weights of pyridine are added to the solution, such as 1 weight to 2 weights, 1.15 weights to 1.73 weights, 1.15 weights, 1.25 weights, 1.5 weights, or 1.73 weights of pyridine.

In some embodiments, the resulting solution is dried by azeotropic distillation and diluted with IPAc addition. In some embodiments, trifluoromethanesulfonic acid anhydride and pyridine are added (e.g., at amounts previously mentioned) to the distilled and diluted solution.

In some embodiments, an IPAc solution of Compound F is washed with water and added to sodium azide and N,N-diisopropylethylamine (DIPEA) in dimethylsulfoxide (DMSO). Some embodiments comprise adding the solution to about 0.05 to about 0.3 weights of sodium azide, such as from about 0.1 to about 0.2, about 0.13 to about 0.19, about 0.13, about 0.15, about 0.17, or about 0.19 weights of sodium azide. Some embodiments comprise adding the solution to 0.05 to 0.3 weights of sodium azide, such as from 0.1 to 0.2, 0.13 to 0.19, 0.13, 0.15, 0.17, or 0.19 weights of sodium azide. Some embodiments comprise adding the solution to about 0.1 to about 0.7 weights of DIPEA, such as about 0.2 to about 0.6 weights, about 0.25 to about 0.5 weights, about 0.28 to about 0.4 weights, about 0.28 weights, about 0.35 weights, or about 0.4 weights of DIPEA. Some embodiments comprise adding the solution to 0.1 to 0.7 weights of DIPEA, such as 0.2 to 0.6 weights, 0.25 to 0.5 weights, 0.28 to 0.4 weights, 0.28 weights, 0.35 weights, or 0.4 weights of DIPEA.

Some embodiments comprise stirring the mixture of Compound F, sodium azide, and DIPEA. In some embodiments, the mixture is stirred for at least about 30 minutes, at least about 45 minutes, or at least about 1 hour. In some embodiments, the mixture is stirred for at least 30 minutes, at least 45 minutes, or at least 1 hour.

In some embodiments, a 5-azido-5-deoxy-1,2,3,6-tetrapivaloyl-D-galactofuranoside mixture is washed with water and the organic layer is concentrated by distillation. In some embodiments, the concentrated mixture is treated with ethanol and water. In some embodiments, the concentrated mixture is treated with from about 3 to about 12 weights of ethanol, such as from about 4 to about 11 weights, about 5 to about 10 weights, about 5.5 to about 9 weights, about 5.64 to about 8.45 weights, about 5.64 weights, about 6 weights, about 7 weights, about 8 weights, or about 8.45 weights of ethanol. In some embodiments, the concentrated mixture is treated with from 3 to 12 weights of ethanol, such as from 4 to 11 weights, 5 to 10 weights, 5.5 to 9 weights, 5.64 to 8.45 weights, 5.64 weights, 6 weights, 7 weights, 8 weights, or 8.45 weights of ethanol. In some embodiments, the concentrated mixture is treated with from about 2 to about 11 weights of water, such as from about 3 to about 10 weights, about 4 to about 9 weights, about 4.5 to about 8 weights, about 4.78 to about 7.17 weights, about 4.78 weights, about 5 weights, about 6 weights, about 7 weights, or about 7.17 weights of water. In some embodiments, the concentrated mixture is treated with from 2 to 11 weights of water, such as from 3 to 10 weights, 4 to 9 weights, 4.5 to 8 weights, 4.78 to 7.17 weights, 4.78 weights, 5 weights, 6 weights, 7 weights, or 7.17 weights of water.

In some embodiments, solid 5-azido-5-deoxy-1,2,3,6-tetrapivaloyl-D-galactofuranoside is isolated by filtration. In some embodiments, the filtration is at a temperature of from about 5° C. to about 35° C., such as from about 10° C. to about 30° C., about 10° C. to about 25° C., about 10° C., about 15° C., about 20° C., or about 25° C. In some embodiments, the filtration is at a temperature of from 5° C. to 35° C., such as from 10° C. to 30° C., 10° C. to 25° C., 10° C., 15° C., 20° C., or 25° C.

Some embodiments comprise washing solid 5-azido-5-deoxy-1,2,3,6-tetrapivaloyl-D-galactofuranoside in methanol. In some embodiments, the solid 5-azido-5-deoxy-1,2,3,6-tetrapivaloyl-D-galactofuranoside is washed in from about 0.5 to about 4 weights of methanol, such as from about 0.6 to about 3 weights, about 0.7 to about 2.5 weights, about 0.79 to about 2.38 weights, about 0.79 weights, about 1 weight, about 1.5 weights, about 2 weights, or about 2.38 weights of methanol. In some embodiments, the solid 5-azido-5-deoxy-1,2,3,6-tetrapivaloyl-D-galactofuranoside is washed in from 0.5 to 4 weights of methanol, such as from 0.6 to 3 weights, 0.7 to 2.5 weights, 0.79 to 2.38 weights, 0.79 weights, 1 weight, 1.5 weights, 2 weights, or 2.38 weights of methanol.

Some embodiments comprise drying the washed 5-azido-5-deoxy-1,2,3,6-tetrapivaloyl-D-galactofuranoside. In some embodiments, the 5-azido-5-deoxy-1,2,3,6-tetrapivaloyl-D-galactofuranoside is dried under vacuum. In some embodiments, the 5-azido-5-deoxy-1,2,3,6-tetrapivaloyl-D-galactofuranoside is dried under vacuum with heating. In some embodiments, the heating is at about 50° C. or less, such as about 45° C. or less, or about 40° C. or less. In some embodiments, the heating is at 50° C. or less, such as 45° C. or less, or 40° C. or less.

In some embodiments, the yield of 5-azido-5-deoxy-1,2,3,6-tetrapivaloyl-D-galactofuranoside is about 45% or more, such as about 50% or more, about 53% or more, about 55% or more, about 60% or more, about 65% or more, about 73% or more, about 75% or more, about 50% to about 75%, about 53% to about 73%, about 53%, about 60%, about 65%, or about 73%. In some embodiments, the yield of 5-azido-5-deoxy-1,2,3,6-tetrapivaloyl-D-galactofuranoside is 45% or more, such as 50% or more, 53% or more, 55% or more, 60% or more, 65% or more, 73% or more, 75% or more, 50% to 75%, 53% to 73%, 53%, 60%, 65%, or 73%.

5-azido-5-deoxy-1,2,3,6-tetrapivaloyl-D-galactofuranoside Purity

Purity of 5-azido-5-deoxy-1,2,3,6-tetrapivaloyl-D-galactofuranoside can be expressed using an amount of total or specific impurities. Amounts can be calculated, inter alia, using % w/w (e.g., based on the weight of the 5-azido-5-deoxy-1,2,3,6-tetrapivaloyl-D-galactofuranoside) or % area (e.g., based on the area under a chromatograph peak, such as an HPLC peak, of the impurity or impurities as compared to the total area under chromatographic peaks). A particularly disclosed impurity percentage is meant to encompass amounts as calculated based on % w/w and/or % area. In other words: in some embodiments, the % impurity is calculated based on % w/w; in some embodiments the % impurity is calculated based on % area; in some embodiments the % impurity is calculated based on % w/w and % area.

In some embodiments, the produced 5-azido-5-deoxy-1,2,3,6-tetrapivaloyl-D-galactofuranoside has about 4% or less of 1,2,3,6-tetrapivaloyl-D-galactofuranoside, such as about 3% or less, about 2.6% or less, about 2% or less, about 1.5% or less, about 1% or less, about 0.75% or less, about 0.6% or less, about 0.5% or less, about 0.36% or less, about 0.25% or less, about 0.16% or less, about 0.1% or less, or about 0.16 to about 0.36% of 1,2,3,6-tetrapivaloyl-D-galactofuranoside. In some embodiments, the produced 5-azido-5-deoxy-1,2,3,6-tetrapivaloyl-D-galactofuranoside has 4% or less of 1,2,3,6-tetrapivaloyl-D-galactofuranoside, such as 3% or less, 2.6% or less, 2% or less, 1.5% or less, 1% or less, 0.75% or less, 0.6% or less, 0.5% or less, 0.36% or less, 0.25% or less, 0.16% or less, 0.1% or less, or 0.16 to 0.36% of 1,2,3,6-tetrapivaloyl-D-galactofuranoside.

In some embodiments, the produced 5-azido-5-deoxy-1,2,3,6-tetrapivaloyl-D-galactofuranoside has about 3% or less of Compound E, such as about 2% or less, about 1.5% or less, about 1.3% or less, about 1% or less, about 0.75% or less, about 0.5% or less, about 0.3% or less, about 0.1% or less, about 0.06% or less, or about 0.05% or less. In some embodiments, the produced 5-azido-5-deoxy-1,2,3,6-tetrapivaloyl-D-galactofuranoside has 3% or less of Compound E, such as 2% or less, 1.5% or less, 1.3% or less, 1% or less, 0.75% or less, 0.5% or less, 0.3% or less, 0.1% or less, 0.06% or less, or 0.05% or less. In some embodiments, the produced 5-azido-5-deoxy-1,2,3,6-tetrapivaloyl-D-galactofuranoside has no detectable amount of Compound E.

In some embodiments, the produced 5-azido-5-deoxy-1,2,3,6-tetrapivaloyl-D-galactofuranoside has about 3% or less of Compound G, such as about 2% or less, about 1.5% or less, about 1.3% or less, about 1% or less, about 0.75% or less, about 0.5% or less, about 0.3% or less, about 0.1% or less, about 0.06% or less, about 0.05% or less, or about 0.03% or less. In some embodiments, the produced 5-azido-5-deoxy-1,2,3,6-tetrapivaloyl-D-galactofuranoside has 3% or less of Compound G, such as 2% or less, 1.5% or less, 1.3% or less, 1% or less, 0.75% or less, 0.5% or less, 0.3% or less, 0.1% or less, 0.06% or less, 0.05% or less, or 0.03% or less. In some embodiments, the produced 5-azido-5-deoxy-1,2,3,6-tetrapivaloyl-D-galactofuranoside has no detectable amount of Compound G.

In some embodiments, the produced 5-azido-5-deoxy-1,2,3,6-tetrapivaloyl-D-galactofuranoside has about 7% or less of Compound J, such as about 6% or less, about 5% or less, about 4% or less, about 3% or less, about 2% or less, about 1% or less, about 0.5% or less, or about 0.86% to about 1.67% of Compound J. In some embodiments, the produced 5-azido-5-deoxy-1,2,3,6-tetrapivaloyl-D-galactofuranoside has 7% or less of Compound J, such as 6% or less, 5% or less, 4% or less, 3% or less, 2% or less, 1% or less, 0.5% or less, or 0.86% to 1.67% of Compound J.

In some embodiments, the produced 5-azido-5-deoxy-1,2,3,6-tetrapivaloyl-D-galactofuranoside has about 3% or less of Compound I, such as about 2% or less, about 1.5% or less, about 1.3% or less, about 1% or less, about 0.9% or less, about 0.75% or less, about 0.6% or less, about 0.5% or less, about 0.35% or less, about 0.3% or less, about 0.1% or less, about 0.06% or less, about 0.05% or less, or about 0.03% or less. In some embodiments, the produced 5-azido-5-deoxy-1,2,3,6-tetrapivaloyl-D-galactofuranoside has 3% or less of Compound I, such as 2% or less, 1.5% or less, 1.3% or less, 1% or less, 0.9% or less, 0.75% or less, 0.6% or less, 0.5% or less, 0.35% or less, 0.3% or less, 0.1% or less, 0.06% or less, 0.05% or less, or 0.03% or less. In some embodiments, the produced 5-azido-5-deoxy-1,2,3,6-tetrapivaloyl-D-galactofuranoside has no detectable amount of Compound I.

In some embodiments, the produced 5-azido-5-deoxy-1,2,3,6-tetrapivaloyl-D-galactofuranoside has about 3% or less of Compound K, such as about 2% or less, about 1.5% or less, about 1.3% or less, about 1% or less, about 0.9% or less, about 0.75% or less, about 0.6% or less, about 0.5% or less, about 0.35% or less, about 0.3% or less, about 0.11% or less, about 0.1% or less, about 0.08% or less, about 0.06% or less, about 0.05% or less, about 0.03% or less, or about 0.08% to about 0.11% of Compound K. In some embodiments, the produced 5-azido-5-deoxy-1,2,3,6-tetrapivaloyl-D-galactofuranoside has 3% or less of Compound K, such as 2% or less, 1.5% or less, 1.3% or less, 1% or less, 0.9% or less, 0.75% or less, 0.6% or less, 0.5% or less, 0.35% or less, 0.3% or less, 0.11% or less, 0.1% or less, 0.08% or less, 0.06% or less, 0.05% or less, 0.03% or less, or 0.08% to 0.11% of Compound K.

In some embodiments, the produced 5-azido-5-deoxy-1,2,3,6-tetrapivaloyl-D-galactofuranoside has about 3% or less of Compound N, such as about 2% or less, about 1.5% or less, about 1% or less, about 0.75% or less, about 0.6% or less, about 0.5% or less, about 0.28% or less, about 0.25% or less, about 0.2% or less, about 0.1% or less, about 0.06% or less, or about 0.06% to about 0.28% of Compound N. In some embodiments, the produced 5-azido-5-deoxy-1,2,3,6-tetrapivaloyl-D-galactofuranoside has 3% or less of Compound N, such as 2% or less, 1.5% or less, 1% or less, 0.75% or less, 0.6% or less, 0.5% or less, 0.28% or less, 0.25% or less, 0.2% or less, 0.1% or less, 0.06% or less, or 0.06% to about 0.28% of Compound N.

In some embodiments, the produced 5-azido-5-deoxy-1,2,3,6-tetrapivaloyl-D-galactofuranoside has about 3% or less of Compound 0, such as about 2% or less, about 1.5% or less, about 1% or less, about 0.75% or less, about 0.6% or less, about 0.5% or less, about 0.3% or less, about 0.17% or less, about 0.12% or less, about 0.1% or less, about 0.05% or less, or about 0.12% to about 0.17% of Compound O. In some embodiments, the produced 5-azido-5-deoxy-1,2,3,6-tetrapivaloyl-D-galactofuranoside has 3% or less of Compound 0, such as 2% or less, 1.5% or less, 1% or less, 0.75% or less, 0.6% or less, 0.5% or less, 0.3% or less, 0.17% or less, 0.12% or less, 0.1% or less, 0.05% or less, or 0.12% to 0.17% of Compound O.

In some embodiments, the produced 5-azido-5-deoxy-1,2,3,6-tetrapivaloyl-D-galactofuranoside has about 5% or less of total impurities, such as about 4% or less, about 3% or less, about 2.9% or less, about 2% or less, about 1% or less, or about 1.5% to about 2.5% of total impurities. In some embodiments, the produced 5-azido-5-deoxy-1,2,3,6-tetrapivaloyl-D-galactofuranoside has 5% or less total impurities, such as 4% or less, 3% or less, 2.9% or less, 2% or less, 1% or less, or 1.5% to 2.5% of total impurities.

In some embodiments, 1,2,3,6-tetrapivaloyl-D-galactofuranoside, Compound D, Compound E, Compound F, 5-azido-5-deoxy-1,2,3,6-tetrapivaloyl-D-galactofuranoside, 1,2,3,6-tetrapivaloyl-α-L-altrofuranoside and/or derivatives thereof are independently purified according to a third purification method. The third purification method can be any of the method known to the person skilled in the art. In some embodiments, the third purification method comprises chromatography, sublimation, crystallization, fractional extraction and distillation. In some embodiments, the chromatography comprises size exclusion chromatography, ion-exchange chromatography, affinity chromatography, normal-phase liquid chromatography and reverse-phase liquid chromatography. In some embodiments, the ion-exchange chromatography comprises anion exchange chromatography and cation exchange chromatography. In some embodiments, the third purification removes one or more impurities, the impurities comprises 1,2,3,6-tetrapivaloyl-Dgalactofuranoside, Compound N, Compound E, Compound G, Compound DD, Compound I, Compound K, Compound J, Compound O and/or derivatives thereof.

In some embodiments, 1,2,3,6-tetrapivaloyl-D-galactofuranoside, Compound D, Compound E, Compound F, 5-azido-5-deoxy-1,2,3,6-tetrapivaloyl-D-galactofuranoside, 1,2,3,6-tetrapivaloyl-α-L-altrofuranoside and/or derivatives thereof are independently converted into a pharmaceutically acceptable salt according to any of the known methods. In some embodiments, the pharmaceutically acceptable salt provides better purification.

In some embodiments, 1,2,3,6-tetrapivaloyl-D-galactofuranoside, Compound D, Compound E, Compound F, 5-azido-5-deoxy-1,2,3,6-tetrapivaloyl-D-galactofuranoside, 1,2,3,6-tetrapivaloyl-α-L-altrofuranoside and/or derivatives thereof are independently treated to protect one or more chemical group of for further purification. In some embodiments, 1,2,3,6-tetrapivaloyl-D-galactofuranoside, Compound D, Compound E, Compound F, 5-azido-5-deoxy-1,2,3,6-tetrapivaloyl-D-galactofuranoside, 1,2,3,6-tetrapivaloyl-α-L-altrofuranoside and/or derivatives thereof with one or more protected chemical groups independently provide better purification.

Stage 3: Preparation of Intermediate Grade 1-deoxygalactonojirimycin Compound Stage 3 of 1-deoxygalactonojirimycin compound production can be performed by reducing 5-azido-5-deoxy-1,2,3,6-tetrapivaloyl-D-galactofuranoside using hydrogen and a palladium catalyst. In some embodiments, following a rearrangement and further hydrogenation, sodium methoxide is added to remove pivaloyl groups. In some embodiments, the product is treated to make N-alkyl substituted intermediate grade 1-deoxygalactonojirimycin compound. In some embodiments, alkylation of the piperidine nitrogen atom with an appropriate alkylating agent forms N-alkyl substituted 1-deoxygalactonojirimycin compound. For example, in some embodiments, alkylation is performed by reductive alkylation of 1-deoxygalactonojirimycin compound with alkylaldehyde in the presence of a reducing agent. Non-limiting examples of suitable reducing agents include hydrogen and a catalyst, sodium cyanoborohydride, and sodium triacetoxyborohydride. In some embodiments, the product is treated with acid and isolated to give salt of intermediate grade 1-deoxygalactonojirimycin compound. For example, in some embodiments, intermediate grade migalastat can be treated with hydrochloric acid to make migalastat hydrochloride. Stage 3 of 1-deoxygalactonojirimycin compound production can be separated into 3 sub-steps, termed Stages 3a, 3b, and 3c. To the extent amounts of Stage 3 components are described using relative terms (e.g., weights, molar equivalents, or volumes), those amounts are relative to 5-azido-5-deoxy-1,2,3,6-tetrapivaloyl-D-galactofuranoside unless indicated otherwise.

Stage 3a

In some embodiments, 5-azido-5-deoxy-1,2,3,6-tetrapivaloyl-D-galactofuranoside and a palladium catalyst on carbon are stirred in methanol under a hydrogen atmosphere. In some embodiments, the palladium catalyst is a 10% palladium catalyst on carbon. Some embodiments comprise using about 0.005 to about 0.05 molar equivalents of the palladium catalyst, such as about 0.006 to about 0.04 molar equivalents, about 0.007 to about 0.03 molar equivalents, about 0.007 to about 0.02 molar equivalents, about 0.007 to about 0.013 molar equivalents, about 0.007 molar equivalents, about 0.008 molar equivalents, about 0.009 molar equivalents, about 0.01 molar equivalents, about 0.011 molar equivalents, about 0.012 molar equivalents, or about 0.013 molar equivalents of palladium catalyst. Some embodiments comprise using 0.005 to 0.05 molar equivalents of the palladium catalyst, such as 0.006 to 0.04 molar equivalents, 0.007 to 0.03 molar equivalents, 0.007 to 0.02 molar equivalents, 0.007 to 0.013 molar equivalents, 0.007 molar equivalents, 0.008 molar equivalents, 0.009 molar equivalents, 0.01 molar equivalents, 0.011 molar equivalents, 0.012 molar equivalents, or 0.013 molar equivalents of palladium catalyst.

In some embodiments, the 5-azido-5-deoxy-1,2,3,6-tetrapivaloyl-D-galactofuranoside and a palladium catalyst on carbon are stirred in about 3 to about 9 weights of methanol, such as about 4 to about 8 weights, about 5 to about 7.5 weights, about 5.54 to about 7.13 weights, about 5.54 weights, about 6 weights, about 6.5 weights, about 7 weights, or about 7.13 weights of methanol. In some embodiments, the 5-azido-5-deoxy-1,2,3,6-tetrapivaloyl-D-galactofuranoside and a palladium catalyst on carbon are stirred in 3 to 9 weights of methanol, such as 4 to 8 weights, 5 to 7.5 weights, 5.54 to 7.13 weights, 5.54 weights, 6 weights, 6.5 weights, 7 weights, or 7.13 weights of methanol.

In some embodiments, the process of stirring the 5-azido-5-deoxy-1,2,3,6-tetrapivaloyl-D-galactofuranoside and the palladium catalyst on carbon in methanol under a hydrogen atmosphere is vented several times (e.g., 2, 3, 4, 5, 6, 7, 8, 9, or 10 or more times) to release nitrogen, and hydrogen pressure is reapplied each time. In some embodiments the mixture is stirred (e.g., after venting) at a temperature of from about 30° C. to about 60° C., such as from about 35° C. to about 55° C., about 40° C. to about 50° C., about 40° C., about 45° C., or about 50° C. In some embodiments the mixture is stirred at a temperature of from 30° C. to 60° C., such as from 35° C. to 55° C., 40° C. to 50° C., 40° C., 45° C., or 50° C.

In some embodiments, the hydrogen pressure is from about 5 bar (absolute) to about 13 bar (absolute), such as from about 6 bar to about 12 bar, about 7 bar to about 11 bar, about 8 bar to about 10 bar, about 8 bar, about 9 bar, or about 10 bar. In some embodiments, the hydrogen pressure is from 5 bar (absolute) to 13 bar (absolute), such as from 6 bar to 12 bar, 7 bar to 11 bar, 8 bar to 10 bar, 8 bar, 9 bar, or 10 bar.

In some embodiments, the stirring is for a time period of about 30 minutes or more, such as about 35 minutes or more, about 40 minutes or more, about 44 minutes or more, about 50 minutes or more, about 55 minutes or more, about 60 minutes or more, about 65 minutes or more, about 68 minutes or more, about 75 minutes or more, about 30 minutes to about 80 minutes, about 35 minutes to about 75 minutes, about 40 minutes to about 70 minutes, about 44 minutes to about 68 minutes, about 44 minutes, about 45 minutes, about 50 minutes, about 55 minutes, about 60 minutes, about 65 minutes, or about 68 minutes. In some embodiments, the stirring is for a time period of 30 minutes or more, such as 35 minutes or more, 40 minutes or more, 44 minutes or more, 50 minutes or more, 55 minutes or more, 60 minutes or more, 65 minutes or more, 68 minutes or more, 75 minutes or more, 30 minutes to 80 minutes, 35 minutes to 75 minutes, 40 minutes to 70 minutes, 44 minutes to 68 minutes, 44 minutes, 45 minutes, 50 minutes, 55 minutes, 60 minutes, 65 minutes, or 68 minutes.

Stage 3b

In some embodiments, a sodium methoxide solution (e.g., 30% sodium methoxide) in methanol is added to a solution of Compound S. In some embodiments, the sodium methoxide solution contains from about 0.5 to about 2 equivalents of methanol, such as from about 0.7 to about 1.5 equivalents, about 0.8 to about 1.2 equivalents, about 0.8 equivalents, about 0.9 equivalents, about 1 equivalent, about 1.1 equivalents, or about 1.2 equivalents of methanol. In some embodiments, the sodium methoxide solution contains from 0.5 to 2 equivalents of methanol, such as from 0.7 to 1.5 equivalents, 0.8 to 1.2 equivalents, 0.8 equivalents, 0.9 equivalents, 1 equivalent, 1.1 equivalents, or 1.2 equivalents of methanol.

In some embodiments, the sodium methoxide/Compound S mixture is concentrated, e.g., by distillation. In some embodiments, the mixture is concentrated to about 0.3 weights, about 0.4 weights, about 0.5 weights, about 0.6 weights, about 0.7 weights, or about 0.8 weights (by volume marker). In some embodiments, the mixture is concentrated to 0.3 weights, 0.4 weights, 0.5 weights, 0.6 weights, 0.7 weights, or 0.8 weights (by volume marker). In some embodiments, an acid, such as hydrochloric acid, is added to the concentrated mixture. In some embodiments, the acid is at a concentration of from about 30% to about 45% acid, such as from about 33% to about 40%, about 35% to about 37%, about 35%, about 36%, or about 37% acid. In some embodiments, the acid is at a concentration of from 30% to 45% acid, such as from 33% to 40%, 35% to 37%, 35%, 36%, or 37% acid.

In some embodiments, about 1.5 to about 4 volumes of the acid, such as hydrochloric acid, is added to the mixture, such as from about 2 to about 3.5 volumes, about 2.9 to about 3.2 volumes, about 2.9 volumes, about 3 volumes, about 3.1 volumes, or about 3.2 volumes. In some embodiments, 1.5 to 4 volumes of the acid, such as hydrochloric acid, are added to the mixture, such as from 2 to 3.5 volumes, 2.9 to 3.2 volumes, 2.9 volumes, 3 volumes, 3.1 volumes, or 3.2 volumes. Without being bound by theory, it is believed that the acid, such as hydrochloric acid, can function as an antisolvent for the by-product sodium salt (e.g., which precipitates out after adding sodium salt, such as sodium chloride, and agitating a batch), which can then be removed by filtration.

In some embodiments, the acid, such as hydrochloric acid, is added at a temperature of from about 10° C. to about 60° C., such as from about 15° C. to about 55° C., about 20° C. to about 50° C., about 20° C. to about 45° C., about 20° C., about 25° C., about 30° C., about 35° C., about 40° C., or about 45° C. In some embodiments, the acid, such as hydrochloric acid, is added at a temperature of from 10° C. to 60° C., such as from 15° C. to 55° C., 20° C. to 50° C., 20° C. to 45° C., 20° C., 25° C., 30° C., 35° C., 40° C., or 45° C.

In some embodiments, the mixture is aged for an age time following addition of the acid, such as hydrochloric acid, to allow precipitation of sodium salt, such as sodium chloride. In some embodiments, the age time is about 15 hours or less, such as about 12 hours or less, about 10 hours or less, about 9 hours or less, about 8 hours or less, about 7 hours or less, about 6 hours of less, or about 5 hours or less. In some embodiments, the age time is 15 hours or less, such as 12 hours or less, 10 hours or less, 9 hours or less, 8 hours or less, 7 hours or less, 6 hours of less, or 5 hours or less.

In some embodiments, the mixture is aged at a temperature of from about 25° C. to about 70° C., such as from about 30° C. to about 65° C., about 35° C. to about 60° C., about 40° C. to about 55° C., about 40° C., about 45° C., about 50° C., or about 55° C. In some embodiments, the mixture is aged at a temperature of from 25° C. to 70° C., such as from 30° C. to 65° C., 35° C. to 60° C., 40° C. to 55° C., 40° C., 45° C., 50° C., or 55° C.

In some embodiments, the suspension formed from aging the mixture is cooled to a filtration temperature and then the sodium salt, such as sodium chloride, is filtered. In some embodiments, the filtration temperature is from about 15° C. to about 50° C., such as from about 20° C. to about 45° C., about 25° C. to about 40° C., about 25° C., about 30° C., about 35° C., or about 40° C. In some embodiments, the filtration temperature is from 15° C. to 50° C., such as from 20° C. to 45° C., 25° C. to 40° C., 25° C., 30° C., 35° C., or 40° C.

Stage 3c

In some embodiments, ethanol is added to the product of Stage 3b. In some embodiments, the ethanol is added over a period of about 15 minutes or more, such as about 20 minutes or more, about 25 minutes or more, about 30 minutes or more, about 35 minutes or more, about 40 minutes or more, about 45 minutes or more, about 50 minutes or more, about 55 minutes or more, about 60 minutes or more, about 20 minutes, about 25 minutes, about 30 minutes, about 35 minutes, about 40 minutes, about 45 minutes, about 50 minutes, about 55 minutes, or about 60 minutes. In some embodiments, the ethanol is added over a period of 15 minutes or more, such as 20 minutes or more, 25 minutes or more, 30 minutes or more, 35 minutes or more, 40 minutes or more, 45 minutes or more, 50 minutes or more, 55 minutes or more, 60 minutes or more, 20 minutes, 25 minutes, 30 minutes, 35 minutes, 40 minutes, 45 minutes, 50 minutes, 55 minutes, or 60 minutes.

In some embodiments, intermediate grade 1-deoxygalactonojirimycin compound is isolated. In some embodiments, the intermediate grade 1-deoxygalactonojirimycin compound is isolated at a temperature of about 5° C. or more, such as about 10° C. or more, about 15° C. or more, about 20° C. or more, about 25° C. or more, about 30° C. or more, about 5° C., about 10° C., about 15° C., about 20° C., about 25° C., or about 30° C. In some embodiments, the intermediate grade 1-deoxygalactonojirimycin compound is isolated at a temperature of 5° C. or more, such as 10° C. or more, 15° C. or more, 20° C. or more, 25° C. or more, 30° C. or more, 5° C., 10° C., 15° C., 20° C., 25° C., or 30° C.

In some embodiments, the isolated intermediate grade 1-deoxygalactonojirimycin compound is washed, e.g., with ethanol. In some embodiments, the washed intermediate grade 1-deoxygalactonojirimycin compound is dried.

In some embodiments, the yield of intermediate grade 1-deoxygalactonojirimycin compound is about 50% or more, such as about 60% or more, about 65% or more, about 70% or more, about 72% or more, about 75% or more, about 80% or more, about 85% or more, about 90% or more, about 92% or more, about 95% or more, about 70% to about 95%, or about 72% to about 92%. In some embodiments, the yield of intermediate grade 1-deoxygalactonojirimycin compound is 50% or more, such as 60% or more, 65% or more, 70% or more, 72% or more, 75% or more, 80% or more, 85% or more, 90% or more, 92% or more, 95% or more, 70% to 95%, or 72% to 92%.

Intermediate Grade 1-deoxygalactonojirimycin Compound Purity

Purity of intermediate grade 1-deoxygalactonojirimycin compound can be expressed using an amount of total or specific impurities. Amounts can be calculated, inter alia, using % w/w (e.g., based on the weight of the intermediate grade 1-deoxygalactonojirimycin compound) or % area (e.g., based on the area under a chromatograph peak, such as an HPLC peak, of the impurity or impurities as compared to the total area under chromatographic peaks). A particularly disclosed impurity percentage is meant to encompass amounts as calculated based on % w/w and/or % area. In other words: in some embodiments, the % impurity is calculated based on % w/w; in some embodiments the % impurity is calculated based on % area; in some embodiments the % impurity is calculated based on % w/w and % area. If an impurity amount is specifically tied to a type of calculation (e.g., % w/w), it is understood that such a calculation is not limiting on the scope of the disclosure, and so the impurity amount additionally or alternatively can be determined using other calculations (e.g., % area) if desired.

In some embodiments, Compound R, Compound S, 1-deoxygalactonojirimycin compound, 1-deoxygalactonojirimycin salt, intermediate grade 1-deoxygalactonojirimycin compound and/or derivatives thereof are independently purified according to a fourth purification method. The fourth purification method can be any of the method known to the person skilled in the art. In some embodiments, the fourth purification method comprises chromatography, sublimation, crystallization, fractional extraction and distillation. In some embodiments, the chromatography comprises size exclusion chromatography, ion-exchange chromatography, affinity chromatography, normal-phase liquid chromatography and reverse-phase liquid chromatography. In some embodiments, the ion-exchange chromatography comprises anion exchange chromatography and cation exchange chromatography. In some embodiments, the fourth purification removes one or more impurities, the impurities comprises Compound U, Compound V, Compound Y, Compound W, Compound BB, Compound Z, Compound AA, Compound X and/or derivatives thereof.

In some embodiments, Compound R, Compound S, 1-deoxygalactonojirimycin compound, intermediate grade 1-deoxygalactonojirimycin compound and/or derivatives thereof are independently converted into a pharmaceutically acceptable salt according to any of the known methods. In some embodiments, the pharmaceutically acceptable salt provides better purification.

In some embodiments, Compound R, Compound S, 1-deoxygalactonojirimycin compound, 1-deoxygalactonojirimycin salt, intermediate grade 1-deoxygalactonojirimycin compound and/or derivatives thereof are independently treated to protect one or more chemical groups for further purification. In some embodiments, one or more of Compound R, Compound S, 1-deoxygalactonojirimycin compound, 1-deoxygalactonojirimycin salt, intermediate grade 1-deoxygalactonojirimycin compound and/or derivatives thereof with one or more protected chemical groups provides better purification.

In some embodiments, the produced intermediate grade 1-deoxygalactonojirimycin compound has about 2% w/w or less of Compound U, such as about 1% w/w or less, about 0.75% w/w or less, about 0.67% w/w or less, about 0.5% w/w or less, about 0.4% w/w or less, about 0.25% w/w or less, or about 0.1% w/w or less of Compound U. In some embodiments, the produced intermediate grade 1-deoxygalactonojirimycin compound has 2% w/w or less of Compound U, such as 1% w/w or less, 0.75% w/w or less, 0.67% w/w or less, 0.5% w/w or less, 0.4% w/w or less, 0.25% w/w or less, or 0.1% w/w or less of Compound U. In some embodiments, the intermediate grade 1-deoxygalactonojirimycin compound has no detectable amount of Compound U.

In some embodiments, the produced intermediate grade 1-deoxygalactonojirimycin compound has about 2% w/w or less of Compound V, such as about 1% w/w or less, about 0.75% w/w or less, about 0.5% w/w or less, about 0.42% w/w or less, about 0.4% w/w or less, about 0.25% w/w or less, about 0.13% w/w or less, or about 0.1% w/w or less of Compound V. In some embodiments, the produced intermediate grade 1-deoxygalactonojirimycin compound has 2% w/w or less of Compound V, such as 1% w/w or less, 0.75% w/w or less, 0.5% w/w or less, 0.42% w/w or less, 0.4% w/w or less, 0.25% w/w or less, 0.13% w/w or less, or 0.1% w/w or less of Compound V. In some embodiments, the intermediate grade 1-deoxygalactonojirimycin compound has no detectable amount of Compound V.

In some embodiments, the produced intermediate grade 1-deoxygalactonojirimycin compound has about 2% w/w or less of Compound Y, such as about 1% w/w or less, about 0.75% w/w or less, about 0.5% w/w or less, about 0.41% w/w or less, about 0.4% w/w or less, about 0.25% w/w or less, or about 0.1% w/w or less of Compound Y. In some embodiments, the produced intermediate grade 1-deoxygalactonojirimycin compound has 2% w/w or less of Compound Y, such as 1% w/w or less, 0.75% w/w or less, 0.5% w/w or less, 0.41% w/w or less, 0.4% w/w or less, 0.25% w/w or less, or 0.1% w/w or less of Compound Y. In some embodiments, the intermediate grade 1-deoxygalactonojirimycin compound has no detectable amount of Compound Y.

In some embodiments, the produced intermediate grade 1-deoxygalactonojirimycin compound has about 2% w/w or less of Compound W, such as about 1% w/w or less, about 0.75% w/w or less, about 0.5% w/w or less, about 0.25% w/w or less, about 0.15% or less, about 0.1% w/w or less, about 0.04% or less, or about 0.01% or less of Compound W. In some embodiments, the produced intermediate grade 1-deoxygalactonojirimycin compound has 2% w/w or less of Compound W, such as 1% w/w or less, 0.75% w/w or less, 0.5% w/w or less, 0.25% w/w or less, 0.15% or less, 0.1% w/w or less, 0.04% or less, or 0.01% or less of Compound W. In some embodiments, the intermediate grade 1-deoxygalactonojirimycin compound has no detectable amount of Compound W.

In some embodiments, the produced intermediate grade 1-deoxygalactonojirimycin compound has about 2% w/w or less of Compound BB, such as about 1% w/w or less, about 0.75% w/w or less, about 0.5% w/w or less, about 0.4% w/w or less, about 0.39% w/w or less, about 0.3% or less, about 0.25% w/w or less, about 0.15% or less, or about 0.1% w/w or less of Compound BB. In some embodiments, the produced intermediate grade 1-deoxygalactonojirimycin compound has 2% w/w or less of Compound BB, such as 1% w/w or less, 0.75% w/w or less, 0.5% w/w or less, 0.4% w/w or less, 0.39% w/w or less, 0.3% or less, 0.25% w/w or less, 0.15% or less, or 0.1% w/w or less of Compound BB. In some embodiments, the intermediate grade 1-deoxygalactonojirimycin compound has no detectable amount of Compound BB.

In some embodiments, the produced intermediate grade 1-deoxygalactonojirimycin compound has about 2% w/w or less of Compound Z, such as about 1% w/w or less, about 0.75% w/w or less, about 0.5% w/w or less, about 0.44% w/w or less, about 0.4% w/w or less, about 0.25% w/w or less, about 0.15% or less, or about 0.1% w/w or less of Compound Z. In some embodiments, the produced intermediate grade 1-deoxygalactonojirimycin compound has 2% w/w or less of Compound Z, such as 1% w/w or less, 0.75% w/w or less, 0.5% w/w or less, 0.44% w/w or less, 0.4% w/w or less, 0.25% w/w or less, 0.15% or less, or 0.1% w/w or less of Compound Z. In some embodiments, the intermediate grade 1-deoxygalactonojirimycin compound has no detectable amount of Compound Z.

In some embodiments, the produced intermediate grade 1-deoxygalactonojirimycin compound has about 2% w/w or less of Compound AA, such as about 1% w/w or less, about 0.75% w/w or less, about 0.5% w/w or less, about 0.41% w/w or less, about 0.4% w/w or less, about 0.25% w/w or less, about 0.15% or less, about 0.1% w/w or less, about 0.09% or less, or about 0.05% or less of Compound AA. In some embodiments, the produced intermediate grade 1-deoxygalactonojirimycin compound has 2% w/w or less of Compound AA, such as 1% w/w or less, 0.75% w/w or less, 0.5% w/w or less, 0.41% w/w or less, 0.4% w/w or less, 0.25% w/w or less, 0.15% or less, 0.1% w/w or less, 0.09% or less, or 0.05% or less of Compound AA. In some embodiments, the intermediate grade 1-deoxygalactonojirimycin compound has no detectable amount of Compound AA.

In some embodiments, the intermediate grade 1-deoxygalactonojirimycin compound contains about 1.2% area or less of Compound CC, such as about 1% or less, about 0.7% or less, about 0.5% or less, about 0.2% or less, or about 0.1% or less of Compound CC. In some embodiments, the intermediate grade 1-deoxygalactonojirimycin compound contains 1.2% area or less of Compound CC, such as 1% or less, 0.7% or less, 0.5% or less, 0.2% or less, or 0.1% or less of Compound CC.

In some embodiments, the intermediate grade 1-deoxygalactonojirimycin compound contains about 1.4% area or less of Compound A, such as about 1.2% or less, about 1% or less, about 0.7% or less, about 0.5% or less, about 0.2% or less, or about 0.1% or less of Compound A. In some embodiments, the intermediate grade 1-deoxygalactonojirimycin compound contains 1.4% area or less of Compound A, such as 1.2% or less, 1% or less, 0.7% or less, 0.5% or less, 0.2% or less, or 0.1% or less of Compound A.

In some embodiments, the intermediate grade 1-deoxygalactonojirimycin compound contains about 0.6% area or less of Compound EE, such as about 0.5% or less, about 0.4% or less, about 0.3% or less, about 0.2% or less, or about 0.1% or less of Compound EE. In some embodiments, the intermediate grade 1-deoxygalactonojirimycin compound contains 0.6% area or less of Compound EE, such as 0.5% or less, 0.4% or less, 0.3% or less, 0.2% or less, or 0.1% or less of Compound EE.

In some embodiments, the intermediate grade 1-deoxygalactonojirimycin compound contains about 4.1% area or less of Compound DD, such as about 3% or less, about 2% or less, about 1% or less, about 0.7% or less, about 0.5% or less, about 0.2% or less, or about 0.1% or less of Compound DD. In some embodiments, the intermediate grade 1-deoxygalactonojirimycin compound contains 4.1% area or less of Compound DD, such as 3% or less, 2% or less, 1% or less, 0.7% or less, 0.5% or less, 0.2% or less, or 0.1% or less of Compound DD.

In some embodiments, the intermediate grade 1-deoxygalactonojirimycin compound has about 5% or less of total impurities, such as about 4% or less, about 3% or less, about 2% or less, about 1.5% or less, about 1% or less, about 0.67% or less, about 0.61% or less, about 0.5% or less, about 0.32% or less, about 0.31% or less, or about 0.25% or less of total impurities. In some embodiments, the intermediate grade 1-deoxygalactonojirimycin compound has 5% or less of total impurities, such as 4% or less, 3% or less, 2% or less, 1.5% or less, 1% or less, 0.67% or less, 0.61% or less, 0.5% or less, 0.32% or less, 0.31% or less, or 0.25% or less of total impurities.

Stage 4: Preparation of Pharmaceutical Grade 1-deoxygalactonojirimycin Compound

In some embodiments, intermediate grade 1-deoxygalactonojirimycin compound is crystallized to form pharmaceutical grade 1-deoxygalactonojirimycin compound. In some embodiments intermediate 1-deoxygalactonojirimycin compound is crystallized twice or more (e.g., two times, three times, four times, or more) to form pharmaceutical grade 1-deoxygalactonojirimycin compound.

In some embodiments, intermediate grade 1-deoxygalactonojirimycin compound is optionally purified according to a fifth purification method before crystallization. The fifth purification method can be any of the method known to the person skilled in the art. In some embodiments, the fifth purification method comprises chromatography, sublimation, crystallization, fractional extraction and distillation. In some embodiments, the chromatography comprises size exclusion chromatography, ion-exchange chromatography, affinity chromatography, normal-phase liquid chromatography and reverse-phase liquid chromatography. In some embodiments, the ion-exchange chromatography comprises anion exchange chromatography and cation exchange chromatography.

In some embodiments, intermediate grade 1-deoxygalactonojirimycin compound is converted into a pharmaceutically acceptable salt according to any of the known methods. In some embodiments, the pharmaceutically acceptable salt provides better purification.

In some embodiments, intermediate grade 1-deoxygalactonojirimycin compound is independently treated to protect one or more chemical groups for further purification. In some embodiments, the intermediate grade 1-deoxygalactonojirimycin compound with one or more protected chemical groups provide better purification.

Stage 4a: First Crystallization Step

To the extent amounts of Stage 4a components are described using relative terms (e.g., weights), those amounts are relative to intermediate grade 1-deoxygalactonojirimycin compound unless indicated otherwise In some embodiments, the crystallization is in a mixture of water and a lower alcohol, for example, a C1-C4 alcohol. Examples of such alcohols include, but are not limited to, methanol, ethanol, n-propanol, isopropanol, and n-butanol. In some embodiments, the lower alcohol is ethanol. Accordingly, in some embodiments, the crystallization is in a mixture of water and ethanol.

In some embodiments, the intermediate grade 1-deoxygalactonojirimycin compound is admixed with water to provide a first slurry or solution of the intermediate grade 1-deoxygalactonojirimycin compound. In some embodiments, the intermediate grade 1-deoxygalactonojirimycin compound is admixed with from about 0.5 to about 4 weights of water, such as from about 0.5 to about 3 weights, about 1 to about 2 weights, about 1.1 to about 1.4 weights, about 1.1 weights, about 1.2 weights, about 1.3 weights, or about 1.4 weights of water. In some embodiments, the intermediate grade 1-deoxygalactonojirimycin compound is admixed with from about 0.5 to about 4 weights of water, such as from about 0.5 to about 3 weights, about 1 to about 2 weights, about 1.1 to about 1.4, about 1.1 weights, about 1.2 weights, about 1.3 weights, or about 1.4 weights of water.

The temperature both during and after the addition may vary. In some embodiments, the temperature is adjusted after the intermediate grade 1-deoxygalactonojirimycin compound is admixed with water, e.g., to a temperature of from about 30° C. to about 70° C., about 35° C. to about 65° C., about 40° C. to about 60° C., about 40° C., about 45° C., about 50° C., about 55° C., or about 60° C. In some embodiments, the temperature is adjusted after the intermediate grade 1-deoxygalactonojirimycin compound is admixed with water, e.g., to a temperature of from about 30° C. to about 70° C., about 35° C. to about 65° C., about 40° C. to about 60° C., about 40° C., about 45° C., about 50° C., about 55° C., or about 60° C. In some embodiments, the intermediate grade 1-deoxygalactonojirimycin compound is admixed with water at a temperature from about 30° C. to about 70° C., and the temperature is maintained or is adjusted, either up or down, to the first crystallization temperature.

A C1-C4 alcohol is added to the first slurry or solution of intermediate grade 1-deoxygalactonojirimycin compound to produce a second slurry or solution of 1-deoxygalactonojirimycin compound and induce crystallization. In some embodiments, the C1-C4 alcohol is ethanol. The amount of the C1-C4 alcohol added may vary, and is generally based on weight, relative to the weight of the intermediate grade 1-deoxygalactonojirimycin compound. In some embodiments, from about 1 to about 15 weights of C1-C4 alcohol, such as ethanol, is added. In some embodiments, from about 1 to about 11.4 weights of C1-C4 alcohol, such as ethanol, is added to the first slurry or solution of 1-deoxygalactonojirimycin compound. In some embodiments, from about 4.8 to about 11.4 weights of C1-C4 alcohol, such as ethanol, is added to the first slurry or solution of 1-deoxygalactonojirimycin compound. In some embodiments, from about 8.4 to about 10.6 weights of C1-C4 alcohol, such as ethanol, is added to the first slurry or solution of 1-deoxygalactonojirimycin compound. In some embodiments, from about 6 to about 15 weights of C1-C4 alcohol, such as ethanol, is added to the first slurry or solution of 1-deoxygalactonojirimycin compound, such as from about 7 to about 12 weights, about 8 to about 11 weights, about 8.5 to about 10.4 weights, about 8.5 weights, about 9 weights, about 9.5 weights, about 10 weights, or about 10.4 weights of C1-C4 alcohol. In some embodiments, from 6 to 15 weights of C1-C4 alcohol, such as ethanol, is added to the first slurry or solution of 1-deoxygalactonojirimycin compound, such as from 7 to 12 weights, 8 to 11 weights, 8.5 to 10.4 weights, 8.5 weights, 9 weights, 9.5 weights, 10 weights, or 10.4 weights of C1-C4 alcohol.

In some embodiments, the first 1-deoxygalactonojirimycin compound is cooled to a first isolation temperature to complete crystallization, providing a first mixture comprising a crystallized 1-deoxygalactonojirimycin compound. In some embodiments, the second slurry or solution is cooled to an isolation temperature, e.g., of from about 3° C. to about 50° C., about 5° C. to about 45° C., about 5° C. to about 40° C., about 5° C. to about 35° C., about 5° C., about 10° C., about 15° C., about 20° C., about 25° C., about 30° C., or about 35° C. In some embodiments, the isolation temperature is from about 3° C. to about 50° C., about 5° C. to about 45° C., about 5° C. to about 40° C., about 5° C. to about 35° C., about 5° C., about 10° C., about 15° C., about 20° C., about 25° C., about 30° C., or about 35° C.

In some embodiments, the Stage 4a product (i.e., the first crystallized 1-deoxygalactonojirimycin compound) is isolated from the first mixture via filtration (e.g., conducted at the isolation temperature). In some embodiments, the isolated Stage 4a product is washed with the C1 to C4 alcohol, e.g., with ethanol. The C1 to C4 alcohol wash can be conducted with about 0.5 weights of C1 to C4 alcohol (relative to the weight of the isolated Stage 4a product) or more, such as about 1 or more weights, about 2 or more weights, about 3 or more weights, about 5 or more weights, or about 10 or more weights. In some embodiments, the C1 to C4 alcohol wash is conducted with about 0.5 weights of C1 to C4 alcohol or more, such as 1 or more weights, 2 or more weights, 3 or more weights, 5 or more weights, or 10 or more weights.

In some embodiments, the Stage 4a product (i.e., the first crystallized 1-deoxygalactonojirimycin compound) is dried, e.g., under vacuum. In some embodiments, the Stage 4a product is dried at a temperature of about 90° C. or less, such as about 80° C. or less, about 70° C. or less, about 60° C. or less, about 50° C. or less, about 80° C., about 70° C., or about 60° C. In some embodiments, Stage 4a product is dried at a temperature or 90° C. or less, such as about 80° C. or less, about 70° C. or less, about 60° C. or less, about 50° C. or less, about 80° C., about 70° C., or about 60° C.

In some embodiments, the Stage 4a product is optionally purified according to a sixth purification method before crystallization. The sixth purification method can be any of the method known to the person skilled in the art. In some embodiments, the purification method comprises chromatography, sublimation, crystallization, fractional extraction and distillation. In some embodiments, the chromatography comprises size exclusion chromatography, ion-exchange chromatography, affinity chromatography, normal-phase liquid chromatography and reverse-phase liquid chromatography. In some embodiments, the ion-exchange chromatography comprises anion exchange chromatography and cation exchange chromatography.

In some embodiments, the Stage 4a product is optionally treated to protect one or more chemical groups for further purification. In some embodiments, the Stage 4a product with one or more protected chemical groups provide better purification.

In some embodiments, the Stage 4a product is converted into a pharmaceutically acceptable salt according to any of the known methods. In some embodiments, the Stage 4a product provides better purification.

Stage 4b: Second Crystallization Step

To the extent amounts Stage 4b components are described using relative terms (e.g., weights), those amounts are relative to the Stage 4a product unless indicated otherwise In some embodiments, the Stage 4a product (i.e., the first crystallized 1-deoxygalactonojirimycin compound) is subjected to a second crystallization. In some embodiments, the second crystallization comprises crystallizing the first crystallized 1-deoxygalactonojirimycin compound in a second mixture comprising water and a C1 to C4 alcohol to give a second crystallized 1-deoxygalactonojirimycin compound; and isolating the second crystallized 1-deoxygalactonojirimycin compound from the second mixture to give active pharmaceutical ingredient (API) grade 1-deoxygalactonojirimycin compound.

In some embodiments, the Stage 4a product (i.e., the first crystallized 1-deoxygalactonojirimycin compound) is admixed with water to produce a third 1-deoxygalactonojirimycin compound slurry or solution. In some embodiments, the Stage 4a product is admixed with from about 0.5 to about 4 weights of water, such as from about 0.5 to about 3 weights, about 1 to about 2 weights, about 1.1 to about 1.4 weights, about 1.1 weights, about 1.2 weights, about 1.3 weights, or about 1.4 weights of water. In some embodiments, the Stage 4a product is admixed with from 0.5 to 4 weights of water, such as from about 0.5 to about 3 weights, 1 to 2 weights, about 1.1 to about 1.4, about 1.1 weights, about 1.2 weights, about 1.3 weights, or about 1.4 weights of water.

The temperature both during and after the addition may vary. In some embodiments, the temperature is adjusted after the Stage 4a product is admixed with water, e.g., to a temperature of from about 30° C. to about 70° C., about 35° C. to about 65° C., about 40° C. to about 60° C., about 40° C., about 45° C., about 50° C., about 55° C., or about 60° C. In some embodiments, the temperature is adjusted after the Stage 4a product is admixed with water, e.g., to a temperature of from about 30° C. to about 70° C., about 35° C. to about 65° C., about 40° C. to about 60° C., about 40° C., about 45° C., about 50° C., about 55° C., or about 60° C. In some embodiments, the first crystallized 1-deoxygalactonojirimycin compound is admixed with water at a temperature from about 30° C. to about 70° C., and the temperature is maintained or is adjusted, either up or down, to the second crystallization temperature.

In some embodiments, a first quantity of a C1-C4 alcohol is added to the Stage 4a product, the third 1-deoxygalactonojirimycin compound slurry or solution, to produce a fourth 1-deoxygalactonojirimycin compound slurry or solution and induce crystallization. In some embodiments, the C1-C4 alcohol is ethanol. In some embodiments, the first quantity of C1-C4 alcohol, such as ethanol, is from about 0.5 to about 4 weights of C1-C4 alcohol, such as from about 0.75 to about 3 weights, about 1 to about 2.5 weights, about 1.8 to about 2 weights, about 1.8 weights, about 1.9 weights, or about 2 weights of C1-C4 alcohol. In some embodiments, the first quantity of C1-C4 alcohol, such as ethanol, is from about 0.5 to about 4 weights of C1-C4 alcohol, such as from about 0.75 to about 3 weights, about 1 to about 2.5 weights, about 1.8 to about 2 weights, about 1.8 weights, about 1.9 weights, or about 2 weights of C1-C4 alcohol.

In some embodiments, the first quantity of C1-C4 alcohol, such as ethanol, is added over a period of about 3 minutes or more, such as about 4 minutes or more, about 5 minutes or more, about 10 minutes or more, or about 15 minutes or more. In some embodiments, the first quantity of C1-C4 alcohol, such as ethanol, is added over a period of about 3 minutes or more, such as about 4 minutes or more, about 5 minutes or more, about 10 minutes or more, or about 15 minutes or more. In some embodiments, the first quantity of C1-C4 alcohol, such as ethanol, is added over a period from about 5 minutes to about 60 minutes.

In some embodiments, a second quantity of the C1-C4 alcohol (e.g., ethanol) is added to the mixture following a hold time. The hold time can be about 3 minutes or more, such as about 4 minutes or more, about 5 minutes or more, about 10 minutes or more, or about 15 minutes or more. In some embodiments, the hold time is a period of about 3 minutes or more, such as 4 minutes or more, about 5 minutes or more, about 10 minutes or more, or about 15 minutes or more. In some embodiments, the hold time is a period of time from about 5 minutes to about 60 minutes.

In some embodiments, the second quantity of the C1-C4 alcohol (e.g., ethanol) comprises about 4 to about 15 weights of the C1-C4 alcohol (e.g., ethanol), such as from about 5 to about 12 weights, about 6 to about 10 weights, about 6.5 to about 9 weights, about 6.7 to about 8.4 weights, about 6.8 weights, about 7 weights, about 7.5 weights, about 8 weights, or about 8.4 weights. In some embodiments, the second quantity of the C1-C4 alcohol comprises about 4 to 15 weights of the C1-C4 alcohol (e.g., ethanol), such as from about 5 to about 12 weights, about 6 to about 10 weights, about 6.5 to about 9 weights, about 6.8 to about 8.4 weights, about 6.8 weights, about 7 weights, about 7.5 weights, about 8 weights, or about 8.4 weights.

In some embodiments, the second quantity of the C1-C4 alcohol (e.g., ethanol) is added over a period of about 10 minutes or more, such as about 15 minutes or more, about 20 minutes or more, about 30 minutes or more, about 45 minutes or more, or about 60 minutes or more. In some embodiments, the second quantity of the C1-C4 alcohol (e.g., ethanol) is added over a period of about 10 minutes or more, such as about 15 minutes or more, about 20 minutes or more, about 30 minutes or more, about 45 minutes or more, or about 60 minutes or more.

The total amount of the C1-C4 alcohol (e.g., ethanol) added may vary, and is generally based on weight, relative to the weight of the intermediate grade 1-deoxygalactonojirimycin compound. In some embodiments, the amount of the C1-C4 alcohol (e.g., ethanol) used in Stage 4b (i.e., the first quantity+the second quantity of the C1-C4 alcohol) is the same as the amount of the C1-C4 alcohol (e.g., ethanol) used in Stage 4a. In some embodiments, the amount of C1-C4 alcohol used in Stage 4b is different from the amount of C1-C4 alcohol used in Stage 4a. In some embodiments, from about 1 to about 15 weights of C1-C4 alcohol, such as ethanol, is added. In some embodiments, from about 1 to about 11.4 weights of C1-C4 alcohol, such as ethanol, is added. In some embodiments, from about 4.8 to about 11.4 weights of C1-C4 alcohol, such as ethanol, is added. In some embodiments, from about 8.4 to about 10.6 weights of C1-C4 alcohol, such as ethanol, is added. In some embodiments, about 9.5 weights of C1-C4 alcohol, such as ethanol, is added.

Some embodiments comprise cooling the Stage 4b slurry or solution in which crystallization has at least partially proceed to a second isolation temperature in order to complete the crystallization, providing the second mixture comprising crystallized 1-deoxygalactonojirimycin compound. In some embodiments, the second isolation temperature is, e.g., of from about 3° C. to about 50° C., about 5° C. to about 45° C., about 5° C. to about 40° C., about 5° C. to about 35° C., about 5° C., about 10° C., about 15° C., about 20° C., about 25° C., about 30° C., or about 35° C. In some embodiments, the second isolation temperature is about 3° C. to about 50° C., about 5° C. to about 45° C., about 5° C. to about 40° C., about 5° C. to about 35° C., about 5° C., about 10° C., about 15° C., about 20° C., about 25° C., about 30° C., or about 35° C.

In some embodiments, the Stage 4b product (i.e., the second crystallized 1-deoxygalactonojirimycin compound) is isolated from the second mixture via filtration (e.g., conducted at the second isolation temperature). In some embodiments, the isolated Stage 4b product is washed with the C1 to C4 alcohol, e.g., with ethanol. The wash can be conducted with about 0.5 weights of C1 to C4 alcohol or more, such as about 1 or more weight, about 2 or more weights, about 3 or more weights, about 5 or more weights, or about 10 or more weights. In some embodiments, the wash is conducted with about 0.5 weights of ethanol or more, such as about 1 or more weight, about 2 or more weights, about 3 or more weights, about 5 or more weights, or about 10 or more weights of ethanol.

In some embodiments, the Stage 4b product is dried, e.g., under vacuum. In some embodiments, the Stage 4b product is dried at a temperature of about 90° C. or less, such as about 80° C. or less, about 70° C. or less, about 60° C. or less, about 50° C. or less, about 80° C., about 70° C., or about 60° C. In some embodiments, Stage 4b product is dried at a temperature of 90° C. or less, such as 80° C. or less, 70° C. or less, 60° C. or less, 50° C. or less, 80° C., 70° C., or 60° C.

In some embodiments, the yield of pharmaceutical grade 1-deoxygalactonojirimycin compound is about 40% or more, such as about 50% or more, about 56% or more, about 60% or more, about 65% or more, about 70% or more, about 80% or more, about 85% or more, about 90% or more, about 95% or more, about 100% or more, about 102% or more, about 50% to about 105%, or about 56% to about 102%. In some embodiments, the yield of pharmaceutical grade 1-deoxygalactonojirimycin compound is 40% or more, such as 50% or more, 56% or more, 60% or more, 65% or more, 70% or more, 80% or more, 85% or more, 90% or more, 95% or more, 100% or more, 102% or more, 50% to 105%, or 56% to 102%.

In some embodiments, the Stage 4b product is optionally purified according to a seventh purification method before crystallization. The seventh purification method can be any of the method known to the person skilled in the art. In some embodiments, the purification method comprises chromatography, sublimation, crystallization, fractional extraction and distillation. In some embodiments, the chromatography comprises size exclusion chromatography, ion-exchange chromatography, affinity chromatography, normal-phase liquid chromatography and reverse-phase liquid chromatography. In some embodiments, the ion-exchange chromatography comprises anion exchange chromatography and cation exchange chromatography.

In some embodiments, the Stage 4b product is optionally treated to protect one or more chemical group for further purification. In some embodiments, the Stage 4b product with one or more protected chemical groups provide better purification.

In some embodiments, the Stage 4b product is converted into a pharmaceutically acceptable salt according to any of the known methods. In some embodiments, the Stage 4b product provides better purification.

Pharmaceutical Grade 1-deoxygalactonojirimycin Compound Purity

The purity of 1-deoxygalactonojirimycin compound produced by the methods disclosed herein may vary. The purity of 1-deoxygalactonojirimycin compound can be expressed using an amount of total or specific impurities. Amounts can be calculated, inter alia, using % w/w (e.g., based on the weight of the 1-deoxygalactonojirimycin compound), % area (e.g., based on the area under a chromatograph peak, such as an HPLC peak, of the impurity or impurities as compared to the 1-deoxygalactonojirimycin compound), parts per million (ppm), etc. A particularly disclosed impurity percentage is meant to encompass amounts as calculated based on % w/w and/or % area. In other words: in some embodiments, the % impurity is calculated based on % w/w; in some embodiments the % impurity is calculated based on % area; in some embodiments the % impurity is calculated based on % w/w and % area. If an impurity amount is specifically tied to a type of calculation (e.g., % w/w), it is understood that such a calculation is not limiting on the scope of the disclosure, and so the impurity amount additionally or alternatively can be determined using other calculations (e.g., % area) if desired.

In some embodiments, pharmaceutical grade, also referred to herein as active pharmaceutical ingredient (API) grade 1-deoxygalactonojirimycin compound, is provided. Generally, providing API grade 1-deoxygalactonojirimycin compound comprises purifying an intermediate grade 1-deoxygalactonojirimycin compound as described herein (e.g., by performing one or more crystallizations as described herein above). In addition to variations in the purity of the pharmaceutical grade 1-deoxygalactonojirimycin compound, the impurity profile of the pharmaceutical grade 1-deoxygalactonojirimycin compound (i.e., the impurity profile of any given batch thereof) may vary.

In some embodiments, the produced pharmaceutical grade 1-deoxygalactonojirimycin compound has about 0.15% w/w or less of Compound W, such as about 0.1% w/w or less, about 0.05 w/w or less, or about 0.025% w/w or less of Compound W. In some embodiments, the produced pharmaceutical grade 1-deoxygalactonojirimycin compound has 0.15% w/w or less of Compound W, such as 0.1% w/w or less, 0.05 w/w or less, or 0.025% w/w or less of Compound W. In some embodiments, the pharmaceutical grade 1-deoxygalactonojirimycin compound has no detectable amount of Compound W.

In some embodiments, the produced pharmaceutical grade 1-deoxygalactonojirimycin compound has about 0.15% w/w or less of Compound U, such as about 0.1% w/w or less, about 0.05 w/w or less, or about 0.025% w/w or less of Compound U. In some embodiments, the produced pharmaceutical grade 1-deoxygalactonojirimycin compound has 0.15% w/w or less of Compound U, such as 0.1% w/w or less, 0.05 w/w or less, or 0.025% w/w or less of Compound U. In some embodiments, the pharmaceutical grade 1-deoxygalactonojirimycin compound has no detectable amount of Compound U.

In some embodiments, the produced pharmaceutical grade 1-deoxygalactonojirimycin compound has about 0.15% w/w or less of Compound V, such as about 0.1% w/w or less, about 0.05 w/w or less, or about 0.025% w/w or less of Compound V. In some embodiments, the produced pharmaceutical grade 1-deoxygalactonojirimycin compound has 0.15% w/w or less of Compound V, such as 0.1% w/w or less, 0.05 w/w or less, or 0.025% w/w or less of Compound V. In some embodiments, the pharmaceutical grade 1-deoxygalactonojirimycin compound has no detectable amount of Compound V.

In some embodiments, the produced pharmaceutical grade 1-deoxygalactonojirimycin compound has about 0.15% w/w or less of Compound Y, such as about 0.1% w/w or less, about 0.05 w/w or less, or about 0.025% w/w or less of Compound Y. In some embodiments, the produced pharmaceutical grade 1-deoxygalactonojirimycin compound has 0.15% w/w or less of Compound Y, such as 0.1% w/w or less, 0.05 w/w or less, or 0.025% w/w or less of Compound Y. In some embodiments, the pharmaceutical grade 1-deoxygalactonojirimycin compound has no detectable amount of Compound Y.

In some embodiments, the produced pharmaceutical grade 1-deoxygalactonojirimycin compound has about 0.15% w/w or less of Compound BB, such as about 0.1% w/w or less, about 0.05 w/w or less, or about 0.025% w/w or less of Compound BB. In some embodiments, the produced pharmaceutical grade 1-deoxygalactonojirimycin compound has 0.15% w/w or less of Compound BB, such as 0.1% w/w or less, 0.05 w/w or less, or 0.025% w/w or less of Compound BB. In some embodiments, the pharmaceutical grade 1-deoxygalactonojirimycin compound has no detectable amount of Compound BB.

In some embodiments, the pharmaceutical grade 1-deoxygalactonojirimycin compound has about 0.3% w/w or less of the C1-C4 alcohol (e.g., methanol), such as about 0.2% w/w or less, about 0.1% w/w or less, or about 0.05% w/w or less of the C1-C4 alcohol (e.g., methanol). In some embodiments, the pharmaceutical grade 1-deoxygalactonojirimycin compound has 0.3% w/w or less of the C1-C4 alcohol (e.g., methanol), such as 0.2% w/w or less, 0.1% w/w or less, or 0.05% w/w or less of the C1-C4 alcohol (e.g., methanol). In some embodiments, the pharmaceutical grade 1-deoxygalactonojirimycin compound has no detectable amount of the C1-C4 alcohol (e.g., methanol).

In some embodiments, the pharmaceutical grade 1-deoxygalactonojirimycin compound has about 0.5% w/w or less of the C1-C4 alcohol (e.g., ethanol), such as about 0.4% w/w or less, about 0.3% w/w, about 0.2% w/w or less, about 0.1% w/w or less, or about 0.05% w/w or less of the C1-C4 alcohol (e.g., ethanol). In some embodiments, the pharmaceutical grade 1-deoxygalactonojirimycin compound has 0.5% w/w or less of the C1-C4 alcohol (e.g., ethanol), such as 0.4% w/w or less, 0.3% w/w, 0.2% w/w or less, 0.1% w/w or less, or 0.05% w/w or less of the C1-C4 alcohol (e.g., ethanol). In some embodiments, the pharmaceutical grade 1-deoxygalactonojirimycin compound has no detectable amount of the C1-C4 alcohol (e.g., ethanol).

In some embodiments, the pharmaceutical grade 1-deoxygalactonojirimycin compound has about 0.2% w/w or less of water, such as about 0.1% w/w or less, or about 0.05% w/w or less of water. In some embodiments, the pharmaceutical grade 1-deoxygalactonojirimycin compound has 0.2% w/w or less of water, such as 0.1% w/w or less, or 0.05% w/w or less of water. In some embodiments, the pharmaceutical grade 1-deoxygalactonojirimycin compound has no detectable amount of water.

In some embodiments, the pharmaceutical grade 1-deoxygalactonojirimycin compound has about 0.2% w/w or less of residue on ignition, such as about 0.1% w/w or less, or about 0.05% w/w or less of residue on ignition. In some embodiments, the pharmaceutical grade 1-deoxygalactonojirimycin compound has 0.2% w/w or less of residue on ignition, such as 0.1% w/w or less, or 0.05% w/w or less of residue on ignition. In some embodiments, the pharmaceutical grade 1-deoxygalactonojirimycin compound has no detectable amount of residue on ignition.

In some embodiments, the pharmaceutical grade 1-deoxygalactonojirimycin compound has about 0.15 ppm or less of arsenic, such as about 0.1 ppm or less, or about 0.05 ppm or less of arsenic. In some embodiments, the pharmaceutical grade 1-deoxygalactonojirimycin compound has 0.15 ppm or less of arsenic, such as 0.1 ppm or less, or 0.05 ppm or less of arsenic. In some embodiments, the pharmaceutical grade 1-deoxygalactonojirimycin compound has no detectable amount of arsenic.

In some embodiments, the pharmaceutical grade 1-deoxygalactonojirimycin compound has about 0.5 ppm or less of cadmium, such as about 0.4 ppm or less, about 0.3 ppm or less, about 0.2 ppm or less, about 0.1 ppm or less, or about 0.05 ppm or less of cadmium. In some embodiments, the pharmaceutical grade 1-deoxygalactonojirimycin compound has 0.5 ppm or less of cadmium, such as 0.4 ppm or less, 0.3 ppm or less, 0.2 ppm or less, 0.1 ppm or less, or 0.05 ppm or less of cadmium. In some embodiments, the pharmaceutical grade 1-deoxygalactonojirimycin compound has no detectable amount of cadmium.

In some embodiments, the pharmaceutical grade 1-deoxygalactonojirimycin compound has about 1.5 ppm or less of mercury, such as about 1 ppm or less, about 0.9 ppm or less, about 0.8 ppm or less, about 0.7 ppm or less, about 0.6 ppm or less, about 0.5 ppm or less, about 0.4 ppm or less, about 0.3 ppm or less, about 0.2 ppm or less, about 0.1 ppm or less, or about 0.05 ppm or less of mercury. In some embodiments, the pharmaceutical grade 1-deoxygalactonojirimycin compound has 1.5 ppm or less of mercury, such as 1 ppm or less, 0.9 ppm or less, 0.8 ppm or les, 0.7 ppm or less, 0.6 ppm or less, 0.5 ppm or less, 0.4 ppm or less, 0.3 ppm or less, 0.2 ppm or less, 0.1 ppm or less, or 0.05 ppm or less of mercury. In some embodiments, the pharmaceutical grade 1-deoxygalactonojirimycin compound has no detectable amount of mercury.

In some embodiments, the pharmaceutical grade 1-deoxygalactonojirimycin compound has about 0.5 ppm or less of lead, such as about 0.4 ppm or less, about 0.3 ppm or less, about 0.2 ppm or less, about 0.1 ppm or less, or about 0.05 ppm or less of lead. In some embodiments, the pharmaceutical grade 1-deoxygalactonojirimycin compound has 0.5 ppm or less of lead, such as 0.4 ppm or less, 0.3 ppm or less, 0.2 ppm or less, 0.1 ppm or less, or 0.05 ppm or less of lead. In some embodiments, the pharmaceutical grade 1-deoxygalactonojirimycin compound has no detectable amount of lead.

In some embodiments, the pharmaceutical grade 1-deoxygalactonojirimycin compound has about 10 ppm or less of palladium, such as about 9 ppm or less, about 8 ppm or less, about 7 ppm or less, about 6 ppm or less, about 5 ppm or less, about 4 ppm or less, about 3 ppm or less, about 2 ppm or less, about 1 ppm or less, or about 0.5 ppm or less of palladium. In some embodiments, the pharmaceutical grade 1-deoxygalactonojirimycin compound has 10 ppm or less of palladium, such as 9 ppm or less, 8 ppm or less, 7 ppm or less, 6 ppm or less, 5 ppm or less, 4 ppm or less, 3 ppm or less, 2 ppm or less, 1 ppm or less, or 0.5 ppm or less of palladium. In some embodiments, the pharmaceutical grade 1-deoxygalactonojirimycin compound has no detectable amount of palladium.

In some embodiments, the pharmaceutical grade 1-deoxygalactonojirimycin compound contains about 0.1% or less of Compound CC, such as about 0.05% or less, or about 0.2% or less of Compound CC. In some embodiments, the pharmaceutical grade 1-deoxygalactonojirimycin compound contains 0.1% or less of Compound CC, such as 0.05% or less, or 0.2% or less of Compound CC. In some embodiments, the pharmaceutical grade 1-deoxygalactonojirimycin compound contains no detectable amount of Compound CC.

In some embodiments, the pharmaceutical grade 1-deoxygalactonojirimycin compound contains about 0.1% or less of Compound A, such as about 0.05% or less, or about 0.2% or less of Compound A. In some embodiments, the pharmaceutical grade 1-deoxygalactonojirimycin compound contains 0.1% or less of Compound A, such as 0.05% or less, or 0.2% or less of Compound A. In some embodiments, the pharmaceutical grade 1-deoxygalactonojirimycin compound contains no detectable amount of Compound A.

In some embodiments, the pharmaceutical grade 1-deoxygalactonojirimycin compound contains about 0.1% or less of Compound EE, such as about 0.05% or less, or about 0.2% or less of Compound EE. In some embodiments, the pharmaceutical grade 1-deoxygalactonojirimycin compound contains 0.1% or less of Compound EE, such as 0.05% or less, or 0.2% or less of Compound EE. In some embodiments, the pharmaceutical grade 1-deoxygalactonojirimycin compound contains no detectable amount of Compound EE.

In some embodiments, the pharmaceutical grade 1-deoxygalactonojirimycin compound contains about 0.1% or less of Compound DD, such as about 0.05% or less, or about 0.2% or less of Compound DD. In some embodiments, the pharmaceutical grade 1-deoxygalactonojirimycin compound contains 0.1% or less of Compound DD, such as 0.05% or less, or 0.2% or less of Compound DD. In some embodiments, the pharmaceutical grade 1-deoxygalactonojirimycin compound contains no detectable amount of Compound DD.

In some embodiments, the pharmaceutical grade 1-deoxygalactonojirimycin compound contains about 12 µg or less of Compound D per gram of pharmaceutical grade 1-deoxygalactonojirimycin compound, such as about 10 µg or less, about 8 µg or less, about 5 µg or less, about 4 µg or less, about 3 µg or less, about 2 µg or less, about 1 µg or less, or about 0.5 µg or less of Compound D per gram of pharmaceutical grade 1-deoxygalactonojirimycin compound. In some embodiments, the pharmaceutical grade 1-deoxygalactonojirimycin compound contains 12 µg or less of Compound D per gram of pharmaceutical grade 1-deoxygalactonojirimycin compound, such as 10 µg or less, 8 µg or less, 5 µg or less, 4 µg or less, 3 µg or less, 2 µg or less, 1 µg or less, or 0.5 µg or less of Compound D per gram of pharmaceutical grade 1-deoxygalactonojirimycin compound. In some embodiments, the pharmaceutical grade 1-deoxygalactonojirimycin compound contains no detectable amount of Compound D per gram of pharmaceutical grade 1-deoxygalactonojirimycin compound.

In some embodiments, the pharmaceutical grade 1-deoxygalactonojirimycin compound contains about 12 µg or less of Compound F per gram of pharmaceutical grade 1-deoxygalactonojirimycin compound, such as about 10 µg or less, about 8 µg or less, about 5 µg or less, about 4 µg or less, about 3 µg or less, about 2 µg or less, about 1 µg or less, or about 0.5 µg or less of Compound F per gram of pharmaceutical grade 1-deoxygalactonojirimycin compound. In some embodiments, the pharmaceutical grade 1-deoxygalactonojirimycin compound contains 12 µg or less of Compound F per gram of pharmaceutical grade 1-deoxygalactonojirimycin compound, such as 10 µg or less, 8 µg or less, 5 µg or less, 4 µg or less, 3 µg or less, 2 µg or less, 1 µg or less, or 0.5 µg or less of Compound F per gram of pharmaceutical grade 1-deoxygalactonojirimycin compound. In some embodiments, the pharmaceutical grade 1-deoxygalactonojirimycin compound contains no detectable amount of Compound F per gram of pharmaceutical grade 1-deoxygalactonojirimycin compound.

In some embodiments, the pharmaceutical grade 1-deoxygalactonojirimycin compound contains about 12 µg or less of 5-azido-5-deoxy-1,2,3,6-tetrapivaloyl-D-galactofuranoside per gram of pharmaceutical grade 1-deoxygalactonojirimycin compound, such as about 10 µg or less, about 8 µg or less, about 5 µg or less, about 4 µg or less, about 3 µg or less, about 2 µg or less, about 1 µg or less, or about 0.5 µg or less of 5-azido-5-deoxy-1,2,3,6-tetrapivaloyl-D-galactofuranoside per gram of pharmaceutical grade 1-deoxygalactonojirimycin compound. In some embodiments, the pharmaceutical grade 1-deoxygalactonojirimycin compound contains 12 µg or less of 5-azido-5-deoxy-1,2,3,6-tetrapivaloyl-D-galactofuranoside per gram of pharmaceutical grade 1-deoxygalactonojirimycin compound, such as 10 µg or less, 8 µg or less, 5 µg or less, 4 µg or less, 3 µg or less, 2 µg or less, 1 µg or less, or 0.5 µg or less of 5-azido-5-deoxy-1,2,3,6-tetrapivaloyl-D-galactofuranoside per gram of pharmaceutical grade 1-deoxygalactonojirimycin compound. In some embodiments, the pharmaceutical grade 1-deoxygalactonojirimycin compound contains no detectable amount of 5-azido-5-deoxy-1,2,3,6-tetrapivaloyl-D-galactofuranoside per gram of pharmaceutical grade 1-deoxygalactonojirimycin compound.

In some embodiments, the pharmaceutical grade 1-deoxygalactonojirimycin compound contains about 12 µg or less of Compound N per gram of pharmaceutical grade 1-deoxygalactonojirimycin compound, such as about 10 µg or less, about 8 µg or less, about 5 µg or less, about 4 µg or less, about 3 µg or less, about 2 µg or less, about 1 µg or less, or about 0.5 µg or less of Compound N per gram of pharmaceutical grade 1-deoxygalactonojirimycin compound. In some embodiments, the pharmaceutical grade 1-deoxygalactonojirimycin compound contains 12 µg or less of Compound N per gram of pharmaceutical grade 1-deoxygalactonojirimycin compound, such as 10 µg or less, 8

µg or less, 5 µg or less, 4 µg or less, 3 µg or less, 2 µg or less, 1 µg or less, or 0.5 µg or less of Compound N per gram of pharmaceutical grade 1-deoxygalactonojirimycin compound. In some embodiments, the pharmaceutical grade 1-deoxygalactonojirimycin compound contains no detectable amount of Compound N per gram of pharmaceutical grade 1-deoxygalactonojirimycin compound.

In some embodiments, the pharmaceutical grade 1-deoxygalactonojirimycin compound contains about 12 µg or less of Compound Q per gram of pharmaceutical grade 1-deoxygalactonojirimycin compound, such as about 10 µg or less, about 8 µg or less, about 5 µg or less, about 4 µg or less, about 3 µg or less, about 2 µg or less, about 1 µg or less, or about 0.5 µg or less of Compound Q per gram of pharmaceutical grade 1-deoxygalactonojirimycin compound. In some embodiments, the pharmaceutical grade 1-deoxygalactonojirimycin compound contains 12 µg or less of Compound Q per gram of pharmaceutical grade 1-deoxygalactonojirimycin compound, such as 10 µg or less, 8 µg or less, 5 µg or less, 4 µg or less, 3 µg or less, 2 µg or less, 1 µg or less, or 0.5 µg or less of Compound Q per gram of pharmaceutical grade 1-deoxygalactonojirimycin compound. In some embodiments, the pharmaceutical grade 1-deoxygalactonojirimycin compound contains no detectable amount of Compound Q per gram of pharmaceutical grade 1-deoxygalactonojirimycin compound.

In some embodiments, the pharmaceutical grade 1-deoxygalactonojirimycin compound contains about 12 µg or less of Compound P per gram of pharmaceutical grade 1-deoxygalactonojirimycin compound, such as about 10 µg or less, about 8 µg or less, about 5 µg or less, about 4 µg or less, about 3 µg or less, about 2 µg or less, about 1 µg or less, or about 0.5 µg or less of Compound P per gram of pharmaceutical grade 1-deoxygalactonojirimycin compound. In some embodiments, the pharmaceutical grade 1-deoxygalactonojirimycin compound contains 12 µg or less of Compound P per gram of pharmaceutical grade 1-deoxygalactonojirimycin compound, such as 10 µg or less, 8 µg or less, 5 µg or less, 4 µg or less, 3 µg or less, 2 µg or less, 1 µg or less, or 0.5 µg or less of Compound P per gram of pharmaceutical grade 1-deoxygalactonojirimycin compound. In some embodiments, the pharmaceutical grade 1-deoxygalactonojirimycin compound contains no detectable amount of Compound P per gram of pharmaceutical grade 1-deoxygalactonojirimycin compound.

In some embodiments, the pharmaceutical grade 1-deoxygalactonojirimycin compound contains about 12 µg or less of Compound X per gram of pharmaceutical grade 1-deoxygalactonojirimycin compound, such as about 10 µg or less, about 8 µg or less, about 5 µg or less, about 4 µg or less, about 3 µg or less, about 2 µg or less, about 1 µg or less, or about 0.5 µg or less of Compound X per gram of pharmaceutical grade 1-deoxygalactonojirimycin compound. In some embodiments, the pharmaceutical grade 1-deoxygalactonojirimycin compound contains 12 µg or less of Compound X per gram of pharmaceutical grade 1-deoxygalactonojirimycin compound, such as 10 µg or less, 8 µg or less, 5 µg or less, 4 µg or less, 3 µg or less, 2 µg or less, 1 µg or less, or 0.5 µg or less of Compound X per gram of pharmaceutical grade 1-deoxygalactonojirimycin compound. In some embodiments, the pharmaceutical grade 1-deoxygalactonojirimycin compound contains no detectable amount of Compound X per gram of pharmaceutical grade 1-deoxygalactonojirimycin compound.

In some embodiments, the pharmaceutical grade 1-deoxygalactonojirimycin compound contains about 12 µg or less of ethyl chloride per gram of pharmaceutical grade 1-deoxygalactonojirimycin compound, such as about 10 µg or less, about 8 µg or less, about 5 µg or less, about 4 µg or less, about 3 µg or less, about 2 µg or less, about 1 µg or less, or about 0.5 µg or less of ethyl chloride per gram of pharmaceutical grade 1-deoxygalactonojirimycin compound. In some embodiments, the pharmaceutical grade 1-deoxygalactonojirimycin compound contains 12 µg or less of ethyl chloride per gram of pharmaceutical grade 1-deoxygalactonojirimycin compound, such as 10 µg or less, 8 µg or less, 5 µg or less, 4 µg or less, 3 µg or less, 2 µg or less, 1 µg or less, or 0.5 µg or less of ethyl chloride per gram of pharmaceutical grade 1-deoxygalactonojirimycin compound. In some embodiments, the pharmaceutical grade 1-deoxygalactonojirimycin compound contains no detectable amount of ethyl chloride per gram of pharmaceutical grade 1-deoxygalactonojirimycin compound.

In some embodiments, the pharmaceutical grade 1-deoxygalactonojirimycin compound contains about 12 µg or less of methyl chloride per gram of pharmaceutical grade 1-deoxygalactonojirimycin compound, such as about 10 µg or less, about 8 µg or less, about 5 µg or less, about 4 µg or less, about 3 µg or less, about 2 µg or less, about 1 µg or less, or about 0.5 µg or less of methyl chloride per gram of pharmaceutical grade 1-deoxygalactonojirimycin compound. In some embodiments, the pharmaceutical grade 1-deoxygalactonojirimycin compound contains 12 µg or less of methyl chloride per gram of pharmaceutical grade 1-deoxygalactonojirimycin compound, such as 10 µg or less, 8 µg or less, 5 µg or less, 4 µg or less, 3 µg or less, 2 µg or less, 1 µg or less, or 0.5 µg or less of methyl chloride per gram of pharmaceutical grade 1-deoxygalactonojirimycin compound. In some embodiments, the pharmaceutical grade 1-deoxygalactonojirimycin compound contains no detectable amount of methyl chloride per gram of pharmaceutical grade 1-deoxygalactonojirimycin compound.

In some embodiments, the pharmaceutical grade 1-deoxygalactonojirimycin compound has about 0.1% or less of any unspecified impurity, such as about 0.05% or less, about 0.03% or less, about 0.02% or less, or about 0.01% or less of unspecified impurity. In some embodiments, the pharmaceutical grade 1-deoxygalactonojirimycin compound has 0.1% or less of any unspecified impurity, such as 0.05% or less, 0.03% or less, 0.02% or less, or 0.01% or less of unspecified impurity.

In some embodiments, the pharmaceutical grade 1-deoxygalactonojirimycin compound has about 0.5% or less of total impurities, such as about 0.4% or less, about 0.3% or less, about 0.2% or less, about 0.1% or less, or about 0.05% or less of total impurities. In some embodiments, the pharmaceutical grade 1-deoxygalactonojirimycin compound has 0.5% or less of total impurities, such as 0.4% or less, 0.3% or less, 0.2% or less, 0.1% or less, or 0.05% or less of total impurities.

Batch 1-deoxygalactonojirimycin Compound Production

Also provided are methods of producing batches of 1-deoxygalactonojirimycin compound, or an intermediate thereof. For instance, in some embodiments 1,2,3,6-tetrapivaloyl-D-galactofuranoside is produced from about 1 kg or more of D-(+)-galactose, such as about 5 kg or more, about 10 kg or more, about 20 kg or more, about 29 kg or more, about 30 kg or more, about 40 kg or more, about 50 kg or more, about 55 kg or more, about 60 kg or more, about 70 kg or more, about 80 kg or more, about 90 kg or more, about 100 kg or more, about 5 kg to about 75 kg, about 10 kg to about 70 kg, about 15 kg to about 65 kg, about 15 kg to about 60 kg, about 20 kg to about 55 kg, about 22 kg to about 55 kg, about 22 kg, about 25 kg, about 30 kg, about 35 kg, about 40 kg, about 45 kg, about 50 kg, or about 55 kg of D-(+)-galactose. In some embodiments 1,2,3,6-tetrapivaloyl-D-galactofuranoside is produced from 1 kg or more of D-(+)-galactose, such as 5 kg or more, 10 kg or more, 20 kg or more, 29 kg or more, 30 kg or more, 40 kg or more, 50 kg or more, 55 kg or more, 60 kg or more, 70 kg or more, 80 kg or more, 90 kg or more, 100 kg or more, 5 kg to 75 kg, 10 kg to 70 kg, 15 kg to 65 kg, 15 kg to 60 kg, 20 kg to 55 kg, 22 kg to 55 kg, 22 kg, 25 kg, 30 kg, 35 kg, 40 kg, 45 kg, 50 kg, or 55 kg of D-(+)-galactose.

In some embodiments, 5-azido-5-deoxy-1,2,3,6-tetrapivaloyl-D-galactofuranoside is produced from about 1 kg or more of 1,2,3,6-tetrapivaloyl-D-galactofuranoside, such as about 5 kg or more, about 10 kg or more, about 20 kg or more, about 30 kg or more, about 36 kg or more, about 40 kg or more, about 50 kg or more, about 60 kg or more, about 70 kg or more, about 80 kg or more, about 84 kg or more, about 90 kg or more, about 100 kg or more, about 5 kg to about 100 kg, about 15 kg to about 95 kg, about 25 kg to about 90 kg, about 36 kg to about 84 kg, about 36 kg, about 45 kg, about 55 kg, about 65 kg, about 75 kg, or about 84 kg of 1,2,3,6-tetrapivaloyl-D-galactofuranoside. In some embodiments, 5-azido-5-deoxy-1,2,3,6-tetrapivaloyl-D-galactofuranoside is produced from 1 kg or more of 1,2,3,6-tetrapivaloyl-D-galactofuranoside, such as 5 kg or more, 10 kg or more, 20 kg or more, 30 kg or more, 36 kg or more, 40 kg or more, 50 kg or more, 60 kg or more, 70 kg or more, 80 kg or more, 84 kg or more, 90 kg or more, 100 kg or more, 5 kg to about 100 kg, 15 kg to 95 kg, 25 kg to 90 kg, 36 kg to 84 kg, 36 kg, 45 kg, 55 kg, 65 kg, 75 kg, or 84 kg of 1,2,3,6-tetrapivaloyl-D-galactofuranoside.

In some embodiments, intermediate grade 1-deoxygalactonojirimycin compound is produced from about 1 kg or more of 5-azido-5-deoxy-1,2,3,6-tetrapivaloyl-D-galactofuranoside, such as about 5 kg or more, about 10 kg or more, about 20 kg or more, about 29 kg or more, about 30 kg or more, about 40 kg or more, about 50 kg or more, about 55 kg or more, about 60 kg or more, about 70 kg or more, about 80 kg or more, about 90 kg or more, about 100 kg or more, about 5 kg to about 50 kg, about 10 kg to about 45 kg, about 15 kg to about 40 kg, about 20 kg to about 35 kg, about 25 kg to about 31 kg, about 25 kg, about 26 kg, about 27 kg, about 28 kg, about 29 kg, about 30 kg, or about 31 kg of 5-azido-5-deoxy-1,2,3,6-tetrapivaloyl-D-galactofuranoside. In some embodiments, intermediate grade 1-deoxygalactonojirimycin compound is produced from 1 kg or more of 5-azido-5-deoxy-1,2,3,6-tetrapivaloyl-D-galactofuranoside, such as 5 kg or more, 10 kg or more, 20 kg or more, 29 kg or more, 30 kg or more, 40 kg or more, 50 kg or more, 55 kg or more, 60 kg or more, 70 kg or more, 80 kg or more, 90 kg or more, 100 kg or more, 5 kg to 50 kg, 10 kg to 45 kg, 15 kg to 40 kg, 20 kg to 35 kg, 25 kg to 31 kg, 25 kg, 26 kg, 27 kg, 28 kg, 29 kg, 30 kg, or 31 kg of 5-azido-5-deoxy-1,2,3,6-tetrapivaloyl-D-galactofuranoside.

In some embodiments, the pharmaceutical grade 1-deoxygalactonojirimycin compound is produced from about 1 kg or more of intermediate grade 1-deoxygalactonojirimycin compound, such as about 5 kg or more, about 10 kg or more, about 20 kg or more, about 29 kg or more, about 30 kg or more, about 40 kg or more, about 50 kg or more, about 55 kg or more, about 60 kg or more, about 70 kg or more, about 80 kg or more, about 90 kg or more, about 100 kg or more, about 5 kg to about 50 kg, about 6 kg to about 40 kg, about 7 kg to about 30 kg, about 8 kg to about 35 kg, about 10 kg to about 20 kg, about 11.5 kg to about 17.3 kg, about 11.5 kg, about 12 kg, about 13 kg, about 14 kg, about 15 kg, about 16 kg, or about 17.3 kg of intermediate grade 1-deoxygalactonojirimycin compound. In some embodiments, the pharmaceutical grade 1-deoxygalactonojirimycin compound is produced from 1 kg or more of intermediate grade 1-deoxygalactonojirimycin compound, such as 5 kg or more, 10 kg or more, 20 kg or more, 29 kg or more, 30 kg or more, 40 kg or more, 50 kg or more, 55 kg or more, 60 kg or more, 70 kg or more, 80 kg or more, 90 kg or more, 100 kg or more, 5 kg to 50 kg, 6 kg to 40 kg, 7 kg to 30 kg, 8 kg to 35 kg, 10 kg to 20 kg, 11.5 kg to 17.3 kg, 11.5 kg, 12 kg, 13 kg, 14 kg, 15 kg, 16 kg, or 17.3 kg of intermediate grade 1-deoxygalactonojirimycin compound.

In some embodiments, the produced batch of pharmaceutical grade 1-deoxygalactonojirimycin compound is from about 1 kg or more, such as about 5 kg or more, about 10 kg or more, about 20 kg or more, about 29 kg or more, about 30 kg or more, about 40 kg or more, about 50 kg or more, about 55 kg or more, about 60 kg or more, about 70 kg or more, about 80 kg or more, about 90 kg or more, about 100 kg or more, about 5 kg to about 50 kg, about 6 kg to about 40 kg, about 7 kg to about 30 kg, about 8 kg to about 35 kg, about 10 kg to about 20 kg, about 11.5 kg to about 17.3 kg, about 11.5 kg, about 12 kg, about 13 kg, about 14 kg, about 15 kg, about 16 kg, or about 17.3 kg. In some embodiments, the produced batch of pharmaceutical grade 1-deoxygalactonojirimycin compound is 1 kg or more, such as 5 kg or more, 10 kg or more, 20 kg or more, 29 kg or more, 30 kg or more, 40 kg or more, 50 kg or more, 55 kg or more, 60 kg or more, 70 kg or more, 80 kg or more, 90 kg or more, 100 kg or more, 5 kg to 50 kg, 6 kg to 40 kg, 7 kg to 30 kg, 8 kg to 35 kg, 10 kg to 20 kg, 11.5 kg to 17.3 kg, 11.5 kg, 12 kg, 13 kg, 14 kg, 15 kg, 16 kg, or 17.3 kg.

Batch Validation and Distribution

Also provided are methods of determining the purity of a batch of pharmaceutical grade 1-deoxygalactonojirimycin compound, or an intermediate thereof. Also provided are methods of validating a batch of pharmaceutical grade 1-deoxygalactonojirimycin compound, or an intermediate thereof. In some embodiments, a batch of pharmaceutical grade 1-deoxygalactonojirimycin compound is validated as suitable for clinical use if it contains levels of impurities within the amounts disclosed herein, or if it does not contain detectable amounts of such impurities.

Impurities can be determined by any suitable method, such as infrared spectroscopy, high performance liquid chromatography (HPLC), hydrophilic interaction liquid chromatography (HILIC), gas chromatography, nuclear magnetic resonance (NMR), mass spectrometry (MS), inductively coupled plasma mass spectroscopy (ICP-MS), Karl Fischer titration, and/or residue on ignition.

Some embodiments comprise using an impurity or a salt thereof as a reference standard to detect amounts (e.g., trace amounts) of the impurity in a batch of 1-deoxygalactonojirimycin compound, or an intermediate thereof. Some embodiments comprise producing the reference standard.

Some embodiments comprise obtaining a sample from a batch of 1-deoxygalactonojirimycin compound, or an intermediate thereof, and determining an amount of one or more impurities in the sample.

In some embodiments, impurities are set forth based on % w/w (e.g., based on the weight of the 1-deoxygalactonojirimycin compound or intermediate in which the impurity is measured). In some embodiments, the impurities are set forth based on % area (e.g., based on the area under an HPLC peak associated with the impurity as compared to the total area under HPLC chromatographic peaks, which can be detected, e.g., using HILIC or UV detection). % area can be calculated as set forth in NORMAN DYSON, CHROMATOGRAPHIC INTEGRATION METHODS (The Royal Society of Chemistry, 2d ed. 1998), which is incorporated herein by reference in its entirety. In some embodiments, impurities are set forth based on an amount or based on ppm. Unless otherwise specified, a particularly disclosed impurity percentage is meant to encompass amounts as calculated based on % w/w and/or % area. In other words: in some embodiments, the % impurity is calculated based on % w/w; in some embodiments the % impurity is calculated based on % area. If an impurity amount is specifically tied to a type of calculation (e.g., % w/w), it is understood that such a calculation is not limiting on the scope of the disclosure, and so the impurity amount can be determined using alternative calculations (e.g., % area) if desired. While exemplary validation components and values are discussed below for particular impurities, other components and values (e.g., provided in preceding paragraphs or in the working examples) can also be used for batch validation.

In some embodiments, a batch of 1,2,3,6-tetrapivaloyl-D-galactofuranoside is validated by determining the amount of Compound B in the batch. In some embodiments, the batch of 1,2,3,6-tetrapivaloyl-D-galactofuranoside has 3% area or less of Compound B.

In some embodiments, a batch of 5-azido-5-deoxy-1,2,3,6-tetrapivaloyl-D-galactofuranoside is validated by determining the amount of one or more (or all) of 1,2,3,6-tetrapivaloyl-D-galactofuranoside, Compound E, Compound G, Compound J, Compound I, Compound K, Compound N, and Compound O in the batch. In some embodiments, the batch contains 0.6% area or less of 1,2,3,6-tetrapivaloyl-D-galactofuranoside, 0.3% area or less of Compound E, 0.3% area or less of Compound G, 3% area or less of Compound J, 0.6% area or less of Compound I, 0.3% area or less of Compound K, 1% area or less of Compound N, and 0.3% area of less of Compound O.

In some embodiments, a batch of intermediate grade 1-deoxygalactonojirimycin compound is validated by determining the amounts of one or more (or all) of Compound U, Compound V, Compound Y, Compound W, and Compound BB in the batch of intermediate grade 1-deoxygalactonojirimycin compound. In some embodiments, the batch contains 0.4% w/w or less of Compound U, 0.4% w/w or less of Compound V, 0.25% w/w or less of Compound Y, 0.15% w/w or less of Compound W, and 0.3% w/w or less of Compound BB. In some embodiments, the batch contains 0.4% area or less of Compound U, 0.4% area or less of Compound V, 0.25% area or less of Compound Y, 0.15% area or less of Compound W, and 0.3% area or less of Compound BB.

In some embodiments, a batch of pharmaceutical grade 1-deoxygalactonojirimycin compound is validated by determining the amounts of one or more (or all) of Compound W, Compound U, Compound V, Compound Y, Compound BB, C1-C4 alcohol(s) (e.g., methanol and/or ethanol), water, residue on ignition, arsenic, cadmium, mercury, lead, and palladium in the batch of 1-deoxygalactonojirimycin compound. In some embodiments, the pharmaceutical grade 1-deoxygalactonojirimycin compound contains 0.15% w/w or less of Compound W, 0.15% w/w or less of Compound U, 0.15% w/w or less of Compound V, 0.15% w/w or less of Compound Y, 0.15% w/w or less of Compound BB, 0.3% w/w or less of the C1-C4 alcohol (e.g., methanol), 0.5% w/w or less of the C1-C4 alcohol (e.g., ethanol), 0.2% w/w or less of water, and 0.2% w/w or less of residue on ignition, each based on the weight of the 1-deoxygalactonojirimycin compound, and 0.15 ppm or less of arsenic, 0.5 ppm or less of cadmium, 1.5 ppm or less of mercury, 0.5 ppm or less of lead, and 10 ppm or less of palladium. Some embodiments comprise validating a batch of 1-deoxygalactonojirimycin compound if it meets the specifications set forth in Example 1 below.

In some embodiments, a validated batch of pharmaceutical grade 1-deoxygalactonojirimycin compound is assessed as suitable for medical use in a subject. In some embodiments, the validated batch of 1-deoxygalactonojirimycin compound is a commercial batch of 1-deoxygalactonojirimycin compound. In some embodiments, the validated batch is distributed. In some embodiments, a batch that does not meet validation standards is not distributed. In some embodiments, a batch that does not meet validation standards is reprocessed until standards are met.

In some embodiments, a pregelatinized starch is added to validated 1-deoxygalactonojirimycin compound and the mixture is screened, e.g. using a rotating impeller screening mill. In some embodiments, the screening is performed using an about a 457-micron screen, such as a 457-micron screen.

In some embodiments, the validated 1-deoxygalactonojirimycin compound is blended. The blending can comprise pre-lubrication and/or lubrication blending steps. Exemplary pre-lubrication blending steps involve blending 1-deoxygalactonojirimycin compound and pregelatinized starch, e.g., using a diffusion mixer. Exemplary 1-deoxygalactonojirimycin compound: pregelatinized starch ratios include about 1:1 to about 5:1, such as about 2:1 to about 4:1, about 3:1 to about 3.5:1, about 3:1, about 3.1:1. About 3.2:1, about 3.3:1, about 3.4:1, or about 3.5:1. Exemplary ratios also include 1:1 to 5:1, such as 2:1 to 4:1, 3:1 to 3.5:1, 3:1, 3.1:1. 3.2:1, 3.3:1, 3.4:1, or 3.5:1. In some embodiments the diffusion mixing is performed at about 100-300 revolutions for about 5 to 15 minutes at a speed of about 20 rpm.

Exemplary lubrication blending steps include adding magnesium stearate to a pre-lubrication mix. Example 1-deoxygalactonojirimycin compound: magnesium stearate ratios include about 100:1 to about 200:1, such as about 125:1 to about 175:1, about 145:1 to about 155:1, about 150:1, about 152:1, about 153:1, about 154:1, or about 155:1. Example 1-deoxygalactonojirimycin compound: magnesium stearate ratios also include 100:1 to 200:1, such as 125:1 to 175:1, 145:1 to 155:1, 150:1, 152:1, 153:1, 154:1, or 155:1. In some embodiments, the lubrication blending step is conducted using a diffusion mixer, e.g., at about 60 revolutions for about 3 minutes at about 20 rpm.

In some embodiments, the validated 1-deoxygalactonojirimycin compound is divided in whole or in part into portions, such as for migalastat hydrochloride with 123 mg portions FBE of migalastat (e.g., 150 mg migalastat hydrochloride). In some embodiments, the portions of 1-deoxygalactonojirimycin compound are encapsulated, e.g., in a capsule. In some embodiments, the encapsulation is with an encapsulation machine. In some embodiments, the encapsulation machine targets a capsule fill weight of about 196 mg.

In some embodiments, the encapsulated 1-deoxygalactonojirimycin compound is packaged, e.g., in a container closure system. The container closure system can be flexible or semirigid, and can be composed entirely, primarily, or partially of plastic. In some embodiments, the 1-deoxygalactonojirimycin compound is packaged in a paperboard package, a flexible pouch, a plastic container (e.g., cup or tray) having a heat-sealed flexible lid, or a plastic container (e.g., can) with double-seamed metal ends. The container closure system can comprise one or more hermetic seals that prevent contamination of the migalastat, oxidation of the migalastat, and/or exposure of the 1-deoxygalactonojirimycin compound to external environmental conditions. In some embodiments, the container closure system comprises primary packaging (the immediate packaging that comes into contact with the consumable 1-deoxygalactonojirimycin compound product). Optionally, the container closure system comprises secondary packaging, which comprises an exterior packaging of the primary packaging.

Some embodiments comprise packaging one or more units of migalastat. Packaging can comprise inserting one or more units of 1-deoxygalactonojirimycin compound (e.g., one or more capsules) into a container closure system. In some embodiments, the secondary packaging may be the smallest sellable unit for commerce.

In some embodiments, the packaging comprises polyvinyl chloride (PVC)/polychlorotrifluoroethylene (PCTFE)/PVC laminate film with aluminum foil lidding blister packs.

Some embodiments comprise sealing the packaging (e.g., forming a hermetic seal on the primary packaging). Some embodiments comprise physical or chemical testing of the packaging integrity. The testing can be performed on packaged migalastat. Integrity testing can be performed, for example, via one or more of air leak testing, biotesting, burst testing, chemical etching, compression, squeeze testing, distribution (abuse) testing, dye penetration, electester, electrolytic testing, gas leak detection, incubation, light testing, machine vision, proximity tester, seam scope projection, sound testing, tensile (peel) testing, or vacuum testing. Some embodiments comprise testing the light transmission of the packaging. Some embodiments comprise testing water vapor permeation of the packaging. Exemplary testing protocols are set forth in the US Pharmacopeia sections <661> and <671>, which are incorporated herein by reference in their entireties.

Manufacturing 1-deoxygalactonojirimycin compound can comprise repackaging 1-deoxygalactonojirimycin compound (e.g., by distributors). Repackaging can comprise removing 1-deoxygalactonojirimycin compound from an original container closure system (e.g., from primary packaging and/or secondary packaging). Repackaging can comprise placing 1-deoxygalactonojirimycin compound into a new container closure system (e.g., placing unpacked 1-deoxygalactonojirimycin compound into a new primary packaging and/or placing packaged 1-deoxygalactonojirimycin compound into a secondary container closure system) and optionally hermetically sealing the new container closure system. If repackaging comprises placing unpacked 1-deoxygalactonojirimycin compound into a new primary container closure system, the amount of 1-deoxygalactonojirimycin compound in each primary container may be the same as or different from the amount in the original packaging. In some embodiments, repackaging comprises packaging 1-deoxygalactonojirimycin compound in unit dose container closure systems. If repackaging comprises placing 1-deoxygalactonojirimycin compound removed from a secondary container closure system into a new secondary container closure system, the amount of 1-deoxygalactonojirimycin compound (e.g., the number of primary containers) in the new secondary container closure system may be the same as or different from the amount in the original secondary packaging. Package integrity testing and/or inspection, as described elsewhere herein, may be performed after the original packaging, after the repackaging, or after both packaging and repackaging. Packaging and/or repackaging may be performed according to Current Good Manufacturing Practices (CGMP). Testing may comprise stability testing on packaged 1-deoxygalactonojirimycin compound used to determine the expiration date of the 1-deoxygalactonojirimycin compound when stored in a specific type of primary container closure system.

During manufacture of migalastat, one or more of a National Drug Code (NDC) number, a bar code, and a product identifier, a unique serial number, an expiration date, and a lot number may be affixed to or imprinted on one or more of the packages (e.g., primary containers and/or secondary containers) containing the migalastat. The NDC is a 10-digit basic identifier for pharmaceutical products. The product identifier may comprise a standardized graphic. The product identifier may be in a human-readable format and/or on a machine-readable data carrier that conforms to the standards developed by an international standards development organization. The product identifier can comprise the standardized numerical identifier (SNI), lot number, and/or expiration date of the product. The standardized numerical identifier can comprise a set of numbers or characters used to uniquely identify each package or homogeneous case (i.e. a sealed case containing only product that has a single NDC number belonging to a single lot) that is composed of the NDC that corresponds to the specific product (including the particular package configuration) combined with a unique alphanumeric serial number (e.g., of up to 20 characters). In some embodiments, an encoded, standardized bar code (e.g., a linear bar code) is affixed to or imprinted on one or more of the packages. The bar code can comprise the NDC number. In some embodiments, the bar code comprises the NDC and/or any other information. In some embodiments, globally accepted GS1 system data structures and/or symbologies are be used to convey the NDC, a unique serial number, expiration date and lot number, as well as optional quantity information. During manufacture of 1-deoxygalactonojirimycin compound a bar code or other machine readable data carrier can be scanned or read by a machine (e.g., by a distributor upon receiving 1-deoxygalactonojirimycin compound from a manufacturer) for processing the transport of the 1-deoxygalactonojirimycin compound through the chain of commerce and/or manufacturing process or for inventorying the migalastat.

Some embodiments comprise tracing or tracking the manufactured 1-deoxygalactonojirimycin compound, e.g., at a batch level, lot level, or package level. In some embodiments, the tracing is performed electronically. In some embodiments, dispensers in a drug supply chain exchange information about a drug and who handled it each time it is sold (e.g., in the US market). In some embodiments, such information comprises transaction information and/or a transaction history. Transaction information can comprise proprietary or established name or names of the product, strength and dosage form of the product, NDC number of the product, container size, number of containers, lot number of the product, date of the transaction, date of the shipment, and/or business name and address of the person from whom and to whom ownership is being transferred.

Tracing can be performed using any suitable system or process. In some embodiments, tracing is performed using paper-based methods. In some embodiments, tracing is performed using electronic-based methods. Examples of tracing methods include paper or electronic versions of invoices, paper versions or packing slips, electronic data interchange (EI) standards, such as advance ship notice (ASN), and electronic product code information services (EPCIS). In some embodiments, email or other web-based platforms are used. In some embodiments, the tracing is performed by scanning a barcode, e.g., that carries transaction information.

Also provided are methods of storing 1-deoxygalactonojirimycin compound (e.g., in packaged form) under conditions that promote stability of the 1-deoxygalactonojirimycin compound and/or reduce degradation of the 1-deoxygalactonojirimycin compound. In some embodiments, the 1-deoxygalactonojirimycin compound is stored at a temperature of from about 20° C. to about 25° C., such as about 20° C., about 21° C., about 22° C., about 23° C., about 24° C., or about 25° C. In some embodiments, the 1-deoxygalactonojirimycin compound is stored at a temperature of from 20° C. to 25° C., such as 20° C., 21° C., 22° C., 23° C., 24° C., or 25° C. In some embodiments, excursions are permitted between about 150 and about 30° C., such as from 15° C. to 30° C. In some embodiments, packaged 1-deoxygalactonojirimycin compound is stored under such conditions for approximately 1, 2, 3, 4, 5, 6, 7, 8, 9, 10, 11, or 12 months. In some embodiments, packaged 1-deoxygalactonojirimycin compound is stored under these conditions for at least 1, 2, 3, 4, 5, 6, 7, 8, 9, 10, 11, or 12 months. In some embodiments, packaged 1-deoxygalactonojirimycin compound is stored under these conditions for no longer than 12, 24, 36, 48, or 60 months. In some embodiments, 1-deoxygalactonojirimycin compound is received from a manufacturer by a distributor and possession can be transferred to a third party (e.g., a pharmacy, hospital, or patient) by the distributor. The distributor may store the 1-deoxygalactonojirimycin compound under controlled conditions (e.g., the temperature described above) for a period of time before transferring possession to the third party. Optionally the distributor may package, repackage, or label the packages (e.g., affix to or imprint on the information described elsewhere herein) prior to transferring possession (distributing) to a third party.

Treatment

Also provided are methods of treating a subject having Fabry disease by administering 1-deoxygalactonojirimycin compound, such as migalastat. In some embodiments, an effective dose of 1-deoxygalactonojirimycin compound is administered to the patient in need thereof. For example, some embodiments comprise administering migalastat or salt thereof in a range of from about 100 mg FBE to about 150 mg FBE. Exemplary doses include about 100 mg FBE, about 105 mg FBE, about 110 mg FBE, about 115 mg FBE, about 120 mg FBE, about 123 mg FBE, about 125 mg FBE, about 130 mg FBE, about 135 mg FBE, about 140 mg FBE, about 145 mg FBE or about 150 mg FBE. Again, it is noted that 150 mg of migalastat hydrochloride is equivalent to 123 mg of the free base form of migalastat. Thus, in one or more embodiments, the dose is 150 mg of migalastat hydrochloride or an equivalent dose of migalastat or a salt thereof other than the hydrochloride salt, administered at a frequency of once every other day.

In some embodiments, 1-deoxygalactonojirimycin compound is administered at a frequency of once every other day. For example, in some embodiments, the migalastat is administered at a frequency of once every other day. For example, a dose of 123 mg of the migalastat free base can be administered at a frequency of once every other day.

In some embodiments, 1-deoxygalactonojirimycin compound is administered for a certain period of time. In some embodiments, 1-deoxygalactonojirimycin compound, migalastat or salt thereof, is administered for a duration of at least 28 days, such as at least 30, 60, or 90 days, or at least 3, 4, 5, 6, 7, 8, 9, 10, 11, 12, 16, 20, 24, 30 or 36 months, or at least 1, 2, 3, 4 or 5 years. In some embodiments, the 1-deoxygalactonojirimycin compound therapy, such as migalastat therapy, is long-term therapy of at least 6 months, such as at least 6, 7, 8, 9, 10, 11, 12, 16, 20, 24, 30 or 36 months or at least 1, 2, 3, 4 or 5 years.

In some embodiments, 1-deoxygalactonojirimycin compound is administered in a formulation suitable for any route of administration. Accordingly, in some embodiments, administration of 1-deoxygalactonojirimycin compound, such as migalastat or salt thereof, may be in a formulation suitable for any route of administration, but is preferably administered in an oral dosage form such as a tablet, capsule or solution. As one example, the patient is orally administered capsules each containing 150 mg migalastat hydrochloride or an equivalent dose of migalastat or a salt thereof other than the hydrochloride salt.

Some embodiments comprise administering 1-deoxygalactonojirimycin compound to a subject having an HEK assay amenable α-galactosidase A mutation. An α-galactosidase A variant can be categorized as amenable if the resultant mutant α-Gal A activity (measured in the cell lysates) meets two criteria in an in vitro HEK assay: 1) it shows a relative increase of at least 20% compared to the pre-treatment α-Gal A activity, and 2) it shows an absolute increase of at least 3% of the wild-type (normal) α-Gal A activity. In some embodiments, the in vitro HEK assay comprises transfecting Human Embryonic Kidney (HEK-293) cell lines with specific α-galactosidase A variants (mutations) which produce mutant α-Gal A proteins. In the transfected cells, amenability of the GLA variants can be assessed after a 5-day incubation with 1-deoxygalactonojirimycin compound, such as 10 micromol/L migalastat. A non-limiting list of HEK assay amenable α-galactosidase A mutations is set forth in Table 55.

Migalastat

Migalastat, also known as 1-deoxygalactonojirimycin or (2R,3S,4R,5S)-2-(hydroxymethyl) piperdine-3,4,5-triol, refers to a compound having the following free base structures:

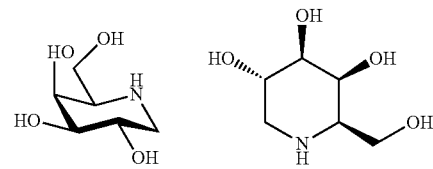

Migalastat hydrochloride is a compound having the following structure:

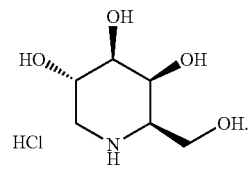 [SMILES: Cl ; OC[C@H]1NC[C@H](O)[C@@H](O)[C@H]1O]

Migalastat salt, such as migalastat hydrochloride, may be prepared by contacting free base migalastat (e.g., migalastat as provided according to the prior paragraph) in solution with at least a molar equivalent of an aqueous solution of acid, such as hydrochloric acid, or a solution of acid gas, such as solution of hydrogen chloride gas, in an appropriate solvent, for example, an alcohol or ether. In some embodiments, the migalastat salt can be isolated by removal of the solvent, for example, by evaporation.

In some embodiments, it may be desirable to purify the migalastat salt. Accordingly, in another aspect of the disclosure is provided a method of purification of migalastat salt.

In some embodiments, intermediate grade migalastat salt, such as intermediate grade migalastat hydrochloride, is crystallized to form pharmaceutical grade migalastat salt. In some embodiments, intermediate grade migalastat salt is crystallized twice or more (e.g., two times, three times, four times, or more) to form pharmaceutical grade migalastat salt.

First Crystallization Step

In some embodiments, the crystallization is in a mixture of water and a lower alcohol, for example, a C1-C4 alcohol. Examples of such alcohols include, but are not limited to, methanol, ethanol, n-propanol, isopropanol, and n-butanol. In some embodiments, the lower alcohol is ethanol.

In some embodiments, the intermediate grade migalastat salt is admixed with water. In some embodiments, the intermediate grade migalastat salt is admixed in from about 0.5 to about 4 weights of water, such as from about 0.5 to about 3 weights, about 1 to about 2 weights, about 1 to about 1.6 weights, about 1.1 to about 1.4 weights, about 1.1 weights, about 1.2 weights, about 1.3 weights, or about 1.4 weights of water. In some embodiments, the intermediate grade migalastat salt is admixed in from 0.5 to 4 weights of water, such as from 0.5 to 3 weights, 1 to 2 weights, 1.1 to about 1.4, 1.1 weights, 1.2 weights, 1.3 weights, or 1.4 weights of water. In some embodiments, the first crystallized migalastat salt is admixed with about 1, 1.1 weights, 1.2 weights, 1.3 weights, 1.4 weights, 1.5 weights or 1.6 weights of water.

The temperature during the mixing and crystallization may vary. In some embodiments, the temperature is adjusted to a first crystallization temperature after the intermediate grade migalastat salt is admixed with water, e.g., to a temperature from about 30° C. to about 70° C., about 35° C. to about 65° C., about 40° C. to about 60° C., about 40° C., about 45° C., about 50° C., about 55° C., or about 60° C. In some embodiments, the temperature is adjusted after the intermediate grade migalastat salt is admixed with water, e.g., to a temperature of from 30° C. to 70° C., 35° C. to 65° C., 40° C. to 60° C., 40° C., 45° C., 50° C., 55° C., or 60° C. In some embodiments, the migalastat salt is admixed with water, at a temperature from about 30° C. to about 70° C., and the temperature is maintained or is adjusted, either up or down, to the first crystallization temperature.

In some embodiments, the C1-C4 alcohol (e.g., ethanol) is added to the intermediate grade migalastat mixture at the first crystallization temperature to induce crystallization. In some embodiments, from about 1 to about 15 weights of C1-C4 alcohol (e.g., ethanol) is added, such as from about 1 to about 12 weights, about 1 to about 11.4 weights, about 4.8 to about 11.4 weights, about 7 to about 12 weights, about 8 to about 11 weights, about 8.4 to about 10.6 weights, about 8.5 to about 10.4 weights, about 8.5 weights, about 9 weights, about 9.5 weights, about 10 weights, or about 10.4 weights of C1-C4 alcohol (e.g., ethanol). In some embodiments, from 1 to 15 weights of C1-C4 alcohol (e.g., ethanol) is added, such as from 1 to 12 weights, 1 to 11.4 weights, 4.8 to 11.4 weights, 7 to 12 weights, 8 to 11 weights, 8.4 to 10.6 weights, 8.5 to 10.4 weights, 8.5 weights, 9 weights, 9.5 weights, 10 weights, or 10.4 weights of C1-C4 alcohol (e.g., ethanol).

In some embodiments, C1-C4 alcohol (e.g., ethanol) is added to the first migalastat salt slurry or solution over a period of time ranging from about 0 to about 65 minutes. In some embodiments, C1-C4 alcohol (e.g., ethanol) is added to the first migalastat salt slurry or solution over a period of time of about 60 minutes.

In some embodiments, the resulting slurry or solution is cooled to an isolation temperature, e.g., of from about 3° C. to about 50° C., about 5° C. to about 45° C., about 5° C. to about 40° C., about 5° C. to about 35° C., about 5° C., about 10° C., about 15° C., about 20° C., about 25° C., about 30° C., or about 35° C. In some embodiments, the isolation temperature is from 3° C. to 50° C., 5° C. to 45° C., 5° C. to 40° C., 5° C. to 35° C., 5° C., 10° C., 15° C., 20° C., 25° C., 30° C., or 35° C. in order to complete the crystallization. In some embodiments, the cooling comprises an active cooling step (e.g. removal of heat by contact with ice, refrigerant, etc). In other embodiments, the cooling comprises a passive cooling step by allowing the slurry or solution to reach the ambient temperature of its surroundings.

In some embodiments, the first crystallized migalastat salt is isolated from the slurry or solution via filtration (e.g., conducted at the isolation temperature). In some embodiments, the first crystallized migalastat salt is washed, e.g., with a C1-C4 alcohol (e.g., ethanol) following isolation. The wash can be conducted with about 0.5 weights of C1-C4 alcohol (e.g., ethanol; relative to the weight of the isolated Stage 4a product) or more, such as about 1 or more weights, about 2 or more weights, about 3 or more weights, about 5 or more weights, or about 10 or more weights. In some embodiments, the wash is conducted with 0.5 weights of C1-C4 alcohol (e.g., ethanol) or more, such as 1 or more weights, 2 or more weights, 3 or more weights, 5 or more weights, or 10 or more weights.

In some embodiments, the first crystallized migalastat salt is dried, e.g., under vacuum. In some embodiments, the first crystallized migalastat salt is dried at a temperature or about 90° C. or less, such as about 80° C. or less, about 70° C. or less, about 60° C. or less, about 50° C. or less, about 80° C., about 70° C., or about 60° C. In some embodiments, the first crystallized migalastat salt is dried at a temperature or 90° C. or less, such as 80° C. or less, 70° C. or less, 60° C. or less, 50° C. or less, including, e.g., a temperature of 80° C., 70° C., or 60° C.

Second Crystallization Step

In some embodiments, the first crystallized migalastat salt is further purified by a second crystallization. In some embodiments, the first crystallized migalastat salt is admixed with water. In some embodiments, the first crystallized migalastat salt is admixed in from about 0.5 to about 4 weights of water, such as from about 0.5 to about 3 weights, about 1 to about 2 weights, about 1 to about 1.6 weights, about 1.1 to about 1.4 weights, about 1.1 weights, about 1.2 weights, about 1.3 weights, or about 1.4 weights of water. In some embodiments, the first crystallized migalastat salt is admixed in from 0.5 to 4 weights of water, such as from 0.5 to 3 weights, 1 to 2 weights, 1.1 to about 1.4, 1.1 weights, 1.2 weights, 1.3 weights, or 1.4 weights of water. In some embodiments, the first crystallized migalastat salt is admixed with about 1, 1.1 weights, 1.2 weights, 1.3 weights, 1.4 weights, 1.5 weights or 1.6 weights of water.

In some embodiments, the temperature is adjusted to a second crystallization temperature after the first crystallized migalastat salt is admixed with water, e.g., to a temperature of from about 30° C. to about 70° C., about 35° C. to about 65° C., about 40° C. to about 60° C., about 40° C., about 45° C., about 50° C., about 55° C., or about 60° C. In some embodiments, the temperature is adjusted after the first crystallized migalastat salt is admixed with water, e.g., to a temperature of from 30° C. to 70° C., 35° C. to 65° C., 40° C. to 60° C., 40° C., 45° C., 50° C., 55° C., or 60° C. In some embodiments, the migalastat salt is admixed with water, at a temperature from about 30° C. to about 70° C., and the temperature is maintained or is adjusted, either up or down, to the second crystallization temperature.

In some embodiments, a first quantity of C1-C4 alcohol (e.g., ethanol) is added to the first crystallized migalastat salt mixture at the first crystallization temperature to induce crystallization. In some embodiments, the first quantity of C1-C4 alcohol (e.g., ethanol) is from about 0.5 to about 4 weights of ethanol relative to the weight of migalastat salt, such as from about 0.75 to about 3 weights, about 1 to about 2.5 weights, about 1.8 to about 2 weights, about 1.8 weights, about 1.9 weights, or about 2 weights of C1-C4 alcohol (e.g., ethanol), relative to the weight of migalastat salt. In some embodiments, the first quantity of C1-C4 alcohol (e.g., ethanol) is from 0.5 to 4 weights, such as from 0.75 to 3 weights, 1 to 2.5 weights, 1.8 to 2 weights, 1.8 weights, 1.9 weights, or 2 weights of C1-C4 alcohol (e.g., ethanol), relative to the weight of migalastat salt.

In some embodiments, the first quantity of C1-C4 alcohol (e.g., ethanol) is added over a period of about 3 minutes or more, such as about 4 minutes or more, about 5 minutes or more, about 10 minutes or more, or about 15 minutes or more. In some embodiments, the first quantity of C1-C4 alcohol (e.g., ethanol) is added over a period of 3 minutes or more, such as 4 minutes or more, 5 minutes or more, 10 minutes or more, or 15 minutes or more. In some embodiments, the first quantity of C1-C4 alcohol (e.g., ethanol) is added over a period of from about 5 to about 65 minutes.

In some embodiments, a second quantity of C1-C4 alcohol (e.g., ethanol) is added to the mixture following a hold time. The hold time can be about 3 minutes or more, such as about 4 minutes or more, about 5 minutes or more, about 10 minutes or more, or about 15 minutes or more. In some embodiments, the hold time is a period of 3 minutes or more, such as 4 minutes or more, 5 minutes or more, 10 minutes or more, or 15 minutes or more.

In some embodiments, the second quantity of C1-C4 alcohol (e.g., ethanol) comprises about 4 to about 15 weights of C1-C4 alcohol (e.g., ethanol) relative to the weight of migalastat salt, such as from about 5 to about 12 weights, about 6 to about 10 weights, about 6.5 to about 9 weights, about 6.7 to about 8.4 weights, about 6.8 to about 8.4 weights, about 6.8 weights, about 7 weights, about 7.5 weights, about 8 weights, or about 8.4 weights. In some embodiments, the second quantity of C1-C4 alcohol (e.g., ethanol) comprises 4 to 15 weights, such as from 5 to 12 weights, 6 to 10 weights, 6.5 to 9 weights, 6.8 to 8.4 weights, 6.8 weights, 7 weights, 7.5 weights, 8 weights, or 8.4 weights of C1-C4 alcohol (e.g., ethanol) relative to the weight of migalastat salt.

In some embodiments, the second quantity of C1-C4 alcohol (e.g., ethanol) is added over a period of about 5 minutes or more, such as about 10 minutes or more, about 15 minutes or more, about 20 minutes or more, about 30 minutes or more, about 45 minutes or more, or about 60 minutes or more. In some embodiments, the second quantity of C1-C4 alcohol (e.g., ethanol) is added over a period of 5 minutes or more, such as 10 minutes of more, 15 minutes or more, 20 minutes or more, 30 minutes or more, 45 minutes or more, or 60 minutes or more.

In some embodiments, the amount of C1-C4 alcohol (e.g., ethanol) used in the second crystallization (i.e., the first quantity+the second quantity) is the same as the amount of C1-C4 alcohol (e.g., ethanol) used in the first crystallization. In some embodiments, the amount of C1-C4 alcohol (e.g., ethanol) used is different from the amount of C1-C4 alcohol (e.g., ethanol) used in the first crystallization.

Some embodiments comprise cooling the resulting slurry or solution (e.g., that contains both the first and second quantities of C1-C4 alcohol (e.g., ethanol)) to an isolation temperature in order to complete the second crystallization. In some embodiments, the slurry or solution is cooled to an isolation temperature, e.g., of from about 3° C. to about 50° C., about 5° C. to about 45° C., about 5° C. to about 40° C., about 5° C. to about 35° C., about 5° C., about 10° C., about 15° C., about 20° C., about 25° C., about 30° C., or about 35° C. In some embodiments, the isolation temperature is 3° C. to 50° C., 5° C. to 45° C., 5° C. to 40° C., 5° C. to 35° C., 5° C., 10° C., 15° C., 20° C., 25° C., 30° C., or 35° C. In some embodiments, the cooling comprises an active cooling step (e.g. removal of heat by contact with ice, refrigerant, etc). In other embodiments, the cooling comprises a passive cooling step by allowing the slurry or solution to reach the ambient temperature of its surroundings.

In some embodiments, the second crystallized migalastat salt is isolated from the slurry or solution via filtration (e.g., conducted at the isolation temperature). In some embodiments, the second crystallized migalastat salt is washed, e.g., with a C1-C4 alcohol (e.g., ethanol). The wash can be conducted with about 0.5 weights of C1-C4 alcohol (e.g., ethanol) or more, such as about 1 or more weight, about 2 or more weights, about 3 or more weights, about 5 or more weights, or about 10 or more weights. In some embodiments, the wash is conducted with 0.5 weights or more, such as 1 or more weight, 2 or more weights, 3 or more weights, 5 or more weights, or 10 or more weights of C1-C4 alcohol (e.g., ethanol).

In some embodiments, the second crystallized migalastat salt is dried, e.g., under vacuum. In some embodiments, the second crystallized migalastat salt is dried at a temperature of about 90° C. or less, such as about 80° C. or less, about 70° C. or less, about 60° C. or less, about 50° C. or less, about 80° C., about 70° C., or about 60° C. In some embodiments, the second crystallized migalastat salt product is dried at a temperature of 90° C. or less, such as 80° C. or less, 70° C. or less, 60° C. or less, 50° C. or less, 80° C., 70° C., or 60° C.

Lucerastat

Lucerastat, also known as N-butyldeoxygalactonojirimycin or (2R,3S,4R,5S)-1-buthyl-2-(hydroxymethyl)piperdine-3,4,5-triol, refers to a compound having the following free base structures:

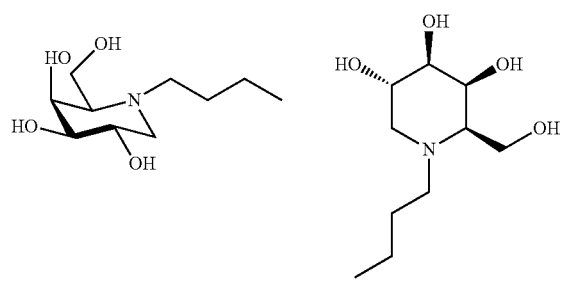

Lucerastat can be produced from migalastat by butylation of the piperidine nitrogen atom with an appropriate alkylating agent. For example, butylation may be performed by reductive alkylation of migalastat with butyraldehyde in the presence of a reducing agent. Non-limiting examples of suitable reducing agents include hydrogen and a catalyst, sodium cyanoborohydride, and sodium triacetoxyborohydride.

Lucerastat hydrochloride is a compound having the following structure:

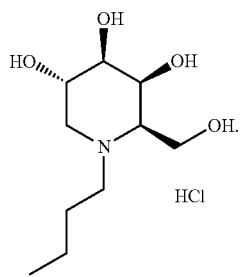

Lucerastat salt, such as lucerastat hydrochloride, may be prepared by contacting free base lucerastat (e.g., lucerastat as provided according to the prior paragraph) in solution with at least a molar equivalent of an aqueous solution of acid, such as hydrochloric acid, or a solution of acid gas, such as solution of hydrogen chloride gas, in an appropriate solvent, for example, an alcohol or ether. Generally, the lucerastat salt, such as lucerastat hydrochloride, is isolated by removal of the solvent, for example, by evaporation.

In some embodiments, it may be desirable to purify the lucerastat salt. Accordingly, in another aspect of the disclosure is provided a method of purification of lucerastat salt.

In some embodiments, intermediate grade lucerastat salt, such as intermediate grade lucerastat hydrochloride, is crystallized to form pharmaceutical grade lucerastat salt. In some embodiments, intermediate grade lucerastat salt is crystallized twice or more (e.g., two times, three times, four times, or more) to form pharmaceutical grade lucerastat salt.

First Crystallization Step

In some embodiments, the crystallization is in a mixture of water and a lower alcohol, for example, a C1-C4 alcohol. Examples of such alcohols include, but are not limited to, methanol, ethanol, n-propanol, isopropanol, and n-butanol. In some embodiments, the lower alcohol is ethanol.

In some embodiments, the intermediate grade lucerastat salt is admixed with water. In some embodiments, the intermediate grade lucerastat salt is admixed in from about 0.5 to about 4 weights of water, such as from about 0.5 to about 3 weights, about 1 to about 2 weights, about 1.1 to about 1.4 weights, about 1.1 weights, about 1.2 weights, about 1.3 weights, or about 1.4 weights of water. In some embodiments, the intermediate grade lucerastat salt is admixed in from 0.5 to 4 weights of water, such as from 0.5 to 3 weights, 1 to 2 weights, 1.1 to about 1.4, 1.1 weights, 1.2 weights, 1.3 weights, or 1.4 weights of water.

The temperature during the mixing and crystallization may vary. In some embodiments, the temperature is adjusted to a first crystallization temperature after the intermediate grade lucerastat salt is admixed with water, e.g., to a temperature from about 30° C. to about 70° C., about 35° C. to about 65° C., about 40° C. to about 60° C., about 40° C., about 45° C., about 50° C., about 55° C., or about 60° C. In some embodiments, the temperature is adjusted after the intermediate grade lucerastat salt is admixed with water, e.g., to a temperature of from 30° C. to 70° C., 35° C. to 65° C., 40° C. to 60° C., 40° C., 45° C., 50° C., 55° C., or 60° C. In some embodiments, the lucerastat salt is admixed with water, at a temperature from about 30° C. to about 70° C., and the temperature is maintained or is adjusted, either up or down, to the first crystallization temperature.

In some embodiments, the C1-C4 alcohol (e.g., ethanol) is added to the intermediate grade lucerastat mixture at the first crystallization temperature to induce crystallization. In some embodiments, from about 6 to about 15 weights of C1-C4 alcohol (e.g., ethanol) is added, such as from about 7 to about 12 weights, about 8 to about 11 weights, about 8.5 to about 10.4 weights, about 8.5 weights, about 9 weights, about 9.5 weights, about 10 weights, or about 10.4 weights of C1-C4 alcohol (e.g., ethanol). In some embodiments, from 6 to 15 weights of C1-C4 alcohol (e.g., ethanol) is added, such as from 7 to 12 weights, 8 to 11 weights, 8.5 to 10.4 weights, 8.5 weights, 9 weights, 9.5 weights, 10 weights, or 10.4 weights of C1-C4 alcohol (e.g., ethanol).

In some embodiments, the resulting slurry or solution is cooled to an isolation temperature, e.g., of from about 3° C. to about 50° C., about 5° C. to about 45° C., about 5° C. to about 40° C., about 5° C. to about 35° C., about 5° C., about 10° C., about 15° C., about 20° C., about 25° C., about 30° C., or about 35° C. In some embodiments, the isolation temperature is from 3° C. to 50° C., 5° C. to 45° C., 5° C. to 40° C., 5° C. to 35° C., 5° C., 10° C., 15° C., 20° C., 25° C., 30° C., or 35° C. in order to complete the crystallization.

In some embodiments, the first crystallized lucerastat salt is isolated from the slurry or solution via filtration (e.g., conducted at the isolation temperature). In some embodiments, the first crystallized lucerastat salt is washed, e.g., with a C1-C4 alcohol (e.g., ethanol) following isolation. The wash can be conducted with about 0.5 weights of C1-C4 alcohol (e.g., ethanol; relative to the weight of the isolated Stage 4a product) or more, such as about 1 or more weights, about 2 or more weights, about 3 or more weights, about 5 or more weights, or about 10 or more weights. In some embodiments, the wash is conducted with 0.5 weights of C1-C4 alcohol (e.g., ethanol) or more, such as 1 or more weights, 2 or more weights, 3 or more weights, 5 or more weights, or 10 or more weights.

In some embodiments, the first crystallized lucerastat salt is dried, e.g., under vacuum. In some embodiments, the first crystallized lucerastat salt is dried at a temperature or about 90° C. or less, such as about 80° C. or less, about 70° C. or less, about 60° C. or less, about 50° C. or less, about 80° C., about 70° C., or about 60° C. In some embodiments, the first crystallized lucerastat salt is dried at a temperature or 90° C. or less, such as 80° C. or less, 70° C. or less, 60° C. or less, 50° C. or less, including, e.g., a temperature of 80° C., 70° C., or 60° C.

Second Crystallization Step

In some embodiments, the first crystallized lucerastat salt is further purified by a second crystallization. In some embodiments, the first crystallized lucerastat salt is admixed with water. In some embodiments, the first crystallized lucerastat salt is admixed in from about 0.5 to about 4 weights of water, such as from about 0.5 to about 3 weights, about 1 to about 2 weights, about 1.1 to about 1.4 weights, about 1.1 weights, about 1.2 weights, about 1.3 weights, or about 1.4 weights of water. In some embodiments, the first crystallized lucerastat salt is admixed in from 0.5 to 4 weights of water, such as from 0.5 to 3 weights, 1 to 2 weights, 1.1 to about 1.4, 1.1 weights, 1.2 weights, 1.3 weights, or 1.4 weights of water.

In some embodiments, the temperature is adjusted to a second crystallization temperature after the first crystallized lucerastat salt is admixed with water, e.g., to a temperature of from about 30° C. to about 70° C., about 35° C. to about 65° C., about 40° C. to about 60° C., about 40° C., about 45° C., about 50° C., about 55° C., or about 60° C. In some embodiments, the temperature is adjusted after the first crystallized lucerastat salt is admixed with water, e.g., to a temperature of from 30° C. to 70° C., 35° C. to 65° C., 40° C. to 60° C., 40° C., 45° C., 50° C., 55° C., or 60° C. In some embodiments, the lucerastat salt is admixed with water, at a temperature from about 30° C. to about 70° C., and the temperature is maintained or is adjusted, either up or down, to the second crystallization temperature.

In some embodiments, a first quantity of C1-C4 alcohol (e.g., ethanol) is added to the first crystallized lucerastat salt mixture at the first crystallization temperature to induce crystallization. In some embodiments, the first quantity of C1-C4 alcohol (e.g., ethanol) is from about 0.5 to about 4 weights of the C1-C4 alcohol (e.g., ethanol) relative to the weight of lucerastat salt, such as from about 0.75 to about 3 weights, about 1 to about 2.5 weights, about 1.8 to about 2 weights, about 1.8 weights, about 1.9 weights, or about 2 weights of C1-C4 alcohol (e.g., ethanol), relative to the weight of lucerastat salt. In some embodiments, the first quantity of C1-C4 alcohol (e.g., ethanol) is from 0.5 to 4 weights, such as from 0.75 to 3 weights, 1 to 2.5 weights, 1.8 to 2 weights, 1.8 weights, 1.9 weights, or 2 weights of C1-C4 alcohol (e.g., ethanol), relative to the weight of lucerastat salt.

In some embodiments, the first quantity of C1-C4 alcohol (e.g., ethanol) is added over a period of about 3 minutes or more, such as about 4 minutes or more, about 5 minutes or more, about 10 minutes or more, or about 15 minutes or more. In some embodiments, the first quantity of C1-C4 alcohol (e.g., ethanol) is added over a period of 3 minutes or more, such as 4 minutes or more, 5 minutes or more, 10 minutes or more, or 15 minutes or more.

In some embodiments, a second quantity of C1-C4 alcohol (e.g., ethanol) is added to the mixture following a hold time. The hold time can be about 3 minutes or more, such as about 4 minutes or more, about 5 minutes or more, about 10 minutes or more, or about 15 minutes or more. In some embodiments, the hold time is a period of 3 minutes or more, such as 4 minutes or more, 5 minutes or more, 10 minutes or more, or 15 minutes or more.

In some embodiments, the second quantity of C1-C4 alcohol (e.g., ethanol) comprises about 4 to about 15 weights of C1-C4 alcohol (e.g., ethanol) relative to the weight of lucerastat salt, such as from about 5 to about 12 weights, about 6 to about 10 weights, about 6.5 to about 9 weights, about 6.8 to about 8.4 weights, about 6.8 weights, about 7 weights, about 7.5 weights, about 8 weights, or about 8.4 weights. In some embodiments, the second quantity of C1-C4 alcohol (e.g., ethanol) comprises 4 to 15 weights, such as from 5 to 12 weights, 6 to 10 weights, 6.5 to 9 weights, 6.8 to 8.4 weights, 6.8 weights, 7 weights, 7.5 weights, 8 weights, or 8.4 weights of C1-C4 alcohol (e.g., ethanol) relative to the weight of lucerastat salt.

In some embodiments, the second quantity of C1-C4 alcohol (e.g., ethanol) is added over a period of about 10 minutes or more, such as about 15 minutes or more, about 20 minutes or more, about 30 minutes or more, about 45 minutes or more, or about 60 minutes or more. In some embodiments, the second quantity of C1-C4 alcohol (e.g., ethanol) is added over a period of 10 minutes or more, such as 15 minutes or more, 20 minutes or more, 30 minutes or more, 45 minutes or more, or 60 minutes or more.

In some embodiments, the amount of C1-C4 alcohol (e.g., ethanol) used in the second crystallization (i.e., the first quantity+the second quantity) is the same as the amount of C1-C4 alcohol (e.g., ethanol) used in the first crystallization. In some embodiments, the amount of C1-C4 alcohol (e.g., ethanol) used is different from the amount of C1-C4 alcohol (e.g., ethanol) used in the first crystallization.

Some embodiments comprise cooling the resulting slurry or solution (e.g., that contains both the first and second quantities of C1-C4 alcohol (e.g., ethanol)) to an isolation temperature in order to complete the second crystallization. In some embodiments, the slurry or solution is cooled to an isolation temperature, e.g., of from about 3° C. to about 50° C., about 5° C. to about 45° C., about 5° C. to about 40° C., about 5° C. to about 35° C., about 5° C., about 10° C., about 15° C., about 20° C., about 25° C., about 30° C., or about 35° C. In some embodiments, the isolation temperature is 3° C. to 50° C., 5° C. to 45° C., 5° C. to 40° C., 5° C. to 35° C., 5° C., 10° C., 15° C., 20° C., 25° C., 30° C., or 35° C.

In some embodiments, the second crystallized lucerastat salt is isolated from the slurry or solution via filtration (e.g., conducted at the isolation temperature). In some embodiments, the second crystallized lucerastat salt is washed, e.g., with a C1-C4 alcohol (e.g., ethanol). The wash can be conducted with about 0.5 weights of C1-C4 alcohol (e.g., ethanol) or more, such as about 1 or more weight, about 2 or more weights, about 3 or more weights, about 5 or more weights, or about 10 or more weights. In some embodiments, the wash is conducted with 0.5 weights or more, such as 1 or more weight, 2 or more weights, 3 or more weights, 5 or more weights, or 10 or more weights of C1-C4 alcohol (e.g., ethanol).

In some embodiments, the second crystallized lucerastat salt is dried, e.g., under vacuum. In some embodiments, the second crystallized lucerastat salt is dried at a temperature of about 90° C. or less, such as about 80° C. or less, about 70° C. or less, about 60° C. or less, about 50° C. or less, about 80° C., about 70° C., or about 60° C. In some embodiments, the second crystallized lucerastat salt product is dried at a temperature of 90° C. or less, such as 80° C. or less, 70° C. or less, 60° C. or less, 50° C. or less, 80° C., 70° C., or 60° C.

The following examples are provided to illustrate embodiments of an invention, but it should be understood that the invention is not limited to the specific conditions or details of these examples.

EXEMPLIFICATION

Example 1: Migalastat Hydrochloride Specification

A batch of pharmaceutical grade migalastat hydrochloride was prepared with the specifications set forth in Table 1:

TABLE 1

Migalastat hydrochloride specifications

| Test | Acceptance Criteria |
| --- | --- |
| Appearance | White to almost white solid |
| Identification of Migalastat Hydrochloride by Infrared Spectroscopy | The spectrum of the sample is concordant with that of migalastat HCl reference material |
| Identification of Migalastat HCl by HPLC | Matches the retention time of the migalastat HCl reference standard |

TABLE 1-continued

Migalastat hydrochloride specifications

| Test | Acceptance Criteria |
|---|---|
| Identification of Chloride | Contains chloride |
| Migalastat HCl Content by HPLC (% w/w, 'as is') | 98.0-102.0 |
| Drug-related Impurities Content by HPLC (% w/w) | |
| Compound W | Not greater than 0.15 |
| Compound U | Not greater than 0.15 |
| Any Unspecified Impurity | Not greater than 0.10 |
| Compound V, Compound Y, and Compound BB Content by HILIC (% w/w) | |
| Compound V | Not greater than 0.15 |
| Compound Y | Not greater than 0.15 |
| Compound BB | Not greater than 0.15 |
| Total Impurities by HPLC and HILIC (% w/w) | Not greater than 0.5 |
| Methanol and Ethanol Content by GC (% w/w) | |
| Methanol | Not greater than 0.3 |
| Ethanol | Not greater than 0.5 |
| Water Content by Karl Fischer (% w/w) | Not greater than 0.2 |
| Residue on Ignition (% w/w) | Not greater than 0.2 |
| Heavy Metals by ICP-MS (ppm) | |
| As | Not greater than 0.15 |
| Cd | Not greater than 0.5 |
| Hg | Not greater than 1.5 |
| Pb | Not greater than 0.5 |
| Palladium Content by ICP-MS (ppm) | Not greater than 10 |

HPLC = High performance liquid chromatography;
HILIC = Hydrophilic interaction liquid chromatography;
GC = gas chromatography;
ICP-MS = Inductively coupled plasma mass spectroscopy The batch was incorporated into capsules, each of which contained 123 mg of migalastat. The specifications for the capsules are set forth in Table 2:

TABLE 2

Migalastat hard capsule specifications

| Test | Acceptance Criteria |
|---|---|
| Description | A size "2" capsule, containing white to pale brown powder. |
| Identification of Migalastat Hydrochloride by IR | The spectrum of the sample is concordant with that of the reference material. |
| Identification of Migalastat Hydrochloride by HPLC | The retention time of the migalastat peak in the sample chromatogram corresponds to that in the standard chromatogram. |
| Migalastat Content by HPLC (% w/w) | 95.0-105.0 |
| Drug-related Impurities Content by HPLC (% w/w) | |
| Any individual degradation product | Not greater than 0.2 |
| Total degradation products | Not greater than 0.5 |
| Uniformity of Dosage Units by Weight/Mass Variation | Complies with Harmonized Pharmacopoeia (USP/Ph. Eur./JP) |
| Dissolution (% migalastat released) | Not less than 80% (Q) at 15 minutes |
| Microbial enumeration tests | |
| Total aerobic microbial count (TAMC) | Not greater than 103 cfu/g |
| Total combined yeast/mold count (TYMC) | Not greater than 102 cfu/g |

TABLE 2-continued

Migalastat hard capsule specifications

| Test | Acceptance Criteria |
|---|---|
| Specific micro-organisms | |
| *Escherichia coli* | Absent in 1 g |

Example 2: Migalastat Hydrochloride Production Parameters

Migalastat hydrochloride was produced using the tolerances set forth in Table 3 unless otherwise defined:

TABLE 3

Tolerances used during production of migalastat hydrochloride

| Variable | Tolerance |
|---|---|
| Batch size if no range is given | ±20% |
| Key raw material and critical quantity (weight or volume) | ±1% |
| Non-critical quantity (weight or volume) | ±2% |
| Solvents (weight or volume) | ±5% |
| Temperature | ±5° C. |
| Time | ±20% |

Equipment: Reactors were glass, glass-lined steel, stainless steel, or Hastelloy C and were equipped with appropriate stirring and temperature controls. Filtrations for the purpose of isolating crystalline products were performed using a Hastelloy Nutsche type filter with a metal filter fabric. Other solid materials, like inorganic salts, were separated from product-containing solutions by use of lens-shaped or GAF-filters (Hastelloy, ECTFE coated or stainless steel) with paper or textile inserts.

A flow diagram for the synthesis of a batch migalastat hydrochloride is shown in FIG. 1. The following abbreviations are used in the flowchart: DMF—N,N-Dimethylformamide; DMSO-Dimethylsulfoxide; IPAc—Isopropyl acetate; MeOH—Methanol; DBU—1,8-Diazabicycloundec-7-ene; NaOMe—Sodium methoxide; NaN₃— Sodium azide; EtOH—Ethanol; DIPEA—N,N-Diisopropylethylamine; PivCl—Pivaloyl chloride; HCl—Hydrochloric acid; Tf2O-Trifluoromethanesulfonic acid; Pd/C Palladium on carbon anhydride. As shown in FIG. 1, the synthesis involved 4 Stages. Batches were produced using the input scale set forth in Table 4 for each of the 4 Stages:

TABLE 4

Manufacturing Batch Scale

| Stage # | Scale Range (Input) |
|---|---|
| 1 | 29-55 kg |
| 2 | 36-84 kg |
| 3 | 25-31 kg |
| 4 | 11.5-17.3 kg |

Stage 1: Preparation of 1,2,3,6-tetrapivaloyl-D-galactofuranoside

Figure 2:
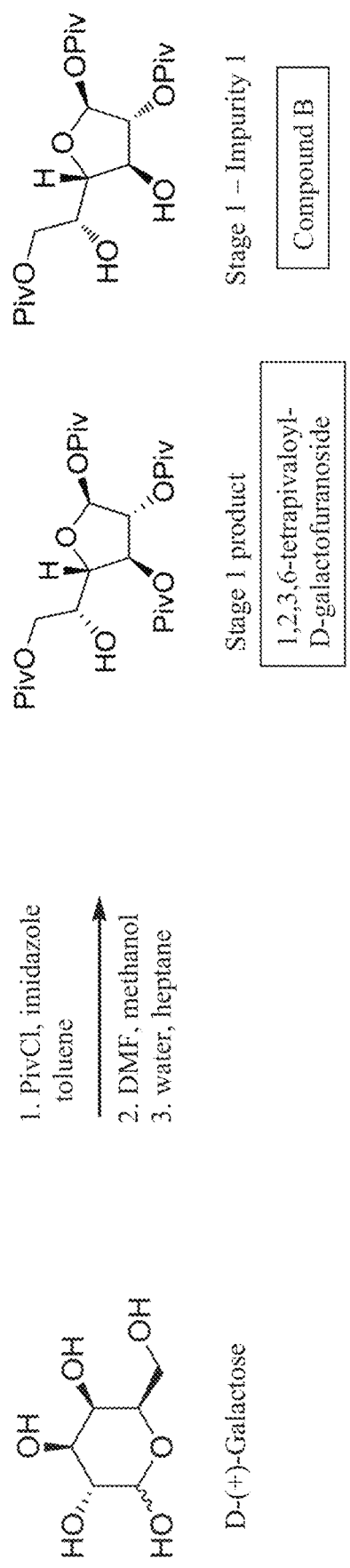
FIG. 2 depicts Stage 1 of an exemplary migalastat hydrochloride synthesis scheme, and shows an impurity that can result from Stage 1.

Stage 1 of migalastat hydrochloride production was performed as shown in FIG. 2, which also demonstrates an impurity formed during Stage 1. Pivaloyl imidazole was reacted with D-(+)-galactose to give 1,2,3,6-tetrapivaloyl- D-galactofuranoside. Pivaloyl imidazole was prepared by mixing pivaloyl chloride and imidazole in toluene. The slurry or solution was filtered and washed with toluene to give a solution of pivaloyl imidazole in toluene (18.4%-28.3% w/w).

Quantities in the following are expressed relative to D-(+)-galactose. 22-55 kg D-(+)-galactose (1 weight) was dissolved by heating in N,N-Dimethylformamide (DMF, 12.10-17.08 weights) at 88-92° C. The solution of pivaloyl imidazole in toluene (4.6-4.8 molar equivalents) was added to the solution of D-(+)-galactose at 77-85° C. The mixture was treated with methanol (0.50-3.0 weights). The resultant mixture was washed with water and the organic layer was separated. The solution was concentrated and heptane (6.27-9.40 weights) added before the mixture was seeded and cooled to −50 to 15° C. Solid 1,2,3,6-tetrapivaloyl-D-galactofuranoside was isolated, washed with heptane, and dried under vacuum with heating at <40° C.

Various batches were produced in which production parameters were varied. It was shown that 1,2,3,6-tetrapivaloyl-D-galactofuranoside could be produced across the production parameter ranges set forth in Table 5. The yield was 23%-33%.

TABLE 5

Summary of Stage 1 process parameters and associated ranges

| Stage | Process Parameter | Range | Units[1] |
|---|---|---|---|
| 1 | Pivaloyl imidazole content | 18.4-28.3 | % w/w |
| | DMF quantity | 12.10-17.08 | weights |
| | Galactose dissolution | 88-92 | ° C. |
| | Pivaloyl-imidazole quantity | 4.6-4.8 | molar equiv |
| | Reaction temperature | 77-85 | ° C. |
| | Methanol quantity | 0.5-3.0 | weights |
| | Heptane quantity | 6.27-9.40 | weights |
| | Crystallization temperature | −50 to −15 | ° C. |

[1]Weights expressed relative to D-(+)-galactose

Figure 3:
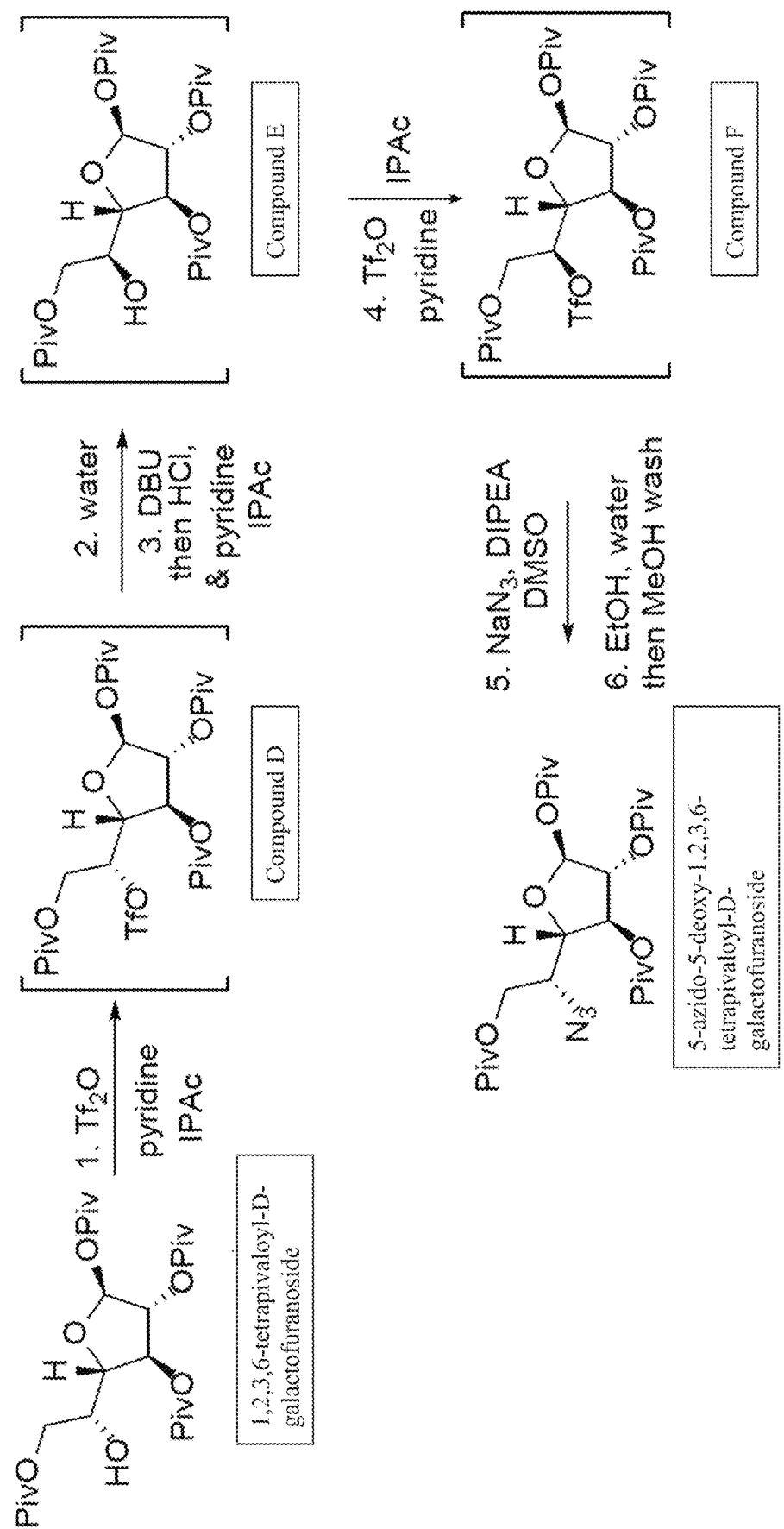
FIG. 3 depicts Stage 2 of an exemplary migalastat hydrochloride synthesis scheme.

Stage 2: Preparation of 5-azido-5-deoxy-1,2,3,6-tetrapivaloyl-D-galactofuranoside Stage 2 of migalastat hydrochloride production was performed as shown in FIG. 3. 1,2,3,6-tetrapivaloyl-D-galactofuranoside was activated with trifluoromethanesulfonic acid anhydride and then reacted with water to give 1,2,3,6-tetrapivaloyl-α-L-altrofuranoside. The resulting intermediate was again activated with trifluoromethanesulfonic acid anhydride and then reacted with sodium azide to give 5-azido-5-deoxy-1,2,3,6-tetrapivaloyl-D-galactofuranoside which was isolated.

Quantities are expressed relative to 1,2,3,6-tetrapivaloyl-D-galactofuranoside. Trifluoromethanesulfonic acid anhydride (1.0-1.6 molar equiv.) and pyridine (1.15-1.73 weights) were added to a solution of 36-84 kg 1,2,3,6-tetrapivaloyl-D-galactofuranoside (1 weight) in isopropyl acetate (IPAc). To the resulting reaction mixture (Compound D), water was added and the mixture heated to 55-60° C. The aqueous layer was separated and the organic layer dried by azeotropic distillation before adding IPAc and then 1,8-diazabicycloundec-7-ene (DBU) (0.033-0.066 weights). The resulting IPAc solution of Compound E was washed with aqueous hydrochloric acid (HCl) and then with aqueous pyridine. The solution was dried by azeotropic distillation and diluted with IPAc addition. Trifluoromethanesulfonic acid anhydride (1.0-1.6 molar equiv.) and pyridine (1.15-1.73 weights) were added. The resulting IPAc solution of Compound F was washed with water and added to sodium azide (0.13-0.19 weights) and N,N-diisopropylethylamine (DIPEA) (0.28-0.40 weights) in dimethylsulfoxide (DMSO). The mixture was stirred for at least 1 hour. The resulting 5-azido-5-deoxy-1,2,3,6-tetrapivaloyl-D-galactofuranoside mixture was washed with water and the organic layer was concentrated by distillation. The mixture was treated with ethanol (5.64-8.45 weights) and water (4.78-7.17 weights). The solid 5-azido-5-deoxy-1,2,3,6-tetrapivaloyl-D-galactofuranoside was isolated by filtration at 10-25° C., washed with methanol (0.79-2.38 weights), and dried under vacuum with heating at ≤40° C.

Figure 4:
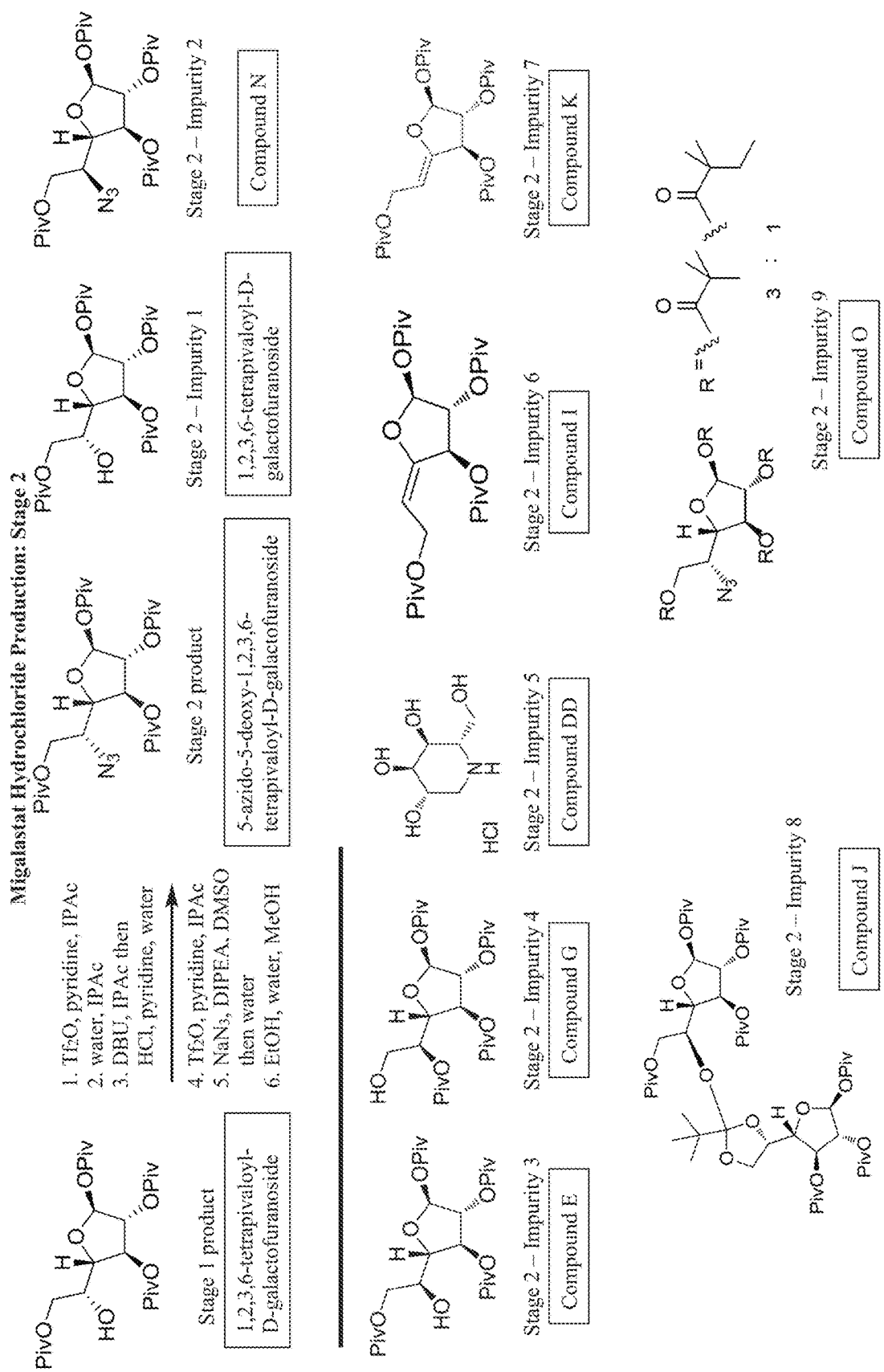
FIG. 4 also depicts Stage 2 of an exemplary migalastat hydrochloride synthesis scheme, and shows impurities that can result from Stage 2.

Various batches were produced in which production parameters were varied. It was shown that 5-azido-5-deoxy-1,2,3,6-tetrapivaloyl-D-galactofuranoside could be produced across the production parameter ranges set forth in Table 6. The yield was 53%-73%. Impurities that are present following Stage 2 are shown in FIG. 4.

TABLE 6

Summary of Stage 2 process parameters and associated ranges

| Stage | Process Parameter | Range | Units[1] |
|---|---|---|---|
| 2 | Trifluoromethanesulfonic acid anhydride quantity | 1.0-1.6 | molar equiv |
| | Pyridine quantity | 1.15-1.73 | weights |
| | Hydrolysis Temperature | 55-60 | ° C. |
| | 1,8-Diazabicycloundec-7-ene quantity | 0.033-0.066 | weights |
| | Trifluoromethanesulfonic acid anhydride quantity | 1.0-1.6 | molar equiv |
| | Pyridine quantity | 1.15-1.73 | weights |
| | Sodium azide quantity | 0.13-0.19 | weights |
| | N,N-diisopropylethylamine quantity | 0.28-0.40 | weights |
| | Ethanol quantity | 5.64-8.45 | weights |
| | Water quantity | 4.78-7.17 | weights |
| | Filtration temperature | 10-25 | ° C. |
| | Methanol wash quantity | 0.79-2.38 | weights |

[1]Weights expressed relative to 1,2,3,6-tetrapivaloyl-D-galactofuranoside

Stage 3: Preparation of Intermediate Grade Migalastat Hydrochloride

Figure 5:
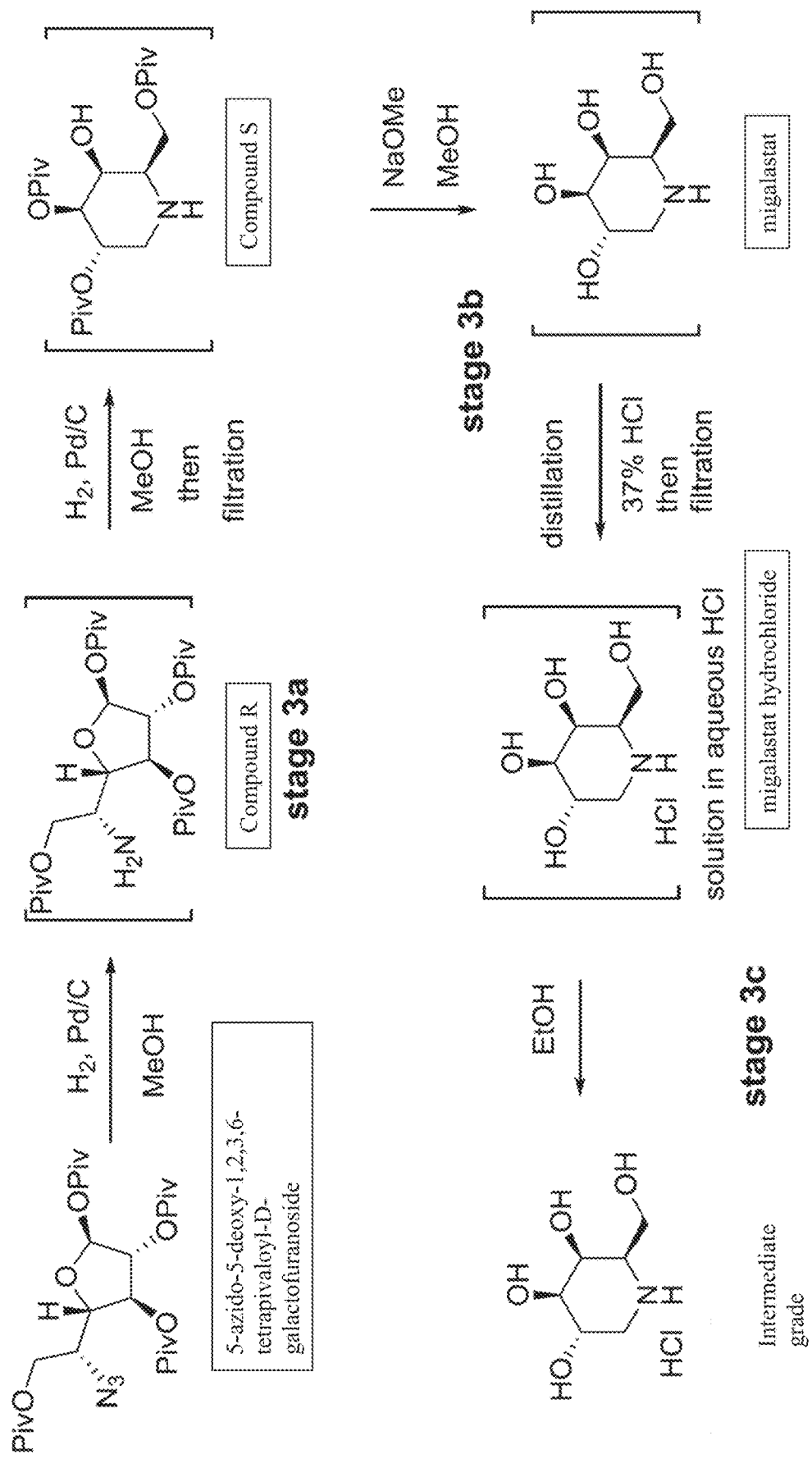
FIG. 5 depicts Stage 3 of an exemplary migalastat hydrochloride synthesis scheme.
Figure 6:
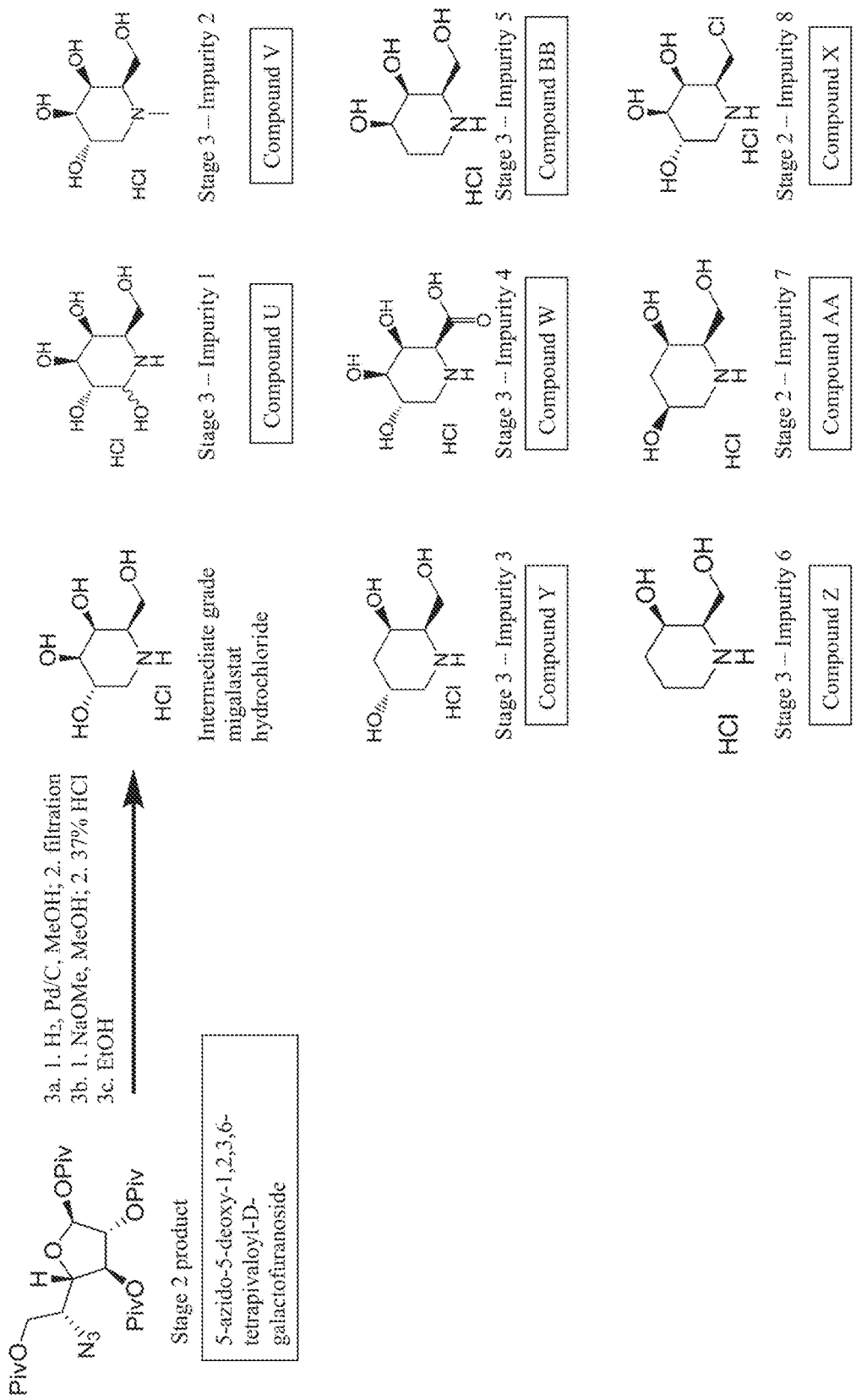
FIG. 6 also depicts Stage 3 of an exemplary migalastat hydrochloride synthesis scheme, and shows impurities that can result from Stage 3.
Figure 7:
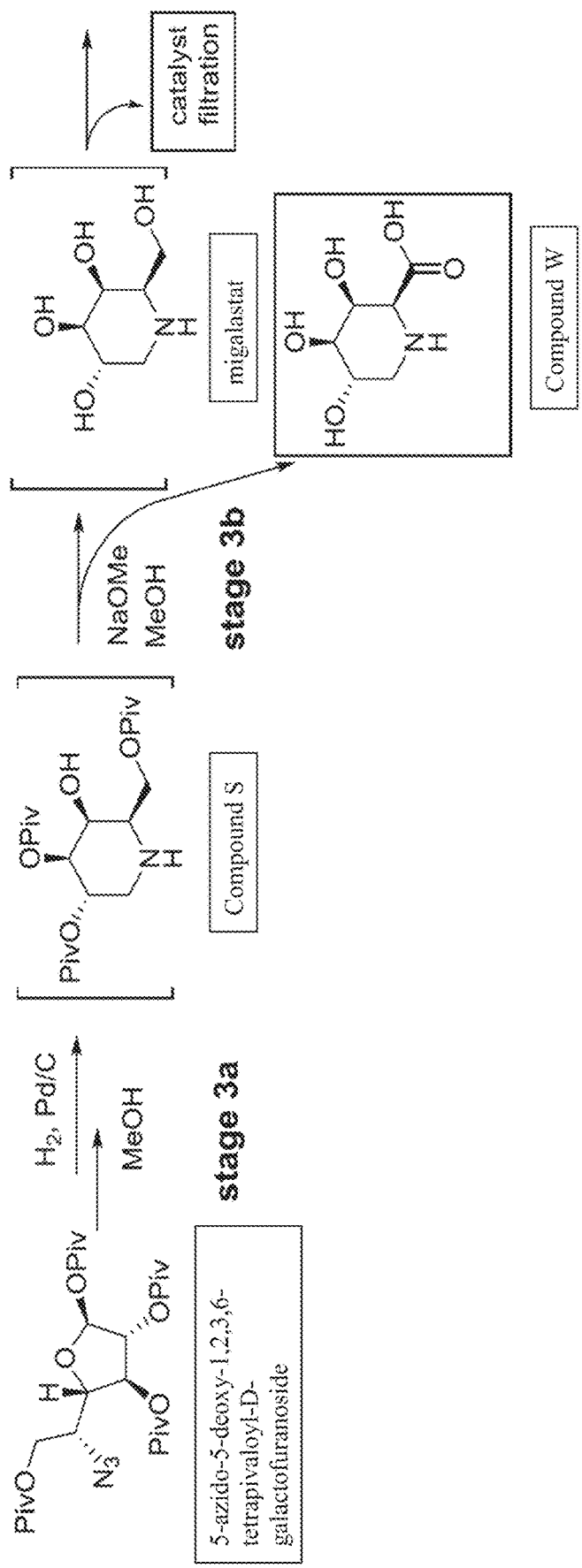
FIG. 7 depicts Stages 3a and 3b of an exemplary migalastat hydrochloride synthesis scheme.
Figure 8:
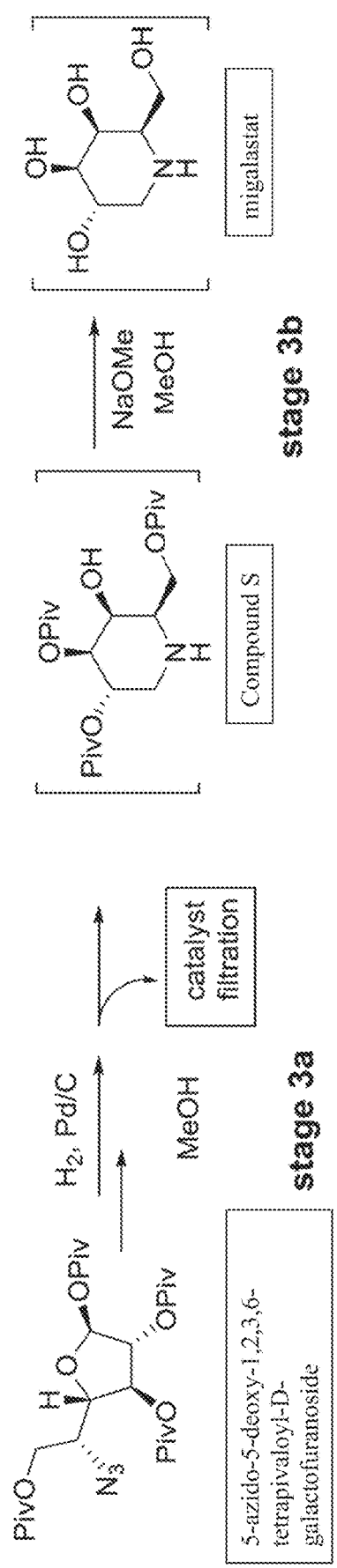
FIG. 8 depicts Stages 3a and 3b of an exemplary migalastat hydrochloride synthesis scheme.
Figure 9:
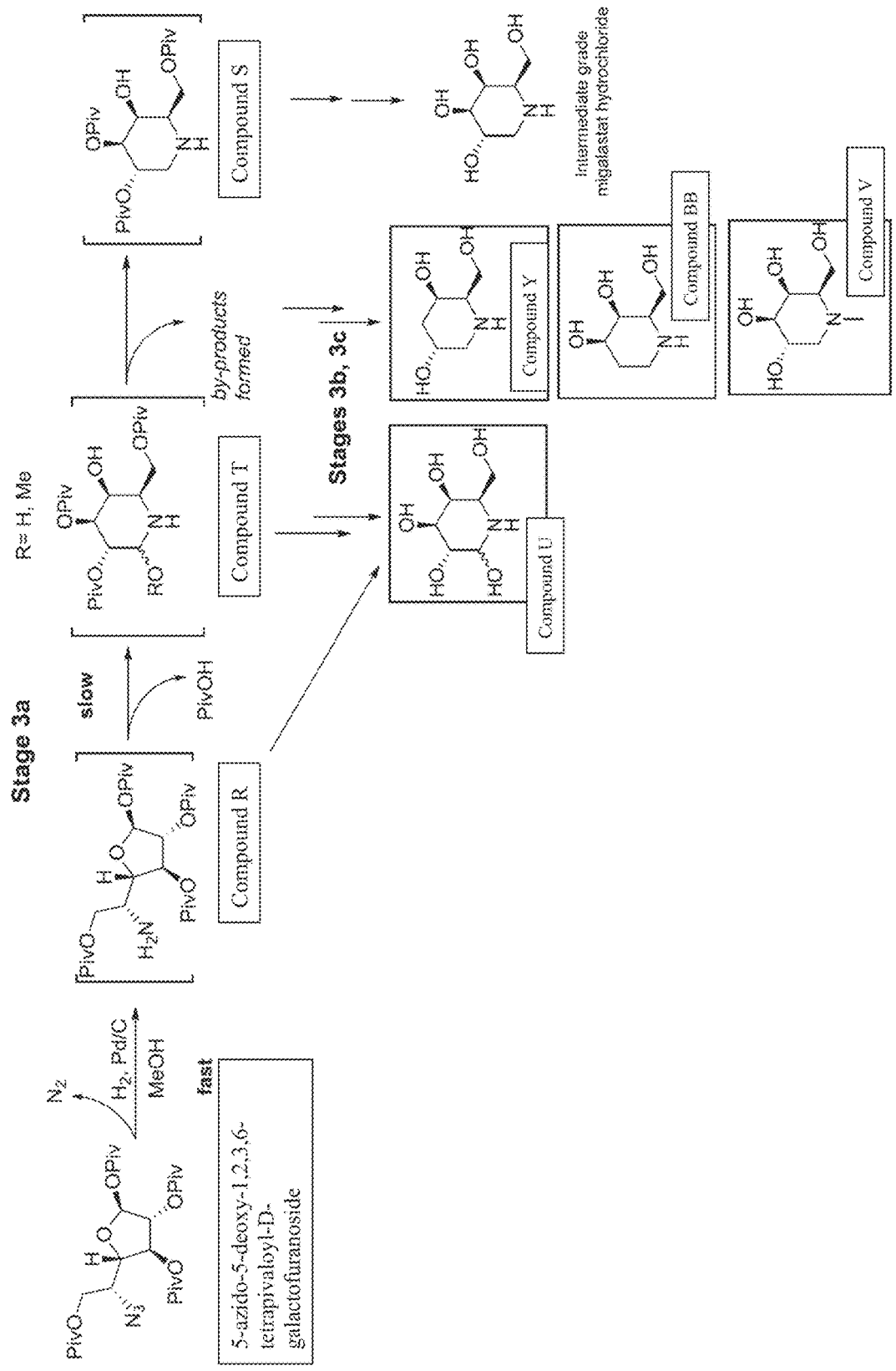
FIG. 9 depicts formation of impurities during Stage 3 of an exemplary migalastat hydrochloride synthesis scheme.

Stage 3 of migalastat hydrochloride production was performed as shown in FIG. 5. Impurities that are present following Stage 3 are shown in FIG. 6. Specific production steps or parameters associated with steps 3a, b, and/or c are shown in FIG. 7-9, which are discussed in greater detail below.

25-31 kg of 5-azido-5-deoxy-1,2,3,6-tetrapivaloyl-D-galactofuranoside was reduced using hydrogen and a palladium catalyst. Following a rearrangement and further hydrogenation, sodium methoxide was added to remove the pivaloyl groups. The product was treated with hydrochloric acid and isolated to give intermediate grade migalastat hydrochloride. Quantities are expressed relative to 5-azido-5-deoxy-1,2,3,6-tetrapivaloyl-D-galactofuranoside.

Stage 3a: 5-azido-5-deoxy-1,2,3,6-tetrapivaloyl-D-galactofuranoside (1 weight) and 10% palladium catalyst on carbon (0.007-0.013 molar equivalents of palladium) were stirred in methanol (5.54-7.13 weights) under a hydrogen atmosphere. The process was vented several times to release nitrogen, and hydrogen pressure was reapplied each time. After venting, the mixture was stirred at a temperature of 40-50° C. under a hydrogen pressure of 8-10 bar (absolute) for a time of not less than 44 hours. The reaction mixture was filtered to remove the catalyst.

Stage 3b: 30% Sodium methoxide solution in methanol (0.8-1.2 equivalents) was added to the solution of Compound S. The mixture was concentrated by distillation to about 0.5 weights (by volume marker) and 37% hydrochloric acid (2.9-3.2 volumes) was added at 20-45° C. before the mixture was aged at a temperature of 40-55° C. for not more than 10 hours to allow precipitation of the sodium chloride. The suspension was cooled to the filtration temperature of 25-40° C. and the sodium chloride was filtered.

Stage 3c: Ethanol was added over not less than 30 minutes. The intermediate grade migalastat hydrochloride was isolated at a temperature of not less than 15° C., washed with ethanol, and dried.

Various batches were produced in which production parameters were varied. It was shown that intermediate grade migalastat could be produced across the production parameter ranges set forth in Tables 7-8. The yield was 72%-92%.

TABLE 7

Summary of Stage 3 critical process parameters and associated ranges

| Stage | Process Parameter | Range | Units[1] |
|---|---|---|---|
| 3a | Palladium catalyst quantity | 0.007-0.013 | molar equiv |
|  | Time | 44-68 | hours |
|  | Temperature | 40-50 | ° C. |
|  | Hydrogen pressure | 8-10 | bar (abs) |
|  | Methanol amount | 5.54-7.13 | weights |
| 3b | Filtration temperature | 25-40 | ° C. |
|  | Residual weight after distillation | about 0.5 | weights (by volume marker) |
|  | Age time | NMT 10 | hours |
|  | Age temperature | 40-55 | ° C. |
| 3c | Time for ethanol addition | NLT 30 | minutes |
|  | Filtration Temperature | NLT 15 | ° C. |

NLT = Not less than;
NMT = Not more than;
[1]Weights expressed relative to 5-azido-5-deoxy-1,2,3,6-tetrapivaloyl-D-galactofuranoside

TABLE 8

Summary of other Stage 3 process parameters and associated ranges

| Stage | Process Parameter | Range | Units[1] |
|---|---|---|---|
| 3b | 30% Sodium methoxide quantity | 0.8-1.2 | molar equiv |
|  | 37% Hydrochloric acid quantity | 2.9-3.2 | volumes (by equivalent weights) |

[1]Weights expressed relative to 5-azido-5-deoxy-1,2,3,6-tetrapivaloyl-D-galactofuranoside Table 9 shows batch analysis data from batches of intermediate grade migalastat hydrochloride manufactured at a range of scales. These data demonstrate that the control of the CQAs in intermediate grade migalastat hydrochloride across a range of scales.

TABLE 9

Impurities Data from Stage 3 at Different Scales

| Attribute of Intermediate Grade Migalastat Hydrochloride[1] | CQA | Specification Limit in IG Migalastat HCl (% w/w) | 70 g batch | 08 kg batch | 31 kg batch 1[2] | 31 kg batch 2[2] |
|---|---|---|---|---|---|---|
| Compound W | Y | 0.15 | <0.05 | <0.05 | ND | ND |
| Compound U | Y | 0.4 | <0.05 | <0.05 | ND | ND |
| Compound AA | N | 0.15 | ND | ND | ND | ND |
| Compound Z | N | 0.25 | <0.05 | 0.07 | 0.08 | 0.05 |
| Any other impurity | N | 0.10 | ND | — | ND | ND |
| Total impurities | N | 1.5 | <0.05 | 0.07 | 0.08 | 0.05 |
| Compound V | Y | 0.40 | 0.13 | 0.08 | 0.21 | 0.07 |

TABLE 9-continued

Impurities Data from Stage 3 at Different Scales

| Attribute of Intermediate Grade Migalastat Hydrochloride[1] | CQA | Specification Limit in IG Migalastat HCl (% w/w) | Batch Numbers and Input Scale | | | |
|---|---|---|---|---|---|---|
| | | | 70 g batch | 08 kg batch | 31 kg batch 1[2] | 31 kg batch 2[2] |
| Compound Y | Y | 0.25 | ND | <0.05 | <0.05 | ND |
| Compound BB | Y | 0.4 | 0.25 | 0.25 | 0.17 | 0.18 |
| Compound X[3] | N | NA | — | — | 4.8 | 1.4 |

NA = Not applicable;
ND = Not detected;
[1]Drug-related impurity CQAs are highlighted in bold text;
[2]6 batches were produced at production scale; Batches have been selected to reflect the minimum and maximum levels for CQAs observed;
[3]Not included on the specification for intermediate grade migalastat hydrochloride.

Stage 4: Preparation of Pharmaceutical Grade Migalastat Hydrochloride

Figure 24:
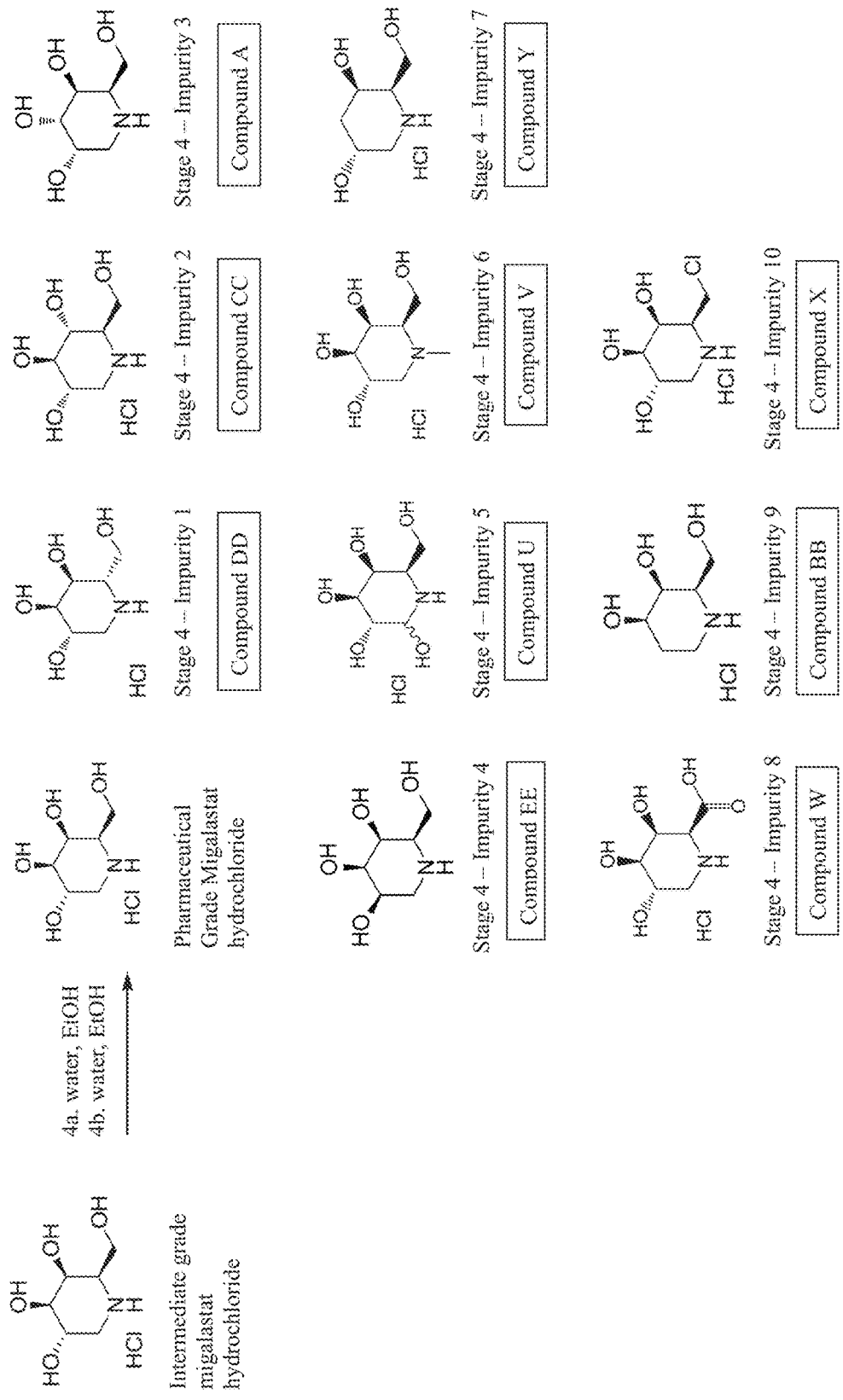
FIG. 24 depicts Stage 4 of an exemplary migalastat hydrochloride synthesis scheme, and shows impurities that can result from Stage 4.

Stage 4 of migalastat hydrochloride production was performed as shown in FIG. 24, which also shows potential impurities that are present following Stage 4. More particularly, intermediate grade migalastat hydrochloride was recrystallized twice from a mixture of water and ethanol to give migalastat hydrochloride.

For Stage 4a, quantities are expressed relative to intermediate grade migalastat hydrochloride. Stage 4a: 11.5-17.3 kg of intermediate grade migalastat hydrochloride (1 weight) was dissolved in water (1.1-1.4 weights). The temperature was adjusted to 40-60° C., ethanol (8.5-10.4 weights) was added, and the slurry or solution cooled to an isolation temperature of 5-35° C. The product was filtered, washed with ethanol (not less than 1 weight), and dried under vacuum at not more than 80° C.

For Stage 4b, quantities are expressed relative to the Stage 4a product. Stage 4b: The Stage 4a product (1 weight) was dissolved in water. The solution was clarified by filtration and water was added to give a total water quantity of (1.1-1.4 weights). The temperature was adjusted to 40-60° C. and ethanol 1 quantity (1.8-2.0 weights) added over not less than 5 minutes to induce crystallization. Following a hold-time of not less than 5 minutes, ethanol 2 quantity (6.8-8.4 weights) was added over not less than 20 minutes and the mixture was cooled to an isolation temperature of 5-35° C. The migalastat hydrochloride was filtered, washed with ethanol (not less than 1 weight), and dried under vacuum at not more than 80° C. (LOD<0.3%).

Various batches were produced in which production parameters were varied. It was shown that pharmaceutical grade migalastat hydrochloride could be produced across the production parameter ranges set forth in Tables 10-11. The yield was 56%-102%.

TABLE 10

Summary of Stage 4 critical process parameters and associated ranges

| Stage | Process Parameter | Range | Units[1] |
|---|---|---|---|
| 4a | Water quantity | 1.1-1.4 | weights |
| 4b | Total water quantity | 1.1-1.4 | weights |
| | Ethanol 1 quantity | 1.8-2.0 | weights |
| | Ethanol 1 addition time | NLT 5 | minutes |

TABLE 10-continued

Summary of Stage 4 critical process parameters and associated ranges

| Stage | Process Parameter | Range | Units[1] |
|---|---|---|---|
| | Hold time | NLT 5 | minutes |
| | Ethanol 1 addition temperature | 40-60 | ° C. |

NLT = Not less than;
[1]Weights expressed relative to input amounts for each Stage

TABLE 11

Summary of other Stage 4 process parameters and associated ranges

| Stage | Process Parameter | Range | Units[1] |
|---|---|---|---|
| 4a | Solution temperature | 40-60 | ° C. |
| | Ethanol quantity | 8.5-10.4 | weights |
| | Filtration temperature | 5-35 | ° C. |
| | Ethanol quantity (wash) | NLT 1 | weights |
| | Drying temperature | ≤80 | ° C. |
| 4b | Ethanol quantity 2 | 6.6-8.4 | weights |
| | Ethanol 2 addition time | NLT 20 | minutes |
| | Filtration temperature | 5-35 | ° C. |
| | Ethanol quantity (wash) | NLT 1 | weights |
| | Drying temperature | ≤80 | ° C. |

NLT = Not less than;
[1]Weights expressed relative to input amounts for each Stage Reprocessing of Intermediate Grade Migalastat Hydrochloride (Stage 3) and Migalastat Hydrochloride (Stage 4):

Stage 3 produces intermediate grade migalastat hydrochloride. Stage 4 recrystallization is a distinct purification process for the final drug substance migalastat hydrochloride. If intermediate grade migalastat hydrochloride does not conform to Stage 3 specifications, it may be processed through the Stage 4a or Stage 4b recrystallization process. The isolated product can be analyzed against both the intermediate grade migalastat hydrochloride and migalastat hydrochloride (API) specifications. The final recrystallization may not have to be repeated if the isolated product from the recrystallization meets the migalastat hydrochloride specification.

If migalastat hydrochloride does not conform to the migalastat hydrochloride specifications, it may be recrystallized by performing the Stage 4b recrystallization process.

Heel of migalastat hydrochloride recovered from the filter drier may be collected in Stage 4a or 4b and reprocessed using the Stage 4b process for the recrystallization of migalastat hydrochloride.

Example 3: Commercial Manufacturing Procedures

Figure 26:
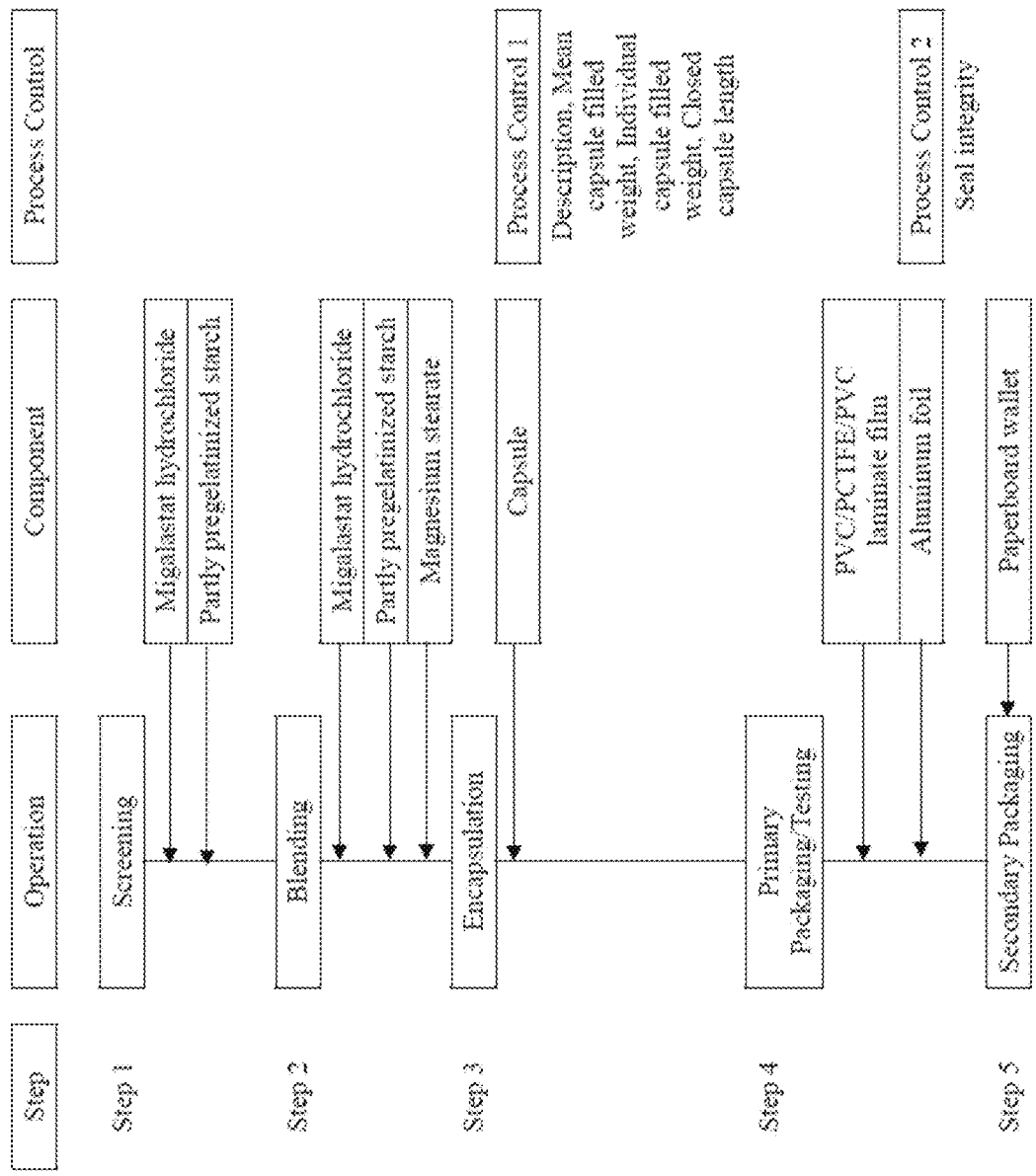
FIG. 26 depicts a flow diagram showing exemplary process controls that can be used for commercial production of migalastat hydrochloride.

FIG. 26 sets forth a flow diagram identifying process controls in place for each unit operation of a commercial process. The controls are a combination of manufacturing operating parameters and in-process control tests. The typical time of manufacture for the drug product is one day for screening and blending of encapsulation blend and two days for encapsulation. Hold time of filled capsules prior to packaging is up to 30 days.

Step 1—Screening

Migalastat hydrochloride and pregelatinized starch were screened using a rotating impeller screening mill (Comil), through a 457 micron screen.

Step 2—Blending of Encapsulation Mix (Pre-lubrication and Lubrication)

Manufacture of the encapsulation mix involved two blending processes, pre-lubrication and lubrication blending.

Pre-lubrication: 4590 g of migalastat hydrochloride and 1380 g of pregelatinized starch were blended using a suitable diffusion mixer, such as 100-300 revolutions, for example 5 to 15 minutes at a speed of 20 rpm.

Lubrication: 30 g of magnesium stearate was added to the pre-lubrication mix and blended for typically 60 revolutions, for example 3 minutes at 20 rpm using a suitable diffusion mixer.

Step 3—Encapsulation

The blend obtained at Step 2 was encapsulated using a suitable encapsulation machine to the target capsule fill weight of 196 mg. In-process control tests for filled capsule weight (individual and mean), closed capsule length, and description were applied at regular intervals throughout the encapsulation run.

Step 4—Primary Packaging and Testing

The capsules from Step 3 were filled into polyvinyl chloride (PVC)/polychlorotrifluoroethylene (PCTFE)/PVC laminate film with aluminum foil lidding blister packs using suitable automated blister packaging equipment. A seal integrity test was performed at the start of packaging and at appropriate intervals for the duration of the packaging process.

Reprocessing Operations

Capsules from blisters failing the seal integrity test may be reprocessed in Step 4.

Example 4: Controlling Stage 1 Impurities

Spiking and purging studies were conducted to determine the maximum tolerated dose of impurities in D-(+)-galactose that could be used to produce 5-azido-5-deoxy-1,2,3,6-tetrapivaloyl-D-galactofuranoside with acceptable levels of purity for producing migalastat hydrochloride. Based on these studies, the specification for D-(+)-galactose was set to total impurities of less than 2% w/w. The tolerable levels of impurities are set forth in Table 12.

TABLE 12

Impurity standards used for setting specification limits in D-(+)-galactose

| Impurity | Maximum Demonstrated Tolerance (% area)[1] | Observed Levels in D-(+)-galactose Batches n = 2 (% area) | Proposed Specification Limit (% area) |
|---|---|---|---|
| 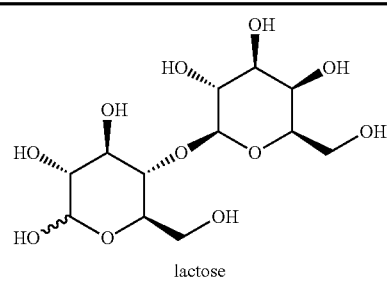 lactose | 4 | <0.1 | 2[2] |
| Largest unidentified disaccharide impurity | 2 | 0.5%-0.66% | 2[2] |
| 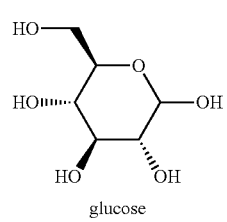 glucose | 4 | <0.1 | 2[2] |

TABLE 12-continued

Impurity standards used for setting specification limits in D-(+)-galactose

| Impurity | Maximum Demonstrated Tolerance (% area)[1] | Observed Levels in D-(+)-galactose Batches n = 2 (% area) | Proposed Specification Limit (% area) |
|---|---|---|---|
| glycerol 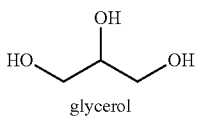 | 3 | <0.1 | 2[2] |
| lactic acid 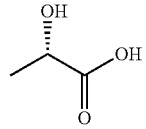 | 2 | <0.1 | 2[2] |

[1]From spiking and purging studies, it was shown that the 5-azido-5-deoxy-1,2,3,6-tetrapivaloyl-D-galactofuranoside specification will be met when the impurity is present in D-(+)-galactose at this level;
[2]Controlled under the specification limit for total impurities.

Impurity standards used in the spiking and purging studies are set forth in Table 13.

TABLE 13

Impurity standards used for setting specification limits in D-(+)-galactose

| Impurity | Brief description of impurity standard origin and quality |
|---|---|
| lactose 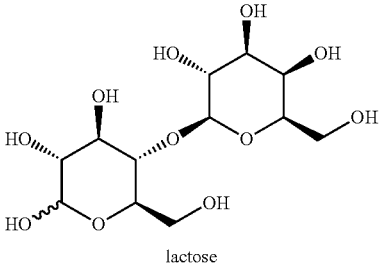 [SMILES: OC[C@H]1O[C@@H](O[C@H]2[C@H](O)[C@@H](O)C(O)O[C@@H]2CO)[C@H](O)[C@@H](O)[C@H]1O] | Commercial material, >98% purity |
| Largest unidentified disaccharide impurity | Commercial disaccharide material, >98% purity |
| glucose 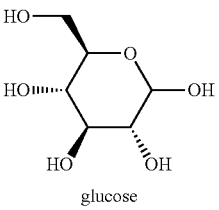 [SMILES: OC[C@H]1OC(O)[C@H](O)[C@@H](O)[C@@H]1O] | Commercial material, >98% purity |

TABLE 13-continued

Impurity standards used for setting specification limits in D-(+)-galactose

| Impurity | Brief description of impurity standard origin and quality |
|---|---|
| glycerol 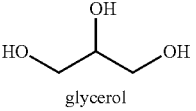 | Commercial material, >98% purity |
| lactic acid 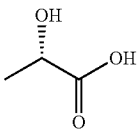 | Commercial material, >98% purity |

Example 5: Controlling Stage 2 Impurities

Spiking and purging studies were conducted to determine the maximum tolerated dose of impurities in 1,2,3,6-tetrapivaloyl-D-galactofuranoside that could be used to produce 5-azido-5-deoxy-1,2,3,6-tetrapivaloyl-D-galactofuranoside with acceptable levels of purity for producing migalastat hydrochloride. Based on these studies, it was determined that Compound B was present in 1,2,3,6-tetrapivaloyl-D-galactofuranoside at greater than 1% area. Compound B is an intermediate in the conversion of D-(+)-galactose to 1,2,3,6-tetrapivaloyl-D-galactofuranoside.

The studies showed that the tolerable levels of this impurity that are set forth in Table 14.

TABLE 14

Data Used for Setting Impurity Specification Limits in 1,2,3,6-tetrapivaloyl-D-galactofuranoside

| Impurity | Maximum Demonstrated Tolerance (% area)[1] | Observed Levels in 1,2,3,6-tetrapivaloyl-D-galactofuranoside Batches n = 14 (% area) | Proposed Specification Limit (% area) |
|---|---|---|---|
| 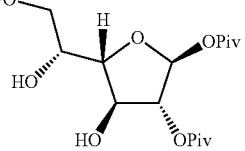 | 2.9 | 1.5-2.5 | 3 |

[1]From spiking and purging studies, it was shown that the 5-azido-5-deoxy-1,2,3,6-tetrapivaloyl-D-galactofuranoside specification will be met when the impurity is present in 1,2,3,6-tetrapivaloyl-D-galactofuranoside at this level.

Impurity standards used in the spiking and purging studies are set forth in Table 15.

TABLE 15

Impurity standards used for setting specification limits in 1,2,3,6-tetrapivaloyl-D-galactofuranoside

| Impurity | Brief description of impurity standard origin and quality |
|---|---|
| 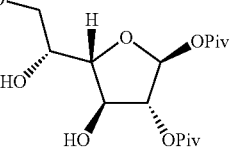 | Synthesized and purified by preparatory chromatography. High performance liquid chromatography (HPLC) purity 92.8% w/w. |

Example 6: Controlling Intermediate Grade Migalastat Hydrochloride Impurities Maximum acceptable levels of each of the impurities potentially present in 5-azido-5-deoxy-1,2,3,6-tetrapivaloyl-D-galactofuranoside were determined by including the impurities in the Stage 3 input at various levels. To demonstrate the purging of Compound J, the impurities Compound G and Compound E were each spiked into Stage 3 at 3% w/w. Compound I and Compound K are both transformed into Compound H in Stage 3a; hence, in order to show that the specification limits of 0.6% and 0.3%, respectively, are acceptable, 0.9% of Compound I was spiked into Stage 3.

Batches of the intermediate grade migalastat hydrochloride produced from 5-azido-5-deoxy-1,2,3,6-tetrapivaloyl-D-galactofuranoside were analyzed against the intermediate grade migalastat hydrochloride specification. Based on these studies, the tolerable doses of impurities set forth in Table 16 were determined.

TABLE 16

Data used for setting impurity specification limits in 5-azido-5-deoxy-1,2,3,6-tetrapivaloyl-D-galactofuranoside

| Impurity | Maximum Demonstrated Tolerance (% w/w)[1] | Observed Levels in 5-azido-5-deoxy-1,2,3,6-tetrapivaloyl-D-galactofuranoside Batches n = 6 (% area) | Proposed Specification Limit (% area) |
|---|---|---|---|
| 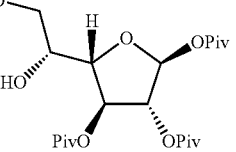 | 2.6 | 0.16-0.36 | 0.6 |
| 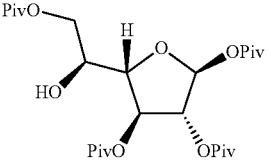 | 1.3 | ND-0.06 | 0.3[2] |

TABLE 16-continued
Data used for setting impurity specification limits in 5-azido-5-deoxy-1,2,3,6-tetrapivaloyl-D-galactofuranoside
| Impurity | Maximum Demonstrated Tolerance (% w/w)[1] | Observed Levels in 5-azido-5-deoxy-1,2,3,6-tetrapivaloyl-D-galactofuranoside Batches n = 6 (% area) | Proposed Specification Limit (% area) |
|---|---|---|---|
| 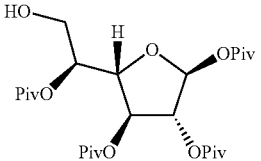 | 1.3 | ND-0.03 | 0.3[2] |
| 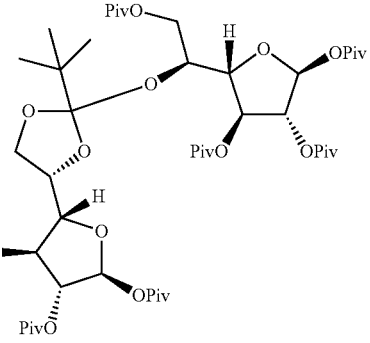 | | 0.86-1.67 | 3.0 |
| 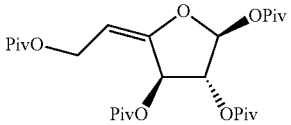 | 0.9% area | ND-0.35 | 0.6 |
| 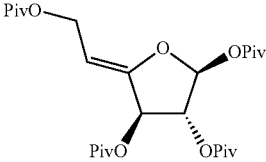 | | 0.08-0.11 | 0.3[2] |
| 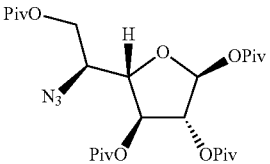 | 1.0 | 0.06-0.28 | 1.0 |

TABLE 16-continued

Data used for setting impurity specification limits in 5-azido-5-deoxy-1,2,3,6-tetrapivaloyl-D-galactofuranoside

| Impurity | Maximum Demonstrated Tolerance (% w/w)[1] | Observed Levels in 5-azido-5-deoxy-1,2,3,6-tetrapivaloyl-D-galactofuranoside Batches n = 6 (% area) | Proposed Specification Limit (% area) |
|---|---|---|---|
| 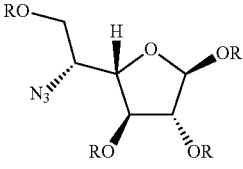 R = 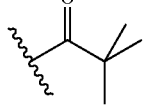 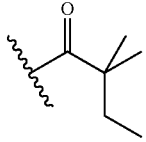 3:1 | NA[3] | 0.12-0.17 | 0.3[2] |

NA = Not applicable;
ND = Not detected, limit of quantitation 0.05% area;
[1]Spiking and purging studies showed that the intermediate grade migalastat hydrochloride specification will be met when the impurity is present in 5-azido-5-deoxy-1,2,3,6-tetrapivaloyl-D-galactofuranoside at this level;
[2]Controlled by the specification limit for any unspecified impurity;
[3]This impurity is converted to migalastat hydrochloride in Stage 3.

The structure of impurities related to those in Table 16 are shown below in Table 17.

TABLE 17

Data used for setting impurity specification limits in 5-azido-5-deoxy-1,2,3,6-tetrapivaloyl-D-galactofuranoside

| Impurity | Structure of Potential Related Impurities Following Stage 3a | Structure of Potential Related Impurities Following Stages 3b and 3c |
|---|---|---|
| 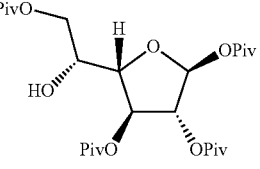 | 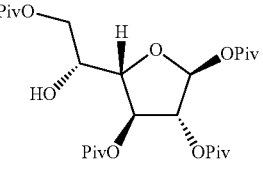 No reaction in Stage 3a | 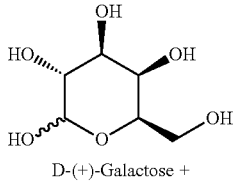 D-(+)-Galactose + By-products of basic and acid decomposition |
| 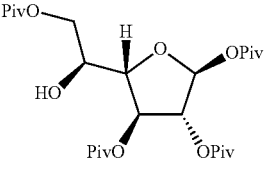 | 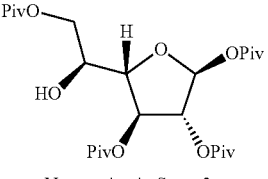 No reaction in Stage 3a | 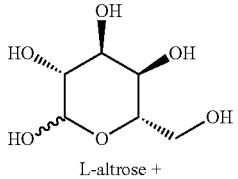 L-altrose + By-products of basic and acid decomposition |

TABLE 17-continued

Data used for setting impurity specification limits in 5-azido-5-deoxy-1,2,3,6-tetrapivaloyl-D-galactofuranoside

| Impurity | Structure of Potential Related Impurities Following Stage 3a | Structure of Potential Related Impurities Following Stages 3b and 3c |
|---|---|---|
| [structure] | [structure] No reaction in Stage 3a | |
| [structure] | [structure] No reaction in Stage 3a | L-altrose + By-products of basic and acid decomposition |
| [structure] | [structure] | By-products of basic and acid decomposition |
| [structure] | [structure] | [structure] · HCl |

TABLE 17-continued

Data used for setting impurity specification limits in 5-azido-5-deoxy-1,2,3,6-tetrapivaloyl-D-galactofuranoside

| Impurity | Structure of Potential Related Impurities Following Stage 3a | Structure of Potential Related Impurities Following Stages 3b and 3c |
|---|---|---|
| 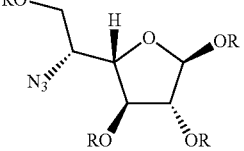 | 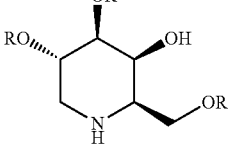 | Intermediate grade migalastat hydrochloride |

Impurity standards used in the spiking and purging studies are set forth in Table 18.

TABLE 18

Impurity standards used for setting specification limits in 5-azido-5-deoxy-1,2,3,6-tetrapivaloyl-D-galactofuranoside

| Impurity | Brief description of impurity standard origin and quality |
|---|---|
| 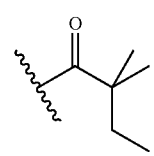 | 1,2,3,6-tetrapivaloyl-D-galactofuranoside is Stage 1 intermediate of the migalastat hydrochloride synthesis and was synthesized from D-(+)-galactose with a >93% w/w purity. |
| 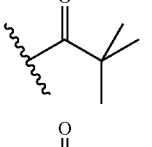 | Compound E is a known intermediate during Stage 2 and it is not isolated during migalastat hydrochloride synthesis. It was prepared from 1,2,3,6-tetrapivaloyl-D-galactofuranoside and purified by silica gel chromatography with a 98% w/w purity. |
| 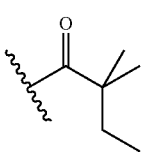 | Compound G is synthesized from 1,2,3,6-tetrapivaloyl-D-galactofuranoside and purified by silica gel chromatography with a 94% area purity. |

TABLE 18-continued

Impurity standards used for setting specification limits in 5-azido-5-deoxy-1,2,3,6-tetrapivaloyl-D-galactofuranoside

| Impurity | Brief description of impurity standard origin and quality |
|---|---|
| (structure) | Compound J was isolated by a preparatory HPLC from a Stage 2 batch. HPLC purity 93%. |
| (structure) | Compound I was synthesized from the triflate Compound D and was recrystallized from heptane. The structure was established by nuclear magnetic resonance (NMR) and mass spectrum (MS) spectroscopy and its purity was determined to be 98% by HPLC. |
| (structure) | Compound K was synthesized from the triflate Compound F and was purified by silica chromatography. Its structure was confirmed by NMR and MS spectroscopy. |
| (structure) | Compound N was synthesized from the epi-triflate Compound F and purified by silica gel chromatography with a 97% purity. |
| (structure), R = (structure), 3:1 | The impurity reference standard was generated by performing preparatory HPLC method on a Stage 2 batch. The fraction corresponding to the desired peak was separated and isolated by the solvent removal. The material was confirmed by NMR and MS spectroscopy. |

Example 7: Controlling Pharmaceutical Grade Migalastat Hydrochloride Impurities

Acceptable levels of impurities in intermediate grade migalastat hydrochloride were determined by spiking various impurities into Stage 4. Based on these studies, the tolerable doses of impurities set forth in Table 19 were determined. Notably, Compound U, Compound V, Compound Y, Compound W, and Compound BB were determined to impact or be linked to pharmaceutical grade migalastat hydrochloride critical quality attributes associated with drug quality.

TABLE 19

Data Used for Setting Impurity Specification Limits in Intermediate Grade Migalastat Hydrochloride

| Impurity | Maximum Demonstrated Tolerance (% w/w)[1] | Typical Levels in IG Migalastat HCl (% w/w) | Proposed Specification Limit (% w/w) |
|---|---|---|---|
| 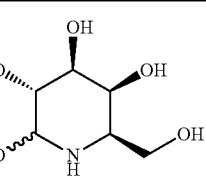 | 0.67 | ND | 0.4 |
| 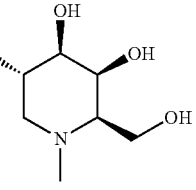 | 0.42 | ND-0.13[2] | 0.40 |
| 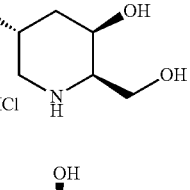 | 0.41 | ND-0.1 | 0.25 |
| 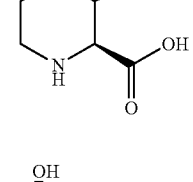 | 0.15 | ND-0.04 | 0.15 |
| 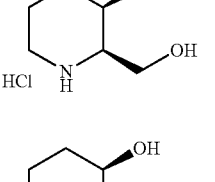 | 0.39 | ND-0.15 | 0.3 |
| 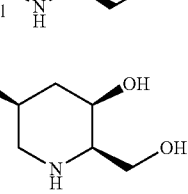 | 0.4 | ND-0.44 | 0.25 |
| 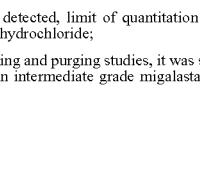 | 0.41 | ND-0.09 | 0.15 |

ND = Not detected, limit of quantitation 0.05% w/w; impurities will be present as the HCl salt in intermediate grade migalastat hydrochloride;

[1]From spiking and purging studies, it was shown that migalastat hydrochloride specification will be met when the impurity is present in intermediate grade migalastat hydrochloride at this level after a single Stage 4a recrystallization;

Impurity standards used in the above-mentioned studies are set forth in Table 20.

TABLE 20

Impurity standards used for setting specification limits in intermediate grade migalastat hydrochloride

| Impurity | Brief description of impurity standard origin and quality |
|---|---|
| 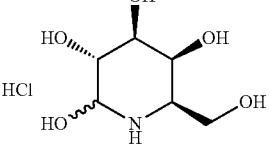 | Stage 2 intermediate 5-azido-5-deoxy-1,2,3,6-tetrapivaloyl-D-galactofuranoside was hydrogenated and then treated with sodium methoxide. The reaction mixture was chromatographed on a silica gel column. The structure of Compound U was determined by NMR spectroscopy. |
| 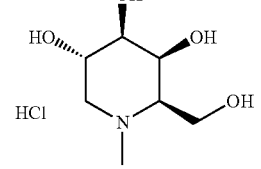 | Compound V was prepared by hydrogenation between migalastat hydrochloride and formaldehyde. The crude was chromatographed on a silica gel column with 97% HPLC purity. The structure was confirmed by NMR spectroscopy. |
| 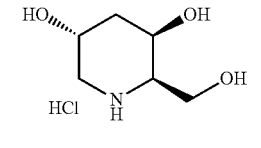 | Compound Y was isolated by a preparative hydrophilic interaction liquid chromatography (HILIC) from the filtrate obtained after recrystallizing of a Stage 3 batch. The structure was confirmed by NMR and MS spectroscopy. |
| 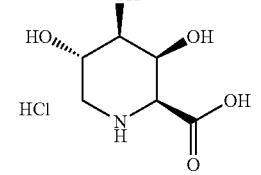 | Compound W was prepared by hydrogenating migalastat hydrochloride in the presence of sodium methoxide. The isolated crude was recrystallized to obtain 89% pure material. The structure was confirmed by NMR spectroscopy. |
| 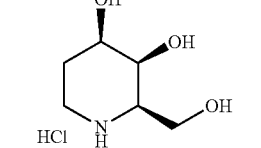 | Compound BB was isolated by a preparative HILIC chromatography from the filtrate obtained after recrystallizing of a Stage 3 batch. The structure was confirmed by NMR and MS spectroscopy. |
| 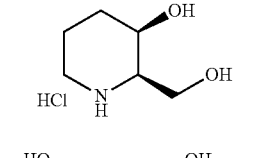 | Compound Z was isolated by a preparative HILIC chromatography from the filtrate obtained after recrystallizing a Stage 3 batch. The structure was confirmed by NMR and MS spectroscopy. |
| 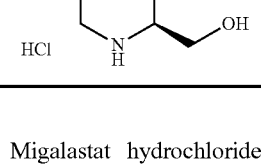 | Compound AA was isolated by a preparative HILIC chromatography from the filtrate obtained after recrystallizing a Stage 3 batch. The structure was confirmed by NMR and MS spectroscopy. |

Migalastat hydrochloride contains four stereocenters, which raise the possibility of impurities related to epimerization. Levels of four epimers were measured in batches of intermediate grade migalastat hydrochloride manufactured at the commercial scale, and the levels were less than 0.1% w/w in all batches.

Compound A, Compound EE, and Compound DD were spiked into the intermediate grade migalastat hydrochloride input to the Stage 4b recrystallization. Levels of each impurity were confirmed to be below 0.1% w/w in the migalastat hydrochloride produced.

Compound CC was spiked at 1.2% w/w into intermediate grade migalastat hydrochloride. It was found that after a single Stage 4b recrystallization, 0.7% w/w was present in the migalastat hydrochloride. Hence, assuming a consistent purge, it has been demonstrated that controlling Compound CC 0.2% w/w in intermediate grade migalastat hydrochloride will yield Compound CC at less than 0.10% w/w in the drug substance.

In view of the above, tolerable levels of diasteroisomeric impurities were determined, as set forth in Table 21.

TABLE 21

Potential Diastereoisomeric Impurities in Intermediate Grade Migalastat Hydrochloride

| Impurity | Maximum Demonstrated Tolerance[1] (% area) | Observed Levels in IG Migalastat HCl Batches n = 6 (% area) |
|---|---|---|
| 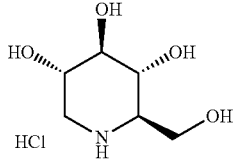 [SMILES: OC[C@H]1NC[C@H](O)[C@@H](O)[C@@H]1O ; Cl] | 0.2 | <0.1 |
| 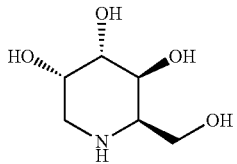 [SMILES: OC[C@H]1NC[C@H](O)[C@H](O)[C@H]1O] | 1.4 | <0.1 |
| 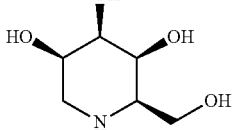 | 0.6 | <0.1 |
| 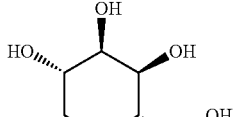 | 4.1 | <0.1 |

[1]From spiking and purging studies, it was shown that migalastat hydrochloride specification will be met when the impurity is present in intermediate grade migalastat hydrochloride at this level.

Impurity standards used to evaluate diastereomer impurities are set forth in Table 22.

TABLE 22

Impurity standards used for potential diastereomer impurities in intermediate grade migalastat hydrochloride

| Impurity | Brief description of impurity standard preparation and quality |
|---|---|
| 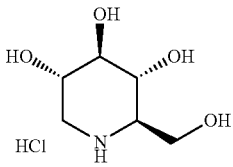 [SMILES: OC[C@H]1NC[C@H](O)[C@@H](O)[C@@H]1O ; Cl] | Compound CC was purchased from Ontario Chemicals Inc. and its Certificate of Analysis (CoA) confirmed that it is 98.3% w/w pure. |
| 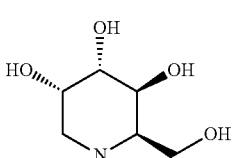 | Compound A was synthesized in six steps based on a literature procedure (Organic Letters 2003, Vol 5, No 14, 2527-2529). The diastereoisomer structure was confirmed by NMR spectroscopy and purity was determined to be 96.2% purity. |
| 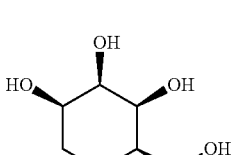 | Compound EE was synthesized following ten step literature procedure (Carbohydrate Research, 2002, 337, 1083-1087). |
| 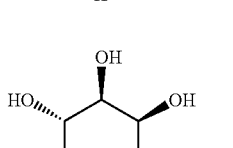 | Compound DD was synthesized using the Stage 2 epimeric azide impurity Compound N. The diastereoisomer structure was confirmed by NMR spectroscopy and purity was determined to be 95% by HPLC. |

Example 8: Control of Genotoxins in Migalastat Hydrochloride

The starting materials, reagents, intermediates, and process impurities generated in the manufacturing process for migalastat hydrochloride were assessed for their potential genotoxicity using in silico (Derek for Windows v13 Lhasa Ltd) screening software. The chemical structures which were DEREK negative were evaluated using Leadscope (Model Applier and Expert Alerts). Materials that were identified through this process that could potentially be genotoxic are set forth below in Table 23. Where possible, the genotoxicity of these materials was then assessed via the use of the bacterial reverse mutation (Ames) test.

TABLE 23

Summary of genotoxic/potentially genotoxic impurities in migalastat hydrochloride

| Potential Genotoxin | Origin | Derek Positive? | Ames Positive? | Designated Genotoxin? |
|---|---|---|---|---|
| [structure: TiO, OPiv, PivO, OPiv, OPiv] | Non-isolated intermediate in Stage 2 | Yes | Insufficiently stable for Ames test | Yes |
| [structure: TiO, OPiv, PivO, OPiv, OPiv] | | Yes | Insufficiently stable for Ames test | Yes |
| [structure: N$_3$, OPiv, PivO, OPiv, OPiv] | Intermediate from Stage 2 | Yes | No | No |
| [structure: N$_3$, OPiv, PivO, OPiv, OPiv] | Potential impurity formed in Stage 2 | Yes | No | No |
| [structure: N$_3$, OH, HO, OH, OH] | Potentially formed from unreacted 5-azido-5-deoxy-1,2,3,6-tetrapivaloyl-D-galactofuranoside in Stage 3 | Yes | Yes | Yes |
| [structure: N$_3$, OH, HO, OH, OH] | | Yes | Yes | Yes |

TABLE 23-continued

Summary of genotoxic/potentially genotoxic impurities in migalastat hydrochloride

| Potential Genotoxin | Origin | Derek Positive? | Ames Positive? | Designated Genotoxin? |
|---|---|---|---|---|
| 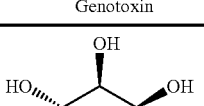 | Impurity formed in Stage 3 | Yes | Yes | Yes |
| Ethyl chloride | Potentially formed in Stages 3 and 4 | Yes | Yes | Yes |
| Methyl chloride | | Yes | Yes | No |

Compound Q, Compound P, and Compound X were confirmed as genotoxins (Ames positive). Compound D and Compound F were not sufficiently stable for Ames testing and, therefore, were also designated as genotoxins. Impurities designated as genotoxins were screened—for using limit tests in suitable intermediates or migalastat hydrochloride drug substance itself. All the designated genotoxins were demonstrated to be below the TTC. Furthermore, confirmatory spiking experiments were completed for each of the designated genotoxins, except for Compound D and Compound F, to demonstrate that the commercial manufacturing process efficiently purges these impurities.

Compound D is transformed in Stage 2 to Compound F. Thus, levels of Compound F were monitored in batches of 5-azido-5-deoxy-1,2,3,6-tetrapivaloyl-D-galactofuranoside manufactured at production scale. In 15 batches of 5-azido-5-deoxy-1,2,3,6-tetrapivaloyl-D-galactofuranoside, Compound F was shown to be not greater than 12 mcg/g.

Levels of Compound Q and Compound P were monitored in batches of intermediate grade migalastat hydrochloride manufactured at production scale. In 11 batches of intermediate grade migalastat hydrochloride, Compound Q and Compound P were each shown to be not greater than 1.0 mcg/g.

Compound X tested positive in a bacterial reverse mutation (Ames) test. Compound X is formed from migalastat hydrochloride in Stage 3b under the harsh process conditions of heating with concentrated hydrochloride acid in the presence of sodium chloride. Levels of up to 5 mcg/g have been detected in batches of intermediate grade migalastat manufactured at production scale. Fourteen batches of intermediate grade migalastat hydrochloride drug substance were tested for levels of Compound X. 12 batches of migalastat hydrochloride drug substance derived from these 14 batches were also tested for Compound X. The results of these tests are shown in Table 24.

TABLE 24

Summary of the Test Results for Compound X in Intermediate Grade Migalastat Hydrochloride and the Corresponding Migalastat Hydrochloride Drug Substance

| Intermediate Grade Migalastat Hydrochloride | | Subsequent Migalastat Hydrochloride | |
|---|---|---|---|
| Batch | Compound X (mcg/g) | Batch | Compound X (mcg/g) |
| 1 | NGT 12[1] | A | NGT 1.0 |
| 2 | NGT 12[1] | | |
| 3 | NGT 12[1] | B | 1.4 |
| 4[2] | NGT 12[1] | C | NGT 1.0 |
| 5 | NGT 12[1] | D | NGT 1.0 |
| 6 | NGT 12[1] | E | NGT 1.0 |
| | | F | NGT 1.0[3] |
| 7 | NGT 12[1] | G | NGT 1.0[3] |
| 8 | NGT 1.0 | H | NGT 1.0 |
| 9 | NGT 2.2 | I | NGT 1.0[4] |
| 10 | 4.8 | | |
| | | J | NGT 1.0[4] |
| 11 | NGT 2.2 | | |
| 12 | 2.2 | K | NGT 1.0[4] |
| 13 | NGT 2.2 | | |
| | | L | NGT 1.0[4] |
| 14 | NGT 2.2 | | |

NGT = Not greater than;

[1]Data generated using a developmental method run as a limit test at 12 mcg/g;

[2]Material was reprocessed;

[3]Data generated on output from Stage 4a Batches F and G;

[4]Analysis run as a 4.0 mcg/g limit test with adequate sensitivity at 1 mcg/g demonstrated.

The tests demonstrated that levels of Compound X in drug substance are not greater than 2 mcg/g for all batches tested. Based on the Threshold of Toxicological Concern (TTC) of less than 1.5 mcg/day for the migalastat therapeutic dose of 123 mg/day, the control limit for Compound X is 12 mcg/g.

Analytical procedures used to determine various genotoxic impurities are set forth in Table 25.

TABLE 25

Summary of Analytical Procedures and Validation Data for Genotoxic Impurities

| Impurity | Origin | Material Tested | Analytical Technique | Method Summary | Method Validation Summary |
|---|---|---|---|---|---|
| Compound F | Non-isolated intermediate in Stage 2 | 5-azido-5-deoxy-1,2,3,6-tetrapivaloyl-D-galactofuranoside | NMR | Compound F Limit Test by $^{19}$F NMR Spectroscopy | Specificity: No significant interferences from blank or sample peaks Detection Limit of 12 µg/g with acceptable signal-to-noise ratio for standard Accuracy: Acceptable recovery (>95%) |
| Compound Q | Potentially formed from unreacted 5-azido-5-deoxy-1,2,3,6-tetrapivaloyl-D-galactofuranoside in Stage 3 | IG migalastat hydrochloride and migalastat hydrochloride drug substance | LC-MS | Gradient reversed-phase HPLC using Hypercarb column with MS SIM detection at 204 Da | Specificity: No significant interferences from blank or sample peaks Accuracy: Acceptable recovery (>95%) Signal-to-noise ratio for standard at 1.0 µg/g > 10 |
| Compound P | | | | | |
| Compound X | Impurity formed in Stage 3 | IG migalastat hydrochloride and migalastat hydrochloride drug substance | LC-MS-MS | Compound X Limit Test by HPLC-MS-MS | Compound X Limit Test by HPLC-MS-MS |

Example 9: Identification of Important Parameters—Stage 2

Parameters impacting the quality of the final drug product were evaluated through experimentation and consideration of batch data to determine critical process parameters and identify parameter ranges.

A series of univariate and multivariate experiments were performed to identify ranges for parameters in the Stage 2 chemical reactions. The development of these ranges focused on ensuring that conversion to each intermediate was appropriate and that the yield of 5-azido-5-deoxy-1,2,3,6-tetrapivaloyl-D-galactofuranoside was consistent.

In addition, residual DMSO in 5-azido-5-deoxy-1,2,3,6-tetrapivaloyl-D-galactofuranoside was identified as impacting the formation of Compound Y in Stage 3a by acting as a poison for the palladium on carbon catalyst. A series of spiking experiments were performed to confirm that the level of DMSO in 5-azido-5-deoxy-1,2,3,6-tetrapivaloyl-D-galactofuranoside is related to levels of Compound Y. Data (not shown) demonstrate that higher levels of DMSO in 5-azido-5-deoxy-1,2,3,6-tetrapivaloyl-D-galactofuranoside will lead to higher levels of Compound Y in migalastat hydrochloride. For this reason, the level of DMSO present in isolated 5-azido-5-deoxy-1,2,3,6-tetrapivaloyl-D-galactofuranoside was controlled to below 0.01% w/w in 5-azido-5-deoxy-1,2,3,6-tetrapivaloyl-D-galactofuranoside.

Conditions impacting the removal of DMSO from the isolated 5-azido-5-deoxy-1,2,3,6-tetrapivaloyl-D-galactofuranoside were investigated. For example, in a multifactorial experiment, summarized in Table 26, the effectiveness of the methanol wash at removing the DMSO from the 5-azido-5-deoxy-1,2,3,6-tetrapivaloyl-D-galactofuranoside filter cake was investigated. In this experiment, after washing the 5-azido-5-deoxy-1,2,3,6-tetrapivaloyl-D-galactofuranoside was dried under vacuum.

TABLE 26

Parameters studied in the Stage 2 washing study

| Parameter | Range Studied | Output Studied |
|---|---|---|
| Wash temperature | −10-10° C. | Levels of DMSO in 5-azido-5-deoxy-1,2,3,6-tetrapivaloyl-D-galactofuranoside |
| Methanol volumes | 1-3 volumes | |
| Wash time | 5-15 minutes | |

Levels of DMSO were controlled to below the specification limit 0.01% w/w in the 5-azido-5-deoxy-1,2,3,6-tetrapivaloyl-D-galactofuranoside produced in each of the experiments. In addition, the 5-azido-5-deoxy-1,2,3,6-tetrapivaloyl-D-galactofuranoside produced was converted to intermediate grade migalastat hydrochloride in each and consistent quality was observed in the quality of the material produced. Thus, the combination of the methanol wash and subsequent drying resulted in sufficient control of the DMSO.

Example 10: Identification of Critical Process Parameters—Stage 3a

Parameters impacting critical quality attributes were evaluated through experimentation and consideration of batch data to determine critical process parameters and identify parameter ranges.

Control of Compound W

It was established that there was a potential risk of formation of increased levels of the critical quality attribute (CQA) Compound W through oxidation in the presence of the palladium on carbon catalyst (FIG. 7). Compound W does not purge in the Stage 4 recrystallization. An alteration in the order of the unit operations in Stage 3a was implemented to mitigate this risk and improve control of Compound W. Earlier filtration of the palladium on carbon catalyst suppresses formation of Compound W and this modification was therefore introduced into the commercial process to provide additional process robustness. FIG. 8 illustrates the commercial process with the catalyst removed at the end of Stage 3a. This is exemplified by the data summarized in Table 27, which shows levels of Compound W from a direct comparison experiment. Compound W was present at 0.6% area in intermediate grade migalastat hydrochloride following manufacture via the process in which the palladium catalyst is present at Stage 3b. In contrast, Compound W was not detected in intermediate grade migalastat hydrochloride produced via the process in which the palladium catalyst is removed before Stage 3b.

TABLE 27

Levels of Compound W in Intermediate Grade Migalastat Hydrochloride Produced via Laboratory Scale Clinical/Stability and Commercial Processes

| Process | Compound W (% w/w) |
| --- | --- |
| Pd catalyst present in Stage 3b | 0.62 |
| Pd catalyst removed before Stage 3b | None detected |

Control of Compound U, Compound V, Compound BB, and Compound Y

In Stage 3a, Compound U is formed as a result of incomplete reduction of the intermediate Compound T (see FIG. 9). Compound Y, Compound BB, and Compound V are formed from by-products of Stage 3a.

In Stage 3a, 5-azido-5-deoxy-1,2,3,6-tetrapivaloyl-D-galactofuranoside is reduced quickly to the first intermediate Compound R. Compound R is then transformed in a slower process via Compound T to the intermediate Compound S. The extent of the Stage 3a reduction is related to the reaction time, and time was identified as a CPP for the control of Compound U derived from residual Compound R and Compound T.

A detailed risk assessment of Stage 3a was undertaken. Through this process, additional parameters in Stage 3a were identified as potentially impacting the drug-related impurity CQAs Compound Y, Compound U, Compound BB, and Compound V. These parameters were then investigated in a series of multifactorial experiments.

A fractional factorial design was performed to identify process parameters and interactions in Stage 3a which had the greatest impact on Compound Y, Compound U, Compound BB, and Compound V. Table 28 shows the parameters and the corresponding ranges that were investigated.

Each reaction was run for 44 hours and the pivaloyl protecting groups were removed under the Stage 3b conditions. The crude reaction mixture was then analyzed prior to Stage 3c, so levels of the impurities were higher than those which would be seen in intermediate grade migalastat hydrochloride after purging during the crystallization.

TABLE 28

Potential CPPs and ranges studied in Stage 3a DOEs

| Parameter | Range Studied | Output studied |
| --- | --- | --- |
| Temperature | 35-55° C. | Levels of Compound Y, Compound U, Compound BB, and Compound V |
| Palladium catalyst quantity | 0.5-2.5 mol % | |
| Methanol volumes | 6-10 volumes | |
| Hydrogen pressure | 6 to 10 bar gauge (5-9 bar absolute) | |

Parameters Impacting Compound V

Figure 10:
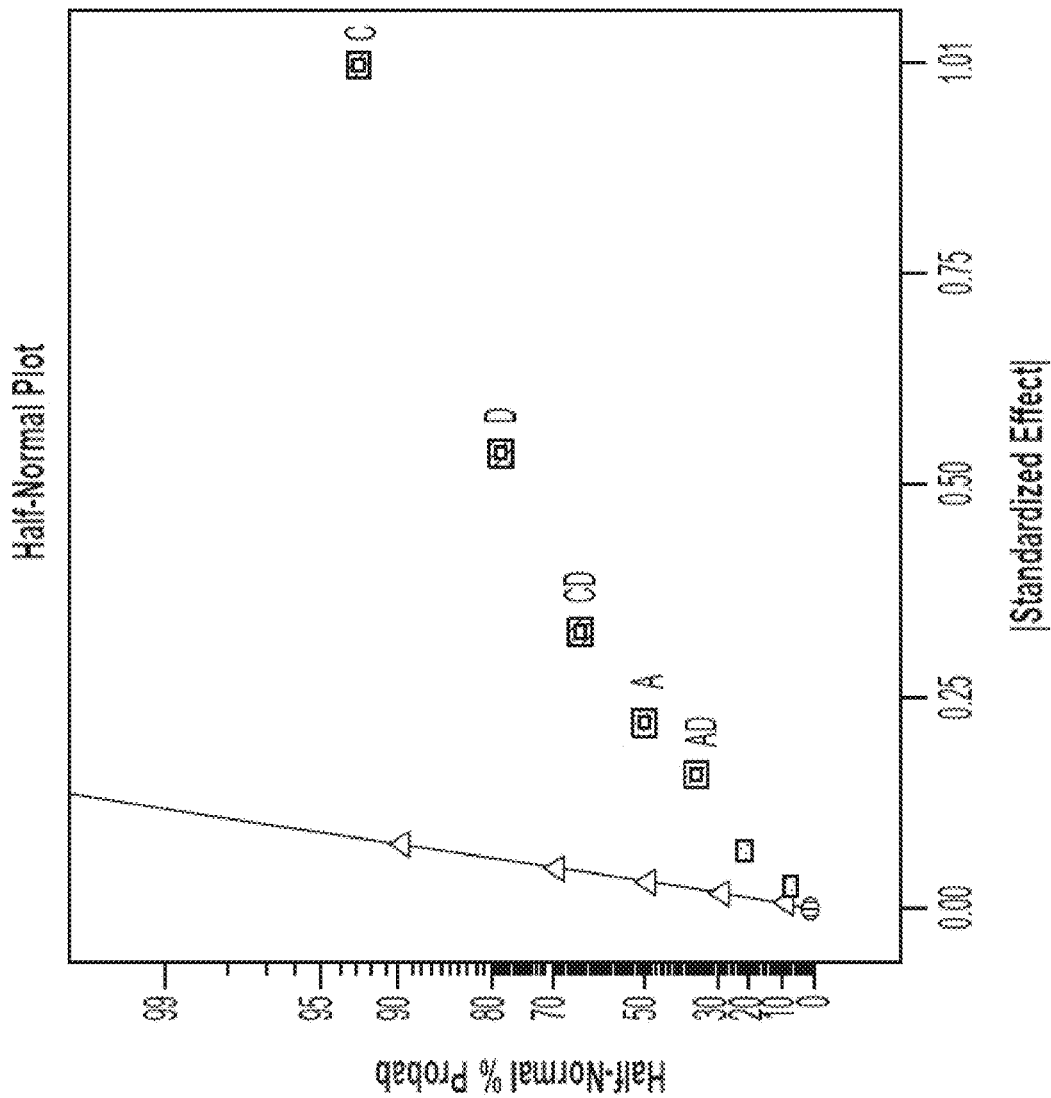
FIG. 10 shows a half-normal effects plot identifying the effects of individual parameters and interactions between parameters on critical quality attributes.

The findings for Compound V from the fractional factorial design are summarized by the half-normal effects plot in FIG. 10. The effects in the fitted model are indicated by a letter on the graph (effects included are all those statistically significant with p<0.05 unless otherwise stated, or included to support hierarchy for a higher order). These half-normal plots are used to identify the effect of individual parameters and interactions between parameters on the CQAs within the ranges investigated in the design. Some parameters have a greater impact on the attribute, indicated by the higher numerical x-axis value on the graph, i.e., they appear further to the right hand side of the half-normal plot. FIG. 10 illustrates that the amount of Compound V formed was impacted primarily by the palladium catalyst quantity. The fractional factorial design indicated that an increased quantity of palladium on carbon catalyst and increased methanol volumes led to increased levels of Compound V. These data also indicated that there was an interaction between these two parameters. There was also a temperature effect on Compound V alongside its interaction with methanol volumes.

Figure 11:
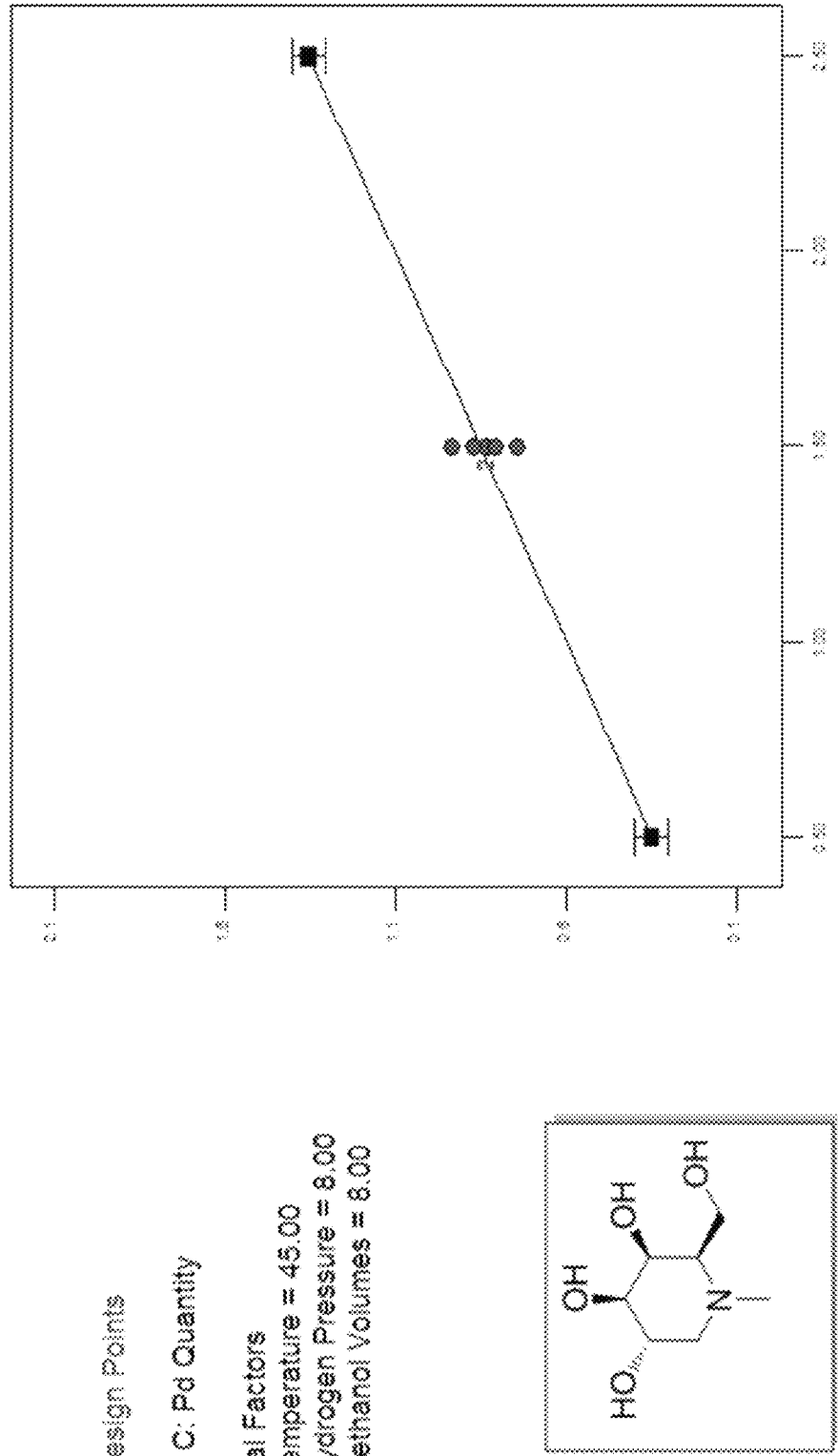
FIG. 11 shows an effects plot illustrating the effect of palladium catalyst quantity on levels of Compound V.

The impact of palladium catalyst quantity on levels of Compound V is exemplified by the effects plot in FIG. 11 which illustrates the effect on Compound V of the palladium catalyst quantity. Error bars represent least significant differences (LSD) at 95% confidence levels. If the response ranges indicated by the LSD bars for two points do not overlap, the points are statistically different. Experimental values run in the design are represented on the effect plot as circles. The specific effect plot is conditional on the level of factors not explicitly displayed (the conditional levels are listed as text to the left of the graphics with a label "Actual Factors"), hence, demonstrating the size of the relationship and not the precise location. Effect plots such as FIG. 11 are used to visualize the predicted relationship between the parameter on the x-axis and the response on the y-axis.

In another study outside the multifactorial experiments, the impact of extended reaction time on Compound V was also investigated. In a single univariate experiment, the Stage 3a reaction was allowed to continue for up to 92 hours prior to removal of the catalyst. Levels of Compound V were higher than typically observed. Palladium catalyst quantity, time, and methanol volumes were therefore identified as CPPs impacting Compound V in Stage 3a.

Parameters Impacting Compound U

Figure 12:
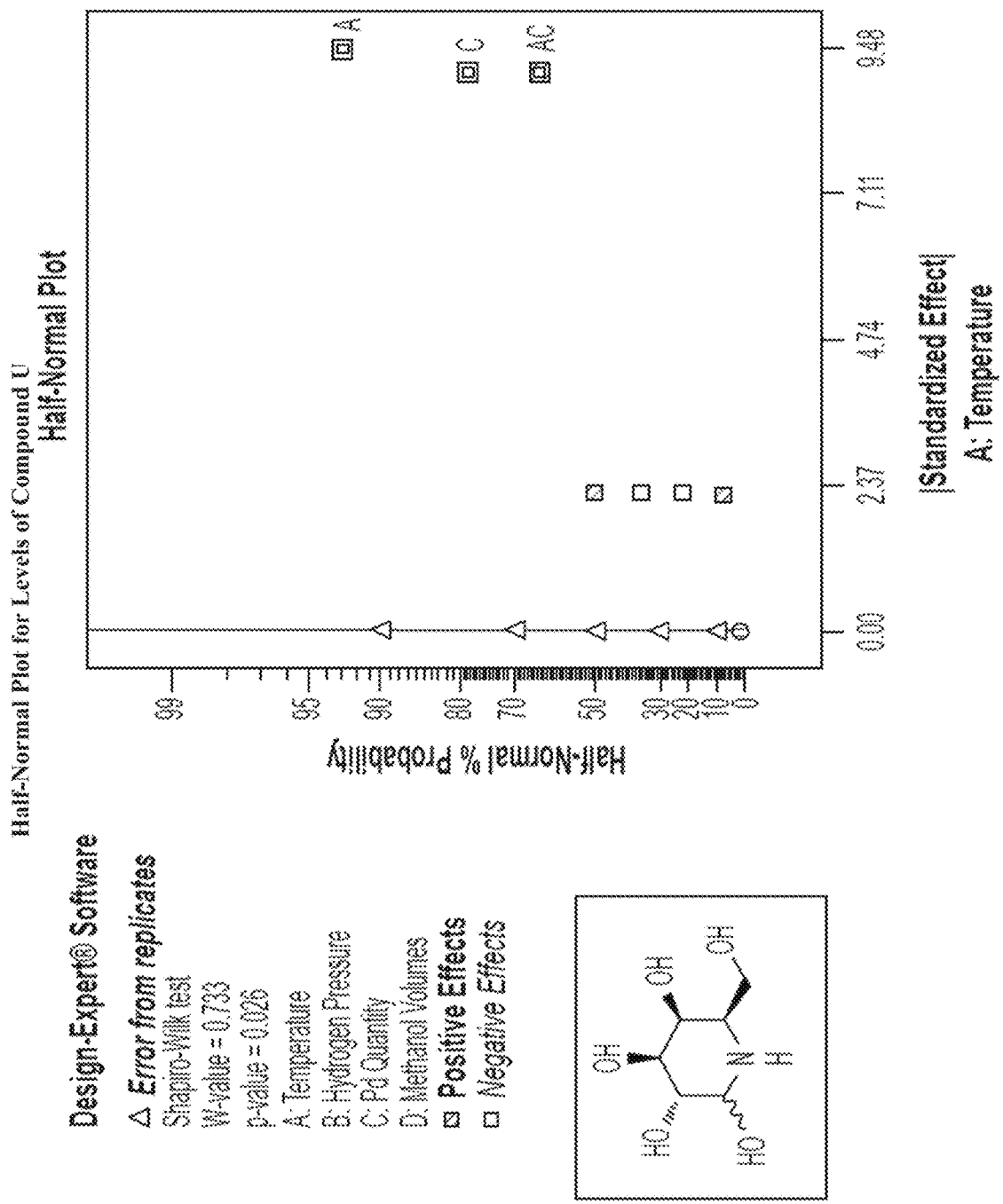
FIG. 12 shows a half-normal effects plot showing how experimental parameters influence Compound U formation.

From the same fractional factorial design, parameters influencing Compound U were also established. The relative impact of the parameters is again illustrated by the half-normal effects plot in FIG. 12, which shows that levels are increased by reducing the palladium catalyst quantity. In several of the design runs, Compound U was not detected in the output. The temperature of the reaction has a similar impact, with lower temperatures leading to increased levels.

Figure 13:
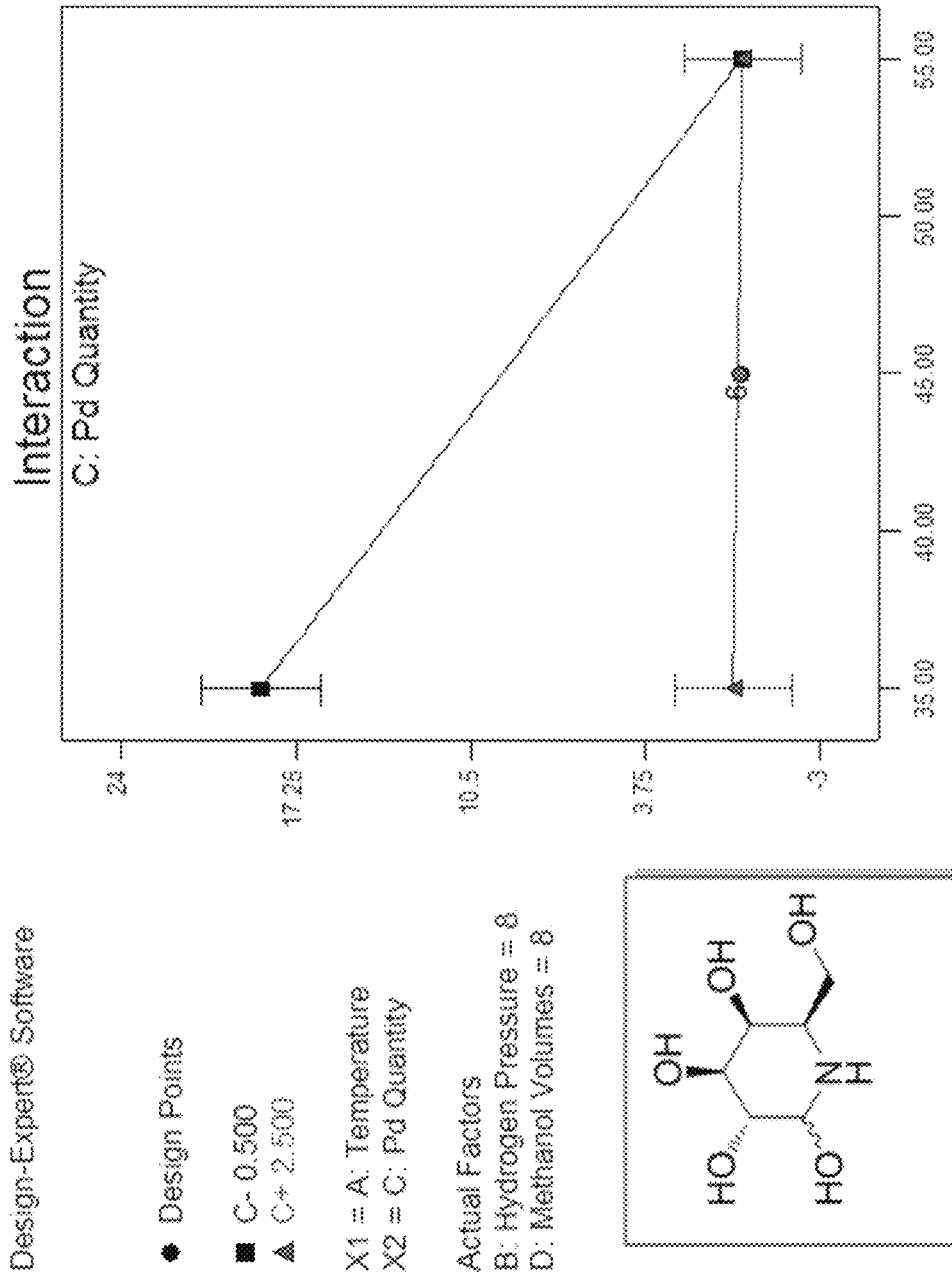
FIG. 13 shows an interaction plot showing the impact of temperature and palladium catalyst quantity on Compound U formation.

There was also an interaction between temperature and the palladium catalyst quantity, which is illustrated by the interaction plot in FIG. 13, which shows that decreasing the quantity of catalyst leads to increased Compound U. The interaction plots are used to visualize the predicted relationship between the factor (on the x-axis) and the response (on the y-axis) and interactions are displayed through two lines appearing within the plot, where the colored square and triangle symbols on the line represent distinct levels of the second parameter in the interaction.

Overall, Compound U is increased most severely when both temperature and palladium catalyst quantity are low. If either of the parameters is maintained at the upper end of the range, the severity is greatly reduced. Palladium catalyst quantity and temperature were therefore identified as CPPs for the control of Compound U in Stage 3a.

The pressure in Stage 3a did not impact levels of Compound U across the range of 6-10 barg studied. In an additional experiment when Stage 3a was performed at the lower pressure of 4 barg, the rate of reaction was significantly slower and levels of Compound U were increased. For this reason, pressure was also identified as a CPP.

Parameters Impacting Compound Y

From the same fractional factorial design, parameters influencing levels of Compound Y were also established. The same parameters which impacted levels of Compound U demonstrated a similar effect on levels of Compound Y, which was most impacted by the palladium catalyst quantity. Overall, where the palladium catalyst quantity was high, Compound Y was undetected in the intermediate grade migalastat hydrochloride. Palladium catalyst quantity and temperature were therefore also shown to be CPPs for the control of Compound Y in Stage 3a. In an additional experiment when Stage 3a was performed at 4 barg, levels of Compound Y were increased. For this reason, pressure was also identified as a CPP impacting Compound Y.

Establishing Ranges for CPPs and Confirming Robustness in Stage 3a

In order to identify operating ranges for the CPPs identified in Stage 3a, a robustness fractional factorial design was carried out. A robustness fractional factorial design was used to show that the process can be operated anywhere within the ranges defined for the CPPs and includes those combinations of parameter setpoints designed to increase impurities to their highest potential levels.

Details of this experiment are summarized in Table 29. Temperature, hydrogen pressure, palladium catalyst quantity, and methanol volumes were included as parameters, and the output was processed through Stages 3b and 3c under standard conditions. All experiments were run for 44 hours and levels of the impurities were measured in the intermediate grade migalastat hydrochloride produced.

TABLE 29

CPPs and ranges studied in Stage 3a robustness design

| Parameter | Range Studied | Output studied |
|---|---|---|
| Temperature | 40-50° C. | Levels of Compound U, Compound Y, Compound BB, and Compound V in intermediate grade migalastat hydrochloride |
| Hydrogen pressure | 7-9 barg (8-10 bar abs) | |
| Palladium catalyst quantity | 0.07-0.013 equiv | |
| Methanol volumes | 7-9 volumes | |

Material from all of the experiments met the specification for drug-related impurity CQAs in intermediate grade migalastat hydrochloride. The fractional factorial design, therefore, confirmed that the ranges in Table 29 are appropriate. In addition, the experiment confirmed that a time of 44 hours or more was an appropriate minimum range.

Palladium catalyst quantity, methanol volumes, and time are CPPs for the control of Compound V, and levels increase with extended time. A maximum time was established in a separate univariate experiment. Table 30 shows the levels of the CPPs for this experiment. The pressure was set at 8 barg and the temperature at 45° C.

TABLE 30

Experiment to define a maximum time for Stage 3a

| CPP | Setpoint | Output studied |
|---|---|---|
| Palladium catalyst quantity | 0.013 equiv | Levels of Compound V |
| Time for Stage 3a | 68 hours | |
| Methanol volumes | 9 volumes | |

Levels of Compound V in the intermediate grade migalastat hydrochloride were within specification and a maximum time of 68 hours was therefore defined.

Impact of Scale and Equipment on Stage 3a

Heterogeneous hydrogenation processes can be sensitive to vessel configuration and impeller speed, which strongly influence the gas/liquid mass transfer properties of the system. For this reason, the design of these reactors usually includes a high speed turbine impeller positioned low in the vessel. In addition, the impeller shafts may be 'gas entrainment' type, i.e., shaft of hollow construction with apertures at the top and bottom extremities which cause gas to be drawn down from the head-space and expelled via the turbine into the liquid vortex causing maximum dispersion and gas transfer.

A series of experiments was conducted to explore the impact of extremes of hydrogen pressure, impeller speed, vessel fill, and gas entrainment on Stage 3a hydrogenation reaction conversion and the profile of isolated intermediate grade migalastat hydrochloride. These experiments are summarized in Table 31.

TABLE 31

Summary of experimental runs and operating conditions

| Parameter | Run 1 | Run 2 | Run 3 | Run 4 | Run 5 |
|---|---|---|---|---|---|
| 5-azido-5-deoxy-1,2,3,6-tetrapivaloyl-D-galactofuranoside (scale) | 50 g | 20 g | 20 g | 20 g | 20 g |
| Volumes of MeOH (scale) | 8 vol | 8 vol | 8 vol | 8 vol | 8 vol |
| Temperature | 45° C. | 45° C. | 45° C. | 45° C. | 45° C. |
| Pressure/barg | 4 | 4 | 8.5 | 8.5 | 8.5 |
| Vessel fill level[1] | 80% | 32% | 32% | 32% | 32% |
| Agitation setpoint | 50 rpm | 50 rpm | 50 rpm | 750 rpm | 750 rpm[2] |

[1]Calculated with respect to the nominal vessel capacity (0.5 L);
[2]Gas entrainment blocked for this run only.

In run 1, even under the conditions of low pressure, low stirrer speed, and high fill level, the rate of reaction (data not shown) was comparable to that of run 4, where conditions for these three parameters were reversed.

Figure 14:
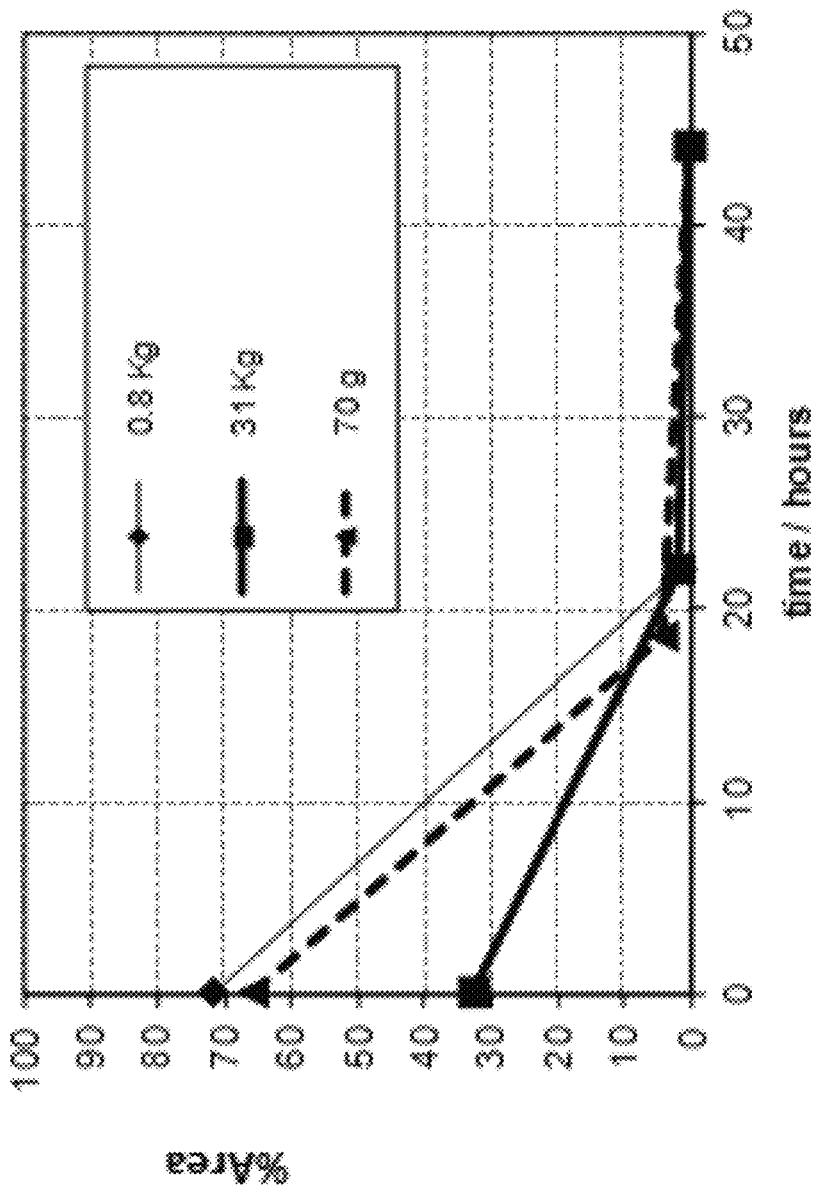
FIG. 14 shows a reaction profile for Stage 3a at various production scales.

In a further assessment of the scalability, FIG. 14 shows the reaction profile for Stage 3a in a 70 g laboratory scale experiment, at 0.8 kg (20 liter) scale and at 31 kg production scale. Zero hours was defined as the time following completion of the venting to release the nitrogen generated during reduction of the 5-azido-5-deoxy-1,2,3,6-tetrapivaloyl-D-galactofuranoside to Compound R. Each of the batches met the reaction endpoint after an equivalent amount of time, and the overall reaction profile at the three scales was comparable. Notably, the plant scale hydrogenator outperformed the lab scale equipment.

Example 11: Identification of Critical Process Parameters—Stages 3b and 3c

Control of Residue on Ignition in Stage 3b

Residue on ignition is a CQA and a measure of inorganic impurity levels. Sodium chloride is an inorganic by-product impurity of Stage 3b that is detected in intermediate grade migalastat hydrochloride. No further inorganic impurities are introduced after this Stage, and the residue on ignition of drug substance is impacted by the levels of sodium chloride in intermediate grade migalastat hydrochloride. Sodium chloride is formed following the addition of 37% hydrochloric acid to the concentrated mixture of migalastat free base and sodium alkoxides. The sodium chloride, which has only partial solubility in the 37% hydrochloric acid solution of migalastat, is then mostly removed by filtration.

Figure 15:
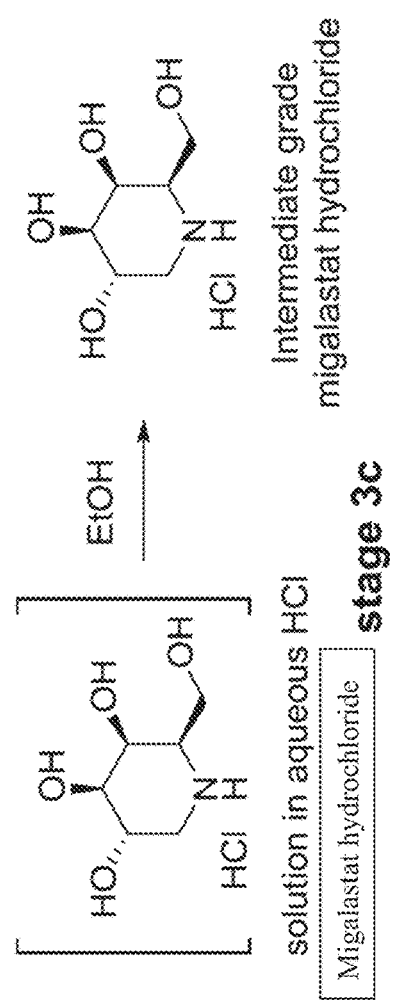
FIG. 15 depicts Stages 3b and 3c of an exemplary migalastat hydrochloride synthesis scheme.
Figure 15:
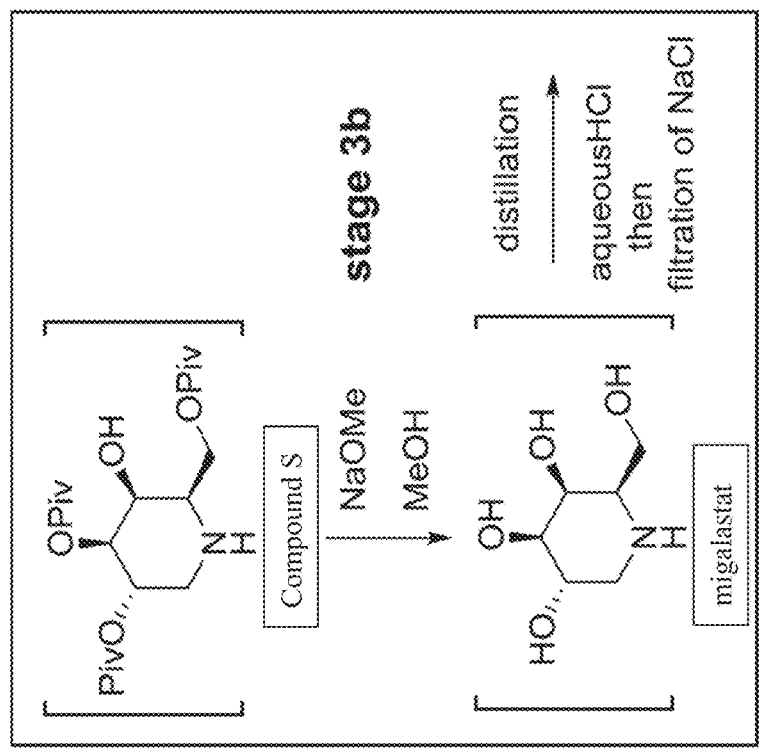
Figure 16:
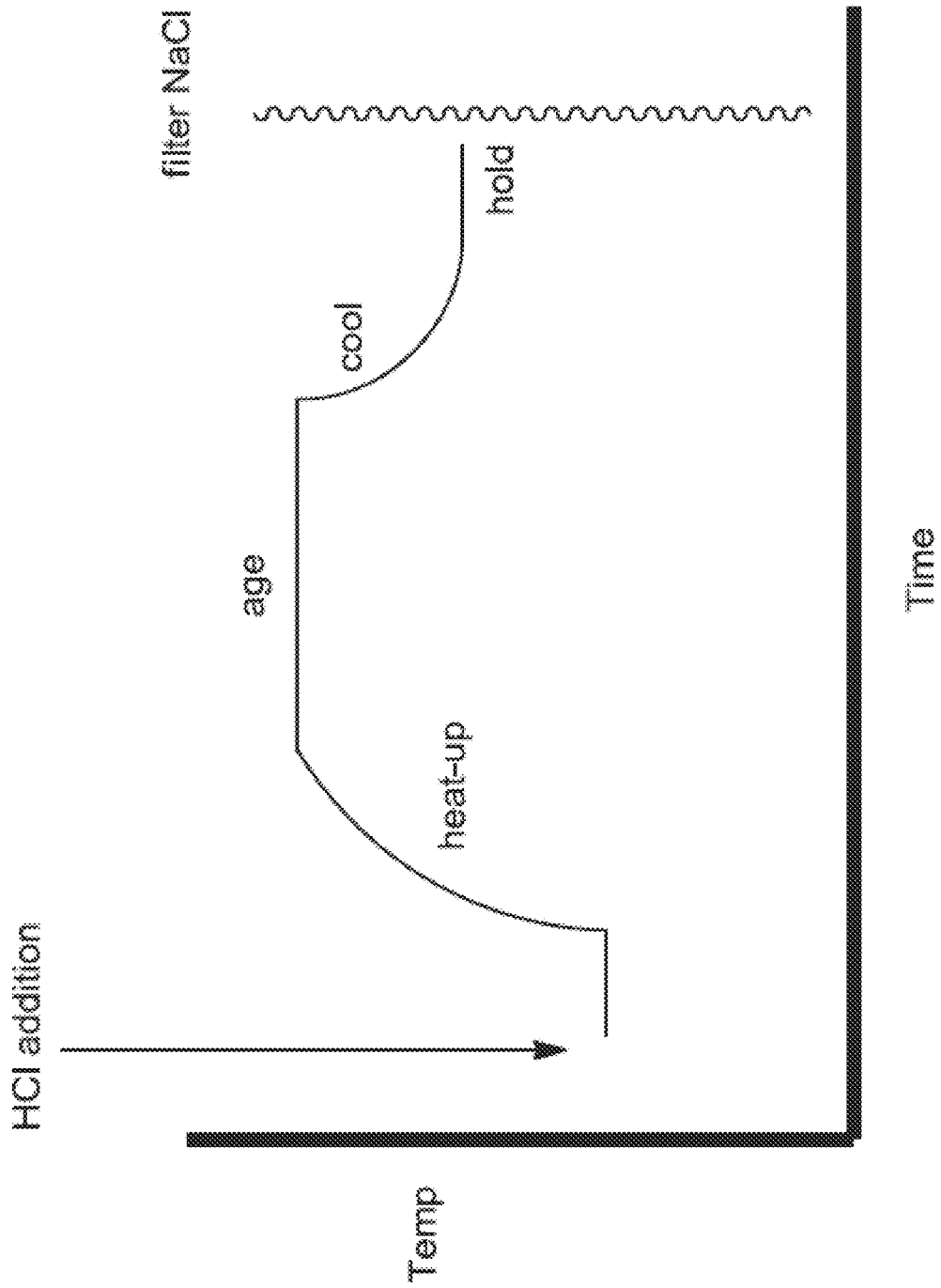
FIG. 16 shows a schematic of an exemplary Stage 3b process in which temperature is varied after addition of hydrochloric acid.

The Stage 3b process is shown in greater detail in FIG. 15. Following addition of the 37% hydrochloric acid, the mixture is heated for an age time to ensure that the migalastat hydrochloride is in solution and the sodium chloride has precipitated prior to the filtration. The mixture is then cooled and the sodium chloride filtered, prior to crystallization in Stage 3c. FIG. 16 is a schematic of the Stage 3b process, showing how the temperature is varied after the addition of the 37% hydrochloric acid.

An investigation of the parameters potentially impacting the removal of sodium chloride in Stage 3b was undertaken. The objective of this investigation was to establish a robust control strategy to ensure that the residue on ignition would always meet the 7% w/w specification limit in intermediate grade migalastat hydrochloride.

Two multifactorial studies were run, investigating the parameters identified as potentially impacting the removal of sodium chloride in the filtration in Stage 3b. The first multifactorial study focused on investigating the potential link between the solution composition and the addition of hydrochloric acid. The conditions evaluated in this are summarized in Table 32. Other parameters in the process were held constant during this study and intermediate grade migalastat hydrochloride was analyzed after isolation under the standard conditions for Stage 3c.

TABLE 32

Parameters and ranges studied in first Stage 3b study

| Parameter | Range studied | Output studied |
|---|---|---|
| 30% Sodium methoxide quantity | 0.8-1.2 equiv | Residue on ignition of intermediate grade migalastat hydrochloride[1] |
| HCl addition time | 30-150 minutes | |
| HCl addition temperature | 20-50° C. | |
| 37% HCl quantity | 2.75-3.25 vol | |
| Hold time after addition | 0-120 min | |
| Heat up time to age temperature | 10-110 min | |
| Residual weight after distillation/methanol quantity | 0.5-0.9 weights | |

[1]Determined via sodium assay.

All of the intermediate grade migalastat hydrochloride produced met the specification for residue on ignition, with levels ranging from 1.2% to 2.1% w/w.

The second multifactorial study focused on investigating the potential link between the solution composition and the age process. The conditions evaluated are summarized in Table 33. Again, intermediate grade migalastat hydrochloride was analyzed after isolation under the standard conditions for Stage 3c.

TABLE 33

Parameters and ranges studied in second Stage 3b study

| Parameter | Range studied | Output studied |
|---|---|---|
| 30% Sodium methoxide quantity | 0.8-1.2 equiv | Residue on ignition of intermediate grade migalastat hydrochloride[1] |
| Age time | 1-10 hrs | |
| Age temperature | 40-55° C. | |
| 37% HCl quantity | 2.75-3.25 vol | |
| Age time prior to filtration | 30-120 min | |
| Filtration temperature | 25-40° C. | |
| Residual weight after distillation/methanol quantity | 0.5-0.9 weights | |

[1]Determined via sodium assay.

Material from all of the experiments met the specification for residue on ignition in intermediate grade migalastat hydrochloride, with levels ranging from 1.0% to 2.5% w/w.

Figure 17:
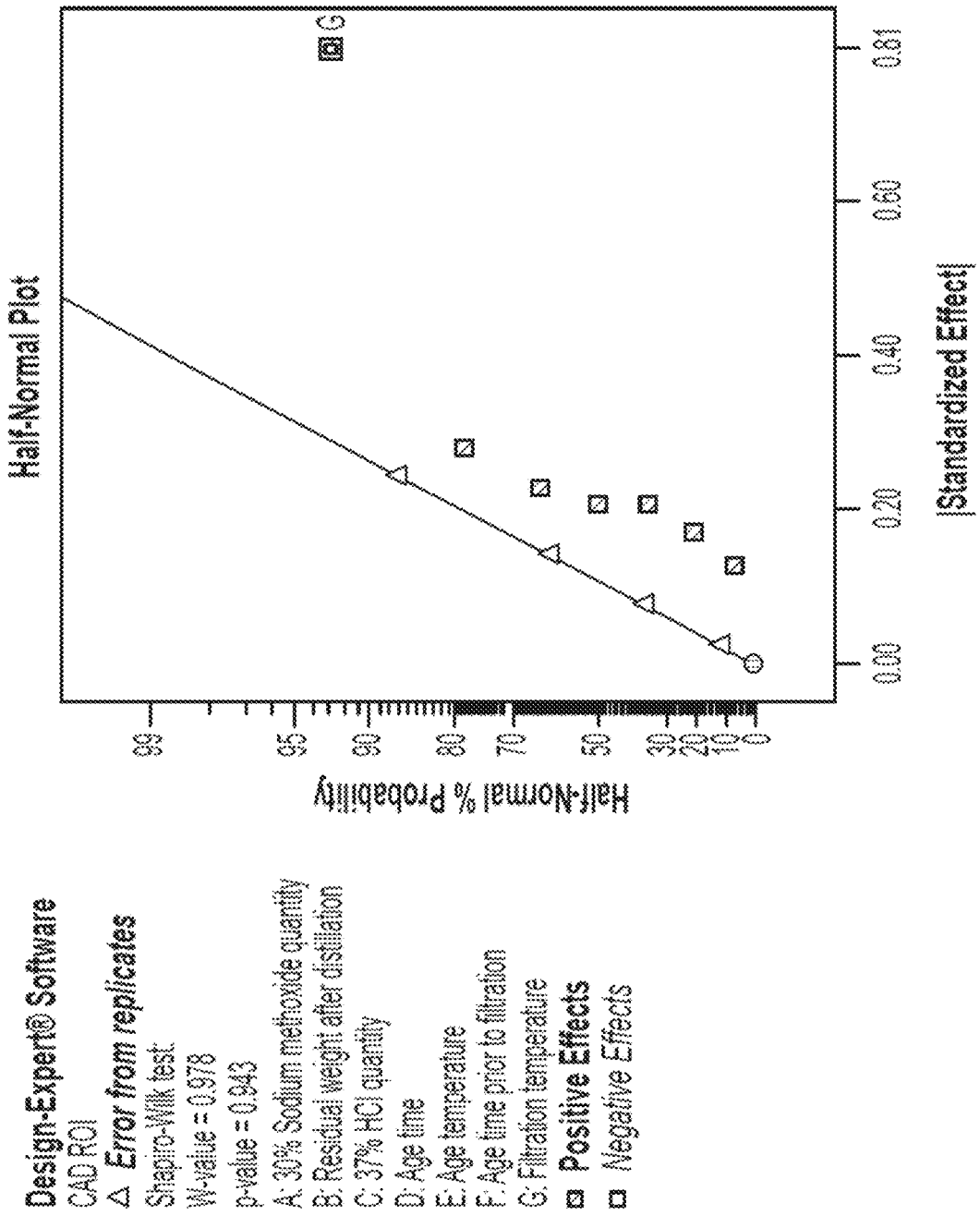
FIG. 17 shows a half normal plot showing the impact of filtration temperature on residue on ignition in intermediate grade migalastat hydrochloride.

However, the data indicated that the residue on ignition was influenced by the filtration temperature, with higher temperatures leading to higher levels of residue on ignition. The significance of the filtration temperature is illustrated in the half normal plot FIG. 17.

Figure 18:
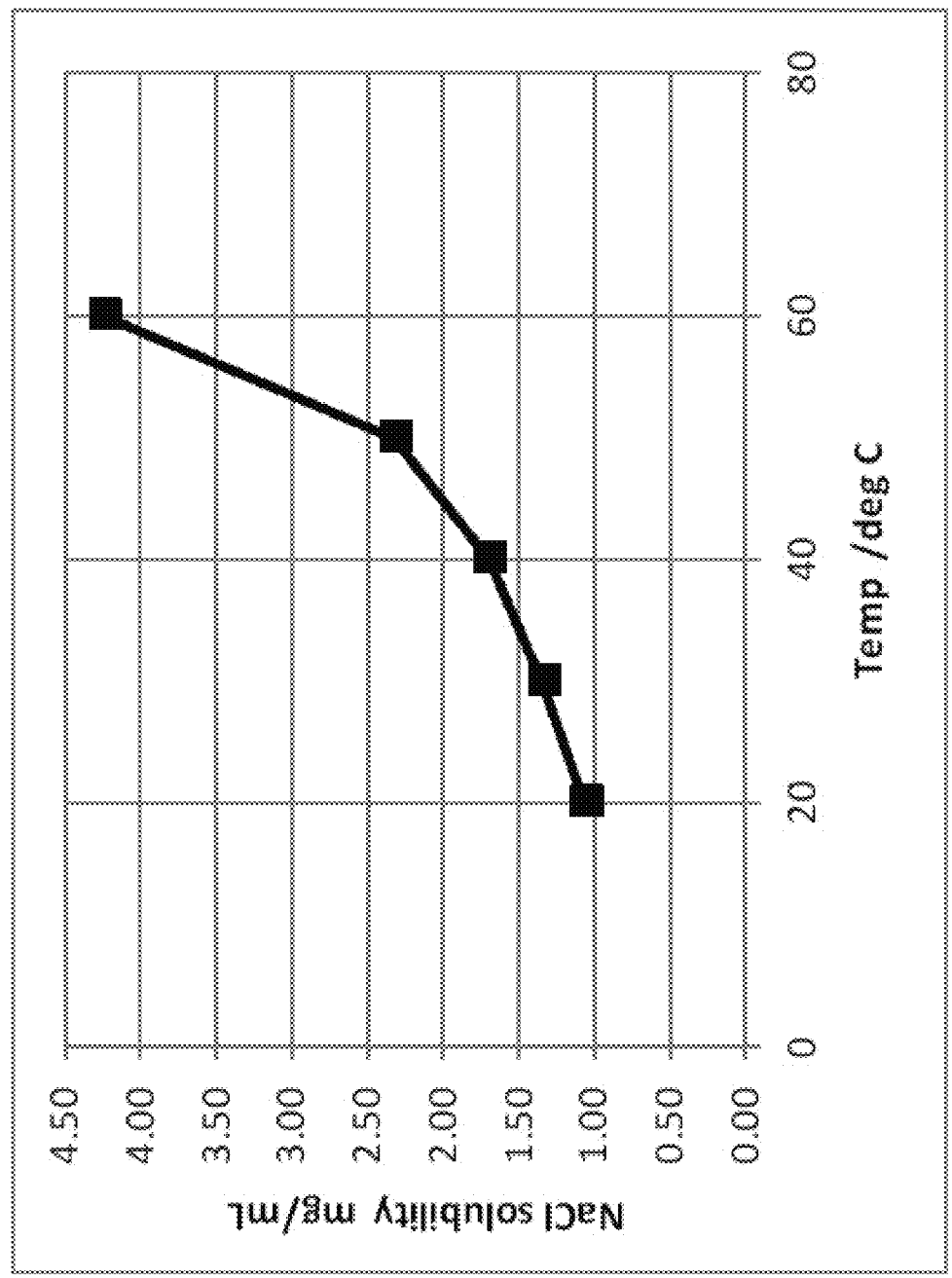
FIG. 18 provides a graphical representation of solubility data associated with sodium chloride across a range of temperatures in a reaction mixture of hydrochloric acid and methanol.

To verify this finding, the solubility of sodium chloride in the reaction mixture of 37% hydrochloric acid and methanol was measured across a range of temperatures. This solubility data is shown in the chart in FIG. 18.

This trend was also confirmed in a univariate experiment where Stage 3b was filtered at 60° C., resulting in a residue on ignition in intermediate grade migalastat hydrochloride of 4.6% w/w. On the basis of these results, the filtration temperature was defined as a CPP for the control of residue on ignition.

It was also shown that the concentration of the 37% hydrochloric acid has an impact, with lower acid concentrations leading to greater solubility of sodium chloride, and therefore, higher residue on ignition. This was confirmed in an experiment where 32% hydrochloric acid was used which led to a residue on ignition in intermediate grade migalastat hydrochloride of 5.2% w/w. For this reason, the concentration of hydrochloric acid was controlled to within the range 35%-37% by the specification.

Control of Compound X in Stage 3b

Figure 19:
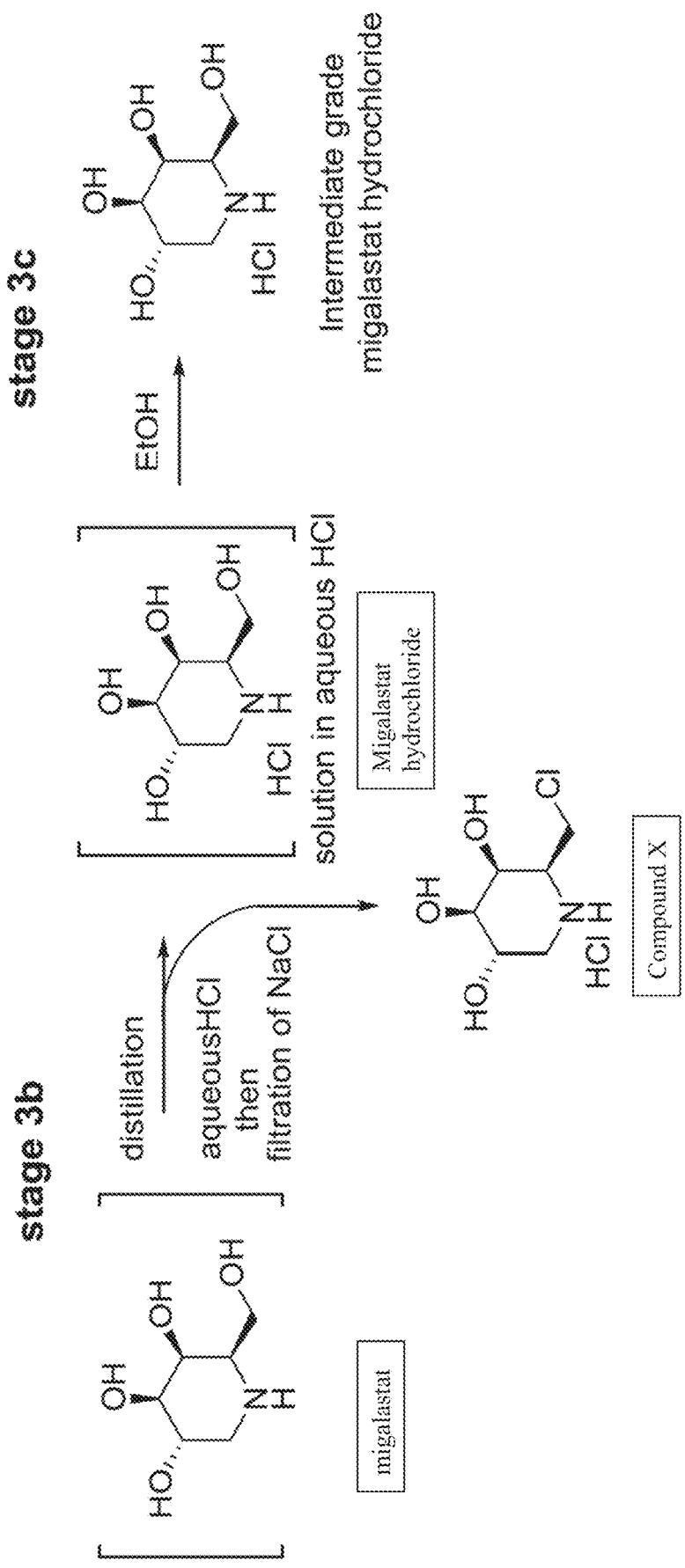
FIG. 19 depicts Stages 3b and 3c of an exemplary migalastat hydrochloride synthesis scheme.

Compound X is a genotoxic impurity which can form in Stage 3, as shown in FIG. 19. Compound X was well controlled in batches of drug substance, being not greater than 2.0 mcg/g, well below the threshold of toxicological concern (TTC) of 12 mcg/g. Compound X can form under the harsh process conditions in Stage 3b where the solution of migalastat hydrochloride in concentrated hydrochloric acid is aged at elevated temperature in a solution saturated with sodium chloride.

Parameters potentially impacting Compound X were all included within a multifactorial study. The intermediate grade migalastat hydrochloride produced in this study, details of which are reproduced in Table 34, was analyzed to determine levels of Compound X.

TABLE 34

Parameters and Ranges Studied to Determine the Impact on Compound X

| Parameter | Range Studied | Output Studied |
| --- | --- | --- |
| 30% Sodium methoxide quantity | 0.8-1.2 equiv | Levels of Compound X in intermediate grade migalastat hydrochloride |
| Age time | 1-10 hrs | |
| Age temperature | 40-55° C. | |
| 37% HCl quantity | 2.75-3.25 vol | |
| Age time prior to filtration | 30-120 min | |
| Filtration temperature | 25-40° C. | |
| Residual weight after distillation/ methanol quantity | 0.5-0.9 weights | |

Figure 20:
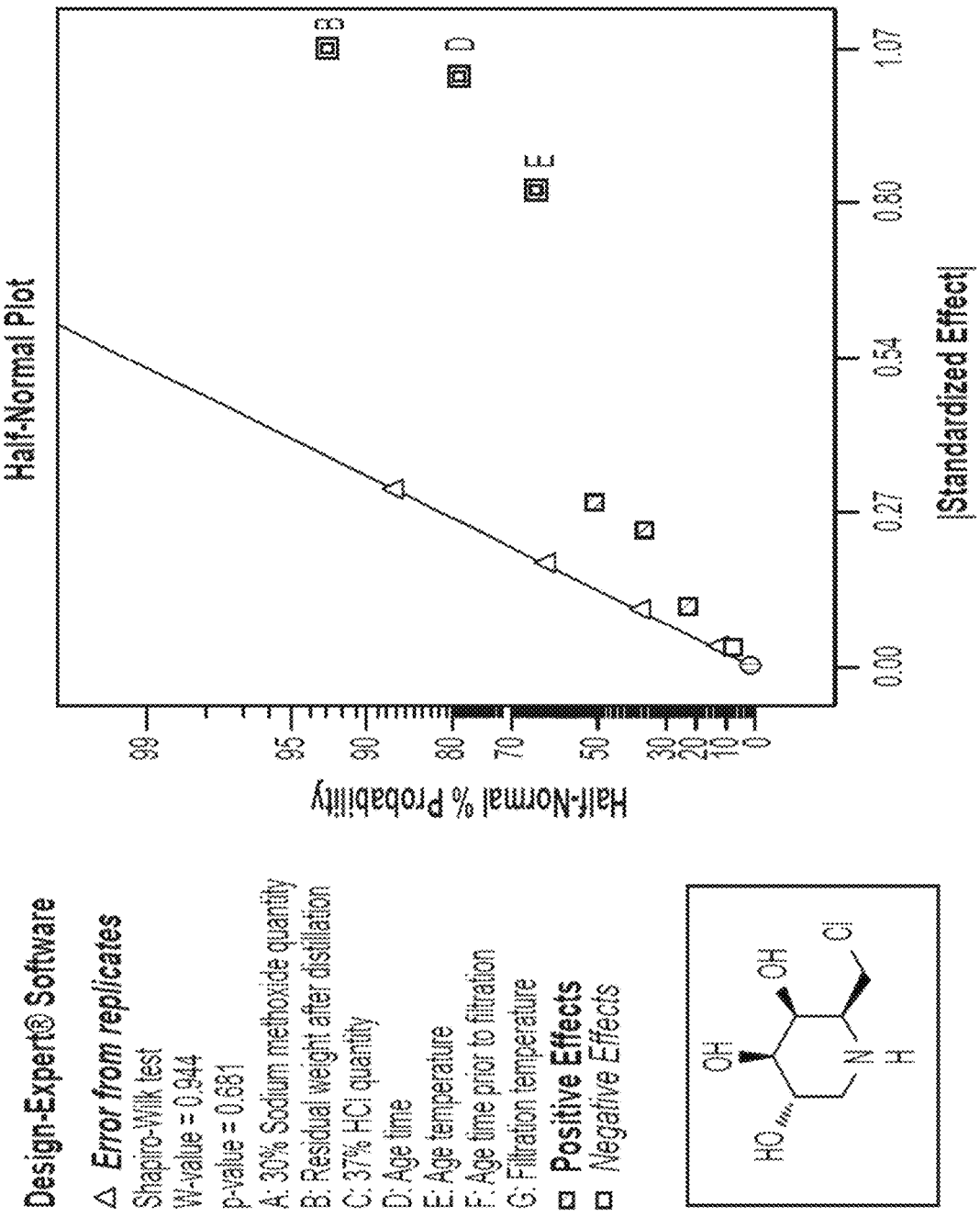
FIG. 20 shows a half normal plot showing the impact of various production parameters on the levels of Compound X.

Levels of Compound X between 2 and 21 mcg/g were detected in the intermediate grade migalastat hydrochloride produced. FIG. 20 illustrates the impact of the parameters studied. Higher levels of Compound X were commonly observed when the residual weight after the distillation was low, the age time was long, or the age temperature was higher. Age time, age temperature, and residual weight after the distillation were therefore concluded to be CPPs for the control of Compound X.

The intermediate grade migalastat hydrochloride containing 21 mcg/g of Compound X was recrystallized via the Stage 4 process and the migalastat hydrochloride produced had Compound X at not greater than 3 mcg/g.

Purging of Drug-related Impurity CQAs in Stages 3b and 3c

Figure 21:
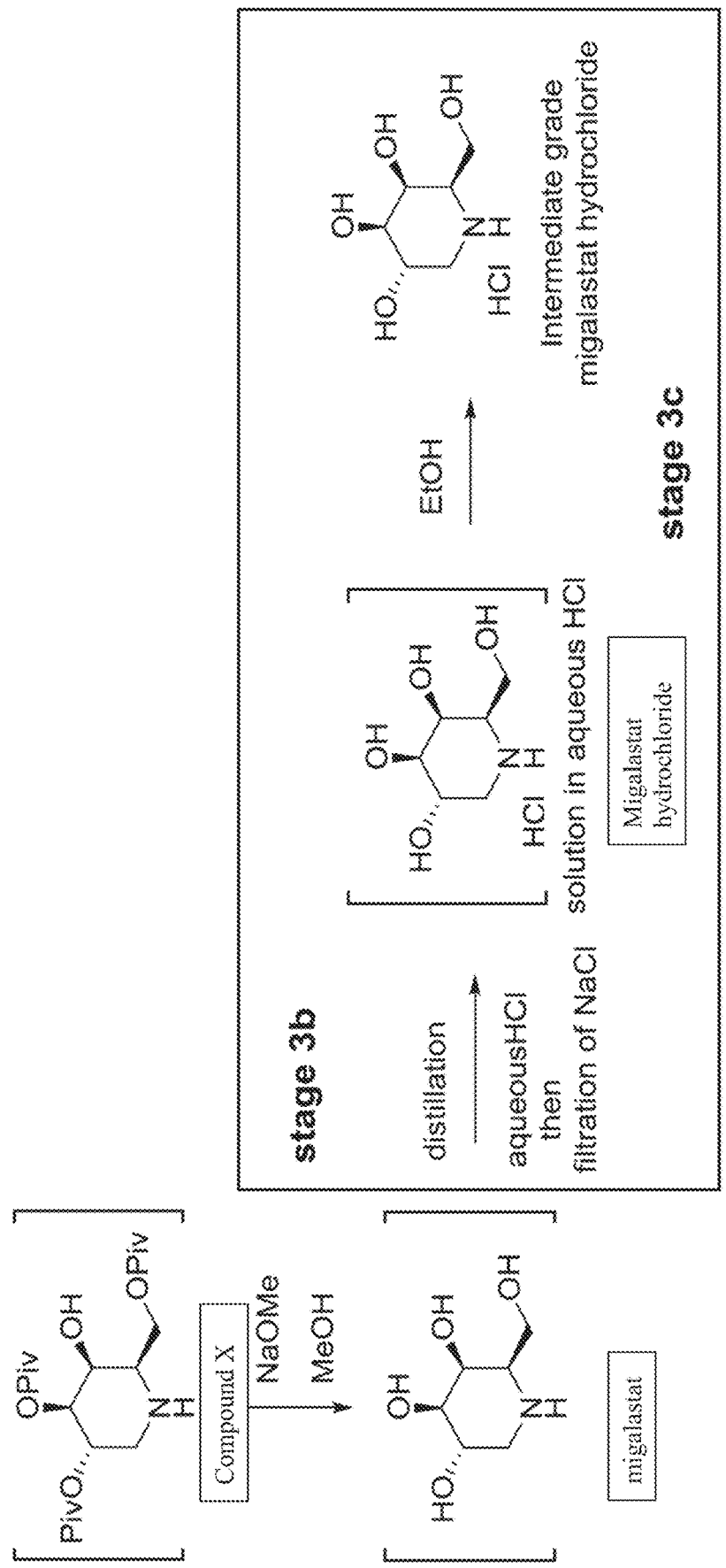
FIG. 21 depicts a process for purging Compound X during Stages 3b and 3c of an exemplary migalastat hydrochloride synthesis scheme.

Some drug-related impurity CQAs are partially purged in the isolation of intermediate grade migalastat hydrochloride. Thus, conditions in Stages 3b and 3c could potentially impact the purging of drug-related impurity CQAs (FIG. 21) and a series of scoping experiments were performed to establish which impurities were influenced. Those drug-related impurity CQAs which are partially purged in the isolation of intermediate grade migalastat hydrochloride in Stages 3b and 3c are shown in Table 35.

TABLE 35

CQA Impurities Partially Purged by the Stage 3c Crystallization of Intermediate Grade Migalastat Hydrochloride

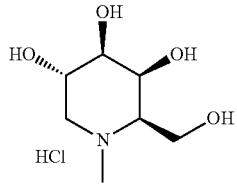

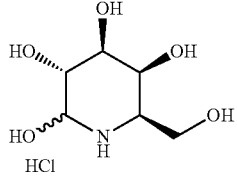 [SMILES: OC[C@H]1NC(O)[C@H](O)[C@@H](O)[C@H]1O ; Cl]

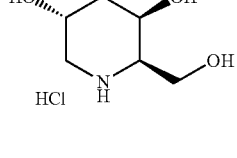

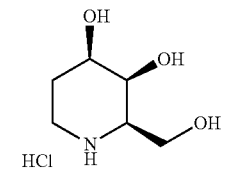

Following the scoping experiments, potential CPPs which might impact the purging of the drug-related impurity CQAs were identified through a further risk assessment. These parameters were then studied in a fractional factorial design to determine their criticality and establish ranges. No assessment of the impact upon Compound BB could be made in this study since levels were uniformly below the limit of detection.

TABLE 36

Parameters studied following risk assessment

| Stage | Parameter | Range Studied | Output Studied |
|---|---|---|---|
| 3b | 37% HCl quantity | 2.7-3.7 vol | Levels of Compound Y, |
| 3c | Temperature | 15-25° C. | Compound V, and Compound |
|  | Time/rate for ethanol addition | 12-50 min | U in intermediate grade |
|  | Volume of ethanol added | 6.5-8.5 vol | migalastat hydrochloride |
|  | Age time | 1-5 hours |  |

Figure 22:
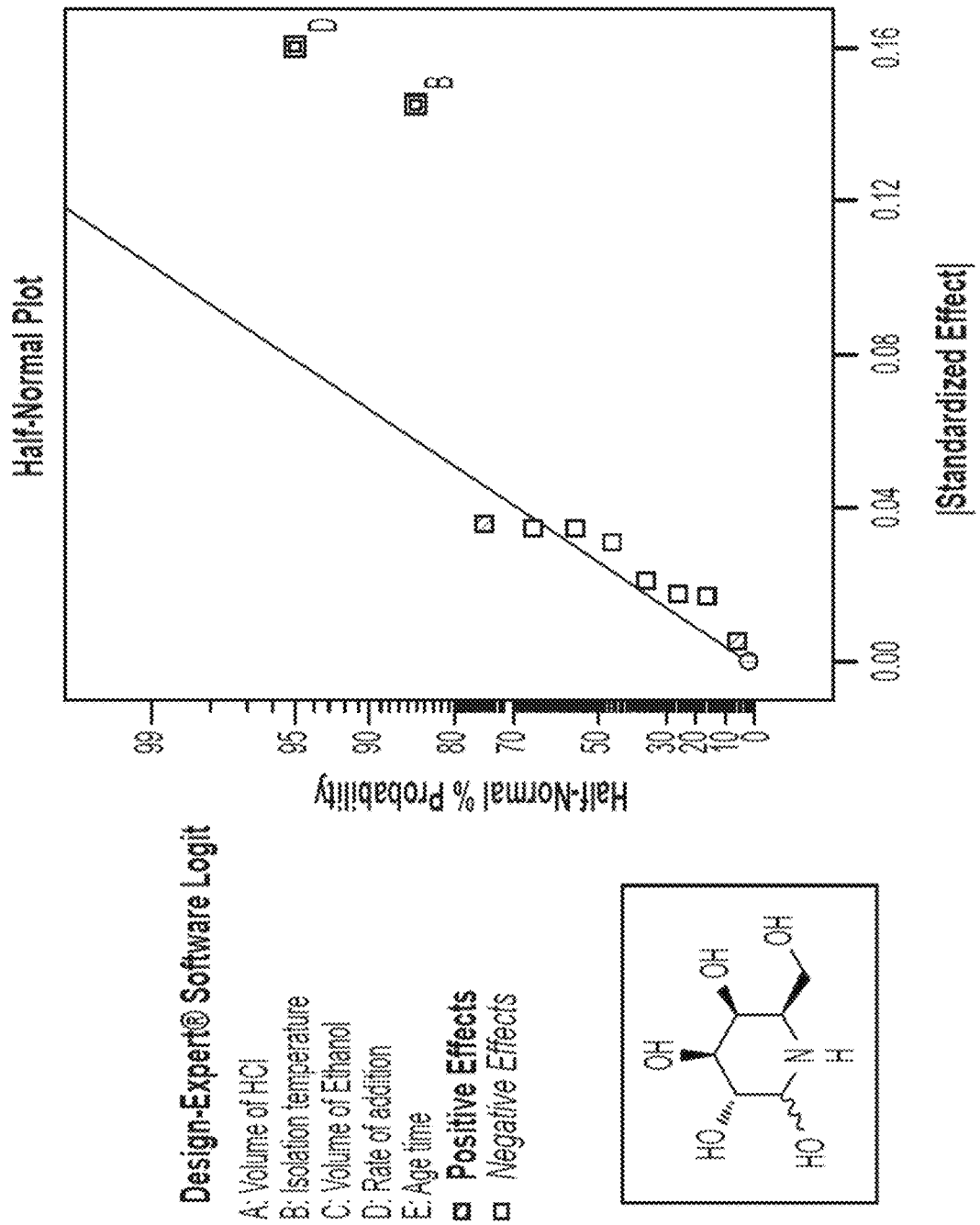
FIG. 22 shows a half-normal plot showing the impact of ethanol addition time and temperature during Stage 3c on levels of Compound U.
Figure 23:
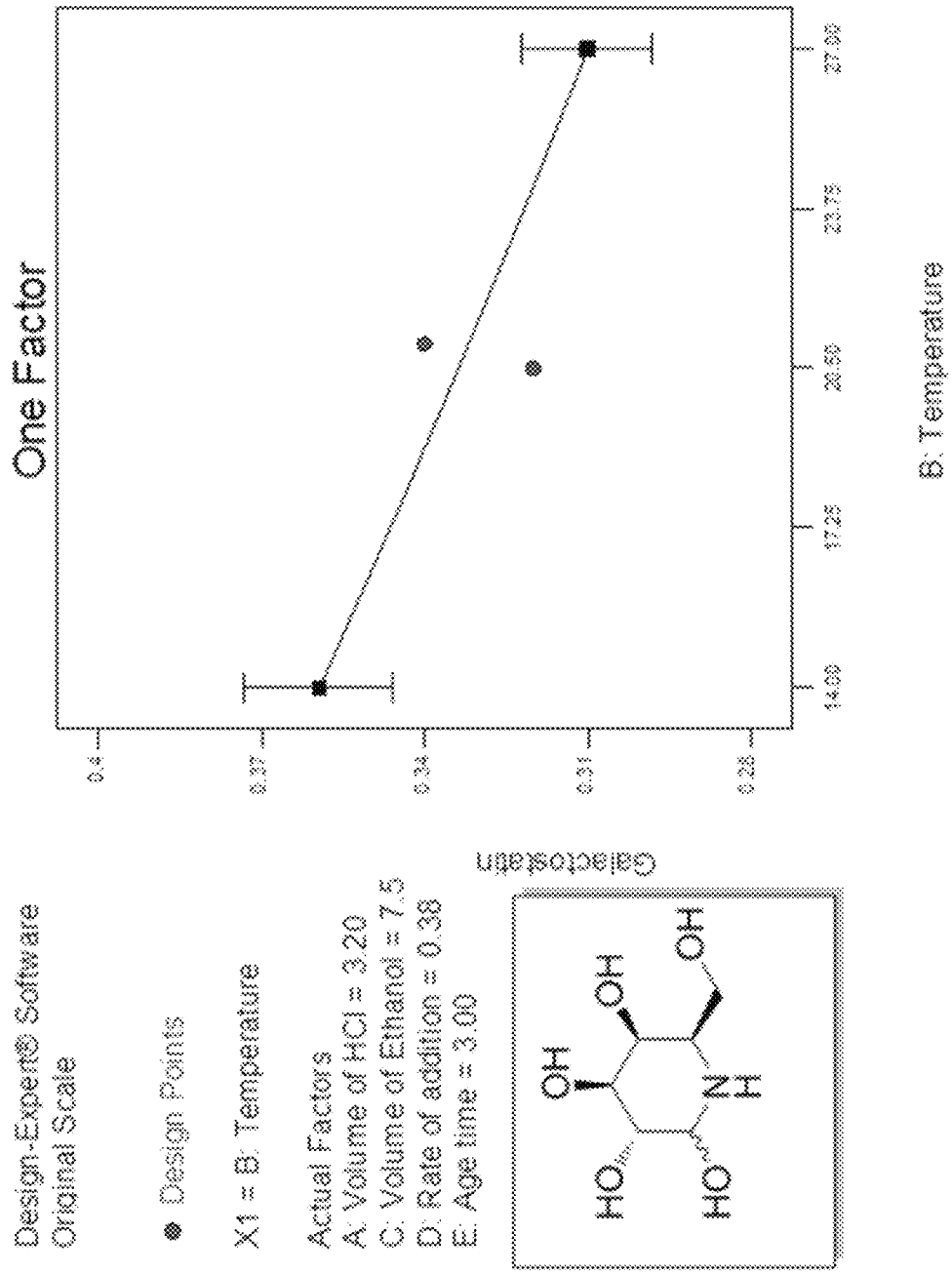
FIG. 23 shows an effects plot illustrating the impact of temperature on levels of Compound U.

The results from the experiments showed that levels of Compound U were impacted by the ethanol addition time and the temperature during Stage 3c. FIG. 22 is a half-normal plot generated using data from this study. It illustrates that decreasing the time of the ethanol addition or decreasing the temperature will lead to higher levels of Compound U in the intermediate grade migalastat hydrochloride. This point is further illustrated in the effects plot in FIG. 23, which illustrates that decreasing the temperature will reduce the degree of purging and hence, increase the level of Compound U in the intermediate grade migalastat hydrochloride.

A similar trend plot was obtained for the rate/time of ethanol addition, showing that faster rate will lead to less purging of Compound U. Hence, a decrease in the time for ethanol addition will lead to higher levels of Compound U. The time of ethanol addition and the isolation temperature were therefore identified as CPPs in Stage 3c.

Similar data was obtained for Compound Y showing that purging of this CQA was also impacted in the same way by the CPPs. Data for Compound V, however, suggested that no parameter had a significant impact on its purging.

For the related impurity CQA Compound BB, a separate study was performed to determine whether the same parameters could impact its purging. Two experiments were run varying the temperature and time for the ethanol addition, as summarized in Table 37.

TABLE 37

Parameters studied following risk assessment

| Stage | Parameter | Range Studied | Output Studied |
|---|---|---|---|
| 3c | Temperature | 17 and 45° C. | Levels of Compound BB |
|  | Time/rate for ethanol addition | 5 and 60 min | in intermediate grade migalastat Time/rate for ethanol addition 5 and 60 min hydrochloride |

At the lower temperature and shorter addition time, Compound BB was observed at 0.5% w/w in the intermediate grade migalastat hydrochloride. When the temperature was higher and the addition time longer, Compound BB was present at 0.2% w/w. These two parameters are therefore also CPPs for the control of the Compound BB.

In summary, two CPPs were identified for the control of the purging of the drug-related impurity CQAs in Stages 3b and 3c. Shorter times for the ethanol addition and lower temperatures will lead to increased levels of Compound U, Compound Y, and Compound BB in intermediate grade migalastat hydrochloride.

Since longer addition times and higher temperatures will lead to reduced levels of the related impurity CQAs, the ranges for these CPPs were defined by one extreme of the ranges in Table 36 and limited to not less than 15° C. and not less than 30 minutes, respectively.

Conclusions: CPPs in Stage 3

Following completion of the evaluating activities for Stage 3, the risk assessment was updated to incorporate data from batches manufactured at commercial scale. The CPPs for control of related impurity CQAs in Stage 3a include temperature, the catalyst quantity, hydrogen pressure, methanol volumes, and time. The CPP for control of residue on ignition in Stage 3b includes filtration temperature. The CPPs for control of the genotoxin Compound X in Stage 3b include the residual weight after the distillation, age time, and age temperature. The CPPs which impact the purging of related impurity CQAs in Stages 3b and 3c include the temperature and time for ethanol addition. These CPPs and their corresponding ranges for Stage 3 are listed in Table 38.

TABLE 38

CPPs in Stage 3

| Stage | Parameter | Range Studied | CQA Impacted | Other Known Attributes Impacted |
|---|---|---|---|---|
| 3a | Palladium catalyst quantity | 0.007-0.013 equivalents | Compound U Compound Y | — |
|  | Time | 44-68 hours | Compound V |  |
|  | Temperature | 40-50° C. |  |  |
|  | Hydrogen pressure | 8-10 bar (abs) |  |  |
|  | Methanol volumes | 7-9 volumes |  |  |
| 3b | Filtration temperature | 25-40° C. | Residue on ignition | — |
|  | Residual weight after distillation | NLT 0.5 weights | — | Compound X |

TABLE 38-continued

CPPs in Stage 3

| Stage | Parameter | Range Studied | CQA Impacted | Other Known Attributes Impacted |
|---|---|---|---|---|
| 3c | Age time | NMT 10 hours | | |
| | Age temperature | 40-55° C. | | |
| | Time for ethanol addition | NLT 30 minutes | Compound U Compound Y | — |
| | Temperature | NLT 15° C. | Compound BB | |

NLT = Not less than;
NMT = Not more than

Example 12: Preparation of Migalastat Hydrochloride

Intermediate grade migalastat hydrochloride was recrystallized twice from a mixture of water and ethanol to give migalastat hydrochloride. The two recrystallization steps are represented as Stage 4a and Stage 4b in the manufacturing process. The main difference between Stage 4a and Stage 4b was the hold time during the ethanol addition in Stage 4b. In Stage 4a, intermediate grade migalastat hydrochloride was dissolved in water by warming to the crystallization temperature. Ethanol was added as an anti-solvent to induce crystallization and the slurry or solution was cooled to the isolation temperature. The migalastat hydrochloride was filtered, washed with ethanol, and dried. In Stage 4b, following the dissolution in water, the solution was clarified. The solution was adjusted to the crystallization temperature and ethanol (ethanol 1 quantity) was added to induce crystallization. Following a hold time, the remainder of the ethanol (ethanol 2 quantity) was added before the slurry or solution was cooled to the isolation temperature. The migalastat hydrochloride was filtered, washed with ethanol, and dried.

Each of the Stage 4 unit operations and process parameters were assessed for their potential impact on the CQAs of migalastat hydrochloride.

Identification of CPPs Impacting the Control of Sodium Chloride

Parameters in the Stage 4 process were assessed for their potential to influence the solubility of sodium chloride, which is soluble in aqueous ethanol mixtures. Table 39 summarizes parameters identified as having the potential to impact the solubility of sodium chloride in both Stage 4a and Stage 4b. The range studied for each parameter is also given. These were defined with reference to solubility data for sodium chloride as well as solubility and metastable limit data for migalastat hydrochloride.

Figure 25:
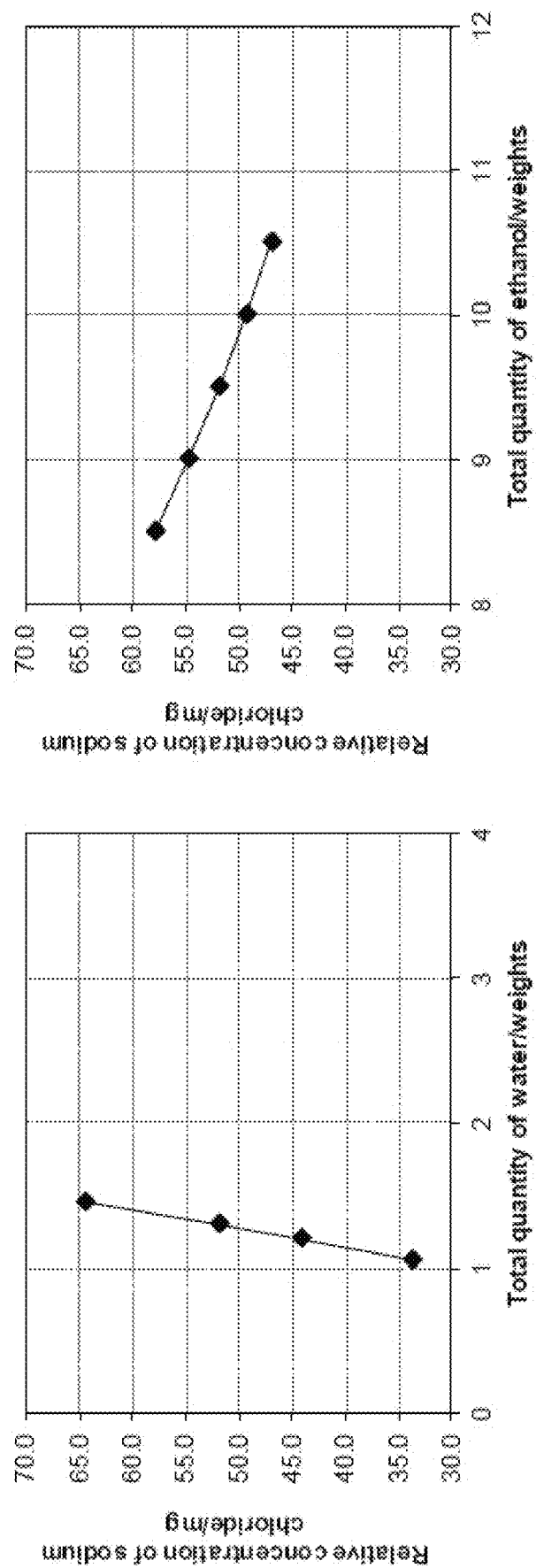
FIG. 25 provides graphical representation of the impact of total quantities of water (left graph) and ethanol (right graph) on the relative concentration of sodium chloride solubilized in a crystallization mixture.

FIG. 25 shows the impact of total quantities of water and ethanol on the relative concentration of sodium chloride solubilized in the crystallization mixture. This shows that a change in the total water quantity between 1.1 and 1.4 weights has a large impact on the concentration of sodium chloride. For this reason, total water quantities in Stage 4a and Stage 4b were assessed to be CPPs for the control of residue on ignition. FIG. 25 also shows that a change in the total ethanol quantity between 8.5 and 10.5 has a smaller impact on the concentration of sodium chloride.

Based on this data, the ranges of from 1.1-1.4 weights were selected for purging of a minimum residue on ignition of 3.5% w/w in each crystallization. This caused the intermediate grade migalastat hydrochloride residue on ignition specification of 7% w/w to be purged in Stages 4a and 4b.

Control of Residual Ethanol in Migalastat Hydrochloride

Ethanol was the main solvent used in the final stage of manufacture and a CQA of migalastat hydrochloride. Low levels of ethanol are generally observed in batches of migalastat hydrochloride. Parameters in the Stage 4b process were assessed for their potential to influence the ethanol content. Table 40 summarizes those parameters identified as having the potential to impact the ethanol content in Stage 4b. The range studied for each parameter is also given. These were set with reference to solubility and metastable limit data for migalastat hydrochloride.

TABLE 39

CPPs in Stage 3

| Parameter | Unit | Setpoint/Target | Range | CQA Impacted |
|---|---|---|---|---|
| Total water quantity | Weights | 1.3 | 1.0-1.6 | Residue on ignition |
| Total ethanol quantity[1] | Weights | 9.5 | 4.8-11.4 | |
| Isolation temperature | ° C. | 20 | 5-35 | |

[1]The Stage 4a parameter of ethanol quantity was equivalent to the sum of the Stage 4b parameters of ethanol 1 quantity and ethanol 2 quantity.

TABLE 40

Parameters and Ranges Assessed for the Control of Ethanol Content

| Parameter | Unit | Setpoint/Target | Range | CQA Impacted |
|---|---|---|---|---|
| Total water quantity | Weights | 1.3 | 1.0-1.6 | Ethanol content |
| Ethanol quantity[1] | Weights | 1.9 | 1.0-11.4 | |
| Ethanol addition time[1] | Minutes | 60 | 0-65 | |
| Ethanol addition temperature[1] | ° C. | 50 | 30-60 | |
| Agitation speed | Rpm | NA | 300-1150 | |

NA = Not applicable;
[1]Prior to introduction of a hold time, the ethanol quantity was considered as a single portion It was demonstrated that the levels of ethanol are strongly impacted by the level of supersaturation at the point of nucleation. In order to control the supersaturation in Stage 4b, a hold time during the addition of ethanol was introduced. Table 41 shows the results of two experiments, both using rapid ethanol addition to generate high supersaturation. In the first experiment, 6 volumes of ethanol were added over 2.5 minutes. This was equivalent to addition of the total ethanol quantity in 5 minutes. In the second experiment, when a 5-minute hold time was incorporated after the addition of the first 1.3 volumes, levels of ethanol were reduced.

TABLE 41

Impact of Hold Time in Stage 4b Process on Ethanol Content

| Details | Ethanol Addition Rate (vols/min) | 5 min Hold Time During Ethanol Addition Utilized | Ethanol Content (% w/w)[1,2] |
|---|---|---|---|
| Rapid ethanol addition without hold time | 2.4 | No | 0.5 |
| Rapid ethanol addition split into 2 portions separated by a 5 min hold time | 2.4 | Yes | 0.2 |

[1]Drug substance specification for ethanol content is not greater than 0.5% w/w;
[2]Migalastat hydrochloride was dried in vacuo to constant weight.

As a result of these data, the hold time, which limited the maximum level of supersaturation, and the ethanol 1 addition time were assessed to be CPPs for the control of ethanol. The parameters of water quantity, ethanol 1 quantity, and ethanol 1 addition temperature were assessed to be CPPs for the control of ethanol content, because the solubility and hence, the level of supersaturation during the crystallization, is strongly impacted by these parameters.

Identification of CPPs and Corresponding Ranges for Control of Ethanol Content

Water quantity, ethanol 1 quantity, ethanol 1 addition temperature, ethanol 1 addition time, and hold time were identified as CPPs for the control of ethanol in Stage 4b as a result of their impact on the supersaturation and nucleation of the system. Table 42 summarizes the ranges that were selected to allow crystallization in Stage 4b whilst preventing high levels of supersaturation. Ranges for water quantity, ethanol 1 quantity, and ethanol 1 addition temperature were defined based on dissolution solubility and metastable limit data. Ranges for ethanol 1 addition time and hold time were defined based on experimental data.

TABLE 42

CPPs and Ranges Impacting the Control of Ethanol in Stage 4

| Stage | CPP | Range | CQA Impacted |
|---|---|---|---|
| 4b | Water quantity | 1.1-1.4 weights | Ethanol content |
| | Ethanol 1 quantity | 1.8-2.0 weights | |
| | Ethanol 1 addition temperature | 40-60° C. | |
| | Ethanol 1 addition time | NLT 5 minutes | |
| | Hold time | NLT 5 minutes | |

NLT = Not less than

Assessment of the Impact of Stage 4 Parameters on the Purging of CQA Impurities

Table 43 shows which of the related impurity CQAs are impacted by Stage 4. Each of these impurities is partially purged in both the Stage 4a and Stage 4b recrystallizations. The genotoxic impurity, Compound X, was demonstrated to be partially purged via the Stage 4 process.

TABLE 43

CQA Impurities Partially Purged in Stage 4

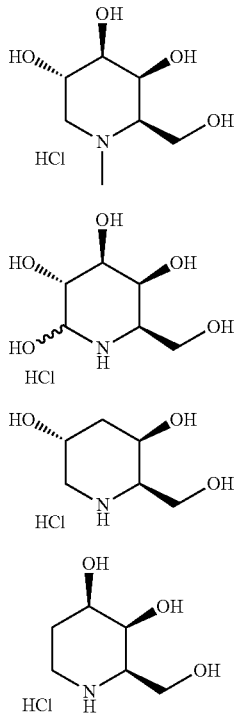

Summary of CQAs Impacted by Stage 4

It was established that the CQA of residue on ignition is controlled in Stages 4a and 4b. The CQA of ethanol is controlled in Stage 4b and the CQAs impurities Compound U, Compound V, Compound Y, and Compound BB are partially purged in both Stage 4a and Stage 4b.

Robustness of the Stage 4a Process

To confirm that the ranges selected for parameters in Stage 4a were appropriate, a fractional factorial study was carried out. Intermediate grade migalastat hydrochloride was used as input. The input residue on ignition was 7% w/w and drug-related impurity CQAs were present at typical levels. In addition to the CPP of water quantity, the parameters of ethanol quantity and isolation temperature, assessed to have an impact on the residue of ignition, were included in the study. Table 44 summarizes the parameters, ranges, and CQAs investigated.

TABLE 44

Parameters and Ranges Selected for the Stage 4a Robustness Study

| Parameter[1] | Range Studied | Output Studied |
|---|---|---|
| Water quantity | 1.1-1.4 weights | Levels of residue on ignition[2], |
| Ethanol quantity | 8.4-10.6 weights | Compound U, Compound W, |
| Isolation temperature | 5-35° C. | Compound V, Compound Y, and Compound BB |

[1]CPPs are highlighted in bold text;
[2]Determined via sodium assay using HILIC/CAD.

Levels of sodium for all the experiments were reduced, with the level removed ranging from 54% to 100%. The highest remaining levels were equal to a residue on ignition of 3.3% w/w. As a minimum residue of ignition of 3.5% w/w is also purged in Stage 4b, this design demonstrated that the identified ranges were appropriate for the control of residue on ignition in Stage 4a. Water quantity was identified as impacting the level of residue on ignition in the design. This confirmed the assessment of water quantity as a CPP and demonstrated that there was no impact of, or interactions with, the other parameters studied. In addition, levels of all drug-related impurity CQAs from the experiments were below the drug substance specification of 0.15% w/w.

Robustness of the Stage 4b Process

A fractional factorial study was carried out to confirm the ranges selected for Stage 4b. Intermediate grade migalastat hydrochloride was used as input. The input residue on ignition was 0.83% w/w and drug-related impurity CQAs were present at typical levels. In addition to the CPPs identified for this stage, other parameters, assessed to have an impact on the CQAs of residual ethanol and residue on ignition, were included in the study. Table 45 summarizes the parameters, ranges, and CQAs investigated.

TABLE 45

Parameters and Ranges Selected for the Stage 4b Robustness Study

| Parameter[1] | Range Studied | Output Studied[2] |
|---|---|---|
| Input quantity of IG migalastat hydrochloride | 0.97-1.03 equivalents | Levels of residue on ignition, ethanol content, |
| Water quantity | 1.1-1.4 weights | Compound U, Compound W, |
| Ethanol 1 addition temperature | 40-60° C. | Compound V, Compound Y, and Compound BB |
| Ethanol 1 quantity | 1.8-2.0 weights | |
| Ethanol 1 addition time | 5-60 minutes | |
| Hold time | 5-60 minutes | |

TABLE 45-continued

Parameters and Ranges Selected for the Stage 4b Robustness Study

| Parameter[1] | Range Studied | Output Studied[2] |
|---|---|---|
| Ethanol 2 quantity | 6.7-8.4 weights | |
| Ethanol 2 addition time | 15-60 minutes | |
| Isolation temperature | 5-35° C. | |

[1]CPPs are highlighted in bold text;
[2]Levels of water were also determined as an output from this study. Levels were <0.10% w/w in all cases.

Material from all the experiments contained levels of residue on ignition at <0.10% w/w, less than the drug substance specification limit of 0.20% w/w. Levels of ethanol ranged from 0.03% to 0.24% w/w, less than the specification limit of 0.5% w/w. In addition, levels of all drug-related impurity CQAs from the experiments were below the drug substance specification of 0.15% w/w.

These studies demonstrated that the investigated ranges were appropriate for the control of residue on ignition and ethanol content in Stage 4. The studies also demonstrated the drug substance specification for CQA impurities was met with a single recrystallization, using typical intermediate grade migalastat hydrochloride as input.

Conclusions: CPPs Identified for Stage 4

The CPPs and the corresponding ranges for Stage 4 are listed in Table 46. A further series of experiments verified the ranges for Stage 4a and Stage 4b and also the impact of including intermediate grade migalastat hydrochloride at the specification limit for CQA impurities and residue on ignition.

TABLE 46

CPPs in Stage 4

| Stage | CPP | Range | CQA Impacted |
|---|---|---|---|
| 4a | Water quantity | 1.1-1.4 weights | Residue on ignition |
| 4b | Water quantity | 1.1-1.4 weights | Ethanol, residue on ignition |
| | Ethanol 1 quantity | 1.8-2.0 weights | Ethanol |
| | Ethanol 1 addition temperature | 40-60° C. | |
| | Ethanol 1 addition time | NLT 5 minutes | |
| | Hold time | NLT 5 minutes | |

NLT = Not less than

Summary of CPPs and Corresponding Ranges for the Manufacture of Migalastat Hydrochloride Following completion of the development activities to identify CPPs and appropriate ranges, the risk assessment was updated with the information that had been generated. Those parameters established as impacting upon CQAs were reassessed for the severity of that impact and were then categorized as CPPs or PPs. The CPPs and their corresponding ranges for the manufacturing process for migalastat hydrochloride drug substance are listed in Table 47.

TABLE 47

CPPs and Corresponding Ranges for the Manufacture of Migalastat Hydrochloride

| Stage | CPP | Range | Unit | CQA Impacted | Other Known Attributes Impacted |
|---|---|---|---|---|---|
| 3a | Palladium catalyst quantity | 0.007-0.013 | Molar equivalents | Compound U Compound Y | — |
| | Time | 44-68 | Hours | Compound V | |
| | Temperature | 40-50 | ° C. | | |
| | Hydrogen pressure | 8-10 | Bar (abs) | | |
| | Methanol volumes | 7-9 | Volumes | | |
| 3b | Residual weight after distillation | NLT 0.5 | Weights | — | Compound X |
| | Age time | NMT 10 | Hours | | |
| | Age temperature | 40-55 | ° C. | | |
| | Filtration temperature | 25-40 | ° C. | Residue on ignition | — |
| 3c | Time for ethanol addition | NLT 30 | Minutes | Compound U Compound Y | — |
| | Temperature | NLT 15 | ° C. | Compound BB | |

TABLE 47-continued

CPPs and Corresponding Ranges for the Manufacture of Migalastat Hydrochloride

| Stage | CPP | Range | Unit | CQA Impacted | Other Known Attributes Impacted |
|---|---|---|---|---|---|
| 4a | Water quantity | 1.1-1.4 | Weight | Residue on ignition | |
| 4b | Water quantity | 1.1-1.4 | Weight | Residue on ignition and ethanol | |
| | Ethanol 1 quantity | 1.8-2.0 | Weight | | |
| | Ethanol 1 addition time | NLT 5 | Minutes | | |
| | Ethanol 1 addition temperature | 40-60 | °C. | | |
| | Hold time | NLT 5 | Minutes | | |

NLT = Not less than;
NMT = Not more than

Commercial Control Strategy

To confirm that the manufacture activities delivered a suitable product, an appropriate control strategy was implemented that included the following: Procedural controls—Controls provided by the nature of the GMP; Attribute controls—These controls were provided through the specification of each reagent, starting material, intermediate, and the drug substance; Parametric controls—These include the CPPs and their associated ranges. The control strategy for each CQA in migalastat hydrochloride drug substance is summarized in Table 48.

TABLE 48

Summary of control strategy

| CQA | Stage or Material | Control Element | Details of Control | Range or Limit |
|---|---|---|---|---|
| Description | Migalastat hydrochloride | Specification | Description | White to pale brown crystal |
| Identity | | Specification | Identity | Concordant with reference material |
| Migalastat hydrochloride content | | Specification | Migalastat hydrochloride content | 98.0-102.0% w/w |
| [structure] | IG migalastat hydrochloride | Specification | Compound W | NGT 0.15% w/w |
| | Migalastat hydrochloride | Specification | | NGT 0.15% w/w |
| [structure] | Stage 3a | CPP | Palladium catalyst quantity | 0.007-0.013 equiv. |
| | | | Time | 44-68 hrs |
| | | | Temperature | 40-50° C. |
| | | | Hydrogen pressure | 8-10 bar |
| | Stage 3c | CPP | Temperature | NLT 30° C. |
| | | | Time for ethanol addition | NLT 30 min |
| | IG migalastat hydrochloride | Specification | Compound U | NGT 0.4% w/w |
| | Migalastat hydrochloride | Specification | Compound U | NGT 0.15% w/w |
| [structure] | 5-azido-5-deoxy-1,2,3,6-tetrapivaloyl-D-galactofuranoside | Specification | DMSO content | <0.01% w/w |
| | Stage 3a | CPP | Palladium catalyst quantity | 0.007-0.013 equiv. |
| | | | Temperature | 40-50° C. |
| | | | Hydrogen pressure | 8-10 bar |
| | Stage 3c | CPP | Temperature | NLT 30° C. |
| | | | Time for ethanol addition | NLT 30 min |

TABLE 48-continued

Summary of control strategy

| CQA | Stage or Material | Control Element | Details of Control | Range or Limit |
|---|---|---|---|---|
| | IG migalastat hydrochloride | Specification | Compound Y | 0.25% w/w |
| | Migalastat hydrochloride | Specification | Compound Y | 0.15% w/w |
| | Stage 3c | CPP | Temperature Time for ethanol addition | NLT 30° C. NLT 30 min |
| | IG migalastat hydrochloride | Specification | Compound BB | 0.3% w/w |
| | Migalastat hydrochloride | Specification | Compound BB | 0.15% w/w |
| Methanol and ethanol content | Stage 4b | CPP | Water quantity | 1.1-1.4 wts |
| | | | Ethanol 1 quantity | 1.8-2.0 wts |
| | | | Ethanol 1 addition time | NLT 5 min |
| | | | Ethanol 1 addition temp | 40-60° C. |
| | | | Hold time | NLT 5 min |
| | Migalastat hydrochloride | Specification | Methanol and ethanol content | 0.3% w/w and 0.5% w/w |
| Water content | Migalastat hydrochloride | Specification | Water content | 0.2% w/w |
| Heavy metals content | Migalastat hydrochloride | Specification | Heavy metals content | 20 mcg/g |
| Residue on ignition | Stage 3b | CPP | Filtration temperature | 25-40° C. |
| | IG migalastat hydrochloride | Specification | Residue on ignition | 7% w/w |
| | Stage 4a | CPP | Water quantity | 1.1-1.4 wts |
| | Stage 4b | CPP | Water quantity | 1.1-1.4 wts |
| | Migalastat hydrochloride | Specification | Residue on ignition | 0.2% w/w |
| Palladium content | Migalastat hydrochloride | Specification | Palladium content | NGT 10 ppm |

NGT = Not greater than; NLT = Not less than

Example 13: Small-Scale Verification Experiments

Verification experiments were conducted for some stages of the manufacturing process to verify that the overall control strategy would deliver intermediates and drug substance meeting specification, and that the ranges defined for CPPs in Stages 3 and 4 are appropriate in the extreme case where impurities are introduced at their specification limits.

The control strategy for the drug-related impurity CQAs was verified for Stages 3 and 4. In addition, studies were conducted to verify the control of residue on ignition in Stages 3 and 4 and the control of ethanol content in Stage 4.

Process impurities impacting CQAs were spiked, where appropriate, at their specification limits in the input materials. At the same time, the CPPs were set at forcing extremes of the ranges most likely to create failure in meeting output specifications (for this reason, not all of the CPPs were run at the limits of their ranges).

Stage 3 Verification Experiments

The objective of the verification experiments for Stage 3 was to demonstrate that the ranges defined for CPPs in Stage 3 will deliver migalastat hydrochloride which meets specification. This is achieved by selecting settings for the PARs which will increase levels of those CQAs impacted by Stage 3. Stage 3 impacts the drug-related impurity CQAs Compound U, Compound V, Compound W, Compound BB, and Compound Y. Stage 3 also impacts the genotoxin Compound X and the residue on ignition of migalastat hydrochloride.

The following verification experiments were undertaken: Experiment A—to confirm that migalastat hydrochloride produced did not fail drug substance specification under conditions selected to increase levels of Compound U, Compound Y, and Compound X; Experiments B and D—to confirm that migalastat hydrochloride produced did not fail drug substance specification under conditions selected to increase levels of Compound V; Experiment C—to confirm that migalastat hydrochloride produced did not fail drug substance specification under conditions selected to increase levels of Compound Y and residue on ignition.

Compound AA, Compound AA, and Compound W are potentially formed in Stage 3, but there are no CPPs for their control. The conditions employed in the Stage 3 experiments are provided in Table 49, alongside the ranges for each CPP and the current process setpoints. DMSO, which impacts the levels of Compound Y, was spiked at its specification limit of 0.01% w/w in experiments A and C. In addition, 35% w/w hydrochloric acid was used in all of the experiments to maximize the impact on residue on ignition. The intermediate grade migalastat hydrochloride produced in these experiments was recrystallized in Stage 4. Analytical data for the intermediate grade migalastat hydrochloride produced in these experiments are provided in Table 50. Data for the subsequent drug substance are provided in Table 51.

For experiments A and C, the intermediate grade migalastat hydrochloride produced after Stage 3 met specification. Furthermore, the drug substance produced after the intermediate grade migalastat hydrochloride was recrystallized in Stage 4 met the specification.

In experiment D, where the CPPs were fixed at setpoints, a higher level of Compound V was observed. In Experiment D, each of the CPPs was at the limit of the specified range. The migalastat hydrochloride produced after recrystallization in Stage 4 met the specification limit for Compound V.

Overall, the experiments verify that the control strategy established for Stage 3 will deliver migalastat hydrochloride within specification. In addition, the results verify that the CPPs have been correctly identified, as levels of the CQAs were increased under the experimental conditions.

TABLE 49

Summary of conditions for Stage 3 verification experiments

| Stage | CPP | Unit | Normal Target/ Setpoint | Range | Experiment A | Experiment B | Experiment C | Experiment D |
|---|---|---|---|---|---|---|---|---|
| 3a | Palladium catalyst quantity | Equiv | 0.01 | 0.007-0.013 | 0.007 | 0.013 | 0.007 | 0.013 |
|  | Time for Stage 3a | Hours | NLT 44 | 44-68 | 44 | 68 | 68 | 44 |
|  | Temperature in Stage 3a | °C. | 45 | 40-50 | 40 | 45 | 40 | 45 |
|  | Pressure in Stage 3a | Barg | 9 | 8-10 | 7 | 8 | 8 | 8 |
|  | Methanol volumes | Volumes | 8 | 7-9 | 8 | 9 | 9 | 9 |
| 3b | Residual weight after distillation | Weights | 0.7 | NLT 0.5 | 0.5 | 0.7 | 0.7 | 0.7 |
|  | Age time | Hours | NLT 1 | NMT 10 | 10 | 5.5 | 5.5 | 5.5 |
|  | Age temperature | °C. | 50 | 40-55 | 50-55 | 45-50 | 45-50 | 45-50 |
|  | Filtration temperature | °C. | 35 | 25-40 | 30-35 | 30-35 | 35-40 | 30-35 |
| 3c | Temperature | °C. | 25 | NLT 15 | 15 | 15 | 15 | 15 |
|  | Time for ethanol addition | Minutes | NLT 5 | NLT 30 | 30 | 30 | 30 | 30 |
|  | Migalastat hydrochloride CQAs and other attributes stressed to potentially challenge process |  |  |  | Compound U, Compound Y, and Compound X | Compound V | Compound Y and residue on ignition | Compound V |

NLT = Not less than;
NMT = Not more than

TABLE 50

Results of Stage 3 verification experiments

| Attribute of Intermediate Grade Migalastat Hydrochloride[1] | CQA | Specification Limit in IG Migalastat Hydrochloride (% w/w) | Experiment A (% w/w) | Experiment B (% w/w) | Experiment C (% w/w) | Experiment D (% w/w) |
|---|---|---|---|---|---|---|
| Compound W | Y | 0.15 | ND | 0.13 | ND | ND |
| Compound U | Y | 0.4 | 0.35 | <0.05 | 0.37 | 0.05 |
| Compound AA | N | 0.15 | 0.06 | 0.05 | 0.06 | 0.05 |
| Compound Z | N | 0.25 | 0.20 | 0.14 | 0.18 | 0.20 |
| Any unspecified impurity[2] | N | 0.10 | 0.06 | <0.05 | <0.05 | <0.05 |
| Total impurities | N | 1.5 | 0.67 | 0.32 | 0.61 | 0.31 |
| Compound V | Y | 0.40 | 0.05 | 0.25 | 0.06 | 0.29 |
| Compound Y | Y | 0.25 | 0.08 | 0.05 | 0.14 | 0.07 |
| Compound BB | Y | 0.3 | 0.28 | 0.23 | 0.24 | 0.27 |
| Compound X[2] | N | NA (mcg/g) | 31 mcg/g[3] | 10.6 mcg/g | 2.6 mcg/g | 18 mcg/g |
| Residue on ignition | Y | 7 | 1.0 | 0.95 | 1.9 | 1.1 |

NA = Not applicable;

ND = Not detected;

[1]CQAs are highlighted in bold text;

[2]Not included on the specification for intermediate grade migalastat hydrochloride;

[3]This level is approximate, as the method for quantification of Compound X is validated for levels up to 18 mcg/g.

TABLE 51

Results of Stage 4b recrystallization of Stage 3 verification experiments

| Attribute of Intermediate Grade Migalastat Hydrochloride[1] | CQA | Specification Limit in IG Migalastat Hydrochloride (% w/w) | Experiment A (% w/w) | Experiment B (% w/w) | Experiment C (% w/w) | Experiment D (% w/w) |
|---|---|---|---|---|---|---|
| Compound W | Y | 0.15 | ND | 0.06 | ND | ND |
| Compound U | Y | 0.15 | <0.05 | ND | <0.05 | ND |
| Compound AA | N | 0.10[2] | ND | ND | ND | ND |
| Compound Z | N | 0.10[2] | ND | ND | ND | ND |
| Any unspecified impurity[3] | N | 0.10 | ND | ND | ND | ND |
| Total impurities[4] | N | 0.5 | <0.05 | 0.06 | <0.05 | ND |
| Compound V | Y | 0.15 | <0.05 | 0.08 | <0.05 | 0.09 |
| Compound Y | Y | 0.15 | <0.05 | ND | <0.05 | <0.05 |
| Compound BB | Y | 0.15 | <0.05 | ND | <0.05 | <0.05 |
| Compound X | N | 12 (mcg/g) | 6.1 mcg/g | 1.4 mcg/g | NGT 1.0 mcg/g | 3.2 mcg/g |
| Residue on ignition | Y | 0.2 (% w/w) | <0.1 | <0.1 | <0.1 | <0.1 |

ND = Not detected;
NGT = Not greater than;
[1]Drug-related impurity CQAs are highlighted in bold text;
[2]Controlled under unspecified impurities limit;
[3]Levels of the epimers Compound A, Compound EE, Compound DD, and Compound CC were all <0.1% w/w in these batches;
[4]The total impurities limit is determined by the drug-related impurities content by HPLC method only and exclude the Compound V, Compound Y, and Compound BB content determined by HPLC.

Stage 4 Verification Experiments

Stage 4 controls the residue on ignition and ethanol content of migalastat hydrochloride, and impacts the drug-related impurity CQAs Compound U, Compound V, Compound Y, and Compound BB. The objective of the verification experiments was to confirm that, at the extremes of the Control Strategy for each CQA impacted by Stage 4, the migalastat hydrochloride produced did not fail the drug substance specification. The experiments were designed to combine CQAs at their specification limit in intermediate grade migalastat hydrochloride with the combination of setpoints for CPPs most likely to cause failure to meet drug substance specification. The following verification experiments were undertaken:

Experiment A—to confirm that migalastat hydrochloride, produced when incorporating levels of Compound W and Compound U at or above their specification limit in intermediate grade migalastat hydrochloride, did not fail drug substance specification. Processing under atypical conditions was used to generate the required levels of Compound U in the intermediate grade migalastat hydrochloride. To confirm the impact of incorporating Compound V, Compound Y, and Compound BB at their specification limit in intermediate grade migalastat hydrochloride with a standard impurity profile, experiment D was also carried out. Experiment B—to confirm that migalastat hydrochloride, produced when incorporating levels of residue on ignition at the specification limit in intermediate grade migalastat hydrochloride, did not fail drug substance specification under conditions designed to maximize levels of residue on ignition and ethanol content. Experiment C—to confirm that migalastat hydrochloride produced did not fail drug substance specification under conditions designed to maximize levels of ethanol content. Stage 4a was not carried out on Experiment C. Experiment D—to confirm that migalastat hydrochloride, produced when incorporating levels of Compound V, Compound Y, and Compound BB at significantly higher levels than typical in intermediate grade migalastat hydrochloride, did not fail drug substance acceptance criteria.

Table 52 shows a summary of the conditions employed in Stage 4 verification experiments. Table 53 shows the analytical data from the migalastat hydrochloride isolated from these experiments.

TABLE 52

Summary of conditions for Stage 4 verification experiments

| Stage | CPP | Unit | Setpoint/ Target | Range | Experiment A | Experiment B | Experiment C | Experiment D |
|---|---|---|---|---|---|---|---|---|
| 4a | Water quantity | Weights | 1.3 | 1.1-1.4 | 1.1 | 1.1 | NA | 1.1 |
| 4b | Water quantity | Weights | 1.3 | 1.1-1.4 | 1.1 | 1.1 | 1.4 | 1.1 |
|  | Ethanol 1 quantity | Weights | 1.9 | 1.8-2.0 | 2.0 | 2.0 | 1.8 | 2.0 |
|  | Ethanol 1 addition time | Minutes | NLT 5 | NLT 5 | 5 | 5 | 5 | 5 |
|  | Ethanol 1 addition temperature | °C. | 50 | 40-60 | 40 | 40 | 60 | 40 |
|  | Hold time | Minutes | NLT 5 | NLT 5 | 5 | 5 | 5 | 5 |
|  | Migalastat hydrochloride CQAs stressed to potentially fail drug substance specification |  |  |  | Compound W Compound U | Residue on ignition and ethanol content | Ethanol content | Compound V, Compound Y, and Compound BB |

NA = Not applicable;
NLT = Not less than

TABLE 53

Spiking Levels and Results of Stage 4 Verification Experiments

| Attribute of Migalastat Hydrochloride[1] | CQA | Specification Limit in IG Migalastat HCl (% w/w) | Specification Limit in Migalastat HCl (% w/w) | Experiment A Input | Experiment A Output | Experiment B Input | Experiment B Output | Experiment C Input | Experiment C Output | Experiment D Input | Experiment D Output |
|---|---|---|---|---|---|---|---|---|---|---|---|
| Compound W | Y | 0.15 | 0.15 | 0.12 | 0.13 | <0.05 | <0.05 | <0.05 | <0.05 | ND | ND |
| Compound U | Y | 0.4 | 0.15 | 0.59 | 0.06 | ND | ND | ND | ND | ND | ND |
| Compound AA[2] | N | 0.15 | 0.10 | 0.41 | ND | ND | ND | ND | ND | <0.05 | ND |
| Compound Z[2] | N | 0.25 | 0.10 | 0.70 | ND | ND | ND | ND | ND | 0.27 | ND |
| Any other impurity | N | 0.10 | 0.10 | 0.15 | <0.05 | ND | ND | ND | ND | 0.06 | ND |
| Total impurities[3] | N | 1.5 | 0.50 | 1.97 | 0.19 | <0.05 | <0.05 | <0.05 | <0.05 | 0.32 | ND |
| Compound V | Y | 0.40 | 0.15 | 0.13 | 0.11 | 0.06 | <0.05 | 0.06 | 0.07 | 0.41 | 0.12 |
| Compound Y | Y | 0.25 | 0.15 | 1.42 | 0.54[4] | <0.05 | ND | <0.05 | ND | 0.32 | <0.05 |
| Compound BB | Y | 0.3 | 0.15 | 0.22 | <0.05 | <0.05 | ND | <0.05 | ND | 0.22 | ND |
| Residue on ignition | Y | 7 | 0.20 | 1.4 | <0.10 | 7.0 | <0.10 | — | <0.10 | 0.28[5] | <0.10 |
| Ethanol | Y | NA | 0.50 | NA | 0.07 | NA | 0.07 | NA | 0.23 | NA | 0.10 |

NA = Not applicable;
ND = Not detected;
[1]Drug-related impurity CQAs are highlighted in bold text;
[2]Controlled in intermediate grade migalastat hydrochloride and migalastat hydrochloride under any unspecified impurity;
[3]The total impurities limit is determined by the drug-related impurities content by HPLC method only and exclude the Compound V, Compound Y, and Compound BB content determined by HPLC;
[4]Due to the conditions used to generate the required levels of Compound U in this experiment, the input level of Compound Y was significantly higher than the intermediate grade migalastat hydrochloride specification limit;
[5]Residue on ignition calculated from constituent input materials.

As shown by the output data in Table 53, except for the level of Compound Y in Experiment A, the migalastat hydrochloride produced met the specification. Due to the conditions used to generate the required level of Compound U in Experiment A, the input level of Compound Y was significantly higher than its specification limit in intermediate grade migalastat hydrochloride. Experiment D was, therefore, also carried out to ensure that the specification limits for Compound Y, Compound V, and Compound BB in intermediate grade migalastat hydrochloride specification were appropriate. The experiments verified that the specification limits for intermediate grade migalastat hydrochloride and the CPP ranges defined for Stage 4 deliver migalastat hydrochloride that meets the drug substance specification.

TABLE 54

Reference Table for Chemical Structures

| Reference No. | Chemical Structure |
|---|---|
| D-(+)-galactose | (structure) |
| 1,2,3,6-tetrapivaloyl-D-galactofuranoside | (structure) |
| 5-azido-5-deoxy-1,2,3,6-tetrapivaloyl-D-galactofuranoside | (structure) |
| migalastat hydrochloride | (structure) |
| L-altrose | (structure) |
| Glucose | (structure) |
| Glycerol | (structure) |

TABLE 54-continued

Reference Table for Chemical Structures

| Reference No. | Chemical Structure |
|---|---|
| Compound A | (piperidine triol with CH2OH) |
| Lactic acid | CH3-CH(OH)-COOH |
| Compound B | furanose with PivO, HO, HO, OPiv, OPiv |
| Compound C | furanose with PivO, PivO, PivO, OPiv, OPiv |
| Compound D | furanose with PivO, TfO, PivO, OPiv, OPiv |
| Compound E | furanose with PivO, HO, PivO, OPiv, OPiv |
| Compound F | furanose with PivO, TfO, PivO, OPiv, OPiv |
| Compound G | furanose with HO, PivO, PivO, OPiv, OPiv |
| Compound H | furanose with PivO-CH2-CH2 (wavy bond), PivO, OPiv, OPiv |
| Compound I | furanose with PivO-CH=, PivO, OPiv, OPiv |
| Compound J | disaccharide-like structure with acetonide, PivO, OPiv groups |
| Compound K | furanose with PivO-CH=CH-, PivO, OPiv, OPiv |
| Compound L | furanose with N3-CH2-, PivO, PivO, OPiv, OPiv |
| Compound M | furanose with pyridinium-CH2-, PivO, PivO, OPiv, OPiv |
| Compound N | furanose with PivO, N3, PivO, OPiv, OPiv |
| Compound O | furanose with RO, N3, RO, OR, OR |

TABLE 54-continued

Reference Table for Chemical Structures

| Reference No. | Chemical Structure |
|---|---|
| R = | (pivaloyl and 2,2-dimethylbutanoyl groups, 3:1 ratio) |
| Compound P | 5-azido-tetrahydropyran-2,3,4-triol with hydroxymethyl |
| Compound Q | azido furanose triol with hydroxymethyl |
| Compound R | amino furanose with OPiv groups and PivO-CH2 |
| Compound S | piperidine with OPiv, OH, OPiv, CH2OPiv substituents |
| Compound T | piperidine with OPiv, OH, OPiv, OPiv, CH2OPiv substituents |
| Compound U | iminosugar hexitol · HCl |
| Migalastat | 1,5-dideoxy-1,5-imino-D-galactitol |
| Compound V | N-methyl piperidine tetraol · HCl |
| Compound W | piperidine triol carboxylic acid · HCl |
| Compound X | piperidine triol with CH2Cl · HCl |
| Compound Y | piperidine diol with CH2OH · HCl |
| Compound Z | piperidine-3-ol with CH2OH · HCl |
| Compound AA | piperidine-3,5-diol with CH2OH · HCl |
| Compound BB | piperidine-3,4-diol with CH2OH · HCl |
| Compound CC | piperidine-3,4,5-triol with CH2OH · HCl |

TABLE 54-continued

Reference Table for Chemical Structures

| Reference No. | Chemical Structure |
|---|---|
| Compound DD | 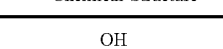 |
| Compound EE | 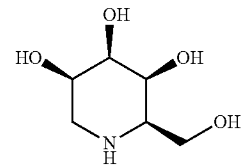 [SMILES: OC[C@H]1NC[C@@H](O)[C@@H](O)[C@H]1O] |

TABLE 55

HEK Amenable Mutations

| DNA Change (Long) | DNA Change (Short) | Protein Change (1-letter Code) | Protein Change (3-letter Code) |
|---|---|---|---|
| c.7C > G | c.C7G | p.(L3V) | p.(Leu3Val) |
| c.8T > C | c.T8C | p.(L3P) | p.(Leu3Pro) |
| c.[11G > T; 620A > C] | c.G11T/A620C | p.(R4M/Y207S) | p.(Arg4Met/Tyr207Ser) |
| c.37G > A | c.G37A | p.(A13T) | p.(Ala13Thr) |
| c.37G > C | c.G37C | p.(A13P) | p.(Ala13Pro) |
| c.43G > A | c.G43A | p.(A15T) | p.(Ala15Thr) |
| c.44C > G | c.C44G | p.(A15G) | p.(Ala15Gly) |
| c.53T > G | c.T53G | p.(F18C) | p.(Phe18Cys) |
| c.58G > C | c.G58C | p.(A20P) | p.(Ala20Pro) |
| c.59C > A | c.C59A | p.(A20D) | p.(Ala20Asp) |
| c.65T > G | c.T65G | p.(V22G) | p.(Val22Gly) |
| c.70T > C or c.70T > A | c.T70C or c.T70A | p.(W24R) | p.(Trp24Arg) |
| c.70T > G | c.T70G | p.(W24G) | p.(Trp24Gly) |
| c.72G > C or c.72G > T | c.G72C or c.G72T | p.(W24C) | p.(Trp24Cys) |
| | | p.(A29D) | p.(Ala29Asp) |
| c.95T > C | c.T95C | p.(L32P) | p.(Leu32Pro) |
| c.97G > T | c.G97T | p.(D33Y) | p.(Asp33Tyr) |
| c.98A > G | c.A98G | p.(D33G) | p.(Asp33Gly) |
| c.100A > C | c.A100C | p.(N34H) | p.(Asn34His) |
| c.100A > G | c.A100G | p.(N34D) | p.(Asn34Asp) |
| c.101A > C | c.A101C | p.(N34T) | p.(Asn34Thr) |
| c.101A > G | c.A101G | p.(N34S) | p.(Asn34Ser) |
| c.102T > G or c.102T > A | c.T102G or c.T102A | p.(N34K) | p.(Asn34Lys) |
| c.103G > C or c.103G > A | c.G103C or c.G103A | p.(G35R) | p.(Gly35Arg) |
| c.104G > A | c.G104A | p.(G35E) | p.(Gly35Glu) |
| c.104G > T | c.G104T | p.(G35V) | p.(Gly35Val) |
| c.107T > C | c.T107C | p.(L36S) | p.(Leu36Ser) |
| c.107T > G | c.T107G | p.(L36W) | p.(Leu36Trp) |
| c.108G > C or c.108G > T | c.G108C or c.G108T | p.(L36F) | p.(Leu36Phe) |
| c.109G > A | c.G109A | p.(A37T) | p.(Ala37Thr) |
| c.110C > T | c.C110T | p.(A37V) | p.(Ala37Val) |
| | | p.(R112L) | p.(Arg112Leu) |
| c.122C > T | c.C122T | p.(T41I) | p.(Thr41Ile) |
| c.124A > C or c.124A > T | c.A124C or c.A124T | p.(M42L) | p.(Met42Leu) |
| c.124A > G | c.A124G | p.(M42V) | p.(Met42Val) |
| c.125T > A | c.T125A | p.(M42K) | p.(Met42Lys) |
| c.125T > C | c.T125C | p.(M42T) | p.(Met42Thr) |
| c.125T > G | c.T125G | p.(M42R) | p.(Met42Arg) |
| c.126G > A or c.126G > C or c.126G > T | c.G126A or c.G126C or c.G126T | p.(M42I) | p.(Met42Ile) |
| c.137A > C | c.A137C | p.(H46P) | p.(His46Pro) |
| c.142G > C | c.G142C | p.(E48Q) | p.(Glu48Gln) |
| c.152T > A | c.T152A | p.(M51K) | p.(Met51Lys) |
| c.153G > A or c.153G > T or c.153G > C | c.G153A or c.G153T or c.G153C | p.(M51I) | p.(Met51Ile) |
| c.[157A > C; 158A > T] | c.A157C/A158T | p.(N53L) | p.(Asn53Leu) |
| c.157A > G | c.A157G | p.(N53D) | p.(Asn53Asp) |
| c.160C > T | c.C160T | p.(L54F) | p.(Leu54Phe) |
| c.161T > C | c.T161C | p.(L54P) | p.(Leu54Pro) |
| c.164A > G | c.A164G | p.(D55G) | p.(Asp55Gly) |
| c.164A > T | c.A164T | p.(D55V) | p.(Asp55Val) |
| c.[164A > T; 170A > T] | c.A164T/A170T | p.(D55V/Q57L) | p.(Asp55Val/Gln57Leu) |
| c.167G > A | c.G167A | p.(C56Y) | p.(Cys56Tyr) |
| c.167G > T | c.G167T | p.(C56F) | p.(Cys56Phe) |
| c.170A > T | c.A170T | p.(Q57L) | p.(Gln57Leu) |
| c.175G > A | c.G175A | p.(E59K) | p.(Glu59Lys) |
| c.178C > A | c.C178A | p.(P60T) | p.(Pro60Thr) |
| c.178C > T | c.C178T | p.(P60S) | p.(Pro60Ser) |

TABLE 55-continued

HEK Amenable Mutations

| DNA Change (Long) | DNA Change (Short) | Protein Change (1-letter Code) | Protein Change (3-letter Code) |
|---|---|---|---|
| c.179C > T | c.C179T | p.(P60L) | p.(Pro60Leu) |
| c.196G > A | c.G196A | p.(E66K) | p.(Glu66Lys) |
| c.197A > G | c.A197G | p.(E66G) | p.(Glu66Gly) |
| c.207C > A or c.207C > G | c.C207A or c.C207G | p.(F69L) | p.(Phe69Leu) |
| c.214A > G | c.A214G | p.(M72V) | p.(Met72Val) |
| c.216G > A or c.216G > T or c.216G > C | c.G216A or c.G216T or c.G216C | p.(M72I) | p.(Met72Ile) |
| c.218C > T | c.C218T | p.(A73V) | p.(Ala73Val) |
| c.227T > C | c.T227C | p.(M76T) | p.(Met76Thr) |
| c.239G > A | c.G239A | p.(G80D) | p.(Gly80Asp) |
| c.239G > T | c.G239T | p.(G80V) | p.(Gly80Val) |
| c.247G > A | c.G247A | p.(D83N) | p.(Asp83Asn) |
| c.253G > A | c.G253A | p.(G85S) | p.(Gly85Ser) |
| c.[253G > A; 254G > A] | c.G253A/G254A | p.(G85N) | p.(Gly85Asn) |
| c.[253G > A; 254G > T; 255T > G] | c.G253A/G254T/T255G | p.(G85M) | p.(Gly85Met) |
| c.254G > A | c.G254A | p.(G85D) | p.(Gly85Asp) |
| c.261G > C or c.261G > T | c.G261C or c.G261T | p.(E87D) | p.(Glu87Asp) |
| c.265C > T | c.C265T | p.(L89F) | p.(Leu89Phe) |
| c.272T > C | c.T272C | p.(I91T) | p.(Ile91Thr) |
| c.288G > A or c.288G > T or c.288G > C | c.G288A or c.G288T or c.G288C | p.(M96I) | p.(Met96Ile) |
| c.289G > C | c.G289C | p.(A97P) | p.(Ala97Pro) |
| c.290C > T | c.C290T | p.(A97V) | p.(Ala97Val) |
| c.305C > T | c.C305T | p.(S102L) | p.(Ser102Leu) |
| c.311G > T | c.G311T | p.(G104V) | p.(Gly104Val) |
| c.316C > T | c.C316T | p.(L106F) | p.(Leu106Phe) |
| c.320A > G | c.A320G | p.(Q107R) | p.(Gln107Arg) |
| c.322G > A | c.G322A | p.(A108T) | p.(Ala108Thr) |
| c.326A > G | c.A326G | p.(D109G) | p.(Asp109Gly) |
| c.334C > G | c.C334G | p.(R112G) | p.(Arg112Gly) |
| c.335G > A | c.G335A | p.(R112H) | p.(Arg112His) |
| c.337T > A | c.T337A | p.(F113I) | p.(Phe113Ile) |
| c.337T > C or c.339T > A or c.339T > G | c.T337C or c.T339A or c.T339G | p.(F113L) | p.(Phe113Leu) |
| c.352C > T | c.C352T | p.(R118C) | p.(Arg118Cys) |
| c.361G > A | c.G361A | p.(A121T) | p.(Ala121Thr) |
| c.368A > G | c.A368G | p.(Y123C) | p.(Tyr123Cys) |
| c.373C > T | c.C373T | p.(H125Y) | p.(His125Tyr) |
| c.374A > T | c.A374T | p.(H125L) | p.(His125Leu) |
| c.376A > G | c.A376G | p.(S126G) | p.(Ser126Gly) |
| c.383G > A | c.G383A | p.(G128E) | p.(Gly128Glu) |
| c.399T > G | c.T399G | p.(I133M) | p.(Ile133Met) |
| c.404C > T | c.C404T | p.(A135V) | p.(Ala135Val) |
| c.408T > A or c.408T > G | c.T408A or c.T408G | p.(D136E) | p.(Asp136Glu) |
| c.416A > G | c.A416G | p.(N139S) | p.(Asn139Ser) |
| c.419A > C | c.A419C | p.(K140T) | p.(Lys140Thr) |
| c.427G > A | c.G427A | p.(A143T) | p.(Ala143Thr) |
| c.431G > A | c.G431A | p.(G144D) | p.(Gly144Asp) |
| c.431G > T | c.G431T | p.(G144V) | p.(Gly144Val) |
| c.434T > C | c.T434C | p.(F145S) | p.(Phe145Ser) |
| c.436C > T | c.C436T | p.(P146S) | p.(Pro146Ser) |
| c.437C > G | c.C437G | p.(P146R) | p.(Pro146Arg) |
| c.454T > C | c.T454C | p.(Y152H) | p.(Tyr152His) |
| c.454T > G | c.T454G | p.(Y152D) | p.(Tyr152Asp) |
| c.455A > G | c.A455G | p.(Y152C) | p.(Tyr152Cys) |
| c.466G > A | c.G466A | p.(A156T) | p.(Ala156Thr) |
| c.466G > T | c.G466T | p.(A156S) | p.(Ala156Ser) |
| c.467C > T | c.C467T | p.(A156V) | p.(Ala156Val) |
| c.471G > C or c.471G > T | c.G471C or c.G471T | p.(Q157H) p.(F159C) | p.(Gln157His) p.(Phe159Cys) |
| c.484T > G | c.T484G | p.(W162G) | p.(Trp162Gly) |
| c.493G > C | c.G493C | p.(D165H) | p.(Asp165His) |
| c.494A > G | c.A494G | p.(D165G) | p.(Asp165Gly) |
| c.496_497delinsTC | c.496_497delinsTC | p.(L166S) | p.(Leu166Ser) |
| c.496C > G | c.C496G | p.(L166V) | p.(Leu166Val) |
| c.[496C > G; 497T > G] | c.C496G/T497G | p.(L166G) | p.(Leu166Gly) |
| c.499C > G | c.C499G | p.(L167V) | p.(Leu167Val) |
| c.506T > C | c.T506C | p.(F169S) | p.(Phe169Ser) |
| c.511G > A | c.G511A | p.(G171S) | p.(Gly171Ser) |
| c.520T > C | c.T520C | p.(C174R) | p.(Cys174Arg) |
| c.520T > G | c.T520G | p.(C174G) | p.(Cys174Gly) |
| c.525C > G or c.525C > A | c.C525G or c.C525A | p.(D175E) | p.(Asp175Glu) |
| c.539T > G | c.T539G | p.(L180W) | p.(Leu180Trp) |
| c.540G > C or c.540G > T | c.G540C or c.G540T | p.(L180F) | p.(Leu180Phe) |
| c.548G > A | c.G548A | p.(G183D) | p.(Gly183Asp) |

TABLE 55-continued

HEK Amenable Mutations

| DNA Change (Long) | DNA Change (Short) | Protein Change (1-letter Code) | Protein Change (3-letter Code) |
|---|---|---|---|
| c.548G > C | c.G548C | p.(G183A) | p.(Gly183Ala) |
| c.550T > A | c.T550A | p.(Y184N) | p.(Tyr184Asn) |
| c.551A > G | c.A551G | p.(Y184C) | p.(Tyr184Cys) |
|  |  | p.(Y184S) | p.(Tyr184Ser) |
| c.553A > G | c.A553G | p.(K185E) | p.(Lys185Glu) |
| c.559_564dup | c.559_564dup | p.(M187_S188dup) | p.(Met187_Ser188dup) |
| c.559A > G | c.A559G | p.(M187V) | p.(Met187Val) |
| c.560T > C | c.T560C | p.(M187T) | p.(Met187Thr) |
| c.561G > T or c.561G > A or c.561G > C | c.G561T or c.G561A or c.G561C | p.(M187I) | p.(Met187Ile) |
| c.567G > C or c.567G > T | c.G567C or c.G567T | p.(L189F) | p.(Leu189Phe) |
| c.572T > A | c.T572A | p.(L191Q) | p.(Leu191Gln) |
| c.581C > T | c.C581T | p.(T194I) | p.(Thr194Ile) |
| c.584G > T | c.G584T | p.(G195V) | p.(Gly195Val) |
| c.586A > G | c.A586G | p.(R196G) | p.(Arg196Gly) |
| c.593T > C | c.T593C | p.(I198T) | p.(Ile198Thr) |
| c.595G > A | c.G595A | p.(V199M) | p.(Val199Met) |
| c.596T > C | c.T596C | p.(V199A) | p.(Val199Ala) |
| c.596T > G | c.T596G | p.(V199G) | p.(Val199Gly) |
| c.599A > G | c.A599G | p.(Y200C) | p.(Tyr200Cys) |
| c.602C > A | c.C602A | p.(S201Y) | p.(Ser201Tyr) |
| c.602C > T | c.C602T | p.(S201F) | p.(Ser201Phe) |
| c.608A > T | c.A608T | p.(E203V) | p.(Glu203Val) |
| c.609G > C or c.609G > T | c.G609C or c.G609T | p.(E203D) | p.(Glu203Asp) |
| c.611C > T | c.G611T | p.(W204L) | p.(Trp204Leu) |
| c.613C > A | c.C613A | p.(P205T) | p.(Pro205Thr) |
| c.613C > T | c.C613T | p.(P205S) | p.(Pro205Ser) |
| c.614C > T | c.C614T | p.(P205L) | p.(Pro205Leu) |
| c.619C > T | c.T619C | p.(Y207H) | p.(Tyr207His) |
| c.620A > C | c.A620C | p.(Y207S) | p.(Tyr207Ser) |
| c.623T > G | c.T623G | p.(M208R) | p.(Met208Arg) |
| c.628C > T | c.C628T | p.(P210S) | p.(Pro210Ser) |
| c.629C > T | c.C629T | p.(P210L) | p.(Pro210Leu) |
| c.638A > G | c.A638G | p.(K213R) | p.(Lys213Arg) |
| c.638A > T | c.A638T | p.(K213M) | p.(Lys213Met) |
| c.640C > T | c.C640T | p.(P214S) | p.(Pro214Ser) |
| c.641C > T | c.C641T | p.(P214L) | p.(Pro214Leu) |
| c.643A > G | c.A643G | p.(N215D) | p.(Asn215Asp) |
| c.644A > G | c.A644G | p.(N215S) | p.(Asn215Ser) |
| c.[644A > G; 937G > T*] | c.A644G/G937T* | p.(N215S/D313Y*) | p.(Asn215Ser/Asp313Tyr*) |
| c.644A > T | c.A644T | p.(N215I) | p.(Asn215Ile) |
| c.646T > G | c.T646G | p.(Y216D) | p.(Tyr216Asp) |
| c.647A > G | c.A647G | p.(Y216C) | p.(Tyr216Cys) |
| c.655A > C | c.A655C | p.(I219L) | p.(Ile219Leu) |
| c.656T > A | c.T656A | p.(I219N) | p.(Ile219Asn) |
| c.656T > C | c.T656C | p.(I219T) | p.(Ile219Thr) |
| c.659G > A | c.G659A | p.(R220Q) | p.(Arg220Gln) |
| c.659G > C | c.G659C | p.(R220P) | p.(Arg220Pro) |
| c.662A > C | c.A662C | p.(Q221P) | p.(Gln221Pro) |
| c.671A > C | c.A671C | p.(N224T) | p.(Asn224Thr) |
| c.671A > G | c.A671G | p.(N224S) | p.(Asn224Ser) |
| c.673C > G | c.C673G | p.(H225D) | p.(His225Asp) |
| c.683A > G | c.A683G | p.(N228S) | p.(Asn228Ser) |
|  |  | p.(N228H) | p.(Asn228His) |
| c.687T > A or c.687T > G | c.T687A or c.T687G | p.(F229L) | p.(Phe229Leu) |
| c.695T > C | c.T695C | p.(I232T) | p.(Ile232Thr) |
| c.712A > G | c.A712G | p.(S238G) | p.(Ser238Gly) |
| c.713G > A | c.G713A | p.(S238N) | p.(Ser238Asn) |
| c.716T > C | c.T716C | p.(I239T) | p.(Ile239Thr) |
| c.717A > G | c.A717G | p.(I239M) | p.(Ile239Met) |
| c.720G > C or c.720G > T | c.G720C or c.G720T | p.(K240N) | p.(Lys240Asn) |
| c.724A > G | c.A724G | p.(I242V) | p.(Ile242Val) |
| c.724A > T | c.A724T | p.(I242F) | p.(Ile242Phe) |
| c.725T > A | c.T725A | p.(I242N) | p.(Ile242Asn) |
| c.725T > C | c.T725C | p.(I242T) | p.(Ile242Thr) |
| c.728T > G | c.T728G | p.(L243W) | p.(Leu243Trp) |
| c.729C > G or c.729C > T | c.G729C or c.G729T | p.(L243F) | p.(Leu243Phe) |
| c.730G > A | c.G730A | p.(D244N) | p.(Asp244Asn) |
| c.730G > C | c.G730C | p.(D244H) | p.(Asp244His) |
| c.733T > G | c.T733G | p.(W245G) | p.(Trp245Gly) |
| c.740C > G | c.C740G | p.(S247C) | p.(Ser247Cys) |
| c.747C > G or c.747C > A | c.C747G or c.C747A | p.(N249K) | p.(Asn249Lys) |
| c.749A > C | c.A749C | p.(Q250P) | p.(Gln250Pro) |
| c.749A > G | c.A749G | p.(Q250R) | p.(Gln250Arg) |
| c.750G > C | c.G750C | p.(Q250H) | p.(Gln250His) |
| c.758T > C | c.T758C | p.(I253T) | p.(Ile253Thr) |

TABLE 55-continued

HEK Amenable Mutations

| DNA Change (Long) | DNA Change (Short) | Protein Change (1-letter Code) | Protein Change (3-letter Code) |
|---|---|---|---|
| c.758T > G | c.T758G | p.(I253S) | p.(Ile253Ser) |
| c.760-762delGTT or c.761763del | c.760_762delGTT or c.761_763del | p.(V254del) | p.(Val254del) |
| c.769G > C | c.G769C | p.(A257P) | p.(Ala257Pro) |
| c.770C > G | c.C770G | p.(A257G) | p.(Ala257Gly) |
| c.770C > T | c.C770T | p.(A257V) | p.(Ala257Val) |
| c.772G > C or c.772G > A | c.G772C or c.G772A | p.(G258R) | p.(Gly258Arg) |
| c.773G > T | c.G773T | p.(G258V) | p.(Gly258Val) |
| c.776C > A | c.C776A | p.(P259Q) | p.(Pro259Gln) |
| c.776C > G | c.C776G | p.(P259R) | p.(Pro259Arg) |
| c.776C > T | c.C776T | p.(P259L) | p.(Pro259Leu) |
| c.779G > A | c.G779A | p.(G260E) | p.(Gly260Glu) |
| c.779G > C | c.G779C | p.(G260A) | p.(Gly260Ala) |
| c.781G > A | c.G781A | p.(G261S) | p.(Gly261Ser) |
| c.781G > C | c.G781C | p.(G261R) | p.(Gly261Arg) |
| c.781G > T | c.G781T | p.(G261C) | p.(Gly261Cys) |
| c.788A > G | c.A788G | p.(N263S) | p.(Asn263Ser) |
| c.790G > T | c.G790T | p.(D264Y) | p.(Asp264Tyr) |
| c.794C > T | c.C794T | p.(P265L) | p.(Pro265Leu) |
| c.800T > C | c.T800C | p.(M267T) | p.(Met267Thr) |
| c.805T > A | c.G805A | p.(V269M) | p.(Val269Met) |
| c.806T > C | c.T806C | p.(V269A) | p.(Val269Ala) |
| c.809T > C | c.T809C | p.(I270T) | p.(Ile270Thr) |
| c.810T > G | c.T810G | p.(I270M) | p.(Ile270Met) |
| c.811G > A | c.G811A | p.(G271S) | p.(Gly271Ser) |
| c.[811G > A; 937G > T*] | c.G811A/G937T* | p.(G271S/D313Y*) | p.(Gly271Ser/Asp313Tyr*) |
| c.812G > A | c.G812A | p.(G271D) | p.(Gly271Asp) |
| c.823C > G | c.C823G | p.(L275V) | p.(Leu275Val) |
| c.827G > A | c.G827A | p.(S276N) | p.(Ser276Asn) |
| c.829T > G | c.T829G | p.(W277G) | p.(Trp277Gly) |
| c.831G > T or c.831G > C | c.G831T or c.G831C | p.(W277C) | p.(Trp277Cys) |
| c.832A > T | c.A832T | p.(N278Y) | p.(Asn278Tyr) |
| c.835C > G | c.C835G | p.(Q279E) | p.(Gln279Glu) |
| c.838C > A | c.C838A | p.(Q280K) | p.(Gln280Lys) |
| c.840A > T or c.840A > C | c.A840T or c.A840C | p.(Q280H) | p.(Gln280His) |
| c.844A > G | c.A844G | p.(T282A) | p.(Thr282Ala) |
| c.845C > T | c.C845T | p.(T282I) | p.(Thr282Ile) |
| c.850A > G | c.A850G | p.(M284V) | p.(Met284Val) |
| c.851T > C | c.T851C | p.(M284T) | p.(Met284Thr) |
| c.860G > T | c.G860T | p.(W287L) | p.(Trp287Leu) |
| c.862G > C | c.G862C | p.(A288P) | p.(Ala288Pro) |
| c.866T > G | c.T866G | p.(I289S) | p.(Ile289Ser) |
| c.868A > C or c.868A > T | c.A868C or c.A868T | p.(M290L) | p.(Met290Leu) |
| c.869T > C | c.T869C | p.(M290T) | p.(Met290Thr) |
| c.870G > A or c.870G > C or c.870G > T | c.G870A or c.G870C or c.G870T | p.(M290I) | p.(Met290Ile) |
| c.871G > A | c.G871A | p.(A291T) | p.(Ala291Thr) |
| c.877C > A | c.C877A | p.(P293T) | p.(Pro293Thr) |
| c.881T > C | c.T881C | p.(L294S) | p.(Leu294Ser) |
| c.884T > G | c.T884G | p.(F295C) | p.(Phe295Cys) |
| c.886A > G | c.A886G | p.(M296V) | p.(Met296Val) |
| c.886A > T or c.886A > C | c.A886T or c.A886C | p.(M296L) | p.(Met296Leu) |
| c.887T > C | c.T887C | p.(M296T) | p.(Met296Thr) |
| c.888G > A or c.888G > T or c.888G > C | c.G888A or c.G888T or c.G888C | p.(M296I) | p.(Met296Ile) |
| c.893A > G | c.A893G | p.(N298S) | p.(Asn298Ser) |
| c.897C > G or c.897C > A | c.C897G or c.C897A | p.(D299E) | p.(Asp299Glu) |
| c.898C > T | c.C898T | p.(L300F) | p.(Leu300Phe) |
| c.899T > C | c.T899C | p.(L300P) | p.(Leu300Pro) |
| c.901C > G | c.C901G | p.(R301G) | p.(Arg301Gly) |
| c.902G > A | c.G902A | p.(R301Q) | p.(Arg301Gln) |
| c.902G > C | c.G902C | p.(R301P) | p.(Arg301Pro) |
| c.902G > T | c.G902T | p.(R301L) | p.(Arg301Leu) |
| c.907A > T | c.A907T | p.(I303F) | p.(Ile303Phe) |
| c.908T > A | c.T908A | p.(I303N) | p.(Ile303Asn) |
|  |  | p.(I303V) | p.(Ile303Val) |
| c.911G > A | c.G911A | p.(S304N) | p.(Ser304Asn) |
| c.911G > C | c.G911C | p.(S304T) | p.(Ser304Thr) |
| c.919G > A | c.G919A | p.(A307T) | p.(Ala307Thr) |
| c.922A > G | c.A922G | p.(K308E) | p.(Lys308Glu) |
| c.924A > T or c.924A > C | c.A924T or c.A924C | p.(K308N) | p.(Lys308Asn) |
| c.925G > C | c.G925C | p.(A309P) | p.(Ala309Pro) |
| c.926C > T | c.C926T | p.(A309V) | p.(Ala309Val) |
| c.928C > T | c.C928T | p.(L310F) | p.(Leu310Phe) |
| c.931C > G | c.C931G | p.(L311V) | p.(Leu311Val) |
| c.935A > G | c.A935G | p.(Q312R) | p.(Gln312Arg) |

TABLE 55-continued

HEK Amenable Mutations

| DNA Change (Long) | DNA Change (Short) | Protein Change (1-letter Code) | Protein Change (3-letter Code) |
|---|---|---|---|
| c.936G > T or c.936G > C | c.G936T or c.G936C | p.(Q312H) | p.(Gln312His) |
| c.937G > T* | c.G937T* | p.(D313Y*) | p.(Asp313Tyr*) |
| c.[937G > T*; 1232G > A] | c.G937T*/G1232A | p.(D313Y*/G411D) | p.(Asp313Tyr*/Gly411Asp) |
| c.938A > G | c.A938G | p.(D313G) | p.(Asp313Gly) |
| c.946G > A | c.G946A | p.(V316I) | p.(Val316Ile) |
| c.947T > G | c.T947G | p.(V316G) | p.(Val316Gly) |
| c.950T > C | c.T950C | p.(I317T) | p.(Ile317Thr) |
| c.955A > T | c.A955T | p.(I319F) | p.(Ile319Phe) |
| c.956T > C | c.T956C | p.(I319T) | p.(Ile319Thr) |
| c.958A > C | c.A958C | p.(N320H) | p.(Asn320His) |
| c.959A > T | c.A959T | p.(N320I) | p.(Asn320Ile) |
| c.962A > G | c.A962G | p.(Q321R) | p.(Gln321Arg) |
| c.962A > T | c.A962T | p.(Q321L) | p.(Gln321Leu) |
| c.963G > C or c.963G > T | c.G963C or c.G963T | p.(Q321H) | p.(Gln321His) |
| c.964G > A | c.G964A | p.(D322N) | p.(Asp322Asn) |
| c.964G > C | c.G964C | p.(D322H) | p.(Asp322His) |
| c.966A > G or c.966C > G | c.C966A or c.C966G | p.(D322E) | p.(Asp322Glu) |
| c.967C > A | c.C967A | p.(P323T) | p.(Pro323Thr) |
| c.968C > G | c.C968G | p.(P323R) | p.(Pro323Arg) |
| c.973G > A | c.G973A | p.(G325S) | p.(Gly325Ser) |
| c.973G > C | c.G973C | p.(G325R) | p.(Gly325Arg) |
| | | p.(G325C) | p.(Gly325Cys) |
| c.978G > C or c.978G > T | c.G978C or c.G978T | p.(K326N) | p.(Lys326Asn) |
| c.979C > G | c.C979G | p.(Q327E) | p.(Gln327Glu) |
| c.980A > T | c.A980T | p.(Q327L) | p.(Gln327Leu) |
| c.983G > C | c.G983C | p.(G328A) | p.(Gly328Ala) |
| c.989A > G | c.A989G | p.(Q330R) | p.(Gln330Arg) |
| | | p.(Q330P) | p.(Gln330Pro) |
| c.1001G > A | c.G1001A | p.(G334E) | p.(Gly334Glu) |
| c.1010T > C | c.T1010C | p.(F337S) | p.(Phe337Ser) |
| c.1012G > A | c.G1012A | p.(E338K) | p.(Glu338Lys) |
| c.1013A > T | c.A1013T | p.(E338V) | p.(Glu338Val) |
| c.1016T > A | c.T1016A | p.(V339E) | p.(Val339Glu) |
| c.1027C > A | c.C1027A | p.(P343T) | p.(Pro343Thr) |
| c.1028C > T | c.C1028T | p.(P343L) | p.(Pro343Leu) |
| c.1033T > C | c.T1033C | p.(S345P) | p.(Ser345Pro) |
| c.1046G > C | c.G1046C | p.(W349S) | p.(Trp349Ser) |
| c.1055C > G | c.C1055G | p.(A352G) | p.(Ala352Gly) |
| c.1055C > T | c.C1055T | p.(A352V) | p.(Ala352Val) |
| c.1061T > A | c.T1061A | p.(I354K) | p.(Ile354Lys) |
| c.1066C > G | c.C1066G | p.(R356G) | p.(Arg356Gly) |
| c.1066C > T | c.C1066T | p.(R356W) | p.(Arg356Trp) |
| c.1067G > A | c.G1067A | p.(R356Q) | p.(Arg356Gln) |
| c.1067G > C | c.G1067C | p.(R356P) | p.(Arg356Pro) |
| c.1072G > C | c.G1072C | p.(E358Q) | p.(Glu358Gln) |
| c.1073A > C | c.A1073C | p.(E358A) | p.(Glu358Ala) |
| c.1073A > G | c.A1073G | p.(E358G) | p.(Glu358Gly) |
| c.1074G > T or c.1074G > C | c.G1074T or c.G1074C | p.(E358D) | p.(Glu358Asp) |
| c.1076T > C | c.T1076C | p.(I359T) | p.(Ile359Thr) |
| c.1078G > A | c.G1078A | p.(G360S) | p.(Gly360Ser) |
| c.1078G > T | c.G1078T | p.(G360C) | p.(Gly360Cys) |
| | | p.(G360R) | p.(Gly360Arg) |
| c.1079G > A | c.G1079A | p.(G360D) | p.(Gly360Asp) |
| c.1082G > A | c.G1082A | p.(G361E) | p.(Gly361Glu) |
| c.1082G > C | c.G1082C | p.(G361A) | p.(Gly361Ala) |
| c.1084C > A | c.C1084A | p.(P362T) | p.(Pro362Thr) |
| c.1085C > T | c.C1085T | p.(P362L) | p.(Pro362Leu) |
| c.1087C > T | c.C1087T | p.(R363C) | p.(Arg363Cys) |
| c.1088G > A | c.G1088A | p.(R363H) | p.(Arg363His) |
| c.1102G > A | c.G1102A | p.(A368T) | p.(Ala368Thr) |
| c.1117G > A | c.G1117A | p.(G373S) | p.(Gly373Ser) |
| c.1124G > A | c.G1124A | p.(G375E) | p.(Gly375Glu) |
| c.1139C > T | c.C1139T | p.(P380L) | p.(Pro380Leu) |
| c.1153A > G | c.A1153G | p.(T385A) | p.(Tyr385Ala) |
| | | p.(L388F) | p.(Leu388Phe) |
| c.1168G > A | c.G1168A | p.(V390M) | p.(Val390Met) |
| c.1172A > C | c.A1172C | p.(K391T) | p.(Lys391Thr) |
| | | p.(L394P) | p.(Leu394Pro) |
| c.1184G > A | c.G1184A | p.(G395E) | p.(Gly395Glu) |
| c.1184G > C | c.G1184C | p.(G395A) | p.(Gly395Ala) |
| c.1192G > A | c.G1192A | p.(E398K) | p.(Glu398Lys) |
| c.1202_1203insGACTTC | c.1202_1203insGACTTC | p.(T400_S401dup) | p.(Thr400_Ser401dup) |
| c.1208T > C | c.T1208C | p.(L403S) | p.(Leu403Ser) |
| c.1225C > A | c.C1225A | p.(P409T) | p.(Pro409Thr) |
| c.1225C > G | c.C1225G | p.(P409A) | p.(Pro409Ala) |
| c.1225C > T | c.C1225T | p.(P409S) | p.(Pro409Ser) |

TABLE 55-continued

HEK Amenable Mutations

| DNA Change (Long) | DNA Change (Short) | Protein Change (1-letter Code) | Protein Change (3-letter Code) |
|---|---|---|---|
| c.1228A > G | c.A1228G | p.(T410A) | p.(Thr410Ala) |
| c.1229C > T | c.C1229T | p.(T410I) | p.(Thr410Ile) |
| c.1232G > A | c.G1232A | p.(G411D) | p.(Gly411Asp) |
| c.1234A > C | c.A1234C | p.(T412P) | p.(Thr412Pro) |
| c.1235C > A | c.C1235A | p.(T412N) | p.(Thr412Asn) |
|  |  | p.(T412I) | p.(Thr412Ile) |
| c.1253A > G | c.A1253G | p.(E418G) | p.(Glu418Gly) |
|  |  | p.(N419D) | p.(Asn419Asp) |
| c.1261A > G | c.A1261G | p.(M421V) | p.(Met421Val) |

Example 14: Preparation of Intermediate Grade Lucerastat Hydrochloride

Lucerastat ([(2R,3S,4R,5S)-1-butyl-2-(hydroxymethyl)piperidine-3,4,5-triol) is provided or is prepared according to any known method. For example, a suitable method of preparation is reported in International Patent Application Publication No. WO1994026714A1, which is incorporated by reference herein in its entirety.

Generally, deoxygalactonojirimycin (DGJ; Migalastat) is reductively N-alkylated using butyraldehyde in sodium acetate buffer, pH 5.0, in the presence of palladium black under hydrogen. The reaction mixture is stirred at room temperature (ca. 20° C.). The reaction mixture is filtered through diatomaceous earth and the solvent removed by evaporation under vacuum. The resulting N-butylated product is purified by ion-exchange chromatography (Dowex® AG50-X12, H$^+$ form), eluting in 2M NH$_3$ (aq). The solvent is removed by evaporation.

The resulting free base lucerastat is converted to the hydrochloride salt. For example, free base lucerastat is treated with excess concentrated HCl (37% aqueous) in a lower alcohol, followed by removal of the solvent by evaporation, to provide the hydrochloride salt of lucerastat.

Example 15: Purification of Intermediate Grade Lucerastat Hydrochloride

Intermediate grade lucerastat hydrochloride, prepared as in Example 14, is purified by recrystallization. Generally, a first crystallization is performed in a first mixture comprising water and a C1 to C4 alcohol to give a first crystallized lucerastat hydrochloride slurry or solution. The first crystallized lucerastat hydrochloride is isolated from the slurry or solution e.g., by filtration. A second recrystallization may be subsequently performed, comprising crystallizing the first crystallized lucerastat hydrochloride in a second mixture comprising water and a C1 to C4 alcohol to give a second crystallized lucerastat hydrochloride slurry or solution, followed by isolating the second crystallized lucerastat hydrochloride from the second crystallized lucerastat hydrochloride slurry or solution to give active pharmaceutical ingredient (API) grade lucerastat hydrochloride.

Example 16: Purification of Intermediate Grade Migalastat Hydrochloride from Diasteroisomeric Impurities Intermediate grade Migalastat hydrochloride, prepared as in Example 7, comprises diasteroisomeric impurities, which are listed in Table 21. The diasteroisomeric impurities may be separated by normal-phase liquid chromatography (NPLC), such as normal-phase flash column chromatography, using a solvent as eluent. The chromatographic method can be run in either isocratic or gradient elution modes. The eluent may be selected from dichloromethane, ethyl acetate, hexane, acetone or combinations thereof. Alternatively, the diasteroisomeric impurities and migalastat may be converted into a pharmaceutically acceptable salt thereof according to known method before performing NPLC. Similarly, the diasteroisomeric impurities and migalastat may be treated with alcohol-protecting group, followed by NPLC purification and treatment to remove the alcohol-protecting group. The alcohol-protecting group may be allyl, acetyl, or benzoly, benzyl. The allyl alcohol-protecting group may be removed by hydrolysis or by hydrogenation in the presence of Pd/C. the acetyl or benzoyl alcohol-protecting group may be removed by hydrolysis under acidic conditions or basic conditions. The benzyl alcohol-protecting group may be removed by catalytic hydrogenation. The catalytic hydrogenation may be performed in the presence of homogenous or heterogenous metal catalyst. The metal catalyst may be based on Pd, Pt, Ni, Rh or Ru. Similarly, the diasteroisomeric impurities and migalastat may be treated with amine-protecting group, followed by NPLC purification and treatment to remove the amine-protecting group. The amino-protecting group may be benzyl, benzhydryl, phenylethyl, benzyloxycarbonyl or tert-butoxycabonyl. The benzyl, benzhydryl, phenylethyl and benzyloxycarbonyl amino-protecting group may be removed by catalytic hydrogenation. The tert-butoxycabonyl amino-protecting group may be removed by treatment with an acid. The acid may include but not limited to trifluoroacetic acid and hydrochloric acid.

Example 17: Purification of Intermediate Grade Lucerastat Hydrochloride from Diasteroisomeric Impurities Using Chromatography Method Intermediate grade lucerastat hydrochloride, prepared as in Example 7, comprises diasteroisomeric impurities, which are listed in Table 21. The diasteroisomeric impurities may be separated by normal-phase liquid chromatography (NPLC), such as normal-phase flash column chromatography, using a solvent as eluent. The chromatographic method can be run in either isocratic or gradient elution modes. The eluent may be selected from dichloromethane, ethyl acetate, hexane, acetone or combinations thereof. Alternatively, the diasteroisomeric impurities and lucerastat may be converted into a pharmaceutically acceptable salt thereof according to known method before performing NPLC. Similarly, the diasteroisomeric impurities and lucerastat may be treated with alcohol-protecting group, followed by NPLC purification and treatment to remove the alcohol-protecting group. The alcohol-protecting group may be allyl, acetyl, or benzoly, benzyl. The allyl alcohol-protecting group may be removed by hydrolysis or by hydrogenation in the presence of Pd/C. the acetyl or benzoyl alcohol-protecting group may be removed by hydrolysis under acidic conditions or basic conditions. The benzyl alcohol-protecting group may be removed by catalytic hydrogenation. The catalytic hydrogenation may be performed in the presence of homogenous or heterogenous metal catalyst. The metal catalyst may be based on Pd, Pt, Ni, Rh or Ru. Similarly, the diastereoisomeric impurities and lucerastat may be treated with amine-protecting group, followed by NPLC purification and treatment to remove the amine-protecting group. The amino-protecting group may be benzyl, benzhydryl, phenylethyl, benzyloxycarbonyl or tert-butoxycabonyl. The benzyl, benzhydryl, phenylethyl and benzyloxycarbonyl amino-protecting group may be removed by catalytic hydrogenation. The tert-butoxycabonyl amino-protecting group may be removed by treatment with an acid. The acid may include but not limited to trifluoroacetic acid and hydrochloric acid.

The invention claimed is:

1. A method of purifying intermediate grade migalastat salt, the method comprising:
   i) performing a first crystallization comprising crystallizing intermediate grade migalastat salt in a first mixture to give a first crystallized migalastat salt;
   ii) isolating the first crystallized migalastat salt from the first mixture to give an isolated first crystallized migalastat salt;
   iii) performing a second crystallization comprising crystallizing the isolated first crystallized migalastat salt in a second mixture to give a second crystallized migalastat salt; and
   iv) isolating the second crystallized migalastat salt from the second mixture to give an active pharmaceutical ingredient (API) grade migalastat salt,
   wherein one or both of the first mixture and the second mixture comprise water and a C1 to C4 alcohol.

2. The method of claim 1, wherein the first crystallization comprises:
   admixing the intermediate grade migalastat salt in water to produce a first migalastat salt slurry or solution;
   adding the C1 to C4 alcohol to the first migalastat salt slurry or solution to produce a second migalastat salt slurry or solution at a first crystallization temperature for inducing crystallization; and
   cooling the second migalastat salt slurry or solution to a first isolation temperature to complete crystallization, providing the first mixture.

3. The method of claim 1, wherein the isolating in ii) comprises:
   filtering the first mixture to provide the first crystallized migalastat salt;
   washing the first crystallized migalastat salt with the C1 to C4 alcohol to provide a washed first crystallized migalastat salt; and
   optionally, drying the washed first crystallized migalastat salt to give the isolated first crystallized migalastat salt.

4. The method of claim 1, wherein the second crystallization comprises:
   admixing the isolated first crystallized migalastat salt in water to produce a third migalastat salt slurry or solution;
   adding a first portion of the C1 to C4 alcohol to the third migalastat salt slurry or solution to produce a fourth migalastat salt slurry or solution at a second crystallization temperature for inducing crystallization;
   adding a second portion of the C1 to C4 alcohol to the fourth migalastat salt slurry or solution after a hold time; and
   cooling the fourth migalastat salt slurry or solution to a second isolation temperature to complete crystallization, providing the second mixture.

5. The method of claim 1, wherein the isolating in iv) comprises:
   filtering the second mixture to isolate the second crystallized migalastat salt;
   washing the second crystallized migalastat salt with the C1 to C4 alcohol; and
   drying the washed second crystallized migalastat salt to give the API grade migalastat salt.

6. The method of claim 1, wherein the C1 to C4 alcohol is ethanol.

7. The method of claim 1, wherein the intermediate grade migalastat salt, the isolated first crystallized migalastat salt, or both, is admixed in an amount of water which is from about 1.0 to about 1.6 times the weight of the corresponding migalastat salt.

8. The method of claim 2, wherein the first crystallization temperature is within a range of from about 30° C. to about 70° C.

9. The method of claim 2, wherein the first isolation temperature is within a range from about 5° C. to about 35° C.

10. The method of claim 4, wherein the second crystallization temperature is within a range of from about 30° C. to about 70° C.

11. The method of claim 4, wherein the second isolation temperature is within a range from about 5° C. to about 35° C.

12. The method of claim 1, wherein the migalastat salt comprises migalastat hydrochloride.

13. The method of claim 2, wherein the migalastat salt comprises migalastat hydrochloride.

14. The method of claim 3, wherein the migalastat salt comprises migalastat hydrochloride.

15. The method of claim 4, wherein the migalastat salt comprises migalastat hydrochloride.

16. The method of claim 5, wherein the migalastat salt comprises migalastat hydrochloride.

17. A method of purifying intermediate grade migalastat hydrochloride, the method comprising:
   i) performing a first crystallization comprising crystallizing intermediate grade migalastat hydrochloride in a first mixture to give a first crystallized migalastat hydrochloride;
   ii) isolating the first crystallized migalastat hydrochloride from the first mixture to give an isolated first crystallized migalastat hydrochloride;
   iii) performing a second crystallization comprising crystallizing the isolated first crystallized migalastat hydrochloride in a second mixture to give a second crystallized migalastat hydrochloride; and
   iv) isolating the second crystallized migalastat hydrochloride from the second mixture to give an active pharmaceutical ingredient (API) grade migalastat hydrochloride,
   wherein one or both of the first mixture and the second mixture comprise water and a C1 to C4 alcohol.

18. The method of claim 17, wherein the second crystallization comprises:
   admixing the isolated first crystallized migalastat hydrochloride in water to produce a third migalastat hydrochloride slurry or solution;

adding a first portion of the C1 to C4 alcohol to the third migalastat hydrochloride slurry or solution to produce a fourth migalastat hydrochloride slurry or solution at a second crystallization temperature for inducing crystallization;

adding a second portion of the C1 to C4 alcohol to the fourth migalastat hydrochloride slurry or solution after a hold time; and cooling the fourth migalastat hydrochloride slurry or solution to a second isolation temperature to complete crystallization, providing the second mixture.

19. The method of claim 18, wherein the second crystallization temperature is within a range of from about 30° C. to about 70° C.

20. The method of claim 18, wherein the second isolation temperature is within a range from about 5° C. to about 35° C.

* * * * *